United States Patent
Arora et al.

(10) Patent No.: US 10,851,133 B2
(45) Date of Patent: Dec. 1, 2020

(54) STABILIZED MINIMAL COILED-COIL MIMETICS

(71) Applicant: NEW YORK UNIVERSITY, New York, NY (US)

(72) Inventors: Paramjit S. Arora, Cold Spring Harbor, NY (US); Michael G. Wuo, Brooklyn, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/580,987

(22) PCT Filed: Jun. 8, 2016

(86) PCT No.: PCT/US2016/036531
§ 371 (c)(1),
(2) Date: Dec. 8, 2017

(87) PCT Pub. No.: WO2016/201007
PCT Pub. Date: Dec. 15, 2016

(65) Prior Publication Data
US 2018/0162907 A1    Jun. 14, 2018

Related U.S. Application Data

(60) Provisional application No. 62/211,603, filed on Aug. 28, 2015, provisional application No. 62/172,669, filed on Jun. 8, 2015.

(51) Int. Cl.
*A61K 38/00* (2006.01)
*C07K 7/06* (2006.01)
(Continued)

(52) U.S. Cl.
CPC .............. *C07K 7/06* (2013.01); *A61P 35/02* (2018.01); *C07K 14/00* (2013.01); *G01N 33/68* (2013.01);
(Continued)

(58) Field of Classification Search
None
See application file for complete search history.

(56) References Cited

FOREIGN PATENT DOCUMENTS

WO    99/16883 A2    4/1999

OTHER PUBLICATIONS

Hadley et al. (Preferred side-chain constellations at antiparallel coiled-coil interfaces. 530-535, PNAS; Jan. 15, 2008, vol. 105, No. 2.*

(Continued)

Primary Examiner — Jeanette M Lieb
(74) Attorney, Agent, or Firm — Troutman Pepper Hamilton Sanders LLP (Rochester)

(57) ABSTRACT

This invention relates to a macrostructure that includes an antiparallel coiled-coil structure shown below or a parallel coiled-coil structure shown below and described in the present application.

(Continued)

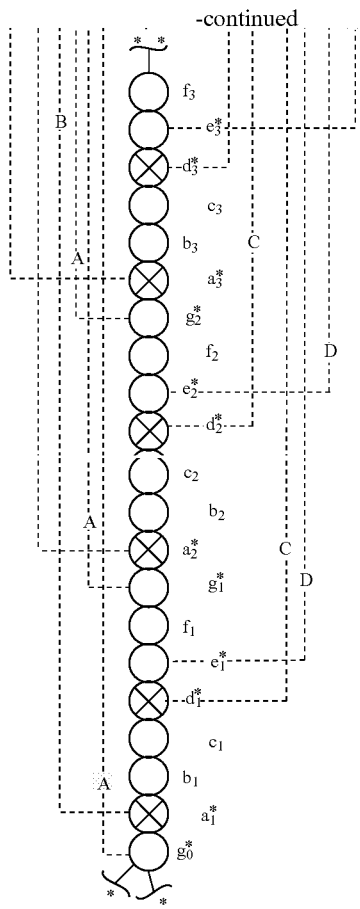
(two-dimensional view);
Parallel
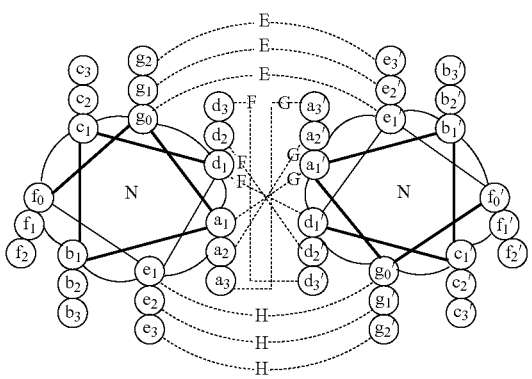
(helical wheel view)
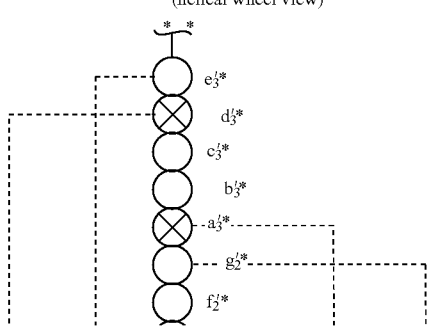
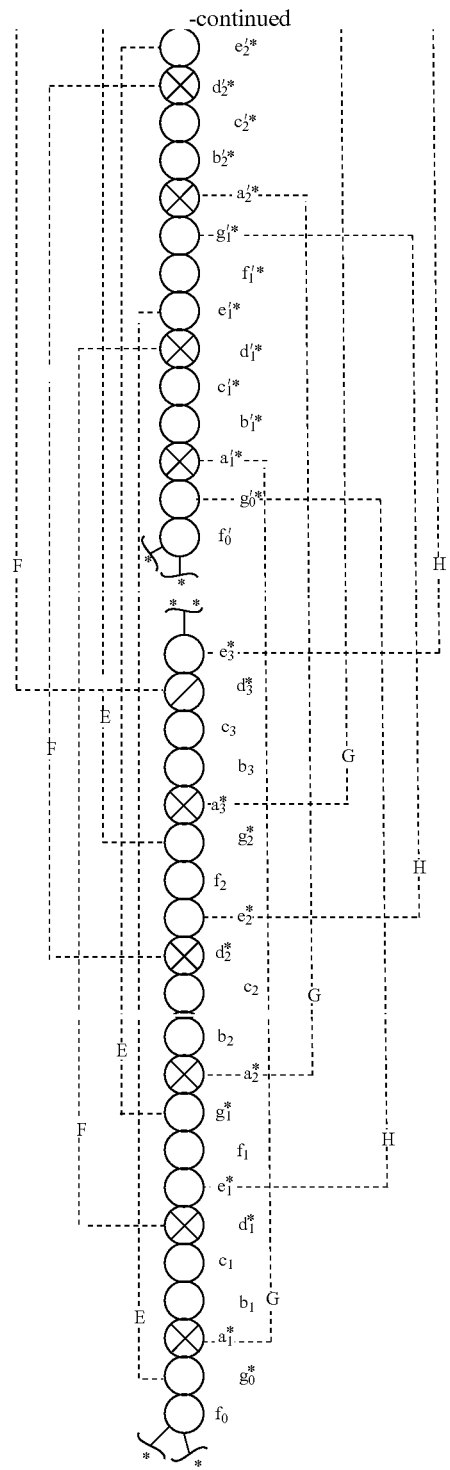
(two-dimensional view)
17 Claims, 23 Drawing Sheets
Specification includes a Sequence Listing.
(51) Int. Cl.
*C07K 14/00* (2006.01)
*G01N 33/68* (2006.01)

| | | |
|---|---|---|
| *A61P 35/02* | (2006.01) | |
| *A61K 48/00* | (2006.01) | |

(52) U.S. Cl.
CPC .............. *A61K 38/00* (2013.01); *A61K 48/00* (2013.01); *C07K 2319/73* (2013.01)

(56) References Cited

OTHER PUBLICATIONS

Hadley et al., "Preferred Side-Chain Constellations at Antiparallel Coiled-Coil Interfaces," PNAS 105(2):530-35 (2008).
Hadley et al., "Preferred Side-Chain Constellations at Antiparallel Coiled-Coil Interfaces," PNAS 105(2):530 (2008), Supporting Information (pp. 1-29).
Keating et al., "Side-Chain Repacking Calculations for Predicting Structures and Stabilities of Heterodimeric Coiled Coils," PNAS 98(26):14825-30 (2001).
Keating et al., "Side-Chain Repacking Calculations for Predicting Structures and Stabilities of Heterodimeric Coiled Coils," PNAS 98(26):14825 (2001), Supporting Information (pp. 1-4).
Mason et al., "Semirational Design of Jun-Fos Coiled Coils with Increased Affinity: Universal Implications for Leucine Zipper Prediction and Design," PNAS 103(24):8989-94 (2006).
Mason et al., "Semirational Design of Jun-Fos Coiled Coils with Increased Affinity: Universal Implications for Leucine Zipper Prediction and Design," PNAS 103(24):8989-94 (2006), Supporting Information (pp. 1-7).
Oberoi et al., "Structural Basis for the Assembly of the SMRT/NCoR Core Transcriptional Repression Machinery," Nat. Struct. Mol. Biol. 18(2):177-84 (2011).
Oberoi et al., "Structural Basis for the Assembly of the SMRT/NCoR Core Transcriptional Repression Machinery," Nat. Struct. Mol. Biol. 18(2):177 (2011), Supplementary Material (pp. 1-8).
PCT/US2016/036531, International Search Report and Written Opinion (dated Oct. 6, 2016).
Poster, Wuo & Arora, "An Effective Strategy for Stabilizing Minimal Coiled-Coil Mimetics," presented at Albany 2015: Conversation 19 (Jun. 9, 2015).
Poster, Wuo & Arora, "Short, Stabilized Coiled Coils as Potential Modulators of Protein-Mediated Interactions," presented at the New York Academy of Sciences (Sep. 15, 2014).
Wuo et al., "An Effective Strategy for Stabilizing Minimal Coiled Coil Mimetics," J. Am. Chem. Soc. 137:11618-21 (2015).
Wuo et al., "An Effective Strategy for Stabilizing Minimal Coiled Coil Mimetics," J. Am. Chem. Soc. 137:11618 (2015), Supporting Information (pp. S1-S23).
PCT/US2016/36531, International Preliminary Report on Patentability (dated Dec. 21, 2017).
EP 16808232.9, Supplemental European Search Report (dated Jan. 22, 2019).
Horne et al, "Heterocyclic Peptide Backbone Modifications in an Alpha-Helical Coiled Coil," J. Amer. Chem. Soc. 126 (47):15366-67 (2004).
Sun et al., "A Stable Transcription Factor Complex Nucleated by Oligomeric AML1-ETO Controls Leukaemogenesis," Nature 500(7460):93-97 (2013).
Del Rizzo et al., "ATP Synthase b Subunit Dimerization Domain: A Right-Handed Coiled Coil with Offset Helices," J. Mol. Biol. 364:735-46 (2006).
European Patent Application No. 16808232.9, Examination Report dated Aug. 27, 2020.
Hodges, "De Novo Design of Alpha-Helical Proteins: Basic Research to Medical Applications," Biochem. Cell Biol. 74:133-54 (1996).
Holub & Kirshenbaum, "Tricks with Clicks: Modification of Peptidomimetic Oligomers via Copper-Catalyzed Azide-Alkyne [3 + 2] Cycloaddition," Chem. Soc. Rev. 39:1325-37 (2010).
Monera et al., "Comparison of Antiparallel and Parallel Two-Stranded Alpha-Helical Coiled-Coils: Design, Synthesis, and Characterization," J. Biol. Chem. 268(26):19218-27 (1993).
Zhou et al., "Disulfide Bond Contribution to Protein Stability: Positional Effects of Substitution in the Hydrophobic Core; of the Two-Stranded Alpha-Helical Coiled-Coil," Biochemistry 32:3178-87 (1993).

\* cited by examiner

Figures 5A-B

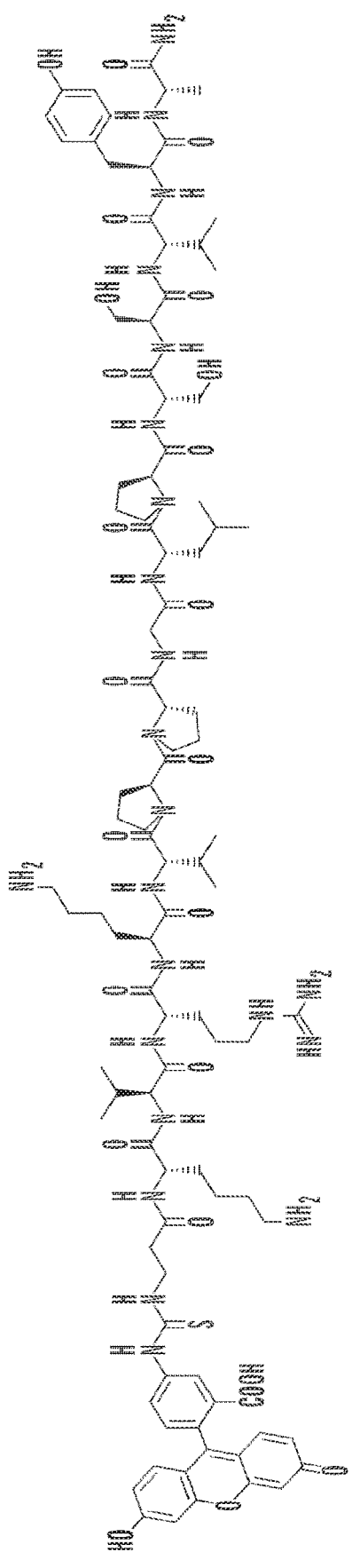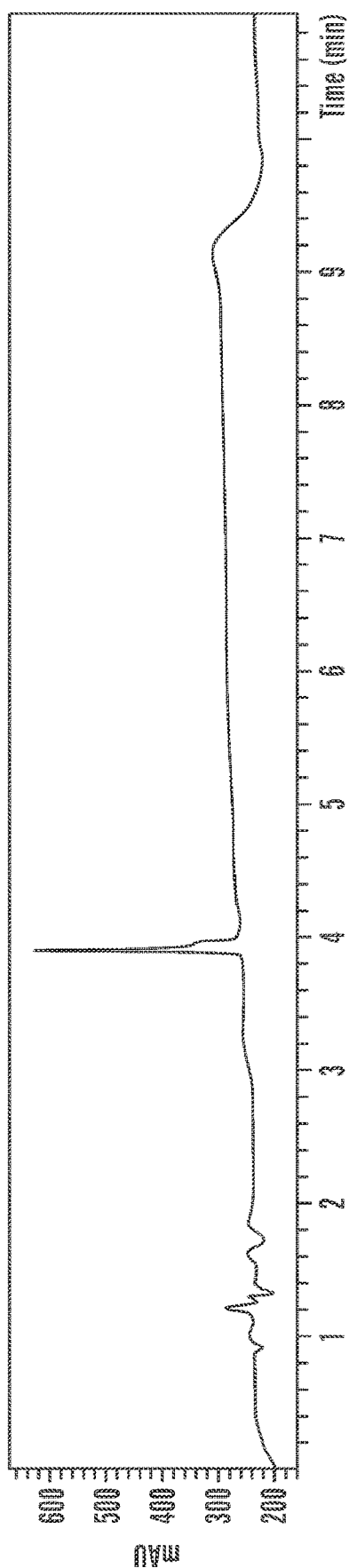
FIG. 7

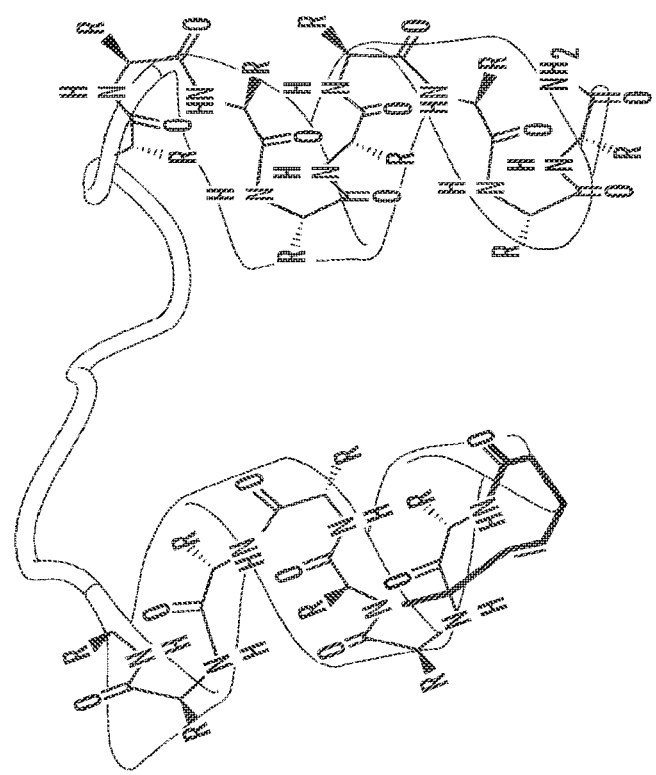
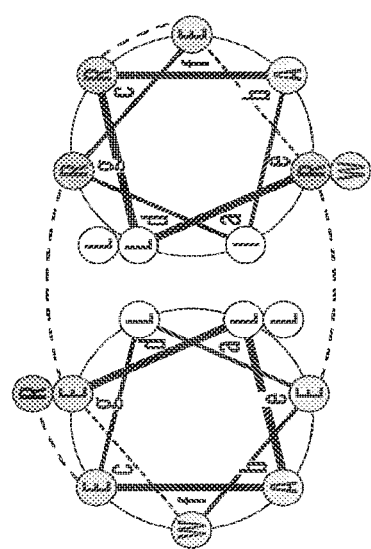
FIG. 10B
FIG. 10A

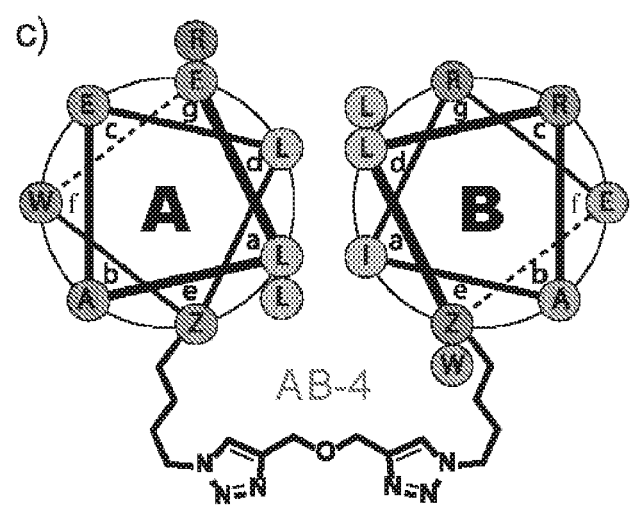
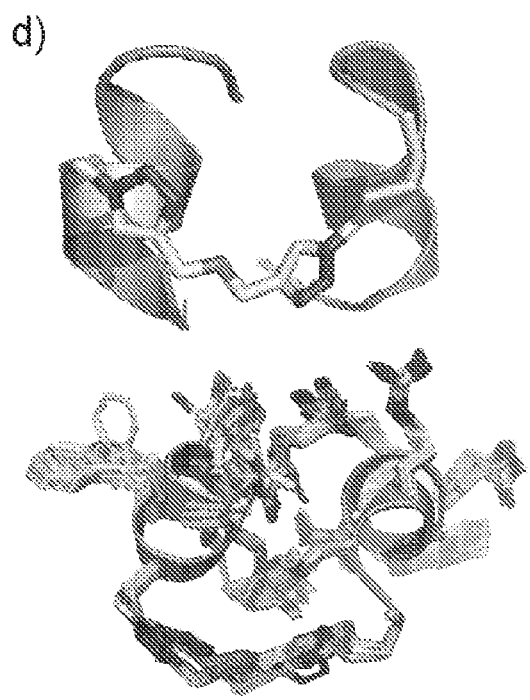
Figures 11C-D

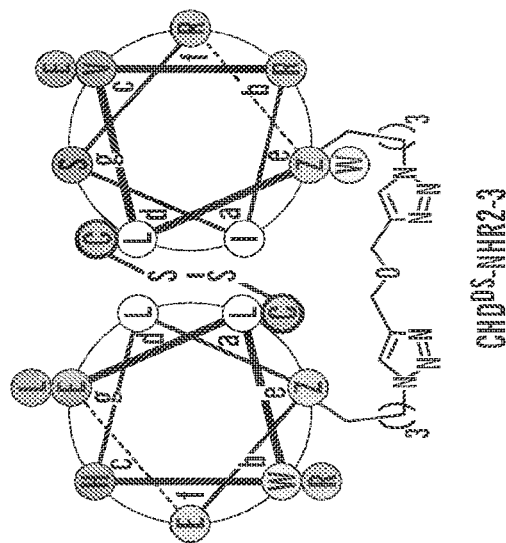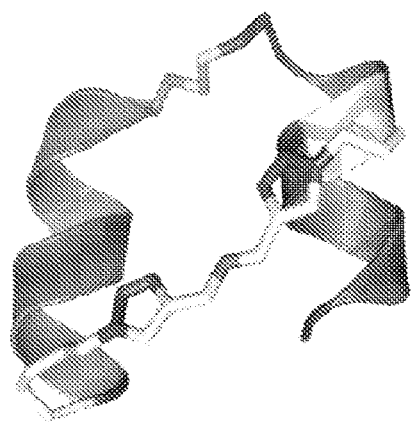
FIG. 12D

SEQUENCE LISTING

```
<160> NUMBER OF SEQ ID NOS: 25

<210> SEQ ID NO 1
<211> LENGTH: 9
<212> TYPE: PRT
<213> ORGANISM: Artificial
<220> FEATURE:
<223> OTHER INFORMATION: Unconstrained peptide A
<220> FEATURE:
<221> NAME/KEY: MISC_FEATURE
<222> LOCATION: (1)..(1)
<223> OTHER INFORMATION: Glu at position 1 is acetylated

<400> SEQUENCE: 1

Glu Leu Ala Glu Leu Glu Trp Arg Leu
1               5

<210> SEQ ID NO 2
<211> LENGTH: 9
<212> TYPE: PRT
<213> ORGANISM: Artificial
<220> FEATURE:
<223> OTHER INFORMATION: Unconstrained peptide B
```

-continued

```
<220> FEATURE:
<221> NAME/KEY: MISC_FEATURE
<222> LOCATION: (1)..(1)
<223> OTHER INFORMATION: Leu at position 1 is acetylated

<400> SEQUENCE: 2

Leu Trp Glu Arg Ile Ala Arg Leu Arg
1               5

<210> SEQ ID NO 3
<211> LENGTH: 25
<212> TYPE: PRT
<213> ORGANISM: Artificial
<220> FEATURE:
<223> OTHER INFORMATION: Hydrogen bond surrogate peptide AB-1
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
<223> OTHER INFORMATION: Xaa at position 4 is N-allylalanine

<400> SEQUENCE: 3

Xaa Glu Leu Xaa Glu Leu Glu Trp Arg Leu Gly Gly Ser Ser Gly Gly
1               5                   10                  15

Leu Ala Glu Arg Ile Ala Arg Leu Arg
            20                  25

<210> SEQ ID NO 4
<211> LENGTH: 30
<212> TYPE: PRT
<213> ORGANISM: Artificial
<220> FEATURE:
<223> OTHER INFORMATION: Cyclic peptide AB-2
<220> FEATURE:
<221> NAME/KEY: MISC_FEATURE
<222> LOCATION: (1)..(1)
<223> OTHER INFORMATION: Position 1 and 30 are linked by a peptide bond
      to form a cyclic peptide
<220> FEATURE:
<221> NAME/KEY: MISC_FEATURE
<222> LOCATION: (30)..(30)
<223> OTHER INFORMATION: Position 1 and 30 are linked by a peptide bond
      to form a cyclic peptide

<400> SEQUENCE: 4

Gly Gly Ser Ser Gly Gly Glu Leu Ala Glu Leu Glu Trp Arg Leu Gly
1               5                   10                  15

Gly Ser Asn Gly Gly Leu Ala Glu Arg Ile Ala Arg Leu Arg
            20                  25                  30

<210> SEQ ID NO 5
<211> LENGTH: 24
<212> TYPE: PRT
<213> ORGANISM: Artificial
<220> FEATURE:
<223> OTHER INFORMATION: Disulfide-bridged peptide AB-3
<220> FEATURE:
<221> NAME/KEY: MISC_FEATURE
<222> LOCATION: (2)..(2)
<223> OTHER INFORMATION: Position 2 and 23 are linked by a disulfide
      bridge
<220> FEATURE:
<221> NAME/KEY: MISC_FEATURE
<222> LOCATION: (23)..(23)
<223> OTHER INFORMATION: Position 2 and 23 are linked by a disulfide
      bridge
```

```
<400> SEQUENCE: 5

Glu Cys Ala Glu Leu Glu Trp Arg Leu Gly Gly Ser Ser Gly Gly Leu
1               5                   10                  15

Ala Glu Arg Ile Ala Arg Cys Arg
            20

<210> SEQ ID NO 6
<211> LENGTH: 10
<212> TYPE: PRT
<213> ORGANISM: Artificial
<220> FEATURE:
<223> OTHER INFORMATION: Strand A of coiled-coil CHD-NHR2-1
<220> FEATURE:
<221> NAME/KEY: MISC_FEATURE
<222> LOCATION: (6)..(6)
<223> OTHER INFORMATION: Xaa at position 6 is linked to SEQ ID NO:7 by a
      triazole bridge
<220> FEATURE:
<221> NAME/KEY: MISC_FEATURE
<222> LOCATION: (6)..(6)
<223> OTHER INFORMATION: Xaa at position 6 is azidolysine

<400> SEQUENCE: 6

Glu Trp Lys His Leu Xaa His Leu Leu Asn
1               5                   10

<210> SEQ ID NO 7
<211> LENGTH: 10
<212> TYPE: PRT
<213> ORGANISM: Artificial
<220> FEATURE:
<223> OTHER INFORMATION: Strand B of coiled-coil CHD-NHR2-1
<220> FEATURE:
<221> NAME/KEY: MISC_FEATURE
<222> LOCATION: (10)..(10)
<223> OTHER INFORMATION: Xaa at position 10 is linked to SEQ ID NO:6 by
      a triazole bridge
<220> FEATURE:
<221> NAME/KEY: MISC_FEATURE
<222> LOCATION: (10)..(10)
<223> OTHER INFORMATION: Xaa at position 10 is azidolysine

<400> SEQUENCE: 7

Lys Thr Arg Arg Ser Leu Thr Val Leu Xaa
1               5                   10

<210> SEQ ID NO 8
<211> LENGTH: 10
<212> TYPE: PRT
<213> ORGANISM: Artificial
<220> FEATURE:
<223> OTHER INFORMATION: Strand A of coiled-coil CHD-NHR2-2 and
      CHD-NHR2-7
<220> FEATURE:
<221> NAME/KEY: MISC_FEATURE
<222> LOCATION: (6)..(6)
<223> OTHER INFORMATION: Xaa at position 6 is linked to SEQ ID NO:9 by a
      triazole bridge
<220> FEATURE:
<221> NAME/KEY: MISC_FEATURE
<222> LOCATION: (6)..(6)
<223> OTHER INFORMATION: Xaa at position 6 is azidolysine

<400> SEQUENCE: 8

Glu Leu Trp His Leu Xaa Glu Leu Leu Arg
1               5                   10
```

```
<210> SEQ ID NO 9
<211> LENGTH: 10
<212> TYPE: PRT
<213> ORGANISM: Artificial
<220> FEATURE:
<223> OTHER INFORMATION: Strand B of coiled-coil CHD-NHR2-2 and
      CHD-NHR2-6
<220> FEATURE:
<221> NAME/KEY: MISC_FEATURE
<222> LOCATION: (10)..(10)
<223> OTHER INFORMATION: Xaa at position 10 is linked to SEQ ID NO:8 by
      a triazole bridge
<220> FEATURE:
<221> NAME/KEY: MISC_FEATURE
<222> LOCATION: (10)..(10)
<223> OTHER INFORMATION: Xaa at position 10 is azidolysine

<400> SEQUENCE: 9

Glu Leu Trp Arg Ser Ile Arg Val Leu Xaa
1               5                   10

<210> SEQ ID NO 10
<211> LENGTH: 10
<212> TYPE: PRT
<213> ORGANISM: Artificial
<220> FEATURE:
<223> OTHER INFORMATION: Strand A of coiled-coil CHD-NHR2-3
<220> FEATURE:
<221> NAME/KEY: MISC_FEATURE
<222> LOCATION: (6)..(6)
<223> OTHER INFORMATION: Xaa at position 6 is linked to SEQ ID NO:11 by
      a triazole bridge
<220> FEATURE:
<221> NAME/KEY: MISC_FEATURE
<222> LOCATION: (6)..(6)
<223> OTHER INFORMATION: Xaa at position 6 is azidolysine
<220> FEATURE:
<221> NAME/KEY: MISC_FEATURE
<222> LOCATION: (9)..(9)
<223> OTHER INFORMATION: Cys at position 9 is linked to SEQ ID NO:11 by
      a disulfide bridge

<400> SEQUENCE: 10

Glu Leu Trp His Leu Xaa Glu Leu Cys Arg
1               5                   10

<210> SEQ ID NO 11
<211> LENGTH: 10
<212> TYPE: PRT
<213> ORGANISM: Artificial
<220> FEATURE:
<223> OTHER INFORMATION: Strand B of coiled-coil CHD-NHR2-3
<220> FEATURE:
<221> NAME/KEY: MISC_FEATURE
<222> LOCATION: (2)..(2)
<223> OTHER INFORMATION: Cys at position 2 is linked to SEQ ID NO:10 by
      a disulfide bridge
<220> FEATURE:
<221> NAME/KEY: MISC_FEATURE
<222> LOCATION: (10)..(10)
<223> OTHER INFORMATION: Xaa at position 10 is linked to SEQ ID NO:10 by
      a triazole bridge
<220> FEATURE:
<221> NAME/KEY: MISC_FEATURE
<222> LOCATION: (10)..(10)
<223> OTHER INFORMATION: Xaa at position 10 is azidolysine

<400> SEQUENCE: 11

Glu Cys Trp Arg Ser Ile Arg Val Leu Xaa
1               5                   10
```

```
<210> SEQ ID NO 12
<211> LENGTH: 10
<212> TYPE: PRT
<213> ORGANISM: Artificial
<220> FEATURE:
<223> OTHER INFORMATION: Strand A of coiled-coil CHD-NHR2-4
<220> FEATURE:
<221> NAME/KEY: MISC_FEATURE
<222> LOCATION: (5)..(5)
<223> OTHER INFORMATION: Cys at position 5 is linked to SEQ ID NO:13 by
      a disulfide bridge
<220> FEATURE:
<221> NAME/KEY: MISC_FEATURE
<222> LOCATION: (6)..(6)
<223> OTHER INFORMATION: Xaa at position 6 is linked to SEQ ID NO:13 by
      a triazole bridge
<220> FEATURE:
<221> NAME/KEY: MISC_FEATURE
<222> LOCATION: (6)..(6)
<223> OTHER INFORMATION: Xaa at position 6 is azidolysine

<400> SEQUENCE: 12

Glu Leu Trp His Cys Xaa Glu Leu Leu Arg
1               5                   10

<210> SEQ ID NO 13
<211> LENGTH: 10
<212> TYPE: PRT
<213> ORGANISM: Artificial
<220> FEATURE:
<223> OTHER INFORMATION: Strand B of coiled-coil CHD-NHR2-4
<220> FEATURE:
<221> NAME/KEY: MISC_FEATURE
<222> LOCATION: (6)..(6)
<223> OTHER INFORMATION: Cys at position 6 is linked to SEQ ID NO:12 by
      a disulfide bridge
<220> FEATURE:
<221> NAME/KEY: MISC_FEATURE
<222> LOCATION: (10)..(10)
<223> OTHER INFORMATION: Xaa at position 10 is linked to SEQ ID NO:12 by
      a triazole bridge
<220> FEATURE:
<221> NAME/KEY: MISC_FEATURE
<222> LOCATION: (10)..(10)
<223> OTHER INFORMATION: Xaa at position 10 is azidolysine

<400> SEQUENCE: 13

Glu Leu Trp Arg Ser Cys Arg Val Leu Xaa
1               5                   10

<210> SEQ ID NO 14
<211> LENGTH: 10
<212> TYPE: PRT
<213> ORGANISM: Artificial
<220> FEATURE:
<223> OTHER INFORMATION: Strand A of coiled-coil CHD-NHR2-5
<220> FEATURE:
<221> NAME/KEY: MISC_FEATURE
<222> LOCATION: (2)..(2)
<223> OTHER INFORMATION: Cys at position 2 is linked to SEQ ID NO:15 by
      a disulfide bridge
<220> FEATURE:
<221> NAME/KEY: MISC_FEATURE
<222> LOCATION: (6)..(6)
<223> OTHER INFORMATION: Xaa at position 6 is linked to SEQ ID NO:15 by
      a triazole bridge
<220> FEATURE:
<221> NAME/KEY: MISC_FEATURE
<222> LOCATION: (6)..(6)
<223> OTHER INFORMATION: Xaa at position 6 is azidolysine

<400> SEQUENCE: 14

Glu Cys Trp His Leu Xaa Glu Leu Leu Arg
1               5                   10
```

```
<210> SEQ ID NO 15
<211> LENGTH: 10
<212> TYPE: PRT
<213> ORGANISM: Artificial
<220> FEATURE:
<223> OTHER INFORMATION: Strand B of coiled-coil CHD-NHR2-5
<220> FEATURE:
<221> NAME/KEY: MISC_FEATURE
<222> LOCATION: (9)..(9)
<223> OTHER INFORMATION: Cys at position 9 is linked to SEQ ID NO:14 by
      a disulfide bridge
<220> FEATURE:
<221> NAME/KEY: MISC_FEATURE
<222> LOCATION: (10)..(10)
<223> OTHER INFORMATION: Xaa at position 10 is linked to SEQ ID NO:14 by
      a triazole bridge
<220> FEATURE:
<221> NAME/KEY: MISC_FEATURE
<222> LOCATION: (10)..(10)
<223> OTHER INFORMATION: Xaa at position 10 is azidolysine

<400> SEQUENCE: 15

Glu Leu Trp Arg Ser Ile Arg Val Cys Xaa
1               5                   10

<210> SEQ ID NO 16
<211> LENGTH: 29
<212> TYPE: PRT
<213> ORGANISM: Artificial
<220> FEATURE:
<223> OTHER INFORMATION: ER transport peptide

<400> SEQUENCE: 16

Met Met Ser Phe Val Ser Leu Leu Leu Val Gly Ile Leu Phe Tyr Ala
1               5                   10                  15

Thr Glu Ala Glu Gln Leu Thr Lys Cys Glu Val Phe Gln
            20                  25

<210> SEQ ID NO 17
<211> LENGTH: 4
<212> TYPE: PRT
<213> ORGANISM: Artificial
<220> FEATURE:
<223> OTHER INFORMATION: ER retention signal

<400> SEQUENCE: 17

Lys Glu Asp Leu
1

<210> SEQ ID NO 18
<211> LENGTH: 8
<212> TYPE: PRT
<213> ORGANISM: Artificial
<220> FEATURE:
<223> OTHER INFORMATION: Nuclear transport peptide

<400> SEQUENCE: 18

Pro Pro Lys Lys Lys Arg Lys Val
1               5

<210> SEQ ID NO 19
<211> LENGTH: 25
<212> TYPE: PRT
<213> ORGANISM: Artificial
<220> FEATURE:
<223> OTHER INFORMATION: Mitochondrial transport peptide
```

```
<400> SEQUENCE: 19

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 20
<211> LENGTH: 6
<212> TYPE: PRT
<213> ORGANISM: Artificial
<220> FEATURE:
<223> OTHER INFORMATION: Peptide linker

<400> SEQUENCE: 20

Gly Gly Ser Ser Gly Gly
1               5

<210> SEQ ID NO 21
<211> LENGTH: 6
<212> TYPE: PRT
<213> ORGANISM: Artificial
<220> FEATURE:
<223> OTHER INFORMATION: Peptide linker

<400> SEQUENCE: 21

Gly Gly Ser Asn Gly Gly
1               5

<210> SEQ ID NO 22
<211> LENGTH: 10
<212> TYPE: PRT
<213> ORGANISM: Artificial
<220> FEATURE:
<223> OTHER INFORMATION: Linear strand A from NHR2

<400> SEQUENCE: 22

Glu Trp Lys His Leu Asp His Leu Leu Asn
1               5                   10

<210> SEQ ID NO 23
<211> LENGTH: 10
<212> TYPE: PRT
<213> ORGANISM: Artificial
<220> FEATURE:
<223> OTHER INFORMATION: Linear strand B from NHR2

<400> SEQUENCE: 23

Lys Thr Arg Arg Ser Leu Thr Val Leu Arg
1               5                   10

<210> SEQ ID NO 24
<211> LENGTH: 10
<212> TYPE: PRT
<213> ORGANISM: Artificial
<220> FEATURE:
<223> OTHER INFORMATION: Strand A of coiled-coil CHD-NHR2-6
<220> FEATURE:
<221> NAME/KEY: MISC_FEATURE
<222> LOCATION: (6)..(6)
<223> OTHER INFORMATION: Xaa at position 6 is linked to SEQ ID NO:9 by a
      triazole bridge
<220> FEATURE:
<221> NAME/KEY: MISC_FEATURE
<222> LOCATION: (6)..(6)
<223> OTHER INFORMATION: Xaa at position 6 is azidolysine
```

```
<400> SEQUENCE: 24

Ala Leu Trp His Leu Xaa Glu Ala Leu Arg
1               5                   10

<210> SEQ ID NO 25
<211> LENGTH: 10
<212> TYPE: PRT
<213> ORGANISM: Artificial
<220> FEATURE:
<223> OTHER INFORMATION: Strand B of coiled-coil CHD-NHR2-7
<220> FEATURE:
<221> NAME/KEY: MISC_FEATURE
<222> LOCATION: (10)..(10)
<223> OTHER INFORMATION: Xaa at position 10 is linked to SEQ ID NO:8 by
      a triazole bridge
<220> FEATURE:
<221> NAME/KEY: MISC_FEATURE
<222> LOCATION: (10)..(10)
<223> OTHER INFORMATION: Xaa at position 10 is azidolysine

<400> SEQUENCE: 25

Glu Leu Trp Arg Ala Ile Arg Ala Leu Xaa
1               5                   10
```

STABILIZED MINIMAL COILED-COIL MIMETICS

This application is a national stage application under 35 U.S.C. § 371 of International Application No. PCT/US2016/036531, filed Jun. 8, 2016, which claims the benefit of U.S. Provisional Patent Application Ser. No. 62/172,669, filed Jun. 8, 2015, and U.S. Provisional Patent Application Ser. No. 62/211,603, filed Aug. 28, 2015, each of which is hereby incorporated by reference in its entirety.

This invention was made with government support under grant number R01GM073943 awarded by the National Institutes of Health. The government has certain rights in this invention.

FIELD OF THE INVENTION

This invention is directed to coiled-coil mimics.

BACKGROUND OF THE INVENTION

Mimicry of critical secondary structure motifs that mediate protein-protein interactions (PPIs) offers a promising approach for the discovery of new classes of therapeutics (Wells et al., *Nature* 450:1001 (2007); Ko et al., *Chem. Soc. Rev.* 40: 4411 (2011); Milroy et al., *Chem. Rev.* 114:4695 (2014); Arkin et al., *Chem. Biol.* 21:1102 (2014)). Several inhibitors of helical protein interfaces have been described owing to the high occurrence of helices at PPI interfaces (Bullock et al., *J. Am. Chem. Soc.* 133:14220 (2011); Jochim et al., *ACS Chem. Biol.* 5:919 (2010)), and development of synthetic approaches that enabled mimicry of this secondary structure (Jayatunga et al., *Bioorg. Med. Chem. Lett.* 24:717 (2014); Azzarito et al., *Nat. Chem.* 5:161 (2013); Henchey et al., *Curr. Opin. Chem. Biol.* 12:692 (2008)). Examination of PPI interfaces suggests that many complexes often utilize contacts from multiple helices, and that these complexes will potentially require inhibitors that are capable of interactions beyond mimicry of a single helix (Watkins et al., "Protein-Protein Interactions Mediated by Helical Tertiary Structure Motifs," *J. Am. Chem. Soc.* 137:11622-11630 (2015); Checco et al., *Proc. Natl. Acad. Sci. USA* 112:4552 (2015)). These multi-helix interfaces are commonly comprised of individual helices from the α-helical coiled-coil motif (Crick, *Acta Crystallographica* 6:689 (1953); Lupas et al., *Adv. Protein Chem.* 70:37 (2005); Burkhard et al., *Trends Cell Biol.* 11:82 (2001); Woolfson, *Adv. Protein Chem.* 70:79 (2005)). An example of such an interface is shown in FIG. 1, where a protein partner presents critical residues for biomolecular recognition from helices that are part of two-strand coiled-coil assemblies. A comprehensive analysis of high-resolution structures in the Protein Data Bank has been undertaken to identify all PPIs mediated by helix dimers (Watkins et al., "Protein-Protein Interactions Mediated by Helical Tertiary Structure Motifs," *J. Am. Chem. Soc.* 137:11622-11630 (2015)).

Formation of coiled-coil assemblies is implicated in many biological processes. Canonical coiled-coils are stabilized by a series of hydrophobic knobs-into-holes (Crick, *Acta Crystallographica* 6:689 (1953)) packing interactions along with inter- and intra-strand electrostatic contacts (Lupas et al., *Adv. Protein Chem.* 70:37 (2005); Burkhard et al., *Trends Cell Biol.* 11:82 (2001); Woolfson, *Adv. Protein Chem.* 70:79 (2005)). Several helical peptides and peptidomimetic inhibitors that target coiled-coil domain assembly in biological processes, such as viral fusion have been described (Dimitrov, *Nat. Rev. Microbiol.* 2:109 (2004); Eckert et al., *Annu. Rev. Biochem.* 70:777 (2001); Horne et al., *Proc. Natl. Acad. Sci. U.S.A.* 106:14751 (2009); Kilby et al., *Nat. Med.* 4:1302 (1998); Wang et al., *Angew. Chem. Int. Ed. Engl.* 47:1879 (2008); Eckert et al., *Cell* 99:103 (1999); Shepherd et al., *J. Am. Chem. Soc.* 128:13284 (2006)). These inhibitors function by inhibiting formation of coiled-coil contacts. This strategy may also be applicable to complexes between globular proteins and pre-formed coiled-coils, such as the one depicted in FIG. 1. However, an alternative strategy could be to utilize coiled-coil mimics or stable helix dimers that display the desired functionality to interact with the globular protein partner.

A survey of the structural data reveals that typical helical dimers in PPIs span 12-18 residues per helix (Watkins et al., "Protein-Protein Interactions Mediated by Helical Tertiary Structure Motifs," *J. Am. Chem. Soc.* 137:11622-11630 (2015)), which is consistent with the average length of helices at protein interfaces (Bullock et al., *J. Am. Chem. Soc.* 133:14220 (2011); Jochim et al., *ACS Chem. Biol.* 5:919 (2010)). A suitable dimeric helix scaffold would therefore be capable of spanning this length. The stability of coiled-coils, however, is directly proportional to the number of heptad repeats and the correct pairing of the hydrophobic and ionic residues. Coiled-coils consisting of less than three heptads are generally not stable (Lau et al., *J. Biol. Chem.* 259:13253 (1984); Burkhard et al., *Protein Sci.* 9:2294 (2000)). Although highly engineered short coiled-coils have been described (Woolfson, *Adv. Protein Chem.* 70:79 (2005); Burkhard et al., *Protein Sci.* 9:2294 (2000); Dong et al., *Biomacromolecules* 7:691 (2006)), these approaches may not be suitable for inhibitor design as at least one face of the dimer is needed to display appropriate functionality to engage the target.

The present invention is directed to overcoming these and other deficiencies in the art.

SUMMARY OF THE INVENTION

One aspect of the present invention relates to a macrostructure. This macrostructure includes:
(i) an antiparallel coiled-coil structure of formula:

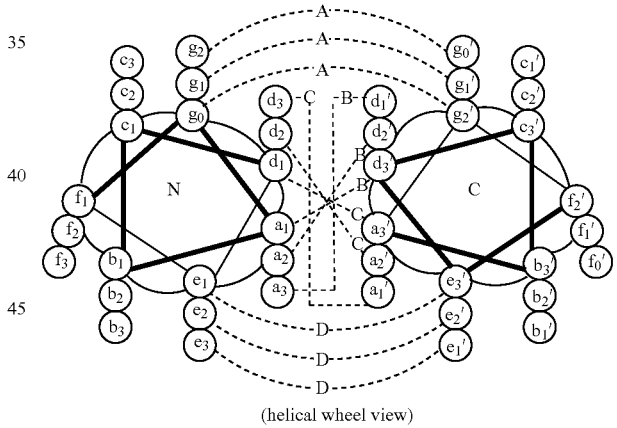

(helical wheel view)

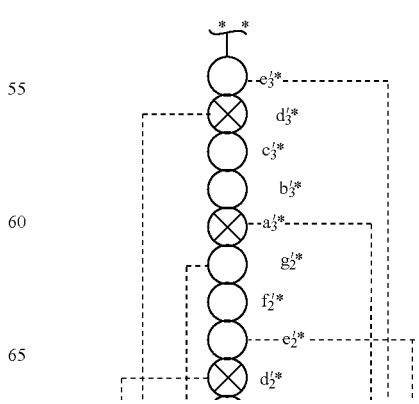

-continued

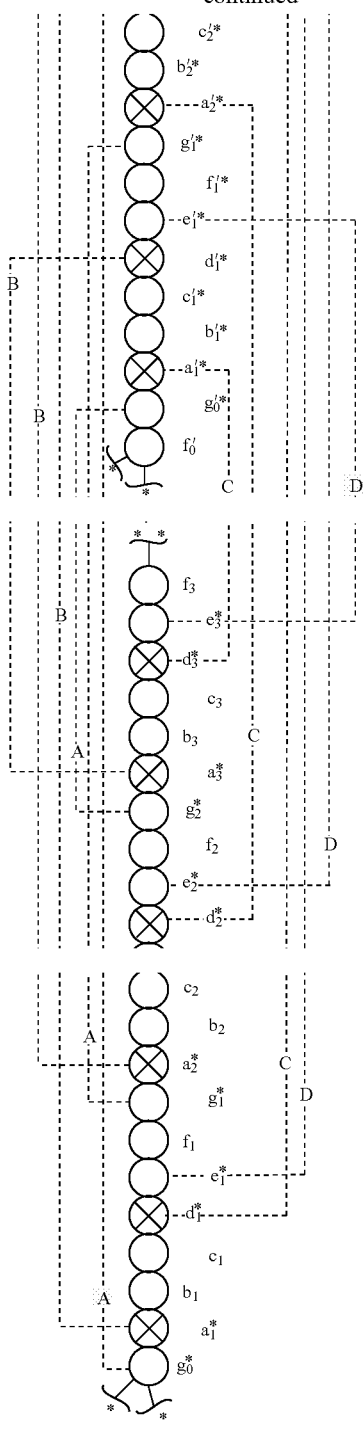

(two-dimensional view);

wherein:

each ○ and each ⊗ is independently absent or a modified or unmodified amino acid residue or analogue thereof, with the proviso that at least seven contiguous amino acid residues/analogues are present in each coil, wherein a, b, c, d, e, f, g, a', b', c', d', e', f', and g' indicate the location of the amino acid residues/analogues within the coiled-coil structure and each ⊗ amino acid residue is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues;

each ⌐ ‾ ‾ ‾ ‾ ¬ is absent or a covalent linker (Linker) between two amino acid residues/analogues, wherein: ⌐ ‾ ‾ ‾ ‾ ¬ each Linker A is independently a linker between a g* amino acid residue and a g'* amino acid residue, wherein the length of the linker is such that the spatial distance between the Cα position of the g* amino acid residue and the Cα position of the g'* amino acid residue is 10-25 Å;

each Linker B is independently a linker between an a* amino acid residue and a d'* amino acid residue, wherein the length of the linker is such that the spatial distance between the Cα position of the a* amino acid residue and the Cα position of the d'* amino acid residue is 5-15 Å;

each Linker C is independently a linker between a d* amino acid residue and an a'* amino acid residue, wherein the length of the linker is such that the spatial distance between the Cα position of the d* amino acid residue and the Cα position of the a'* amino acid residue is 5-15 Å;

each Linker D is independently a linker between an e* amino acid residue and an e'* amino acid residue, wherein the length of the linker is such that the spatial distance between the Cα position of the e* amino acid residue and the Cα position of the e'* amino acid residue is 10-25 Å;

and at least one Linker A or Linker D is present;

each

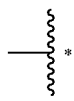

is a point of attachment from a terminal nitrogen to H, $-PG_1$, $-C(O)R$, $-C(O)NR_2$, $-C(O)NH_2$, $-R$, $-C(O)OR$, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein $PG_1$ is a protecting group for protection of an amine; and each

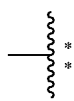

is a point of attachment from a terminal carbonyl to H, —OPG$_2$, —NPG$_2$, —OR, —OH, —NR$_2$, —NH$_2$, —NRC(O)C$_{1-6}$ alkyl, —NHC(O)C$_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_2$ is a protecting group for protection of a carboxylic acid;

or (ii) a parallel coiled-coil structure of formula

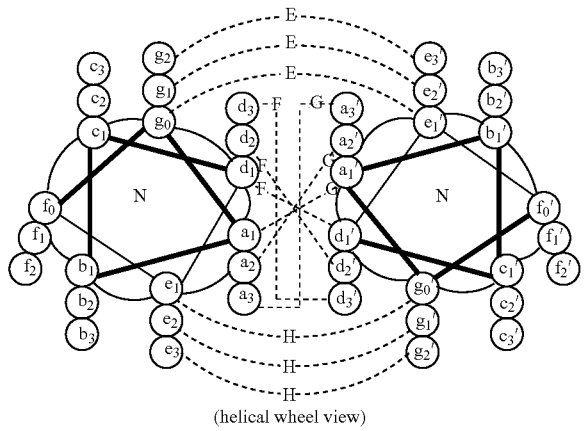

(helical wheel view)

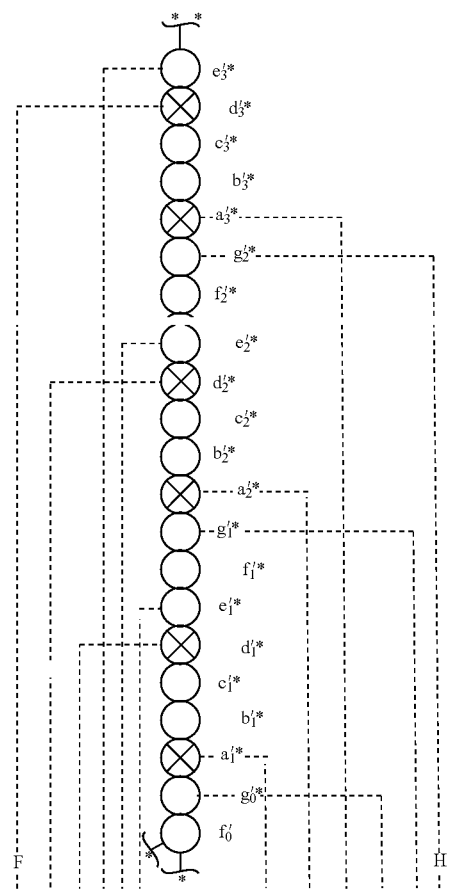

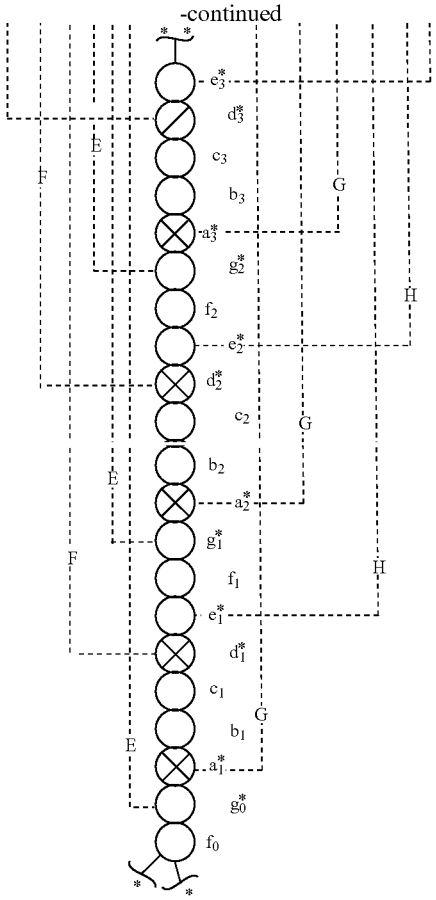

(two-dimensional view);

wherein:
each ○ and each ⊗ is independently absent or a modified or unmodified amino acid residue or analogue thereof, with the proviso that at least seven contiguous amino acid residues/analogues are present in each coil, wherein
a, b, c, d, e, f, g, a', b', c', d', e', f', and g' indicate the location of the amino acid residues/analogues within the coiled-coil structure and
each ⊗ amino acid residue is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues;

each ⌐ ⌐ is absent or a covalent linker (Linker) between two amino acid residues/analogues, wherein:
each Linker E is independently a linker between a g* amino acid residue and an e'* amino acid residue, wherein the length of the linker is such that the spatial distance between the Cα position of the g* amino acid residue and the Cα position of the e'* amino acid residue is 10-25 Å;
each Linker F is independently a linker between a d* amino acid residue and a d'* amino acid residue, wherein the length of the linker is such that the spatial distance between the Cα position of the d* amino acid residue and the Cα position of the d'* amino acid residue is 5-15 Å;

each Linker G is independently a linker between an a* amino acid residue and an a'* amino acid residue, wherein the length of the linker is such that the spatial distance between the Cα position of the a* amino acid residue and the Cα position of the a'* amino acid residue is 5-15 Å;

each Linker H is independently a linker between an e* amino acid residue and a g'* amino acid residue, wherein the length of the linker is such that the spatial distance between the Cα position of the e* amino acid residue and the Cα position of the g'* amino acid residue is 10-25 Å; and at least one Linker E or Linker H is present; and each

is a point of attachment from a terminal nitrogen to H, —PG$_1$, —C(O)R, —C(O)NR$_2$, —C(O)NH$_2$, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_1$ is a protecting group for protection of an amine; and each

is a point of attachment from a terminal carbonyl to H, —OPG$_2$, —NPG$_2$, —OR, —OH, —NR$_2$, —NH$_2$, —NRC(O)C$_{1-6}$ alkyl, —NHC(O)C$_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_2$ is a protecting group for protection of a carboxylic acid.

Another aspect of the present invention is an antiparallel coiled-coil of formula I:

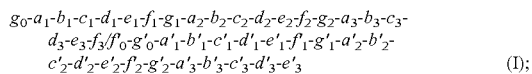

wherein each $b_{1-3}$, $c_{1-3}$, $e_{1-3}$, $f_{1-3}$, $g_{0-2}$, $b'_{1-3}$, $c'_{1-3}$, $e'_{1-3}$, $f'_{0-2}$, and $g'_{0-2}$ is independently absent or is a modified or unmodified amino acid residue or an analogue thereof, and each $a_{1-3}$, $d_{1-3}$, $a'_{1-3}$, and $d'_{1-3}$, is independently absent or is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding amino acids, with the proviso that at least seven contiguous amino acid residues/analogues are present in each coil;

wherein one or more of the following pairs are covalently bound by a linker: $g_0$-$g'_2$, $g_1$-$g'_1$, $g_2$-$g'_0$, $a_1$-$d'_3$, $a_2$-$d'_2$, $a_3$-$d'_1$, $d_1$-$a'_3$, $d_2$-$a'_2$, $d_3$-$a'_1$, $e_1$-$e'_3$, $e_2$-$e'_2$, and $e_3$-$e'_1$.

Another aspect of the present invention is an antiparallel coiled-coil of formula I:

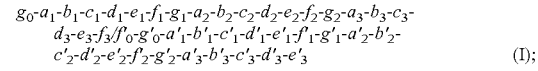

wherein each $b_{1-3}$, $c_{1-3}$, $e_{1-3}$, $f_{1-3}$, $g_{0-2}$, $b'_{1-3}$, $c'_{1-3}$, $e'_{1-3}$, $f'_{0-2}$, and $g'_{0-2}$ is independently absent or is a modified or unmodified amino acid residue or an analogue thereof, and each $a_{1-3}$, $d_{1-3}$, $a'_{1-3}$, and $d'_{1-3}$, is independently absent or is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding amino acids, with the proviso that at least seven contiguous amino acid residues/analogues are present in each coil;

wherein one or more of the following pairs are covalently bound by a linker: $g_0$-$g'_2$, $g_1$-$g'_1$, $g_2$-$g'_0$, $a_1$-$d'_3$, $a_2$-$d'_2$, $a_3$-$d'_1$, $d$-$a'_3$, $d_2$-$a'_2$, $d_3$-$a'_1$, $e_1$-$e'_3$, $e_2$-$e'_2$, and $e_3$-$e'_1$;

wherein the terminal nitrogen of each coil is covalently bound to one or more H, —PG$_1$, —C(O)R, —C(O)NR$_2$, —C(O)NH$_2$, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_1$ is a protecting group for protection of an amine; and wherein the terminal carbonyl of each coil is covalently bound to H, —OPG$_2$, —NPG$_2$, —OR, —OH, —NR$_2$, —NH$_2$, —NRC(O)C$_{1-6}$ alkyl, —NHC(O)C$_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_2$ is a protecting group for protection of a carboxylic acid.

Another aspect of the present invention is an antiparallel coiled-coil of formula I wherein the length of the linker for $g_0$-$g'_2$, $g_1$-$g'_1$, and $g_2$-$g'_0$ is such that the spatial distance between the Cα positions of the $g_0$-$g'_2$, $g_1$-$g'_1$, and $g_2$-$g'_0$ amino acid residue pairs is 10-25 Å;

wherein the length of the linker for $a_1$-$d'_3$, $a_2$-$d'_2$, and $a_3$-$d'_1$ is such that the spatial distance between the Cα positions of the $a_1$-$d'_3$, $a_2$-$d'_2$, and $a_3$-$d'_1$ amino acid residue pairs is 5-15 Å;

wherein the length of the linker for $d_1$-$a'_3$, $d_2$-$a'_2$, and $d_3$-$a'_1$ is such that the spatial distance between the Cα positions of the $d_1$-$a'_3$, $d_2$-$a'_2$, and $d_3$-$a'_1$ amino acid residue pairs is 5-15 Å; and wherein the length of the linker for the $e_1$-$e'_3$, $e_2$-$e'_2$ and $e_3$-$e'_1$ is such that the spatial distance between the Cα positions of the $e_1$-$e'_3$, $e_2$-$e'_2$ and $e_3$-$e'_1$ amino acid residue pairs is 10-25 Å.

Another aspect of the present invention is an antiparallel coiled-coil of formula I:

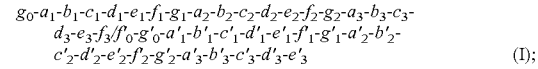

wherein each $b_{1-3}$, $c_{1-3}$, $e_{1-3}$, $f_{1-3}$, $g_{0-2}$, $b'_{1-3}$, $c'_{1-3}$, $e'_{1-3}$, $f'_{0-2}$, and $g'_{0-2}$ is independently absent or is a modified or unmodified amino acid residue or an analogue thereof, and each $a_{1-3}$, $d_{1-3}$, $a'_{1-3}$, and $d'_{1-3}$, is independently absent or is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding amino acids, with the proviso that at least seven contiguous amino acid residues/analogues are present in each coil; wherein one or more of the following pairs are covalently bound by a linker: $g_0$-$g'_2$, $g_1$-$g'_1$, $g_2$-$g'_0$, $a_1$-$d'_3$, $a_2$-$d'_2$, $a_3$-$d'_1$, $d_1$-$a'_3$, $d_2$-$a'_2$, $d_3$-$a'_1$, $e_1$-$e'_3$, $e_2$-$e'_2$, and $e_3$-$e'_1$; wherein the length of the linker for $g_0$-$g'_2$, $g_1$-$g'_1$, and $g_2$-$g'_0$ is such that the spatial distance between the Cα positions of the $g_0$-$g'_2$, $g_1$-$g'_1$, and $g_2$-$g'_0$ amino acid residue pairs is 10-25 Å; wherein the length of the linker for $a_1$-$d'_3$, $a_2$-$d'_2$, and $a_3$-$d'_1$ is such that the spatial distance between the Cα positions of the $a_1$-$d'_3$, $a_2$-$d'_2$, and $a_3$-$d'_1$ amino acid residue pairs is 5-15 Å; wherein the length of the linker for $d_1$-$a'_3$, $d_2$-$a'_2$, and $d_3$-$a'_1$ is such that the spatial distance between the Cα positions of the $d_1$-$a'_3$, $d_2$-$a'_2$, and $d_3$-$a'_1$ amino acid residue pairs is 5-15 Å; wherein the length of the linker for the $e_1$-$e'_3$, $e_2$-$e'_2$ and $e_3$-$e'_1$ is such that the spatial distance between the Cα positions of the $e_1$-$e'_3$, $e_2$-$e'_2$ and $e_3$-$e'_1$ amino acid residue pairs is 10-25 Å; wherein the terminal nitrogen of each coil is bound to one or more H, —$PG_1$, —C(O)R, —C(O)$NR_2$, —C(O)$NH_2$, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein $PG_1$ is a protecting group for protection of an amine; and wherein the terminal carbonyl of each coil is bound to H, —$OPG_2$, —$NPG_2$, —OR, —OH, —$NR_2$, —$NH_2$, —NRC(O)$C_{1-6}$ alkyl, —NHC(O)$C_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein $PG_2$ is a protecting group for protection of a carboxylic acid.

Another aspect of the present invention is an antiparallel coiled-coil of formula I wherein (1) at least $a_1$, $b_1$, $c_1$, $d_1$, $e_1$, $f_1$, $g_0$ and at least $a'_3$, $b'_3$, $c'_3$, $d'_3$, $e'_3$, $f'_2$, and $g'_2$ are present, (2) at least $a_2$, $b_2$, $c_2$, $d_2$, $e_2$, $f_2$, $g_1$ and at least $a'_2$, $b'_2$, $c'_2$, $d'_2$, $e'_2$, $f'_1$, and $g'_1$ are present, or (3) at least $a_3$, $b_3$, $c_3$, $d_3$, $e_3$, $f_3$, $g_2$ and at least $a'_1$, $b'_1$, $c'_1$, $d'_1$, $e'_1$, $f'_0$, and $g'_0$ are present.

Another aspect of the present invention is an antiparallel coiled-coil of formula I wherein each linker is independently selected from the group consisting of alkylene, alkenylene, arylene, heteroarylene, ethers, thioethers, amides, maleimides, esters, disulfides, diselenides, —O—, —S—, —Se—, and any combination thereof.

Another aspect of the present invention is an antiparallel coiled-coil of formula I

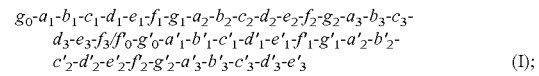

wherein each $b_{1-3}$, $c_{1-3}$, $e_{1-3}$, $f_{1-3}$, $g_{0-2}$, $b'_{1-3}$, $c'_{1-3}$, $e'_{1-3}$, $f'_{0-2}$, and $g'_{0-2}$ is independently absent or is a modified or unmodified amino acid residue or an analogue thereof, and each $a_{1-3}$, $d_{1-3}$, $a'_{1-3}$, and $d'_{1-3}$, is independently absent or is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding amino acids, with the proviso that at least seven contiguous amino acid residues/analogues are present in each coil; wherein one or more of the following pairs are covalently bound by a linker: $g_0$-$g'_2$, $g_1$-$g'_1$, $g_2$-$g'_0$, $a_1$-$d'_3$, $a_2$-$d'_2$, $a_3$-$d'_1$, $d_1$-$a'_3$, $d_2$-$a'_2$, $d_3$-$a'_1$, $e_1$-$e'_3$, $e_2$-$e'_2$, and $e_3$-$e'_1$; wherein the terminal nitrogen of each coil is covalently bound to one or more H, —$PG_1$, —C(O)R, —C(O)$NR_2$, —C(O)$NH_2$, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein $PG_1$ is a protecting group for protection of an amine; wherein the terminal carbonyl of each coil is covalently bound to H, —$OPG_2$, —$NPG_2$, —OR, —OH, —$NR_2$, —$NH_2$, —NRC(O)$C_{1-6}$ alkyl, —NHC(O)$C_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein $PG_2$ is a protecting group for protection of a carboxylic acid; and wherein at least one of the linkers for $g_0$-$g'_2$, $g_1$-$g'_1$, $g_2$-$g'_0$, $e_1$-$e'_3$, $e_2$-$e'_2$, and $e_3$-$e'_1$ has the formula —$Z_n$—, wherein n is a number from 1 to 25 and each Z is independently selected at each occurrence thereof from the group consisting of alkylene, alkenylene, arylene, heteroarylene, triazole-diyl, thiazole-diyl, oxazole-diyl, ethers, amides, esters, maleimides, thioethers, O, S, and Se.

Another aspect of the present invention is an antiparallel coiled-coil of formula I wherein at least one of the linkers for $g_0$-$g'_2$, $g_1$-$g'_1$, $g_2$-$g'_0$, $e_1$-$e'_3$, $e_2$-$e'_2$, and $e_3$-$e'_1$ is selected from the group consisting of:

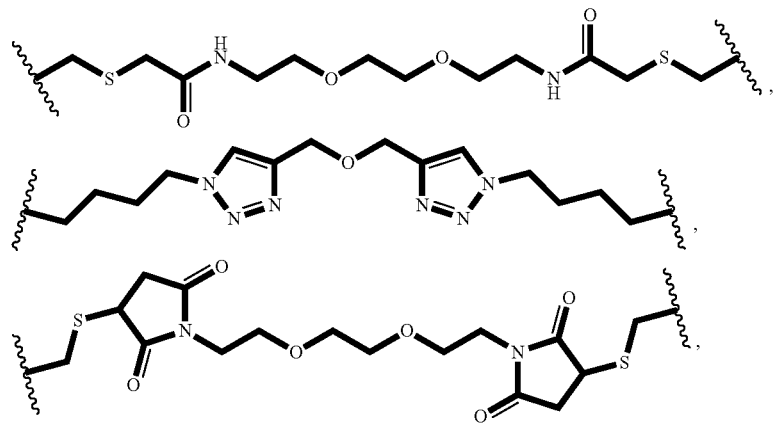

-continued

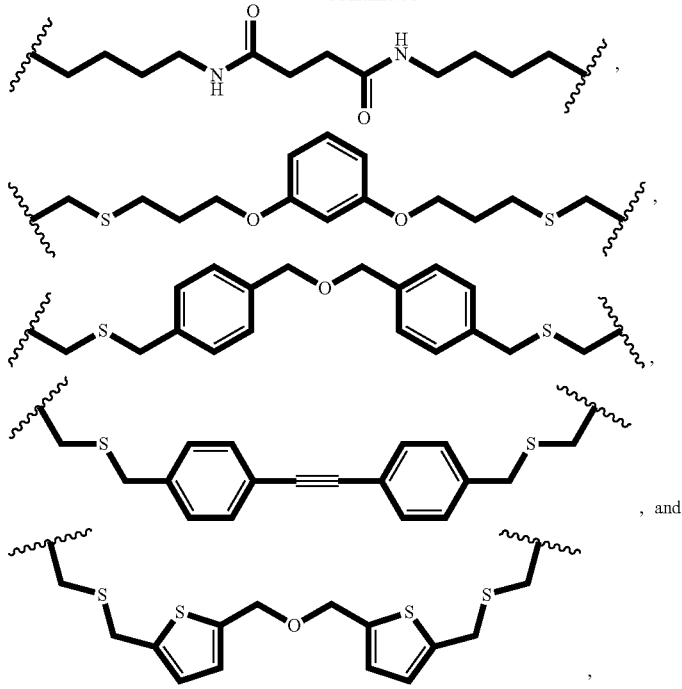

, and wherein each

marks a connection point to the Cα carbon in a linked residue/analogue.

Another aspect of the present invention is an antiparallel coiled-coil of formula I wherein at least one of the linkers for $g_0$-$g'_2$, $g_1$-$g'_1$, $g_2$-$g'_0$, $e_1$-$e_3$, $e_2$-$e'_2$, and $e_3$-$e'_1$ has the formula

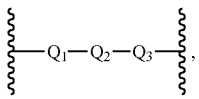

wherein:
  $Q_1$ is a $C_{1-8}$ alkylene or a moiety of formula ($C_{1-8}$ alkylene-X—$C_{0-8}$ alkylene)$_n$;
  $Q_2$ is $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, a moiety of formula $C_{1-8}$ alkylene-X—$C_{1-8}$ alkylene, or a moiety of formula -$Q_4$-$Q_5$-$Q_6$-; wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;
  $Q_3$ is a $C_{1-8}$ alkylene or a moiety of formula ($C_{1-8}$ alkylene-X—$C_{0-8}$ alkylene)$_n$;
  $Q_4$ is selected from the group consisting of O, —C(O)—NR—, —NR—C(O)—, —C(O)—O—, —O—C(O)—, —C(O)—S—, —S—C(O)—, $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;
  $Q_5$ is selected from the group consisting of —C(O)—NR—, —NR—C(O)—, —C(O)—O—, —O—C(O)—, —C(O)—S—, —S—C(O)—, $C_{1-8}$ alkylene, $C_{2-8}$ alkynylene, monocyclic carbocycle, fused bicyclic carbocycle, non-aromatic heterocycle, arylene, and heteroarylene, or is a moiety of formula $C_{1-8}$ alkylene-(X—$C_{1-8}$ alkylene)$_n$, wherein each of $C_{1-8}$ alkylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;
  $Q_6$ is selected from the group consisting of O, —C(O)—NR—, —NR—C(O)—, —C(O)—O—, —O—C(O)—, —C(O)—S—, —S—C(O)—, $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, $N(R)_2$, OR, and SR;

each X is selected from the group consisting of O, S, $CR_2$, NR, P, $C_{2-8}$ alkynylene, arylene, and heteroarylene (preferably O, S, $CH_2$, NR, or CR≡CR);

each R is independently H, $C_{1-8}$ alkyl, or aryl;

n is 1 to 10; and each

marks a connection point to the Cα carbon in a linked residue/analogue.

Another aspect of the present invention is an antiparallel coiled-coil of formula I wherein at least one of the linkers for $g_0\text{-}g'_2$, $g_1\text{-}g'_1$, $g_2\text{-}g'_0$, $e_1\text{-}e'_3$, $e_2\text{-}e'_2$, and $e_3\text{-}e'_1$ has the following formula

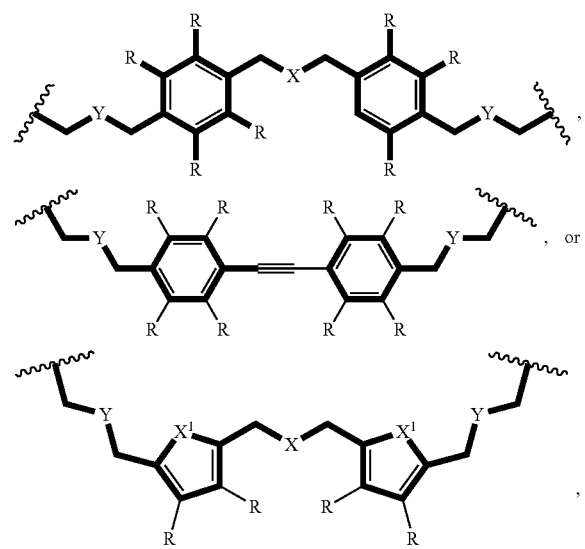

wherein X is O, S, $CR_2$, NR, or P (preferably O, S, $CH_2$ or NR), wherein $X^1$ is O, S, NH, and NR, wherein each R is independently H, alkyl, or aryl, wherein Y is S, and wherein each

marks a connection point to the Cα carbon in a linked residue/analogue.

Another aspect of the present invention is an antiparallel coiled-coil of formula I wherein at least one of the linkers for $g_0\text{-}g'_2$, $g_1\text{-}g'_1$, $g_2\text{-}g'_0$, $e_1\text{-}e'_3$, $e_2\text{-}e'_2$, and $e_3\text{-}e'_1$ has the following formula

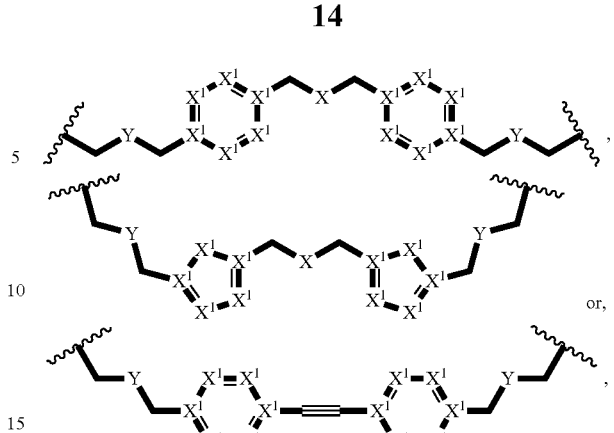

wherein X is O, S, $CR_2$, NR, or P (preferably O, S, $CH_2$ or NR), wherein $X^1$ is O, S, C, CR, N, NH, and NR, wherein each R is independently H, alkyl, or aryl, wherein Y is S, and wherein each

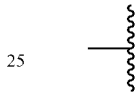

marks a connection point to the Cα carbon in a linked residue/analogue.

Another aspect of the present invention is an antiparallel coiled-coil of formula I wherein at least one of the linkers for $a_1\text{-}d'_3$, $a_2\text{-}d'_2$, $a_3\text{-}d'_1$, $d_1\text{-}a'_3$, $d_2\text{-}a'_2$, and $d_3\text{-}a'_1$ is independently selected from the group consisting of disulfides, diselenides, $C_{1-8}$ alkylene, $C_{2-8}$ alkenylene, arylene, heteroarylene, triazole-diyl, and thiazole-diyl.

Another aspect of the present invention is an antiparallel coiled-coil of formula I wherein at least one of the linkers for $a_1\text{-}d'_3$, $a_2\text{-}d'_2$, $a_3\text{-}d'_1$, $d_1\text{-}a'_3$, $d_2\text{-}a'_2$, and $d_3\text{-}a'_1$ is independently a disulfide bond from a cysteine or homocysteine residue, a diselenide from a selenocysteine residue, an alkylene from an allylglycine residue, or an arylene linker.

Another aspect of the present invention is an antiparallel coiled-coil of formula I wherein one linker is present or two linkers are present.

Another aspect of the present invention is an antiparallel coiled-coil of formula I wherein at least one of the linkers for $g_0\text{-}g'_2$, $g_1\text{-}g'_1$, $g_2\text{-}g'_0$, $e_1\text{-}e'_3$, $e_2\text{-}e'_2$, and $e_3\text{-}e'_1$ is present and at least one of the linkers for $a_1\text{-}d'_3$, $a_2\text{-}d'_2$, $a_3\text{-}d'_1$, $d_1\text{-}a'_3$, $d_2\text{-}a'_2$, and $d_3\text{-}a'_1$ is present.

Another aspect of the present invention is an antiparallel coiled-coil of formula I wherein one of the linkers for $g_0\text{-}g'_2$, $g_1\text{-}g'_1$, $g_2\text{-}g'_0$, $e_1\text{-}e'_3$, $e_2\text{-}e'_2$, and $e_3\text{-}e'_1$ is present and one of the linkers for $a_1\text{-}d'_3$, $a_2\text{-}d'_2$, $a_3\text{-}d'_1$, $d_1\text{-}a'_3$, $d_2\text{-}a'_2$, and $d_3\text{-}a'_1$ is present.

Another aspect of the present invention is an antiparallel coiled-coil of formula I wherein: $a_1$, $a_2$, $a_3$, $d_1$, $d_2$, $d_3$, $a'_1$, $a'2$, $a'_3$, $d'_1$, $d'_2$, and $d'_3$ each independently have the formula (a)

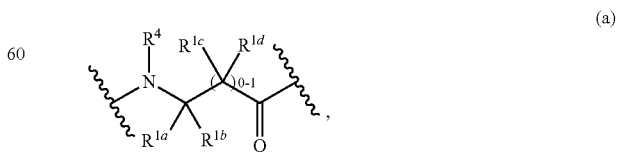

wherein:

$R^{1a}$, $R^{1b}$, $R^{1c}$, and $R^{1d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —$OR^5$, or —$SR^5$; and at least one of $R^{1a}$ and $R^{1c}$ is a side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues; and when a linker covalently binds $a_1$-$d'_3$, $a_2$-$d'_2$, $a_3$-$d'_1$, $d_1$-$a'_3$, $d_2$-$a'_2$, or $d_3$-$a'_1$, the linker is attached to or replaces one of $R^{1a}$, $R^{1b}$, $R^{1c}$, and $R^{1d}$ of formula (a);

$e_1$, $e_2$, $e_3$, $g_1$, $g_2$, $e'_1$, $e'_2$, $e'_3$, $g'_0$, $g'_1$, and $g'_2$ each independently have the formula (b) and $g_0$ has the formula (b')

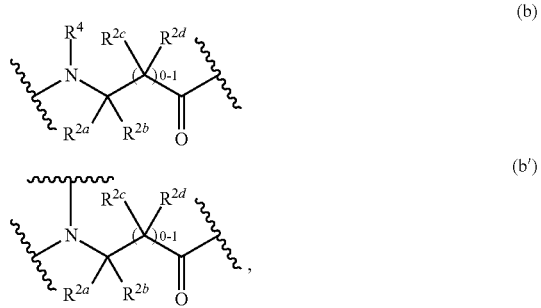

wherein:

$R^{2a}$, $R^{2b}$, $R^{2c}$, and $R^{2d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —$OR^5$, or —$SR^5$; and at least one of $R^{2a}$ and $R^{2c}$ is an amino acid side chain; and when a linker covalently binds $g_0$-$g'_2$, $g_1$-$g'_1$, $g_2$-$g'_0$, $e_1$-$e'_3$, $e_2$-$e'_2$, or $e_3$-$e'_1$, the linker is attached to or replaces one of $R^{2a}$, $R^{2b}$, $R^{2c}$, and $R^{2d}$ of formula (b) or formula (b');

$b_1$, $b_2$, $b_3$, $c_1$, $c_2$, $c_3$, $f_1$, $f_2$, $f_3$, $b'_1$, $b'_2$, $b'_3$, $c'_1$, $c'_2$, $c'_3$, $f'_1$, and $f'_2$ each independently have the formula (c) and $f_0'$ has the formula (c')

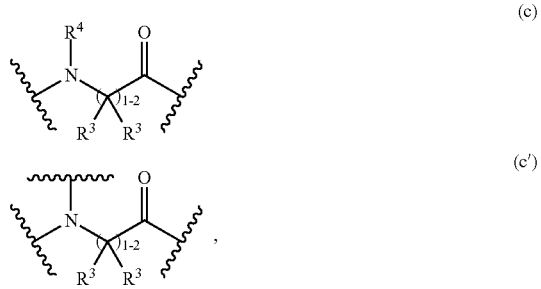

wherein each $R^3$ is independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an alkynyl, an azide, —$OR^5$, or —$SR^5$;

each $R^4$ is independently hydrogen, an alkyl, an alkenyl, an alkynyl, a cycloalkyl, a heterocyclyl, an aryl, a heteroaryl, or an arylalkyl; and each $R^5$ is independently selected from the group consisting of H, —PG (where PG is a protecting group), an alkyl, an alkenyl, an alkynyl, a cycloalkyl, an aryl, a heteroaryl, a heterocyclyl, and an arylalkyl.

Another aspect of the present invention is an antiparallel coiled-coil of formula I wherein at least one of the following conditions is met:

(A) in at least one residue of formula (a), (i) one of $R^{1a}$ and $R^{1c}$ is the side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues, and (ii) $R^{1b}$, $R^{1d}$, and the other of $R^{1a}$ and $R^{1c}$ are each independently hydrogen, a $C_{1-3}$ alkyl, or a $C_{2-3}$ alkenyl;

(B) in at least one residue of formula (b), (i) one of $R^{2a}$ and $R^{2c}$ is an amino acid side chain and (ii) $R^{2b}$, $R^{2d}$, and the other of $R^{2a}$ and $R^{2c}$ are each independently hydrogen or a $C_{1-3}$ alkyl.

Another aspect of the present invention is an antiparallel coiled-coil of formula I wherein the compound has an antiparallel coiled-coil tertiary structure.

Another aspect of the present invention is an antiparallel coiled-coil of formula I wherein (i) the first strand of the antiparallel coiled-coil structure comprises at least ten contiguous modified or unmodified amino acid residues (or analogues thereof), wherein the at least ten contiguous amino acid residues/analogues have the formula $^gX_1$-$X_2$-$X_3$-$X_4$-$X_5$-$X_6$-$X_7$-$X_8$-$X_9$-$X_{10}^b$, wherein $X_1$ is Glu, Leu, Arg, Lys, Thr, or Val (or analogues of each of the preceding residues); $X_2$ is Cys, HCys, Leu, Ile, allylleucine, Val, allylglycine, Thr, selenocysteine, hexafluoroleucine, or hexafluorovaline (or analogues of each of the preceding residues); $X_3$ is any residue/analogue; $X_4$ is His, Tyr, Phe, Lys, Gln, or Trp (or analogues of each of the preceding residues); $X_5$ is Cys, HCys, Leu, Ile, allylleucine, Val, allylglycine, Thr, selenocysteine, hexafluoroleucine, or hexafluorovaline (or analogues of each of the preceding residues); $X_6$ is any residue/analogue; $X_7$ is Glu, Asn, Trp, Leu, Glu, or Gln (or analogues of each of the preceding residues); $X_8$ is Leu, Met, Ala, His, or Ser (or analogues of each of the preceding residues); $X_9$ is Cys, HCys, Leu, Ile, allylleucine, Val, allylglycine, Thr, selenocysteine, hexafluoroleucine, or hexafluorovaline (or analogues of each of the preceding residues); and $X_{10}$ is any residue/analogue;

(ii) the second strand of the antiparallel coiled-coil structure comprises at least ten contiguous modified or unmodified amino acid residues (or analogues thereof), wherein the at least ten contiguous amino acid residues/analogues have the formula $^{c'}X_1'$-$X_2'$-$X_3'$-$X_4'$-$X_5'$-$X_6'$-$X_7'$-$X_8'$-$X_9'$-$X_{10}^{b'}$, wherein $X_1'$ is Glu, Asn, Leu, Gln, Met, or Ala (or analogues of each of the preceding residues); $X_2'$ is Cys, HCys, Leu, Ile, allylleucine, Val, allylglycine, Thr, selenocysteine, hexafluoroleucine, or hexafluorovaline (or analogues of each of the preceding residues); $X_3'$ is any residue/analogue; $X_4'$ is any residue/analogue; $X_5'$ is Ala, Ser, Thr, Gly, or Asp (or analogues of each of the preceding residues); $X_6'$ is Cys, HCys, Leu, Ile, allylleucine, Val, allylglycine, Thr, selenocysteine, hexafluoroleucine, or hexafluorovaline (or analogues of each of the preceding residues); $X_7'$ is Arg, Leu, Gln, Met, Glu, or Asp (or analogues of each of the preceding residues); $X_8'$ is Tyr, Val, Phe, Trp, or Met (or analogues of each of the preceding residues); $X_9'$ is Cys, HCys, Leu, Ile, allylleucine, Val, allylglycine, Thr, selenocysteine, hexafluoroleucine, or hexafluorovaline (or analogues of each of the preceding residues); and $X_{10}'$ is any residue/analogue;

(iii)$^g$, $^b$, $^{c'}$, and $^{e'}$ indicate where the ten contiguous amino acids/analogues appear within the antiparallel coiled-coil structure;

(iv) residues in the e/e' and g/g' positions can be optionally modified to facilitate attachment of a linker or replaced with a linker, if present; and (v) residues in the a/a' and d/d' positions can be optionally modified to facilitate attachment of a linker, if present.

Another aspect of the present invention is an antiparallel coiled-coil of formula I wherein $g_1$ is Glu, Leu, Arg, Lys, Thr or Val; $a_2$ is Cys, HCys, Leu, Ile, allylleucine, Val, allylglycine, Thr, selenocysteine, hexafluoroleucine, or hexafluorovaline; $b_2$ is any residue; $c_2$ is His, Tyr, Phe, Lys, Gln, or Trp; $d_2$ is Cys, HCys, Leu, Ile, allylleucine, Val, allylglycine, Thr, selenocysteine, hexafluoroleucine, or hexafluorovaline; $e_2$ is any residue; $f_2$ is Glu, Asn, Trp, Leu, Glu, or Gln; $g_2$ is Leu, Met, Ala, His, or Ser; $a_3$ is Cys, HCys, Leu, Ile, allylleucine, Val, allylglycine, Thr, selenocysteine, hexafluoroleucine, or hexafluorovaline; $b_3$ is any residue; $c'_1$ is Glu, Asn, Leu, Gln, Met, or Ala; $d'_1$ is Cys, HCys, Leu, Ile, allylleucine, Val, allylglycine, Thr, selenocysteine, hexafluoroleucine, or hexafluorovaline; $e'_1$ is any residue; $f'_1$ is any residue; $g'_1$ is Ala, Ser, Thr, Gly, or Asp; $a'_2$ is Cys, HCys, Leu, Ile, allylleucine, Val, allylglycine, Thr, selenocysteine, hexafluoroleucine, or hexafluorovaline; $b'_2$ is Arg, Leu, Gln, Met, Glu, or Asp; $c'_2$ is Tyr, Val, Phe, Trp, or Met; $d'_2$ is Cys, HCys, Leu, Ile, allylleucine, Val, allylglycine, Thr, selenocysteine, hexafluoroleucine, or hexafluorovaline, $e'_2$ is any residue, where any amino acid residue may be modified for attachment of Z, which is a covalent linker (e.g., a bis-triazole linker) between pair g-g' or $e_2$-$e'_2$.

Another aspect of the present invention is an antiparallel coiled-coil of formula I wherein $g_1$ is Glu, $a_2$ is Leu, $b_2$ is Trp, $c_2$ is His, $d_2$ is Leu, $e_2$ is Z, $f_2$ is Glu, $g_2$ is Leu, $a_3$ is Leu, $b_3$ is Arg, $c'_1$ is Glu, $d'_1$ is Leu, $e'_1$ is Trp, $f'_1$ is Arg, $g'_1$ is Ser, $a'_2$ is Ile, $b'_2$ is Arg, $c'_2$ is Val, $d'_2$ is Leu, $e'_2$ is Z, and each Z is a lysine residue that has been modified for attachment of a covalent linker (e.g., a bis-triazole linker) between pair $e_2$-$e'_2$.

Another aspect of the present invention is an antiparallel coiled-coil of formula I wherein $g_1$ is Glu, $a_2$ is Leu, $b_2$ is Trp, $c_2$ is His, $d_2$ is Leu, $e_2$ is Z, $f_2$ is Glu, $g_2$ is Leu, $a_3$ is Z', $b_3$ is Arg, $c'_1$ is Glu, $d'_1$ is Z', $e'_1$ is Trp, $f'_1$ is Arg, $g'_1$ is Ser, $a'_2$ is Ile, $b'_2$ is Arg, $c'_2$ is Val, $d'_2$ is Leu, $e'_2$ is Z, each Z is a lysine residue that has been modified for attachment of a covalent linker (e.g., a bis-triazole linker) between pair $e_2$-$e'_2$, and each Z' is a cysteine residue that has been modified for attachment of a covalent linker (e.g., a disulfide linker) between pair $a_3$-$d'_1$.

Another aspect of the present invention is an antiparallel coiled-coil of formula I selected from the group consisting of CHD-NHR2-2 and CHD$^{DS}$-NHR2-3.

Another aspect of the present invention is an antiparallel coiled-coil of formula I, wherein the antiparallel coiled-coil is CHD-NHR2-2.

Another aspect of the present invention is an antiparallel coiled-coil of formula I, wherein the antiparallel coiled-coil is CHD$^{DS}$-NHR2-3.

Another aspect of the present invention is a parallel coiled-coil of formula II:

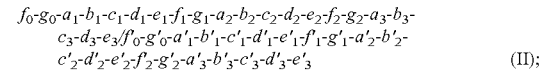

(II);

wherein each $b_{1-3}$, $c_{1-3}$, $e_{1-3}$, $f_{0-2}$, $g_{0-2}$, $b'_{1-3}$, $c'_{1-3}$, $e'_{1-3}$, $f'_{0-2}$, and $g'_{0-2}$ is independently absent or is a modified or unmodified amino acid residue or an analogue thereof, and each $a_{1-3}$, $d_{1-3}$, $a'_{1-3}$, and $d'_{1-3}$, is independently absent or is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding amino acids, with the proviso that at least seven contiguous amino acid residues/analogues are present in each coil;

wherein one or more of the following pairs are covalently bound by a linker: $g_0$-$e'_1$, $g_1$-$e'_2$, $g_2$-$e_3$, $d_1$-$d'_1$, $d_2$-$d'_2$, $d_3$-$d'_3$, $a_1$-$a'_1$, $a_2$-$a'_2$, $a_3$-$a_3$, $e_1$-$g'_0$, $e_2$-$g'_1$, and $e_3$-$g'_2$.

Another aspect of the present invention is a parallel coiled-coil of formula II:

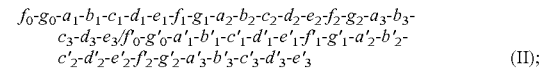

(II);

wherein each $b_{1-3}$, $c_{1-3}$, $e_{1-3}$, $f_{0-2}$, $g_{0-2}$, $b'_{1-3}$, $c'_{1-3}$, $e'_{1-3}$, $f'_{0-2}$, and $g'_{0-2}$ is independently absent or is a modified or unmodified amino acid residue or an analogue thereof, and each $a_{1-3}$, $d_{1-3}$, $a'_{1-3}$, and $d'_{1-3}$, is independently absent or is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding amino acids, with the proviso that at least seven contiguous amino acid residues/analogues are present in each coil;

wherein one or more of the following pairs are covalently bound by a linker: $g_0$-$e'_1$, $g_1$-$e'_2$, $g_2$-$e_3$, $d_1$-$d'_1$, $d_2$-$d'_2$, $d_3$-$d'_3$, $a_1$-$a'_1$, $a_2$-$a_2$, $a_3$-$a_3$, $e_1$-$g'_0$, $e_2$-$g'_1$, and $e_3$-$g'_2$;

wherein the terminal nitrogen of each coil is covalently bound to one or more H, —PG$_1$, —C(O)R, —C(O)NR$_2$, —C(O)NH$_2$, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_1$ is a protecting group for protection of an amine; and wherein the terminal carbonyl of each coil is covalently bound to H, —OPG$_2$, —NPG$_2$, —OR, —OH, —NR$_2$, —NH$_2$, —NRC(O)C$_{1-6}$ alkyl, —NHC(O)C$_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_2$ is a protecting group for protection of a carboxylic acid.

Another aspect of the present invention is a parallel coiled-coil of formula II wherein the length of the linker for $g_0$-$e'_1$, $g_1$-$e'_2$, and $g_2$-$e'_3$ is such that the spatial distance between the Cα positions of the $g_0$-$e'_1$, $g_1$-$e'_2$, and $g_2$-$e'_3$ amino acid residue pairs is 10-25 Å;

wherein the length of the linker for $d_1$-$d'_1$, $d_2$-$d'_2$, and $d_3$-$d'_3$ is such that the spatial distance between the Cα positions of the $d_1$-$d'_1$, $d_2$-$d'_2$, and $d_3$-$d'_3$ amino acid residue pairs is 5-15 Å;

wherein the length of the linker for a₁-a'₁, a₂-a'₂, and a₃-a'₃ is such that the spatial distance between the Cα positions of the a₁-a'₁, a₂-a'₂, and a₃-a'₃ amino acid residue pairs is 5-15 Å; and wherein the length of the linker for the e₁-g'₀, e₂-g'₁, and e₃-g'₂ is such that the spatial distance between the Cα positions of the e₁-g'₀, e₂-g'₁, and e₃-g'₂ amino acid residue pairs is 10-25 Å.

Another aspect of the present invention is a parallel coiled-coil of formula II:

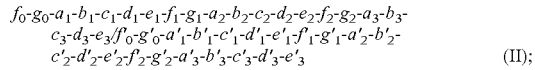
(II);

wherein each $b_{1-3}$, $c_{1-3}$, $e_{1-3}$, $f_{0-2}$, $g_{0-2}$, $b'_{1-3}$, $c'_{1-3}$, $e'_{1-3}$, $f'_{0-2}$, and $g'_{0-2}$ is independently absent or is a modified or unmodified amino acid residue or an analogue thereof, and each $a_{1-3}$, $d_{1-3}$, $a'_{1-3}$, and $d'_{1-3}$, is independently absent or is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding amino acids, with the proviso that at least seven contiguous amino acid residues/analogues are present in each coil;

wherein one or more of the following pairs are covalently bound by a linker: $g_0$-$e'_1$, $g_1$-$e'_2$, $g_2$-$e_3$, $d_1$-$d'_1$, $d_2$-$d'_2$, $d_3$-$d'_3$, $a_1$-$a'_1$, $a_2$-$a'_2$, $a_3$-$a_3$, $e_1$-$g'_0$, $e_2$- $g'_1$, and $e_3$-$g'_2$;

wherein the length of the linker for $g_0$-$e'_1$, $g_1$-$e'_2$, and $g_2$-$e'_3$ is such that the spatial distance between the Cα positions of the $g_0$-$e'_1$, $g_1$-$e'_2$, and $g_2$-$e'_3$ amino acid residue pairs is 10-25 Å;

wherein the length of the linker for $d_1$-$d'_1$, $d_2$-$d'_2$, and $d_3$-$d'_3$ is such that the spatial distance between the Cα positions of the $d_1$-$d'_1$, $d_2$-$d'_2$, and $d_3$-$d'_3$ amino acid residue pairs is 5-15 Å;

wherein the length of the linker for $a_1$-$a'_1$, $a_2$-$a'_2$, and $a_3$-$a'_3$ is such that the spatial distance between the Cα positions of the $a_1$-$a'_1$, $a_2$-$a'_2$, and $a_3$-$a'_3$ amino acid residue pairs is 5-15 Å;

wherein the length of the linker for the $e_1$-$g'_0$, $e_2$-$g'_1$, and $e_3$-$g'_2$ is such that the spatial distance between the Cα positions of the $e_1$-$g'_0$, $e_2$-$g'_1$, and $e_3$-$g'_2$ amino acid residue pairs is 10-25 Å;

wherein the terminal nitrogen of each coil is covalently bound to one or more H, —PG₁, —C(O)R, —C(O)NR₂, —C(O)NH₂, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG₁ is a protecting group for protection of an amine; and wherein the terminal carbonyl of each coil is covalently bound to H, —OPG₂, —NPG₂, —OR, —OH, —NR₂, —NH₂, —NRC(O)C₁₋₆ alkyl, —NHC(O)C₁₋₆ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG₂ is a protecting group for protection of a carboxylic acid.

Another aspect of the present invention is a parallel coiled-coil of formula II wherein (1) at least a₁, b₁, c₁, d₁, e₁, f₀, g₀ and at least a'₁, b'₁, c'₁, d'₁, e'₁, f'₀, and g'₀ are present, (2) at least a₂, b₂, c₂, d₂, e₂, f₁, g₁ and at least a'₂, b'₂, c'₂, d'₂, e'₂, f'₁, and g'₁ are present, or (3) at least a₃, b₃, c₃, d₃, e₃, f₂, g₂ and at least a'₃, b'₃, c', d'₃, e'₃, f'₂, and g'₂ are present.

Another aspect of the present invention is a parallel coiled-coil of formula II wherein: a₁, a₂, a₃, d₁, d₂, d₃, a'₁, a'₂, a'₃, d'₁, d'₂, and d'₃ each independently have the formula (a)

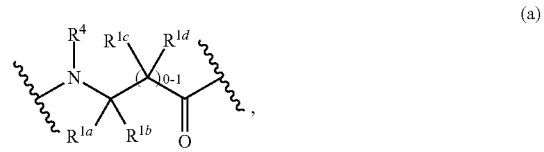

wherein:

$R^{1a}$, $R^{1b}$, $R^{1c}$, and $R^{1d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —OR⁵, or —SR⁵; and at least one of $R^{1a}$ and $R^{1c}$ is a side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues; and when a linker covalently binds d₁-d'₁, d₂-d'₂, d₃-d'₃, a₁-a'₁, a₂-a'₂, a₃-a'₃, the linker is attached to or replaces one of $R^{1a}$, $R^{1b}$, $R^{1c}$, and $R^{1d}$ of formula (a);

e₁, e₂, e₃, g₁, g₂, e'₁, e'₂, e'₃, g'₀, g'₁, and g'₂ each independently have the formula (b) and g₀ has the formula (b')

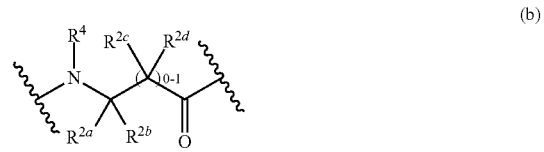

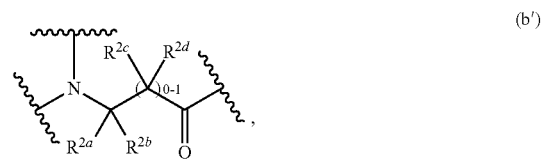

wherein:

$R^{2a}$, $R^{2b}$, $R^{2c}$, and $R^{2d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —OR⁵, or —SR⁵; and at least one of $R^{2a}$ and $R^{2c}$ is an amino acid side chain; and when a linker covalently binds g₀-e'₁, g₁-e'₂, g₂-e'₃, e₁-g'₀, e₂-g'₁, and e₃-g'₂, the linker is attached to or replaces one of $R^{2a}$, $R^{2b}$, $R^{2c}$, and $R^{2d}$ of formula (b) or formula (b');

b₁, b₂, b₃, c₁, c₂, c₃, f₁, f₂, f₃, b'₁, b'₂, b'₃, c'₁, c'₂, c'₃, f'₁, and f'₂ each independently have the formula (c) and f'₀ has the formula (c')

(c)

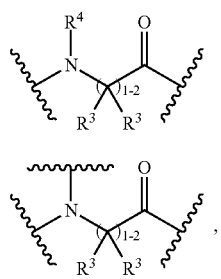

(c')

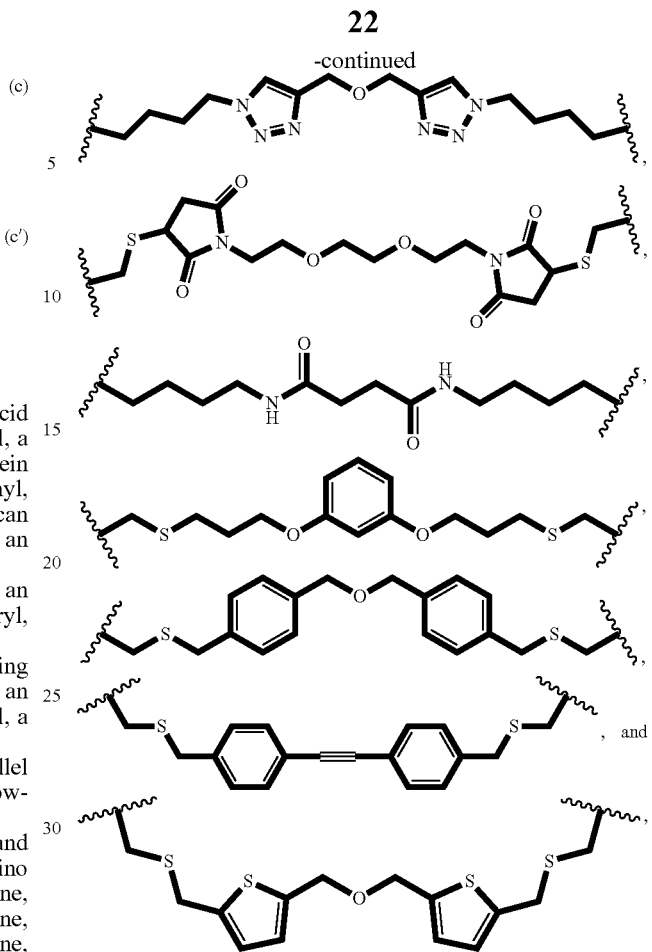

wherein each R³ is independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —$OR^5$, or —$SR^5$;

each R⁴ is independently hydrogen, an alkyl, an alkenyl, an alkynyl, a cycloalkyl, a heterocyclyl, an aryl, a heteroaryl, or an arylalkyl; and each R⁵ is independently selected from the group consisting of H, —PG (where PG is a protecting group), an alkyl, an alkenyl, an alkynyl, a cycloalkyl, an aryl, a heteroaryl, a heterocyclyl, and an arylalkyl.

Another aspect of the present invention is a parallel coiled-coil of formula II wherein at least one of the following conditions is met:

(A) in at least one residue of formula (a), (i) one of $R^{1a}$ and $R^{1c}$ is the side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues, and (ii) $R^{1b}$, $R^{1d}$, and the other of $R^{1a}$ and $R^{1c}$ are each independently hydrogen, a $C_{1-3}$ alkyl, or a $C_{2-3}$ alkenyl;

(B) in at least one residue of formula (b), (i) one of $R^{2a}$ and $R^{2c}$ is an amino acid side chain and (ii) $R^{2b}$, $R^{2d}$, and the other of $R^{2a}$ and $R^{2c}$ are each independently hydrogen or a $C_{1-3}$ alkyl.

Another aspect of the present invention is a parallel coiled-coil of formula II wherein each linker is independently selected from the group consisting of alkylene, alkenylene, arylene, heteroarylene, ethers, thioethers, amides, maleimides, esters, disulfides, diselenides, —O—, —S—, —Se—, and any combination thereof.

Another aspect of the present invention is a parallel coiled-coil of formula II wherein at least one of the linkers for $g_0$-$e'_1$, $g_1$-$e'_2$, $g_2$-$e'_3$, $e_1$-$g'_0$, $e_2$-$g'_1$, and $e_3$-$g'_2$ has the formula —$Z_n$—, wherein n is a number from 1 to 25 and each Z is independently selected at each occurrence thereof from the group consisting of alkylene, alkenylene, arylene, heteroarylene, triazole-diyl, thiazole-diyl, oxazole-diyl, ethers, amides, esters, maleimides, thioethers, O, S, and Se.

Another aspect of the present invention is a parallel coiled-coil of formula II wherein at least one of the linkers for $g_0$-$e'_1$, $g_1$-$e'_2$, $g_2$-$e'_3$, $e_1$-$g'_0$, $e_2$-$g'_1$, and $e_3$-$g'_2$ is selected from the group consisting of wherein each

marks a connection point to the Cα carbon in a linked residue/analogue.

Another aspect of the present invention is a parallel coiled-coil of formula II wherein at least one of the linkers for $g_0$-$e'_1$, $g_1$-$e'_2$, $g_2$-$e'_3$, $e_1$-$g'_0$, $e_2$-$g'_1$, and $e_3$-$g'_2$ has the formula

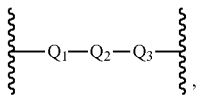

wherein:

$Q_1$ is a $C_{1-8}$ alkylene or a moiety of formula ($C_{1-8}$ alkylene-X—$C_{0-8}$ alkylene)$_n$;

$Q_2$ is $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, a moiety of formula $C_{1-8}$ alkylene-X—$C_{1-8}$ alkylene, or a moiety of formula -$Q_4$-$Q_5$-$Q_6$-; wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;

$Q_3$ is a $C_{1-8}$ alkylene or a moiety of formula ($C_{1-8}$ alkylene-X—$C_{0-8}$ alkylene)$_n$;

$Q_4$ is selected from the group consisting of O, —C(O)—NR—, —NR—C(O)—, —C(O)—O—, —O—C(O)—, —C(O)—S—, —S—C(O)—, $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;

$Q_5$ is selected from the group consisting of —C(O)—NR—, —NR—C(O)—, —C(O)—O—, —O—C(O)—, —C(O)—S—, —S—C(O)—, $C_{1-8}$ alkylene, $C_{2-8}$ alkynylene, monocyclic carbocycle, fused bicyclic carbocycle, non-aromatic heterocycle, arylene, and heteroarylene, or is a moiety of formula $C_{1-8}$ alkylene-(X—$C_{1-8}$ alkylene)$_n$, wherein each of $C_{1-8}$ alkylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;

$Q_6$ is selected from the group consisting of O, —C(O)—NR—, —NR—C(O)—, —C(O)—O—, —O—C(O)—, —C(O)—S—, —S—C(O)—, $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;

each X is selected from the group consisting of O, S, CR$_2$, NR, P, $C_{2-8}$ alkynylene, arylene, and heteroarylene (preferably O, S, CH$_2$, NR, or CR=CR);

each R is independently H, $C_{1-8}$ alkyl, or aryl;

n is 1 to 10; and each

marks a connection point to the Cα carbon in a linked residue/analogue.

Another aspect of the present invention is a parallel coiled-coil of formula II wherein at least one of the linkers for $g_0$-$e'_1$, $g_1$-$e'_2$, $g_2$-$e_3$, $e_1$-$g'_0$, $e_2$-$g'_1$, and $e_3$-$g'_2$ has the following formula

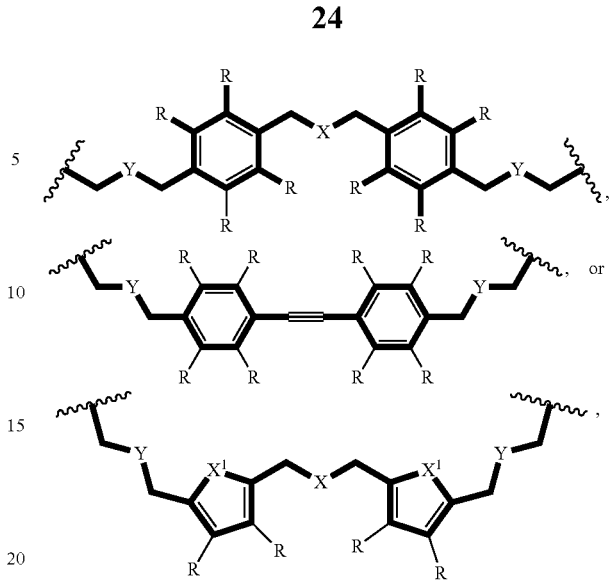

wherein X is O, S, CR$_2$, NR, or P (preferably O, S, CH$_2$ or NR), wherein X$^1$ is O, S, NH, and NR, wherein each R is independently H, alkyl, or aryl, wherein Y is S, and wherein each

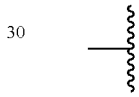

marks a connection point to the Cα carbon in a linked residue/analogue.

Another aspect of the present invention is a parallel coiled-coil of formula II wherein at least one of the linkers for $g_0$-$e'_1$, $g_1$-$e'_2$, $g_2$-$e_3$, $e_1$-$g'_0$, $e_2$-$g'_1$, and $e_3$-$g'_2$ has the following formula

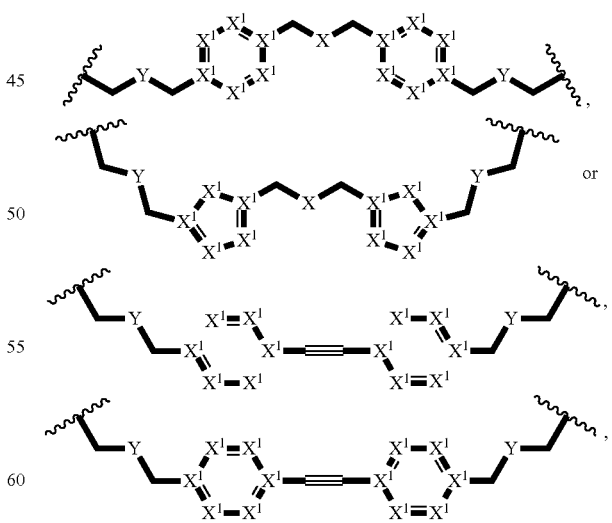

wherein X is O, S, CR$_2$, NR, or P (preferably O, S, CH$_2$ or NR), wherein X$^1$ is O, S, C, CR, N, NH, and NR, wherein each R is independently H, alkyl, or aryl, wherein Y is S, and wherein each marks a connection point to the Cα carbon in a linked residue/analogue.

Another aspect of the present invention is a parallel coiled-coil of formula II wherein at least one of the linkers for $d_1$-$d'_1$, $d_2$-$d'_2$, $d_3$-$d'_3$, $a_1$-$a'_1$, $a_2$-$a'_2$, and $a_3$-$a'_3$ is independently selected from the group consisting of disulfides, diselenides, $C_{1-8}$ alkylene, $C_{2-8}$ alkenylene, arylene, heteroarylene, triazole-diyl, and thiazole-diyl.

Another aspect of the present invention is a parallel coiled-coil of formula II wherein at least one of the linkers for $d_1$-$d'_1$, $d_2$-$d'_2$, $d_3$-$d'_3$, $a_1$-$a'_1$, $a_2$-$a'_2$, and $a_3$-$a'_3$ is independently a disulfide bond from a cysteine or homocysteine residue, a diselenide from a selenocysteine residue, an alkylene from an allylglycine residue, or an arylene linker.

Another aspect of the present invention is a parallel coiled-coil of formula II wherein one linker is present or two linkers are present.

Another aspect of the present invention is a parallel coiled-coil of formula II wherein as least one of the linkers for $g_0$-$e'_1$, $g_1$-$e'_2$, $g_2$-$e_3$, $e_1$-$g'_0$, $e_2$-$g'_1$ and $e_3$-$g'_2$ is present and at least one of the linkers for $d_1$-$d'_1$, $d_2$-$d'_2$, $d_3$-$d'_3$, $a_1$-$a'_1$, $a_2$-$a'_2$, and $a_3$-$a'_3$ is present.

Another aspect of the present invention is a parallel coiled-coil of formula II wherein one of the linkers for $g_0$-$e'_1$, $g_1$-$e'_2$, $g_2$-$e_3$, $e_1$-$g'_0$, $e_2$-$g'_1$, and $e_3$-$g'_2$ is present and one of the linkers for $d_1$-$d'_1$, $d_2$-$d'_2$, $d_3$-$d'_3$, $a_1$-$a'_1$, $a_2$-$a'_2$, and $a_3$-$a'_3$ is present.

Another aspect of the present invention is a parallel coiled-coil of formula II wherein the compound has a parallel coiled-coil tertiary structure.

Another aspect of the present invention is a parallel coiled-coil of formula II wherein $f_0$ is any residue; $g_0$ is Trp, Met, Phe, Ala, Glu, or His; $a_1$ is Cys, HCys, Leu, Ile, allylleucine, Val, allylglycine, Thr, selenocysteine, hexafluoroleucine, or hexafluorovaline; $b_1$ is any residue; $c_1$ is Gln, Trp, Leu, Phe, Tyr, or Met; $d_1$ is Cys, HCys, Leu, Ile, allylleucine, Val, allylglycine, Thr, selenocysteine, hexafluoroleucine, or hexafluorovaline; $e_1$ is any residue; $f_1$ is any residue; $g_1$ is any residue; $a_2$ is Cys, HCys, Leu, Ile, allylleucine, Val, allylglycine, Thr, selenocysteine, hexafluoroleucine, or hexafluorovaline; $b_2$ is any residue; $c_2$ is any residue; $d_2$ is Cys, HCys, Leu, Ile, allylleucine, Val, allylglycine, Thr, selenocysteine, hexafluoroleucine, or hexafluorovaline; $e_2$ is any residue; $g'_0$ is any residue; $a'_1$ is Cys, HCys, Leu, Ile, allylleucine, Val, allylglycine, Thr, selenocysteine, hexafluoroleucine, or hexafluorovaline; $b'_1$ is His, Phe, Trp, Tyr, Val, Leu, or Ile; $c'_1$ is any residue; $d'_1$ is Cys, HCys, Leu, Ile, allylleucine, Val, allylglycine, Thr, selenocysteine, hexafluoroleucine, or hexafluorovaline; $e'_1$ is His, Phe, Trp, Tyr, Val, Leu, or Ile, $e'_1$ is any residue; $f'_1$ is any residue; $g'_1$ is any residue; $a'_2$ is Cys, HCys, Leu, Ile, allylleucine, Val, allylglycine, Thr, selenocysteine, hexafluoroleucine, or hexafluorovaline; $b'_2$ Asp, Asn, Glu, Gln, Tyr, Ser, or Thr; $c'_2$ is any residue; $d'_2$ is Cys, HCys, Leu, Ile, allylleucine, Val, allylglycine, Thr, selenocysteine, hexafluoroleucine, or hexafluorovaline, $e'_2$ is His, Phe, Trp, Tyr, Val, Leu, or Ile; $f'_2$ is any residue; where any amino acid residue may be modified for attachment of Z, which is a covalent linker (e.g., a bis-triazole linker) between pair $e_2$-$g'_1$.

Another aspect of the present invention is a parallel coiled-coil of formula II wherein $c_1$ is Glu; $d_1$ is Leu; $e_1$ is Glu; $f_1$ is Arg; $g_1$ is Glu; $a_2$ is Ile; $b_2$ is Arg; $c_2$ is Trp; $d_2$ is Leu; ea is Z; $c'_1$ is Glu; $d'_1$ is Leu; $e'_1$ is Glu; $f'_1$ is Arg; $g'_1$ is Z; $a'_1$, is Ile; $b'_2$, is Arg; $c'_2$, is Trp; $d'_2$ is Leu, $e'_2$ is Arg; where any amino acid residue may be modified for attachment of Z, which is a covalent linker (e.g., a bis-triazole linker) between pair $g_1$-$e'_2$.

Another aspect of the present invention is a parallel coiled-coil of formula II wherein $c_1$ is Glu; $d_1$ is Cys; $e_1$ is Glu; $f_1$ is Arg; $g_1$ is Glu; $a_2$ is Ile; $b_2$ is Arg; $c_2$ is Trp; $d_2$ is Leu; $e_2$ is Z; $c'_1$ is Glu; $d'_1$ is Cys; $e'_1$ is Glu; $f'_1$ is Arg; $g'_1$ is Z; $a'_2$ is Ile; $b'_2$ is Arg; $c'_2$ is Trp; $d'_2$ is Leu, $e'_2$ is Arg; where any amino acid residue may be modified for attachment of Z, which is a covalent linker (e.g., a bis-triazole linker) between pair $g_1$-$e'_2$.

Another aspect of the present invention is a method of inhibiting interaction between the AML1-ETO-containing transcription factor complex (AETFC) and an NHR2 binding motif. This method involves contacting the transcription factor complex and/or the NHR2 binding motif with a compound of Formula I that mimics the NHR2 domain, as described below, under conditions effective to inhibit interaction between the AML1-ETO-containing transcription factor complex and the NHR2 binding motif.

Another aspect of the present invention relates to a method of modulating transcription of a gene in a cell, wherein transcription of the gene is regulated by interaction between AETFC and an NHR2 binding motif. This method involves contacting the cell with a compound of Formula I that mimics the NHR2 domain, as described below, under conditions effective to modulate transcription of the gene.

Another aspect of the present invention relates to a method of treating leukemia in a subject. This method involves administering to the subject a compound of Formula I that mimics the NHR2 domain, as described below, under conditions effective to treat leukemia in the subject.

Coiled-coils are a major motif in proteins and orchestrate multimerization of various complexes important for biological processes. Inhibition of coiled-coil-mediated interactions has significant biomedical potential. However, general approaches that afford short peptides with defined coiled-coil conformation have remained elusive. As described more fully herein, several strategies to stabilize minimal helical bundles with the dimer motif as the initial focus were evaluated. A stable dimeric scaffold was realized in a synthetic sequence by replacing an interhelical ionic bond with a covalent bond. For a native protein-protein interaction with a less stable native coiled-coil, an additional constraint, a disulfide bond at the internal a/d' position along with a linker at the e/e' positions, was used to enhanced conformational stability. It is expected that the coiled-coil stabilization methodology described herein can yield new classes of modulators for the subset of protein-protein interactions that utilize this motif for complex formation and that this synthetic approach could be applied to stabilize a range of helical dimers in a sequence-independent manner.

BRIEF DESCRIPTION OF THE DRAWINGS

FIG. 7 shows the structure of flu-N2B used in the peptide-binding assays (top) and its analytical UV trace measured at 220 nm on an XTerra RP18 3.5 μm 2.1×150 mm column (Part No. 186000410) (bottom). 10% B to 90% B over 10 min; A: 0.1% aqueous TFA, B: acetonitrile; flow rate 400 μL/min. Exact mass calcd [M+H]$^+$ (m/z): 2056.0; found: 2055.9 m/z.

FIGS. 10A-E show strategies to template coiled-coil formation of designed peptides. FIG. 10A shows a potential antiparallel coiled-coil assembly between peptides A and B. FIG. 10B shows use of hydrogen bond surrogate helices to stabilize helical dimers. FIG. 10C shows macrocyclization of peptides. FIG. 10D shows the utilization of interhelical disulfide bridges in place of hydrophobic contacts to aid assembly. FIG. 10E shows placement of covalent bonds in place of interstrand ionic interactions. See Table 1 below.

TABLE 1

Strategies used to stabilize antiparallel coiled coil mimics and their characteristics

| Compound | Modification (location) | Minimum at 222/208 | $|\theta_{222}|$ |
|---|---|---|---|
| AB* | N/A | 0.58 | 9510 |
| AB-1 | N-terminal HBS constraint | 0.73 | 8475 |
| AB-2 | Two GGSSGG linkers at the N and C termini | 0.62 | 8950 |
| AB-3 | Interhelical cysteine disulfide bridges at the A-D' positions | 0.62 | 9460 |
| AB-4‡ | Bis-triazole azidolysine | 0.86 | 9935 |
| AB-5‡ | Bis-triazole azidohomoalanine | 0.71 | 11450 |
| AB-6‡ | Bis-triazole azidoalanine | 0.46 | 8505 |

Figure 11A:
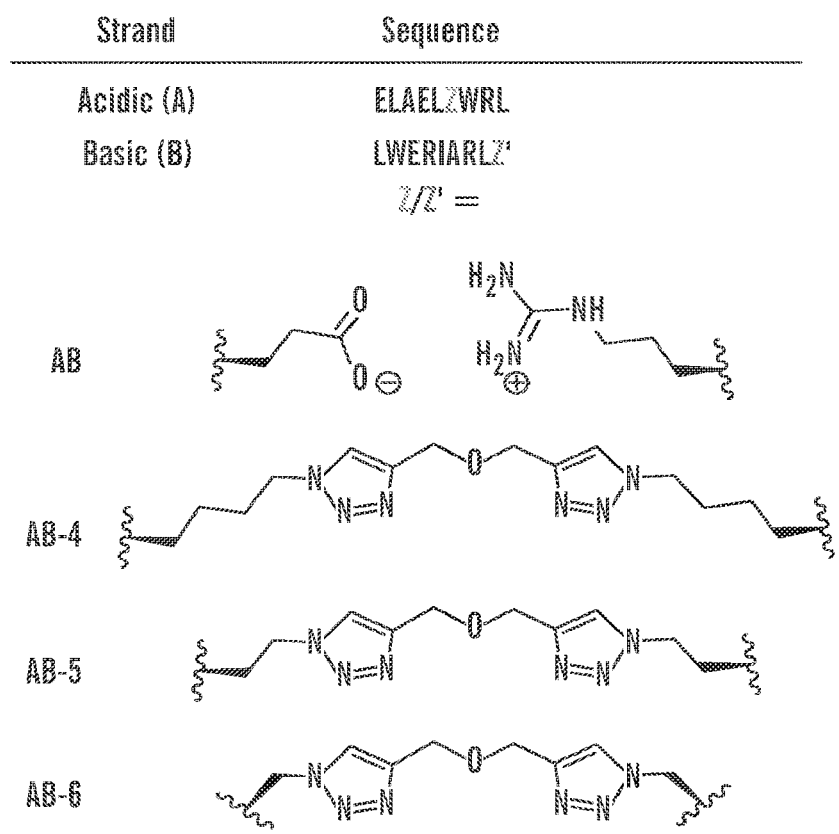
Figure 11B:
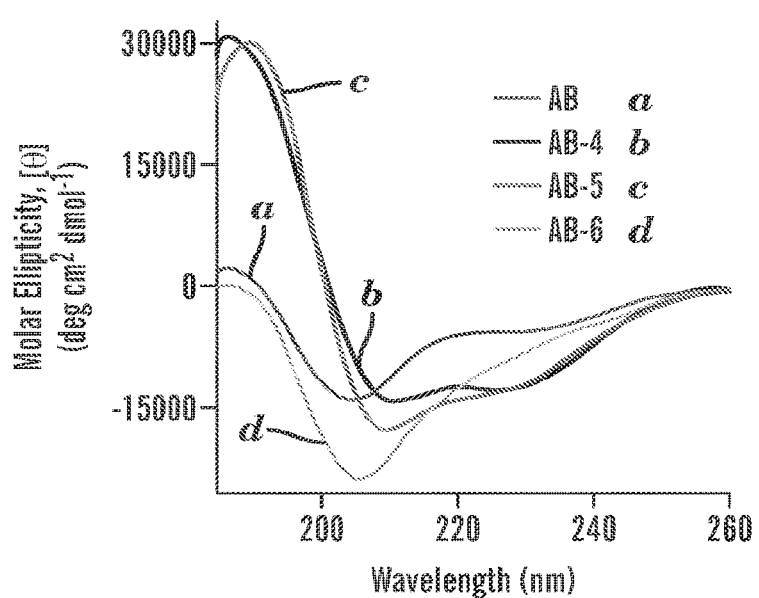

*Exhibits random coil-like signature;
‡Click reaction performed with propargyl ether FIGS. 11A-D relate to the design of crosslinked helix dimers by replacement of an interstrand ionic contact with bistriazole linkers. As shown in FIG. 11A, the acidic strand A (SEQ ID NO:1) and the basic strand B (SEQ ID NO:2) were used to synthesize the crosslinked helix dimers. Bis-triazole linkers of varying lengths resulting from azidoalanine, azidohomoalanine, and azidolysine residues were incorporated at coiled-coil positions e/e' to obtain dimers AB-4, AB-5, and AB-6, respectively. FIG. 11B shows CD spectra of AB-4-AB-6 in 50 mM aqueous KF, pH 7.4. FIG. 11C shows a helical wheel diagram of AB-4. FIG. 11D depicts NMR-derived structure of AB-4. The lowest conformer (top) and ensemble of 20 lowest conformers (bottom) are shown.

Figure 12A:
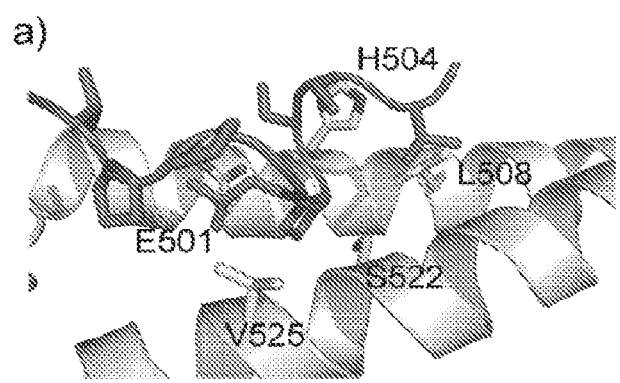
Figure 12B:
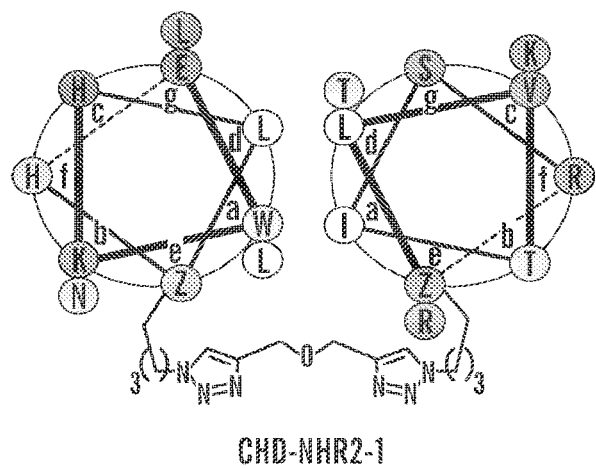
Figure 12C:
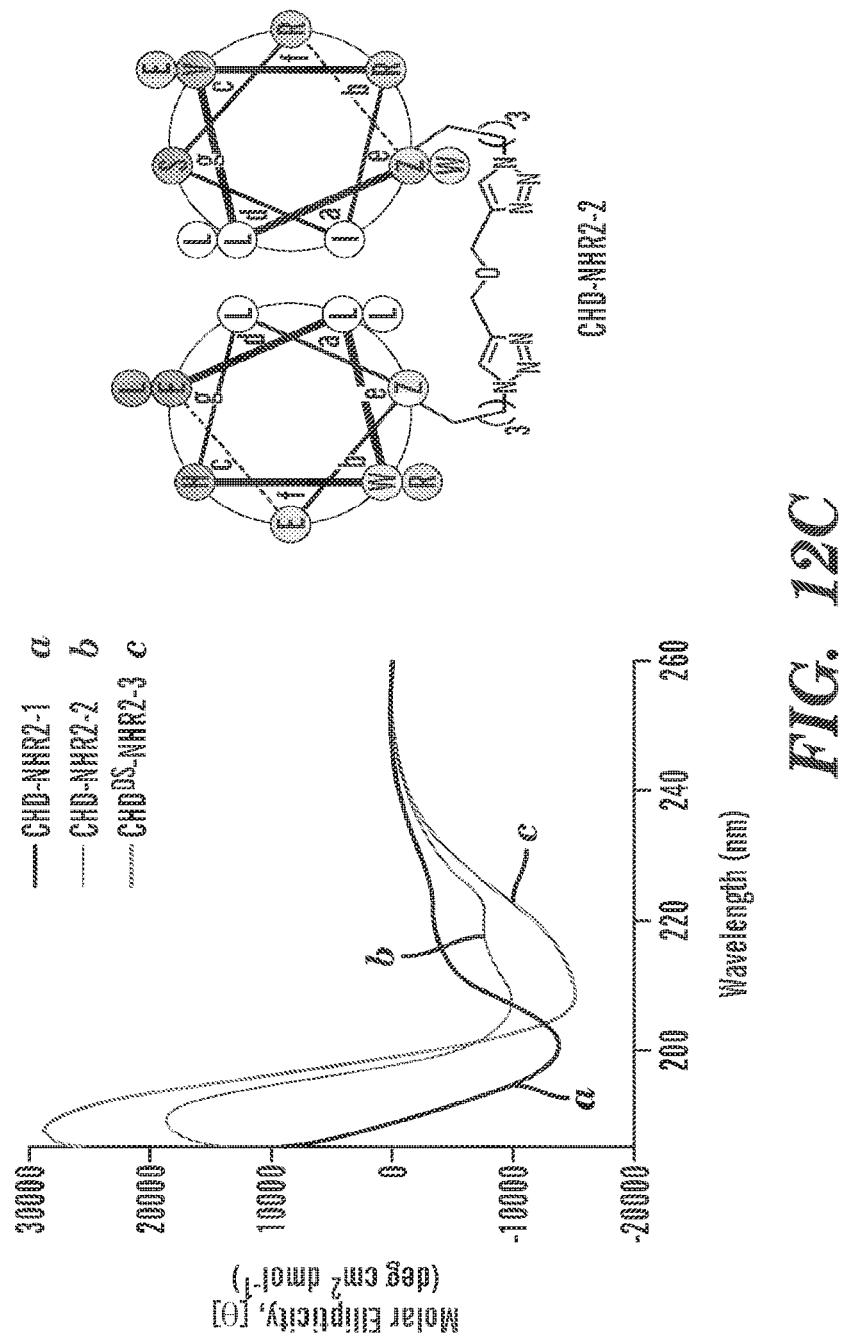

FIGS. 12A-D relate to the design of coiled-coil mimics of NHR2. FIG. 12A is a model depicting binding of NHR2 to N2B with critical residues labeled. PDB code: 4JOL. FIG. 12B are helical wheel diagrams depicting sequences for the native (CHD-NHR2-1) (FIG. 12B, top), the redesigned (CHD-NHR2-2) (FIG. 12B, middle), and disulfide-linked (CHD$^{DS}$-NHR2-3) (FIG. 12B, bottom) NHR2 coiled-coil mimetics. Z denotes azidolysine derived bis-triazole linker. FIG. 12C is the CD spectra of CHD-NHR2-1, CHD-NHR2-2, and CHD$^{DS}$-NHR2-3 in 50 mM aqueous KF, pH 7.4. FIG. 12D shows a computational model of CHD$^{DS}$-NHR2-3.

Figure 13A:
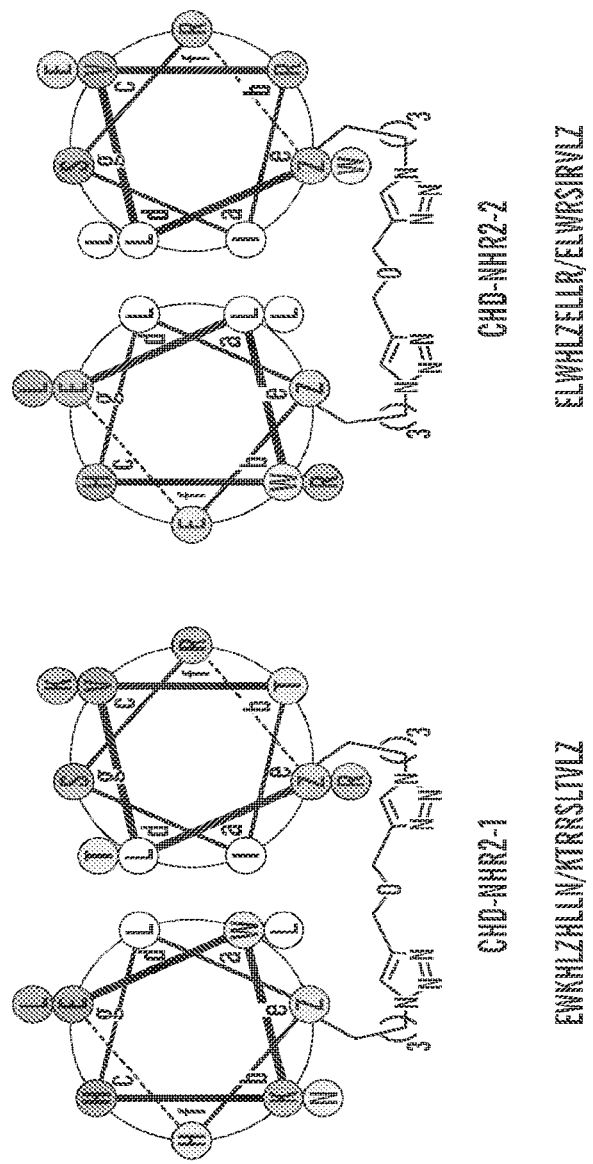
Figure 13B:
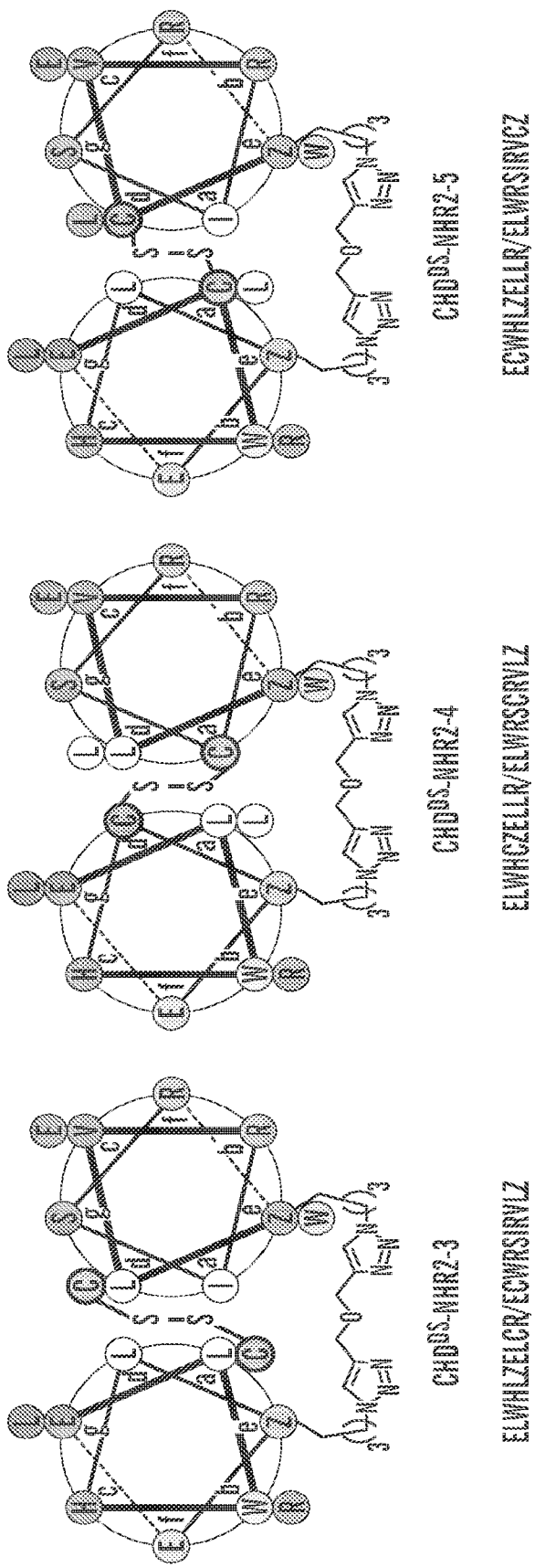
Figure 13C:
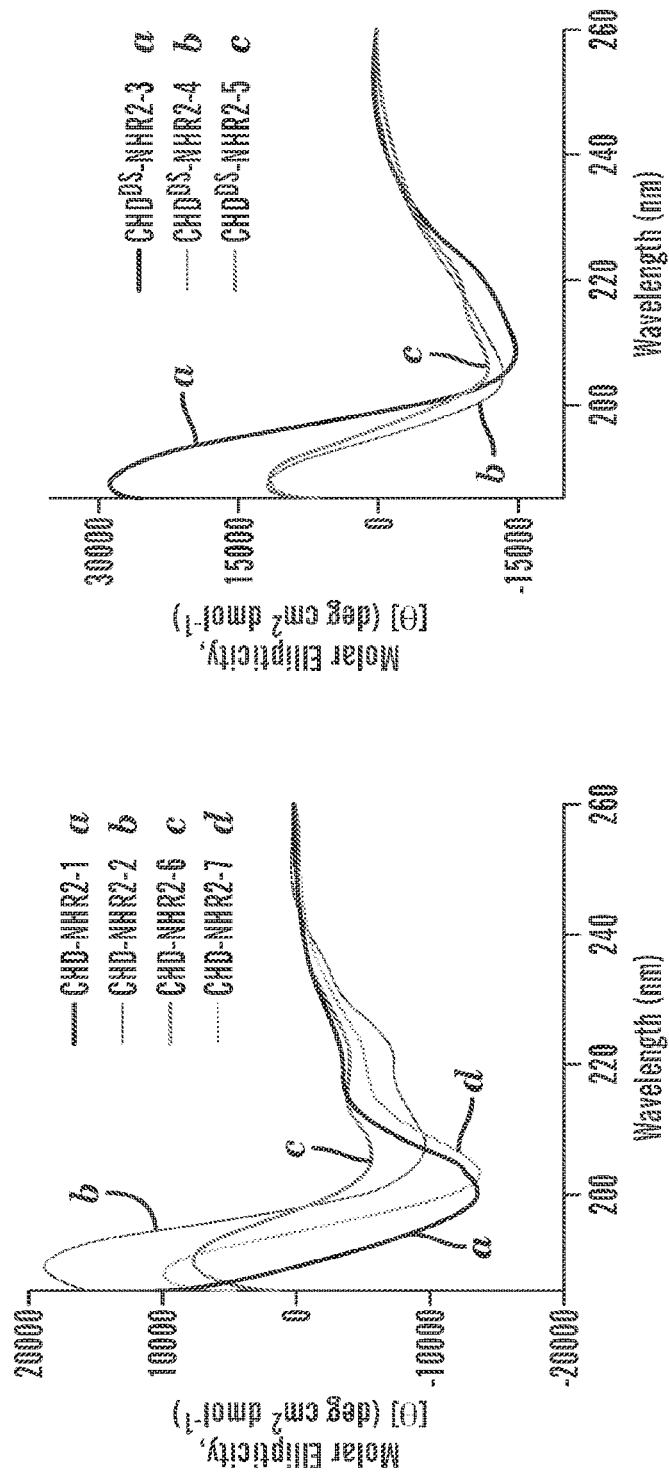

FIGS. 13A-C show helical wheel diagrams of mono-crosslinked NHR2 helix dimers CHD-NHR2-1 (SEQ ID NO:6/SEQ ID NO:7) and CHD-NHR2-2 (SEQ ID NO:8/SEQ ID NO:9) (FIG. 13A) and disulfide-stabilized double crosslinked NHR2 helix dimers CHD$^{DS}$-NHR2-3 (SEQ ID NO:10/SEQ ID NO:11), CHD$^{DS}$-NHR2-4 (SEQ ID NO:12/SEQ ID NO:13), and CHD$^{DS}$-NHR2-5 (SEQ ID NO:14/SEQ ID NO:15) (FIG. 13B), and CD spectra of designed CHD-NHR2 peptides (FIG. 13C). CD spectra were acquired in 50 mM aqueous KF, pH 7.4.

DETAILED DESCRIPTION OF THE INVENTION

One aspect of the present invention relates to a macrostructure that comprises:
(i) an antiparallel coiled-coil structure of formula:

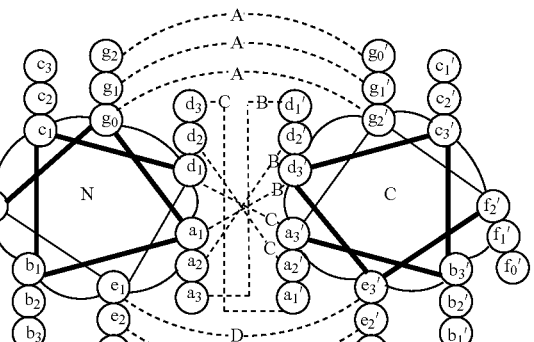

(helical wheel view)

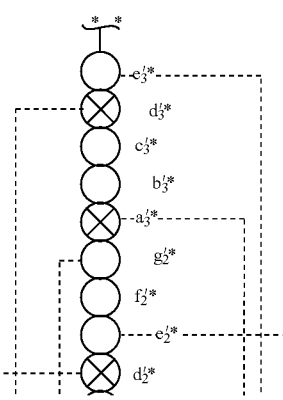

-continued

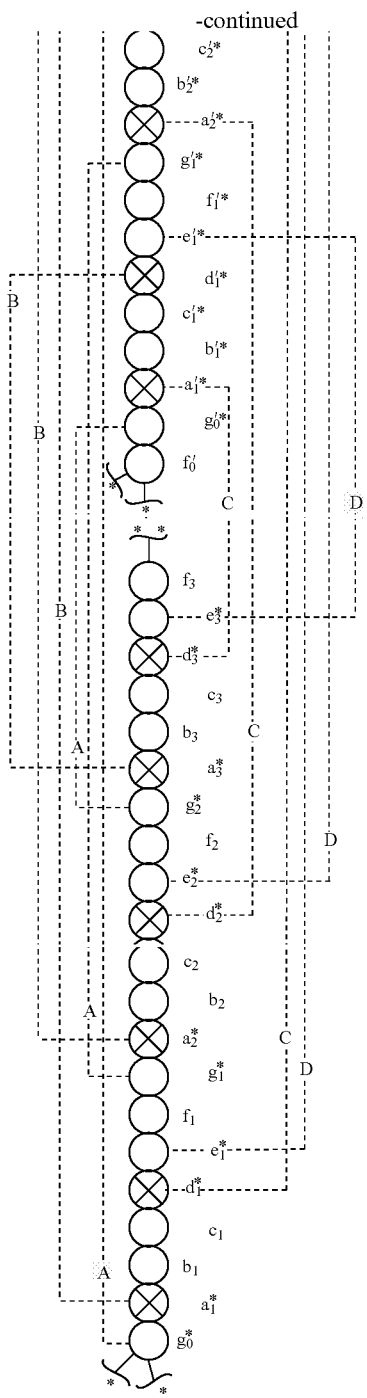

(two-dimensional view);

wherein:
each ○ and each ⊗ is independently absent or a modified or unmodified amino acid residue or analogue thereof, with the proviso that at least seven contiguous amino acid residues/analogues are present in each coil, wherein
a, b, c, d, e, f, g, a'$_1$, b', c', d', e', f', and g' indicate the location of the amino acid residues/analogues within the coiled-coil structure and
each ⊗ amino acid residue is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues;

each ⌐ ─ ─ ─ ─ ┐ is absent or a covalent linker (Linker) between two amino acid residues/analogues, wherein:
  each Linker A is independently a linker between a g* amino acid residue and a g'* amino acid residue, wherein the length of the linker is such that the spatial distance between the Cα position of the g* amino acid residue and the Cα position of the g'* amino acid residue is 10-25 Å;
  each Linker B is independently a linker between an a* amino acid residue and a d'* amino acid residue, wherein the length of the linker is such that the spatial distance between the Cα position of the a* amino acid residue and the Cα position of the d'* amino acid residue is 5-15 Å;
  each Linker C is independently a linker between a d* amino acid residue and an a'* amino acid residue, wherein the length of the linker is such that the spatial distance between the Cα position of the d* amino acid residue and the Cα position of the a'* amino acid residue is 5-15 Å;
  each Linker D is independently a linker between an e* amino acid residue and an e'* amino acid residue, wherein the length of the linker is such that the spatial distance between the Cα position of the e* amino acid residue and the Cα position of the e'* amino acid residue is 10-25 Å;
  and
at least one Linker A or Linker D is present; each $$\text{—}\xi\text{*}$$

is a point of attachment from a terminal nitrogen to H, —PG$_1$, —C(O)R, —C(O)NR$_2$, —C(O)NH$_2$, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_1$ is a protecting group for protection of an amine; and each $$\text{—}\xi\text{*}\text{*}$$

is a point of attachment from a terminal carbonyl to H, —OPG$_2$, —NPG$_2$, —OR, —OH, —NR$_2$, —NH$_2$, —NRC(O)C$_{1-6}$ alkyl, —NHC(O)C$_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_2$ is a protecting group for protection of a carboxylic acid;

or (ii) a parallel coiled-coil structure of formula

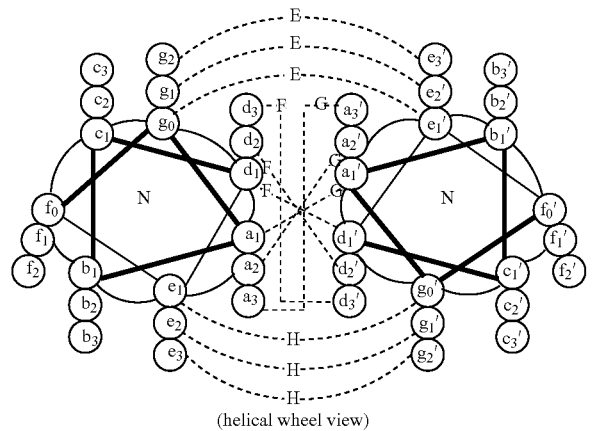

(helical wheel view)

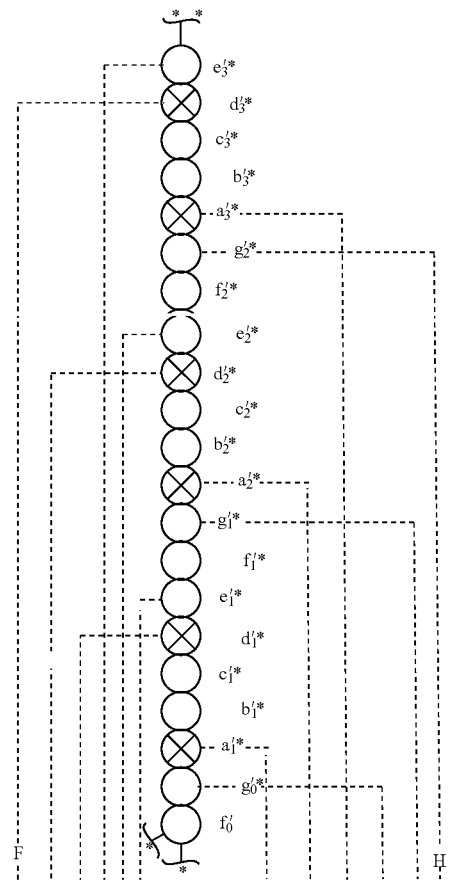

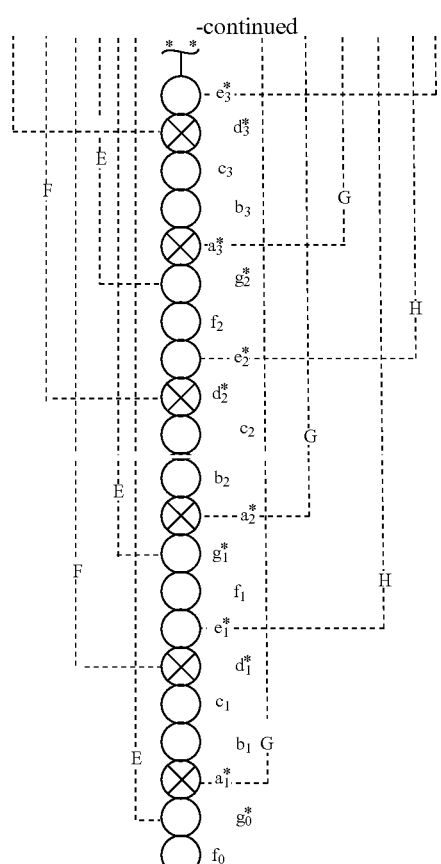

(two-dimensional view);

wherein:
each ○ and each ⊗ is independently absent or a modified or unmodified amino acid residue or analogue thereof, with the proviso that at least seven contiguous amino acid residues/analogues are present in each coil, wherein
  a, b, c, d, e, f, g, a'$_1$, b', c', d', e', f', and g' indicate the location of the amino acid residues/analogues within the coiled-coil structure and
each ⊗ amino acid residue is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues;

each ⌐‾‾‾‾¬
      ⌊____⌋
is absent or a covalent linker (Linker) between two amino acid residues/analogues, wherein: ⌐‾‾‾‾‾¬
                                                                                              ⌊____⌋
  each Linker E is independently a linker between a g* amino acid residue and an e'* amino acid residue, wherein the length of the linker is such that the spatial distance between the Cα position of the g* amino acid residue and the Cα position of the e'* amino acid residue is 10-25 Å;
  each Linker F is independently a linker between a d* amino acid residue and a d'* amino acid residue, wherein the length of the linker is such that the spatial distance between the Cα position of the d* amino acid residue and the Cα position of the d'* amino acid residue is 5-15 Å;

each Linker G is independently a linker between an a* amino acid residue and an a'* amino acid residue, wherein the length of the linker is such that the spatial distance between the Cα position of the a* amino acid residue and the Cα position of the a'* amino acid residue is 5-15 Å;

each Linker H is independently a linker between an e* amino acid residue and a g'* amino acid residue, wherein the length of the linker is such that the spatial distance between the Cα position of the e* amino acid residue and the Cα position of the g'* amino acid residue is 10-25 Å; and at least one Linker E or Linker H is present; and
each

is a point of attachment from a terminal nitrogen to H, —PG$_1$, —C(O)R, —C(O)NR$_2$, —C(O)NH$_2$, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_1$ is a protecting group for protection of an amine; and
each

is a point of attachment from a terminal carbonyl to H, —OPG$_2$, —NPG$_2$, —OR, —OH, —NR$_2$, —NH$_2$, —NRC(O)C$_{1-6}$ alkyl, —NHC(O)C$_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_2$ is a protecting group for protection of a carboxylic acid.

Another aspect of the present invention is an antiparallel coiled-coil of formula I:

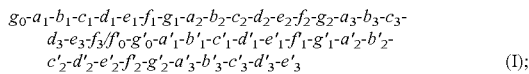  (I);

wherein each $b_{1-3}$, $c_{1-3}$, $e_{1-3}$, $f_{1-3}$, $g_{0-2}$, $b'_{1-3}$, $c'_{1-3}$, $e'_{1-3}$, $f'_{0-2}$, and $g'_{0-2}$ is independently absent or is a modified or unmodified amino acid residue or an analogue thereof, and each $a_{1-3}$, $d_{1-3}$, $a'_{1-3}$, and $d'_{1-3}$, is independently absent or is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding amino acids, with the proviso that at least seven contiguous amino acid residues/analogues are present in each coil;

wherein one or more of the following pairs are covalently bound by a linker: $g_0$-$g'_2$, $g_1$-$g'_1$, $g_2$-$g'_0$, $a_1$-$d'_3$, $a_2$-$d'_2$, $a_3$-$d'_1$, $d_1$-$a'_3$, $d_2$-$a'_2$, $d_3$-$a'_1$, $e_1$-$e'_3$, $e_2$-$e'_2$, and $e_3$-$e'_1$;

Another aspect of the present invention is an antiparallel coiled-coil of formula I:

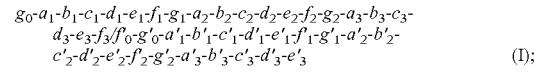  (I);

wherein each $b_{1-3}$, $c_{1-3}$, $e_{1-3}$, $f_{1-3}$, $g_{0-2}$, $b'_{1-3}$, $c'_{1-3}$, $e'_{1-3}$, $f'_{0-2}$, and $g'_{0-2}$ is independently absent or is a modified or unmodified amino acid residue or an analogue thereof, and each $a_{1-3}$, $d_{1-3}$, $a'_{1-3}$, and $d'_{1-3}$, is independently absent or is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding amino acids, with the proviso that at least seven contiguous amino acid residues/analogues are present in each coil;

wherein one or more of the following pairs are covalently bound by a linker: $g_0$-$g'_2$, $g_1$-$g'_1$, $g_2$-$g'_0$, $a_1$-$d'_3$, $a_2$-$d'_2$, $a_3$-$d'_1$, $d_1$-$a'_3$, $d_2$-$a'_2$, $d_3$-$a'_1$, $e_1$-$e'_3$, $e_2$-$e'_2$, and $e_3$-$e'_1$;

wherein the terminal nitrogen of each coil is covalently bound to one or more H, —PG$_1$, —C(O)R, —C(O)NR$_2$, —C(O)NH$_2$, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_1$ is a protecting group for protection of an amine; and wherein the terminal carbonyl of each coil is covalently bound to H, —OPG$_2$, —NPG$_2$, —OR, —OH, —NR$_2$, —NH$_2$, —NRC(O)C$_{1-6}$ alkyl, —NHC(O)C$_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein PG$_2$ is a protecting group for protection of a carboxylic acid.

Another aspect of the present invention is a parallel coiled-coil of formula II:

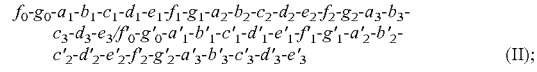  (II);

wherein each $b_{1-3}$, $c_{1-3}$, $e_{1-3}$, $f_{0-2}$, $g_{0-2}$, $b'_{1-3}$, $c'_{1-3}$, $e'_{1-3}$, $f'_{0-2}$, and $g'_{0-2}$ is independently absent or is a modified or unmodified amino acid residue or an analogue thereof, and each $a_{1-3}$, $d_{1-3}$, $a'_{1-3}$, and $d'_{1-3}$, is independently absent or is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding amino acids, with the proviso that at least seven contiguous amino acid residues/analogues are present in each coil;

wherein one or more of the following pairs are covalently bound by a linker: $g_0$-$e'_1$, $g_1$-$e'_2$, $g_2$-$e_3$, $d_1$-$d'_1$, $d_2$-$d'_2$, $d_3$-$d'_3$, $a_1$-$a'_1$, $a_2$-$a'_2$, $a_3$-$a_3$, $e_1$-$g'_0$, $e_2$-$g'_1$, and $e_3$-$g'_2$.

Another aspect of the present invention is a parallel coiled-coil of formula II:

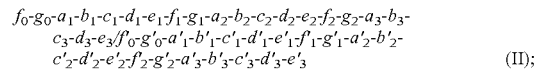  (II);

wherein each $b_{1-3}$, $c_{1-3}$, $e_{1-3}$, $f_{0-2}$, $g_{0-2}$, $b'_{1-3}$, $c'_{1-3}$, $e'_{1-3}$, $f'_{0-2}$, and $g'_{0-2}$ is independently absent or is a modified or unmodified amino acid residue or an analogue thereof, and each $a_{1-3}$, $d_{1-3}$, $a'_{1-3}$, and $d'_{1-3}$, is independently absent or is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding amino acids, with the proviso that at least seven contiguous amino acid residues/analogues are present in each coil;

wherein one or more of the following pairs are covalently bound by a linker: $g_0$-$e'_1$, $g_1$-$e'_2$, $g_2$-$e_3$, $d_1$-$d'_1$, $d_2$-$d'_2$, $d_3$-$d'_3$, $a_1$-$a'_1$, $a_2$-$a'_2$, $a_3$-$a_3$, $e_1$-$g'_0$, $e_2$- $g'_1$, and $e_3$-$g'_2$;

wherein the terminal nitrogen of each coil is covalently bound to one or more H, —$PG_1$, —C(O)R, —C(O)$NR_2$, —C(O)$NH_2$, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein $PG_1$ is a protecting group for protection of an amine; and wherein the terminal carbonyl of each coil is covalently bound to H, —$OPG_2$, —$NPG_2$, —OR, —OH, —$NR_2$, —$NH_2$, —NRC(O)$C_{1-6}$ alkyl, —NHC(O)$C_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein $PG_2$ is a protecting group for protection of a carboxylic acid.

Antiparallel coiled-coil structures and parallel coiled-coil structures each have a first amino acid strand (or first coil) and a second amino acid strand (or second coil). As will be readily apparent to the skilled artisan, the following conventions are commonly used to characterize coiled-coil structures and are used throughout this application. The convention "A/B" or "$^xA^y$/$^xB^y$" is used to identify the sequence of each strand (either specifically or generically), where A is the sequence ($X_1$-$X_2$-$X_3$ . . . ) of the first strand, B is the sequence ($X_1'$-$X_2'$-$X_3'$ . . . ) of the second strand, x, x', y, and y' identify the starting (x, x') and ending (y, y') locations of the corresponding sequences relative to heptad(s) in each strand, and "/" separates one sequence from the other. Conventionally, for both antiparallel and parallel coiled-coil structures, the A and B sequences are both written, left to right, in an N-to-C orientation. However, as will be readily apparent to the skilled artisan, the strands in an antiparallel coiled-coil structure are spatially aligned in opposite directions, e.g., in a top view taken perpendicular to the axis of an antiparallel coiled-coil, the N-terminal of the first strand will be top-most and the C-terminal of the second strand will be top-most; conversely, as will be readily apparent to the skilled artisan, the strands in a parallel coiled-coil structure are spatially aligned in the same direction, e.g., in a top view taken perpendicular to the axis of a parallel coiled-coil, the N-terminal of the first strand will be top-most and the N-terminal of the second strand will be top-most. As will be readily apparent to the skilled artisan, in the compounds of the present invention, there is also at least one covalent linker between a residue in the first strand and a residue in the second strand. The location and structure of the linker(s) are sometimes identified using "Z" and "Z'" in place of X and X', respectively, in the A and B sequences. Alternatively, the location and structure of the linker(s) are identified by additional explanation (e.g., "there is a disulfide linker between residue $X_n$ and residue $X_n'$").

As will be readily apparent to the skilled artisan, the helical wheel views herein show the spatial orientation of each coil in the antiparallel or parallel coiled-coil structure, while the two-dimensional views show the connections between residues.

As used above, and throughout the description of the invention, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

As used herein, the term "alkyl" means an aliphatic hydrocarbon group which may be straight or branched having about 1 to about 8 (e.g., 1-2, 1-3, 1-4, 1-5, 1-6, 1-7, 1-8) carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 8 (e.g., 2-3, 2-4, 2-5, 2-6, 2-7, 2-8) carbon atoms in the chain. Preferred alkenyl groups have 2 to about 4 carbon atoms in the chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 8 (e.g., 2-3, 2-4, 2-5, 2-6, 2-7, 2-8) carbon atoms in the chain. Preferred alkynyl groups have 2 to about 4 carbon atoms in the chain. Exemplary alkynyl groups include ethynyl, propynyl, n-butynyl, 2-butynyl, 3-methylbutynyl, and n-pentynyl.

As used herein, the term "cycloalkyl" refers to a non-aromatic saturated or unsaturated mono- or polycyclic ring system which may contain 3 to 8 (3, 4, 5, 6, 7, 8, 3-4, 3-5, 3-6, 3-7, 4-5, 4-6, 4-7, 4-8, 5-6, 5-7, 5-8, 6-7, 6-8, 7-8) carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, the term "alkane" refers to aliphatic hydrocarbons of formula $C_nH_{2n+2}$, which may be straight or branched having about 1 to about 8 (e.g., 1-2, 1-3, 1-4, 1-5, 1-6, 1-7, 1-8) carbon atoms in the chain. Branched means that one or more lower alkyl groups such as methyl, ethyl, or propyl are attached to a linear alkyl chain. Exemplary alkanes include methane, ethane, n-propane, i-propane, n-butane, t-butane, n-pentane, and 3-pentane. The term "alkylene" refers to a divalent group formed from an alkane by removal of two hydrogen atoms. Exemplary alkylene groups include, but are not limited to, divalent groups derived from the alkanes described above.

As used herein, the term "alkene" refers to aliphatic unsaturated hydrocarbons of formula $C_nH_{2n}$, which may be straight or branched having about 2 to about 8 (e.g., 2-3, 2-4, 2-5, 2-6, 2-7, 2-8) carbon atoms in the chain. Exemplary alkenes include ethylene, propylene, n-butylene, and i-butylene. The term "alkenylene" refers to a divalent group formed from an alkene by removal of two hydrogen atoms. Alkenylenes contain a carbon-to-carbon double bond and are represented by the formula —$(C_nH_{n-2})$—. Exemplary alkenylene groups include, but are not limited to, divalent groups derived from the alkenes described above.

As used herein, the term "alkyne" refers to aliphatic unsaturated hydrocarbons of formula $C_nH_{2n-2}$, which may be straight or branched having about 2 to about 8 (e.g., 2-3, 2-4, 2-5, 2-6, 2-7, 2-8) carbon atoms in the chain. Exemplary alkynes include acetylene, propyne, butyne, and pentyne. The term "alkynylene" refers to a divalent groups formed from alkynes by removal of two hydrogen atoms. Alkynylene contains a carbon-to-carbon triple bond and is represented by the formula —$(C_nH_{2n-4})$—. Exemplary alkynylene groups include, but are not limited to, divalent groups derived from the alkynes described above.

Aromatic rings and heteroaromatic rings can be any single, multiple, or fused ring structures. For example, aromatic or heteroaromatic rings include 5- or 6-membered aromatic or heteroaromatic rings containing 0-3 (0, 1, 2, or 3) heteroatoms selected from O, N, and S; a bicyclic 9- or 10-membered aromatic or heteroaromatic ring system containing 0-3 (0, 1, 2, or 3) heteroatoms selected from O, N, and S; or a tricyclic 13- or 14-membered aromatic or heteroaromatic ring system containing 0-3 (0, 1, 2, or 3) heteroatoms selected from O, N, and S. Aromatic 5- to 14-membered (5-, 6-, 7-, 8-, 9-, 10-, 11-, 12-, 13-, or 14-membered) carbocyclic rings include, e.g., cyclopenta-1,3-diene, benzene, naphthalene, indane, tetralin, and anthracene. 5- to 10-Membered (5-, 6-, 7-, 8-, 9-, or 10-membered) aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole, pyrazole, benzimidazole, pyridazine, pyrrole, imidazole, oxazole, isooxazole, indazole, isoindole, imidazole, purine, triazine, quinazoline, cinnoline, benzoxazole, acridine, benzisooxazole, and benzothiazole. The term "arylene" refers to a divalent group derived from an aromatic ring by removal of a hydrogen atom from two ring carbon atoms. Exemplary arylene groups include, but are not limited to, divalent groups derived from the aromatic rings described above. The term "heteroarylene" refers to a divalent group derived from a heteroaromatic ring. Exemplary heteroarylene groups include, but are not limited to, divalent groups derived from the heteroaromatic rings described above.

The term "ether" means a group having the formula —R—O—R—. Each R can be independently selected from the group consisting of a bond, $C_{1-8}$ alkylene, $C_{2-8}$ alkenylene, arylene, and heteroarylene. Exemplary ethers include, but are not limited to, $C_{1-8}$ alkylene-O—$C_{1-8}$ alkylene- (e.g., —$(CH_2)_2$—O—$(CH_2)_2$—), —$C_{2-8}$ alkenylene-O—$C_{2-8}$ alkenylene-, -arylene-O-arylene-, -heteroarylene-O-heteroarylene-, and —$C_{1-8}$ alkylene-O-heteroarylene-.

The term "thioether" means a group having the formula —R—S—R—. Each R can be independently selected from the group consisting of a bond, $C_{1-8}$ alkylene, $C_{2-8}$ alkenylene, arylene, and heteroarylene. Exemplary thioethers include, but are not limited to, —$C_{1-8}$ alkylene-S—$C_{1-8}$ alkylene- (e.g., —$(CH_2)_2$—S—$(CH_2)_2$—), —$C_{2-8}$ alkenylene-S—$C_{2-8}$ alkenylene-, -arylene-S-arylene-, -heteroarylene-S-heteroarylene-, and —$C_{1-8}$ alkylene-S-heteroarylene.

The term "amide" means a group having the formula —C(O)N($R^1$)($R^1$) or —C(O)N($R^1$)—. Amides include, e.g., —C(O)N($R^1$)R—, —R—C(O)N($R^1$)R—, —CH$R^1$—C(O)N($R^1$)R—, and —C($R^1$)($R^1$)—C(O)N($R^1$)R—. Each R can be independently selected from the group consisting of a bond, $C_{1-8}$ alkylene, $C_{2-8}$ alkenylene, arylene, and heteroarylene, and each $R^{1c}$ an be independently selected from the group consisting of hydrogen, $C_{1-8}$ alkyl, $C_{2-8}$ alkenyl, $C_{2-8}$ alkynyl, $C_{3-8}$ cycloalkyl, aryl, heteroaryl, heterocyclyl, and arylalkyl. Exemplary amides include, but are not limited to, —$C_{1-8}$ alkylene-C(O)N(aryl)-, —$C_{2-8}$ alkenylene-C(O)N(aryl)-, and —$C_{1-8}$ alkylene-C(O)N($C_{1-8}$ alkyl)- (e.g., —$(CH_2)_2$—C(O)N($CH_3$)—).

The term "ester" means a group having the formula —C(O)O—. Esters include, e.g., —R—C(O)O—R—, —CH$R^1$—C(O)O—R—, and —C($R^1$)($R^1$)—C(O)O—R—. Each R can be independently selected from the group consisting of a bond, $C_{1-8}$ alkylene, $C_{2-8}$ alkenylene, arylene, and heteroarylene, and each $R^{1c}$ an be independently selected from the group consisting of hydrogen, $C_{1-8}$ alkyl, $C_{2-8}$ alkenyl, $C_{2-8}$ alkynyl, $C_{3-8}$ cycloalkyl, aryl, heteroaryl, heterocyclyl, and arylalkyl. Exemplary esters include, but are not limited to, —$C_{1-8}$ alkylene-C(O)O-arylene-, —$C_{2-8}$ alkenylene-C(O)O-arylene-, —$C_{1-8}$ alkylene-C(O)O-heteroarylene-, —$C_{1-8}$ alkylene-C(O)O—$C_{1-8}$ alkylene- (e.g., —$(CH_2)_2$—C(O)O—$(CH_2)_2$—), and $C_{1-8}$ alkylene-C(O)O— (e.g., —$(CH_2)_2$—C(O)O—).

As used herein, the term "heterocyclyl" refers to a stable 3- to 18-membered (3-, 4-, 5-, 6-, 7-, 8-, 9-, 10-, 11-, 12-, 13-, 14-, 15-, 16-, 17-, or 18-membered) ring system that consists of carbon atoms and from one to five (1, 2, 3, 4, 5, 1-2, 1-3, 1-4, 2-3, 2-4, 2-5, 3-4, 3-5, 4-5) heteroatoms selected from the group consisting of nitrogen, oxygen, and sulfur. The heterocyclyl may be a monocyclic or a polycyclic ring system, which may include fused, bridged, or spiro ring systems; and the nitrogen, carbon, or sulfur atoms in the heterocyclyl may be optionally oxidized; the nitrogen atom may be optionally quaternized; and the ring may be partially or fully saturated. Representative monocyclic heterocyclyls include piperidine, piperazine, pyrimidine, morpholine, thiomorpholine, pyrrolidine, tetrahydrofuran, pyran, tetrahydropyran, oxetane, and the like. Representative polycyclic heterocyclyls include indole, isoindole, indolizine, quinoline, isoquinoline, purine, carbazole, dibenzofuran, chromene, xanthene, and the like.

As used herein, the term "aryl" refers to an aromatic monocyclic or polycyclic ring system containing from 6 to 19 (6, 7, 8, 9, 10, 11, 12, 13, 14, 15, 16, 17, 18, 19, 6-7, 6-8, 6-9, 6-10, 6-11, 6-12, 6-13, 6-14, 6-15, 6-16, 1-17, 6-18, 7-8, 7-9, 7-10, 7-11, 7-12, 7-13, 7-14, 7-15, 7-16, 7-18, 7-19, 8-9, 8-10, 8-11, 8-12, 8-13, 8-14, 8-15, 8-16, 8-17, 8-18, 8-19, 9-10, 9-11, 9-12, 9-13, 9-14, 9-15, 9-16, 9-17, 9-18, 9-19, 10-11, 10-12, 10-13, 10-14, 10-15, 10-16, 10-17, 10-18, 10-19, 11-12, 11-13, 11-14, 11-15, 11-16, 11-17, 11-18, 11-19, 12-13, 12-14, 12-15, 12-16, 12-17, 12-18, 12-19, 13-14, 13-15, 13-16, 13-17, 13-18, 13-19, 14-15, 14-16, 14-17, 14-18, 14-19, 15-16, 15-17, 15-18, 15-19, 16-17, 16-18, 16-19, 17-18, 17-19, 18-19) carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

As used herein, "heteroaryl" refers to an aromatic ring radical which consists of carbon atoms and from one to five heteroatoms selected from the group consisting of nitrogen, oxygen, and sulfur. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. Additional heteroaryls are described in COMPREHENSIVE HETEROCYCLIC CHEMISTRY: THE STRUCTURE, REACTIONS, SYNTHESIS AND USE OF HETEROCYCLIC COMPOUNDS (Katritzky et al. eds., 1984), which is hereby incorporated by reference in its entirety.

The term "arylalkyl" refers to a moiety of the formula —$R^aR^b$ where $R^a$ is an alkyl or cycloalkyl as defined above and $R^b$ is an aryl or heteroaryl as defined above.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. This technology is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "monocyclic carbocycle" means a monocyclic ring system of 5 to about 8 (e.g., 5, 6, 7, 8, 5-6, 5-7, 6-7, 6-8, 7-8) ring carbon atoms, preferably 5 or 6. The ring is nonaromatic, but may contain one or more carbon-carbon double bonds. The term "monocyclic carbocycle" also includes divalent groups derived from a monocyclic ring system. Representative monocyclic carbocycles include divalent groups derived from cyclopentane, cyclohexane, cyclopentene, cyclohexene, and the like.

The term "fused bicyclic carbocycle" means a bicyclic ring system consisting of about 8 to 11 (e.g., 8, 9, 10, 11, 8-9, 8-10, 9-10, 9-11, 10-11) ring carbon atoms, preferably 9 or 10. One or both of the rings is/are aromatic. The term "fused bicyclic carbocycle" also encompasses divalent groups derived from a bicyclic ring system. Representative monocyclic carbocycles include divalent groups derived from dihydronaphthalene, tetrahydronaphthalene, tetrahydrobenzoannulene, and the like.

The term "non-aromatic heterocycle" means a non-aromatic monocyclic system containing 3 to 10 atoms (e.g., 3, 4, 5, 6, 7, 8, 9, 10, 3-4, 3-5, 3-6, 3-7, 3-8, 3-9, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, 9-10), preferably 4 to about 7 carbon atoms, in which one or more of the atoms in the ring system is/are element(s) other than carbon, for example, nitrogen, oxygen, or sulfur. The term "non-aromatic heterocycle" also includes divalent groups derived from a non-aromatic heterocyclic rings. Representative non-aromatic heterocycle groups include divalent groups derived from pyrrolidine, 2-oxopyrrolidine, piperidine, 2-oxopiperidine, azepane, 2-oxoazepane, 2-oxooxazolidine, morpholine, 3-oxomorpholine, thiomorpholine, 1,1-dioxothiomorpholine, piperazine, tetrahydro-2H-oxazine, and the like.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "halogen" means fluorine, chlorine, bromine, or iodine.

A "peptide" as used herein is any oligomer of two or more natural or non-natural amino acids, including alpha amino acids, beta amino acids, gamma amino acids, L-amino acids, D-amino acids, and combinations thereof. In preferred embodiments, the peptide is ~2 to ~30 (e.g., ~2 to ~5, ~2 to ~10, ~5 to ~10, ~2 to ~17, ~5 to ~17, ~10 to ~17, ~5 to ~30, ~10 to ~30, or ~18 to ~30) amino acids in length. Typically, the peptide is 10-17 amino acids in length. In at least one embodiment, the peptide contains a mixture of alpha and beta amino acids, preferably in the pattern α3/β1.

An amino acid as used herein can be any natural or non-natural amino acid, including alpha amino acids, beta amino acids, gamma amino acids, L-amino acids, and D-amino acids. Amino acid side chains can be any amino acid side chain of such an amino acid.

An amino acid according to the present invention also includes an analogue of a natural or non-natural amino acid. An amino acid analogue is an alpha amino acid with a nonnatural side chain consisting of alkyl, cycloalkyl, aryl, cycloaryl, alkenyl, or alkynyl; or a beta3-amino acid with a side chain consisting of alkyl, cycloalkyl, aryl, cycloaryl, alkenyl, or alkynyl. As used herein, an amino acid analogue also refers to a natural or nonnatural amino acid that may be substituted for an amino acid residue in the coiled-coil without loss of function relative to the native coiled-coil sequence. Suitable amino acid analogues/substitutions include the natural amino acid substitutions described in Betts & Russell, "Amino Acid Properties and Consequences of Substitutions," in Bioinformatics for Geneticists 289-316 (Michael R. Barnes & Ian C. Gray eds. 2003), which is hereby incorporated by reference in its entirety, as well as the nonnatural substitutions set forth below (all available from Sigma Aldrich) and the nonnatural substitutions described in Gfeller et al., "SwissSidechain: A Molecular and Structural Database of Non-Natural Sidechains," *Nucl. Acids Res.* 41:D327-D332 (2013), which is hereby incorporated by reference in its entirety. As will be understood by the skilled artisan, analogues in the table below that are listed as having a protecting group at the N- and/or C-terminal would be deprotected during conjugation to an adjacent residue.

| Amino Acid | Exemplary Non-Natural Analogue(s) |
|---|---|
| Alanine | N-Acetyl-3-(3,4-dimethoxyphenyl)-D-alanine, H-β-Ala-β-naphthalene, Albizziin, (R)-(+)-α-Allylalanine, (S)-(−)-α-Allylalanine, D-2-Aminobutyric acid, L-2-Aminobutyric acid, DL-2-Aminobutyric acid, DL-2-Aminobutyric acid, 2-Aminoisobutyric acid, α-Aminoisobutyric acid, (S)-(+)-2-Amino-4-phenylbutyric acid ethyl ester, Benzyl α-aminoisobutyrate, Boc-Abu-OH, Boc-D-Abu-OH, Boc-Aib-OH, Boc-β-(9-anthryl)-Ala-OH, Boc-β-(3-benzothienyl)-Ala-OH, Boc-β-(3-benzothienyl)-D-Ala-OH, Boc-Cha-OH, Boc-Cha-OMe, Boc-β-(2-furyl)-Ala-OH, Boc-β-(2-furyl)-D-Ala-OH, Boc-β-iodo-Ala-OBzl, Boc-β-iodo-D-Ala-OBzl, Boc-3-iodo-D-Ala-OMe, Boc-β-iodo-Ala-OMe, Boc-β-iodo-Ala-OMe, Boc-1-Nal-OH, Boc-D-1-Nal-OH, Boc-D-1-Nal-OH, Boc-2-Nal-OH, Boc-D-2-Nal-OH, (R)-Boc-3-(2-naphthyl)-β-Ala-OH, (S)-Boc-3-(2-naphthyl)-β-Ala-OH, Boc-β-phenyl-Phe-OH, Boc-3-(2-pyridyl)-Ala-OH, Boc-3-(3-pyridyl)-Ala-OH, Boc-3-(3-pyridyl)-D-Ala-OH, (S)-Boc-3-(3-pyridyl)-β-Ala-OH, Boc-3-(4-pyridyl)-Ala-OH, Boc-3-(4-pyridyl)-D-Ala-OH, Boc-β-(2-quinolyl)-Ala-OH, Boc-3-(2-quinolyl)-DL-Ala-OH, Boc-3-(3-quinolyl)-DL-Ala-OH, Boc-3-(2-quinoxalyl)-DL-Ala-OH, Boc-β-(4-thiazolyl)-Ala-OH, Boc-β-(2-thienyl)-Ala-OH, Boc-β-(2-thienyl)-D-Ala-OH, Boc-β-(3-thienyl)-Ala-OH, Boc-β-(3-thienyl)-D-Ala-OH, 3-Chloro-D-alanine methyl ester, N-[(4-Chlorophenyl)sulfonyl]-β-alanine, 3-Cyclohexyl-D-alanine, 3-Cyclopentyl-DL-alanine, (−)-3-(3,4-Dihydroxyphenyl)-2-methyl-L-alanine, 3,3-Diphenyl-D-alanine, 3,3-Diphenyl-L-alanine, N-[(S)-(+)-1-(Ethoxycarbonyl)-3-phenylpropyl]-L-alanine, N-[1-(S)-(+)-Ethoxycarbonyl-3-phenylpropyl]-L-alanyl carboxyanhydride, N-(3-fluorobenzyl)alanine, Fmoc-Abu-OH, Fmoc-3-(9-anthryl)-Ala-OH, Fmoc-β-azido-Ala-OH, Fmoc—(S)-2-(4-azidobutane)Ala-OH, Fmoc—(S)-2-(2-azidoethane)Ala-OH, Fmoc—(S)-2-(6-azidohexane)Ala-OH, Fmoc—(S)-2-(5-azidopentane)Ala-OH, Fmoc-Cha-OH, Fmoc-3-cyclopentyl-DL-Ala-OH, Fmoc-β-(2-furyl)-Ala-OH, Fmoc-β-(2-furyl)-D-Ala-OH, Fmoc-α-Me-Ala-OH, Fmoc-1-Nal-OH, Fmoc-D-1-Nal-OH, Fmoc-2-Nal-OH, Fmoc-D-2-Nal-OH, Fmoc—(S)-2-(7-octenyl)Ala-OH, Fmoc—(R)-2-(pentenyl)Ala-OH, Fmoc—(S)-2-(4-pentenyl)Ala-OH, Fmoc-β-phenyl-Phe-OH, Fmoc—(R)-2-(2-propenyl)Ala-OH, Fmoc-β-(2-pyridyl)-Ala-OH ≥97.0% (HPLC), Fmoc-β-(2-pyridyl)-D-Ala-OH, Fmoc-β-(3-pyridyl)-Ala-OH, Fmoc-β-(3-pyridyl)-D-Ala-OH, Fmoc-β-(4-pyridyl)-Ala-OH, Fmoc-β-(4-pyridyl)-D-Ala-OH, Fmoc-3-(2-quinolyl)-DL-Ala-OH, Fmoc-β-(4-thiazolyl)-Ala-OH, Fmoc-β-(2-thienyl)-Ala-OH, Fmoc-β-(3-thienyl)-Ala-OH, Fmoc-β-(3-thienyl)-D-Ala-OH, N-(3-Indolylacetyl)-L-alanine, Methyl (RS)-2-(aminomethyl)-3-phenylpropionate, 3-(2-Oxo-1,2-dihydro-4-quinolinyl)alanine, 3-(1-Pyrazolyl)-L-alanine, 3-(2-Pyridyl)-D-alanine, 3-(2-Pyridyl)-L-alanine, 3-(3-Pyridyl)-L-alanine, 3-(4-Pyridyl)-D-alanine, 3-(4-Pyridyl)-L-alanine, 3-(2-Quinolyl)-DL-alanine, 3-(4-Quinolyl)-DL-alanine, D-styrylalanine, L-styrylalanine, 3-(2-Thienyl)-L-alanine, 3-(2-Thienyl)-DL-alanine, 3-(2-Thienyl)-DL-alanine, 3,3,3-Trifluoro-DL-alanine, 3-Ureidopropionic acid, Z-Aib-OH, Z-Cha-OH, Z-Dehydro-Ala-OMe, Z-dehydro-Ala-OH, Z-D-2-Nal-OH. |
| Isoleucine | Boc-allo-Ile-OH, D-allo-Isoleucine, D-allo-Isoleucine, DL-allo-Isoleucine. |
| Leucine | Homoleucine, N-[(2S,3R)-3-Amino-2-hydroxy-4-phenylbutyryl]-L-leucine, Boc-4,5-dehydro-Leu-OH, Boc-Ile-Osu, Cycloleucine, N-(3,5-Dinitrobenzoyl)-DL-leucine, Fmoc-tBu-Gly-OH, N-Formyl-Leu-OH, N-(3-lndolylacetyl)-L-isoleucine, D-tert-Leucine, D-tert-Leucine, L-tert-Leucine, L-tert-Leucine, DL-tert-Leucine, DL-tert-Leucine, L-tert-Leucine methyl ester, 5,5,5-Trifluoro-DL-leucine. |
| Valine | 3-Fluoro-DL-valine, 4,4,4,4',4',4'-Hexafluoro-DL-valine, (R)-(+)-α-Methylvaline, (S)-(−)-α-Methylvaline. |
| Phenylalanine | Boc-Homophenylalanine-OH, Boc-D-Homophenylalanine-OH, Fmoc-Homophenylalanine-OH, Fmoc-D-Homophenylalanine-OH, Z-Homophenylalanine-OH, Boc-(R)-β52-homophenylalanine, DL-homophenylalanine methyl ester, D-Homophenylalanine, L-Homophenylalanine, DL-Homophenylalanine, D-Homophenylalanine ethyl ester, Ac-p-bromo-DL-Phe-OH, (S)-N-acetyl-4-bromophenylalanine, N-Acetyl-2-fluoro-DL-phenylalanine, N-Acetyl-4-fluoro-DL-phenylalanine, 4-Amino-L-phenylalanine, Boc-4-azido-Phe-OH, Boc-Bpa-OH, Boc-D-Bpa-OH, Boc-4-tert-butyl-Phe-OH, Boc-4-tert-butyl-D-Phe-OH, Boc-4-(Fmoc-amino)-L-phenylalanine, rac-Boc-β2-homophenylalanine, (S)-Boc-4-methoxy-β-Phe-OH, Boc-2-nitro-L-phenylalanine, Boc-pentafluoro-D-phenylalanine, Boc-pentafluoro-L-phenylalanine, Boc-Phe(4-Br)—OH, Boc-D-Phe(4-Br)—OH, Boc-Phe(2-CF3)—OH, Boc-D-Phe(2-CF3)—OH, Boc-Phe(3-CF3)—OH, Boc-D-Phe(3-CF3)—OH, Boc-Phe(4-CF3)—OH, Boc-D-Phe(4-CF3)—OH, Boc-Phe(2-Cl)—OH, Boc-D-Phe(2-Cl)—OH, Boc-Phe(2,4-Cl2)—OH, Boc-D-Phe(2,4-Cl2)—OH, Boc-D-Phe(3-Cl)—OH, Boc-Phe(3,4-Cl2)—OH, Boc-D-Phe(3,4-Cl2)—OH, Boc-Phe(4-Cl)—OH, Boc-D-Phe(4-Cl)—OH, Boc-Phe(2-CN)—OH, Boc-D-Phe(2-CN)—OH, Boc-Phe(3-CN)—OH, Boc-D-Phe(3-CN)—OH, Boc-Phe(4-CN)—OH, Boc-D-Phe(4-CN)—OH, Boc-Phe(2-Me)—OH, Boc-D-Phe(2-Me)—OH, Boc-Phe(3-Me)—OH, Boc-D-Phe(3-Me)—OH, Boc-Phe(4-Me)—OH, Boc-Phe(4-NH2)—OH, Boc-Phe(4-NO2)—OH, Boc-D-Phe(4-NO2)—OH, Boc-Phe(2-F)—OH, Boc-D-Phe(2-F)—OH, Boc-Phe(3-F)—OH, Boc-D-Phe(3-F)—OH, Boc-Phe(3,4-F2)—OH, Boc-D-Phe(3,4-F2)—OH, Boc-Phe(3,5-F2)—OH, Boc-Phe(4-F)—OH, Boc-D-Phe(4-F)—OH, Boc-Phe(4-I)—OH, Boc-D-Phe(4-I)—OH, Boc-D-3,4,5-trifluorophenylalanine, 4-Borono-D-phenylalanine, 4-Borono-L-phenylalanine, 4-Borono-DL-phenylalanine, p-Bromo-DL-phenylalanine, 4-Bromo-L-phenylalanine, N-(tert-Butoxycarbonyl)-β-phenyl-D-phenylalanine, 4-Chloro-L-phenylalanine, DL-2,3-Difluorophenylalanine, DL-3,5-Difluorophenylalanine, 3,4-Dihydroxy-L-phenylalanine, 3-(3,4-Dimethoxyphenyl)-L-alanine, N-[(9H-Fluoren-9-ylmethoxy)carbonyl]-2-methoxy-L-phenylalanine, o-Fluoro-DL-phenylalanine, m-Fluoro-L-phenylalanine, m-Fluoro-DL-phenylalanine, p-Fluoro-D-phenylalanine, p-Fluoro-D-phenylalanine, p-Fluoro-L-phenylalanine, p-Fluoro-DL-phenylalanine, 4-Fluoro-D-phenylalanine, 2-fluoro-L-phenylalanine methyl ester, H-p-fluoro-DL-Phe-OMe, Fmoc-Bpa-OH, Fmoc-D-Bpa-OH, Fmoc-D-3-bromophenylalanine, Fmoc-4-bromophenylalanine, L-Fmoc-β-(6-chloro-4-pyridinyl)alanine, Fmoc-D-3,5-difluorophenylalanine, L-Fmoc-3-fluorophenylalanine, L-Fmoc-4-fluorophenylalanine, L-Fmoc-β-(1H-5-indolyl)alanine, |

| Amino Acid | Exemplary Non-Natural Analogue(s) |
| --- | --- |
| | Fmoc-2-nitro-L-phenylalanine, Fmoc-pentafluoro-L-phenylalanine, Fmoc-Phe(4-Boc2-guanidino)—OH, Fmoc-Phe(3-Br)—OH, Fmoc-Phe(4-Br)—OH, Fmoc-Phe(2-CF3)—OH, Fmoc-D-Phe(2-CF3)—OH, Fmoc-Phe(3-CF3)—OH, Fmoc-D-Phe(3-CF3)—OH, Fmoc-Phe(4-CF3)—OH, Fmoc-D-Phe(4-CF3)—OH, Fmoc-Phe(2-Cl)—OH, Fmoc-D-Phe(2-Cl)—OH, Fmoc-Phe(2,4-Cl2)—OH, Fmoc-D-Phe(2,4-Cl2)—OH, Fmoc-Phe(3,4-Cl2)—OH, Fmoc-D-Phe(3,4-Cl2)—OH, Fmoc-Phe(4-Cl)—OH, Fmoc-D-Phe(4-Cl)—OH, Fmoc-Phe(2-CN)—OH, Fmoc-D-Phe(2-CN)—OH, Fmoc-Phe(3-CN)—OH, Fmoc-D-Phe(3-CN)—OH, Fmoc-Phe(4-CN)—OH, Fmoc-Phe(2-Me)—OH, Fmoc-Phe(3-Me)—OH, Fmoc-D-Phe(3-Me)—OH, Fmoc-Phe(4-NO2)—OH, Fmoc-D-Phe(4-NO2)—OH, Fmoc-D-Phe(2-F)—OH, Fmoc-Phe(3-F)—OH, Fmoc-D-Phe(3-F)—OH, Fmoc-Phe(3,4-F2)—OH, Fmoc-Phe(3,5-F2)—OH, Fmoc-Phe(4-F)—OH, Fmoc-D-Phe(4-F)—OH, Fmoc-Phe(4-I)—OH, Fmoc-D-Phe(4-I)—OH, Fmoc-4-(phosphonomethyl)-Phe-OH, L-Fmoc-4-trifluoromethylphenylalanine, Fmoc-3,4,5-trifluoro-D-phenylalanine, Fmoc-L-3,4,5-trifluorophenylalanine, 6-Hydroxy-DL-DOPA, 4-(Hydroxymethyl)-D-phenylalanine, N-(3-Indolylacetyl)-L-phenylalanine, p-Iodo-D-phenylalanine, 4-Iodo-L-phenylalanine, α-Methyl-D-phenylalanine, α-Methyl-L-phenylalanine, α-Methyl-DL-phenylalanine, α-Methyl-DL-phenylalanine methyl ester, 4-Nitro-D-phenylalanine, 4-Nitro-L-phenylalanine, 4-Nitro-DL-phenylalanine, (S)-(+)-4-Nitrophenylalanine methyl ester, 2-(Trifluoromethyl)-D-phenylalanine, 2-(Trifluoromethyl)-L-phenylalanine, 3-(Trifluoromethyl)-D-phenylalanine, 3-(Trifluoromethyl)-L-phenylalanine, 4-(Trifluoromethyl)-D-phenylalanine, 3,3',5-Triiodo-L-thyronine, Z-L-Phe chloromethyl ketone. |
| Tryptophan | 5-Fluoro-L-tryptophan, 5-Fluoro-DL-tryptophan, 5-Hydroxy-L-tryptophan, 5-Methoxy-DL-tryptophan, 5-Methyl-DL-tryptophan tryptophan analog, H-Tpi-Ome. |
| Tyrosine | 3-Amino-L-tyrosine, Boc-3-chloro-D-Tyr-OH, Boc-Tyr(3,5-I2)-Osu, 3-Chloro-L-tyrosine, Fmoc-Tyr(3-NO2)—OH, Fmoc-Tyr(3,5-I2)—OH, α-Methyl-DL-tyrosine, 3-Nitro-L-tyrosine, 3-Nitro-L-tyrosine ethyl ester, 3-Nitro-L-tyrosine ethyl ester, DL-o-Tyrosine. |
| Asparagine | Boc-Asn(Xan)-OH, Nα-Boc-Nβ-xanthenyl-L-asparagine. |
| Cysteine | Homocysteine, DL-Homocysteine, L-Homocysteine thiolactone, L-Homocysteine thiolactone, L-Homocystine, BOC-CYS(ME)-OH, L-Cysteic acid, L-Cysteinesulfinic acid, D-Ethionine, Fmoc-Cys(Boc-methyl)-OH, Seleno-L-cystine, S-(2-Thiazolyl)-L-cysteine, S-(4-Tolyl)-L-cysteine. |
| Glutamine | Boc-Cit-OH, D-Citrulline, Fmoc-Cit-OH, Thio-L-citrulline. |
| Serine | Fmoc-Homoser(Trt)-OH, Fmoc-D-Homoser(Trt)-OH, D-Homoserine, L-3-Homoserine, N-Trityl-L-homoserine, N-Benzoyl-(2R,3S)-3-phenylisoserine, D-Cycloserine, Fmoc-Gly-Val-OH, Fmoc-Ser[GalNAc(Ac)3-α-D]-OH, L-Isoserine, DL-Isoserine, DL-3-Phenylserine, N-Z-L-Homoserine lactone. |
| Threonine | Fmoc-Thr[GalNAc(Ac)3-α-D]-OH, L-allo-Threonine, D-Thyroxine. |
| Aspartic acid | (S)-(−)-4-tert-Butyl hydrogen 2-azidosuccinate, N-Z-L-aspartic anhydride. |
| Glutamic acid | (S)-5-tert-Butyl hydrogen 2-azidoglutarate, γ-Carboxy-DL-glutamic acid, 4-Fluoro-DL-glutamic acid, (4S)-4-(4-Trifluoromethyl-benzyl)-L-glutamic acid. |
| Arginine | L-Homoarginine hydrochloride unnatural arginine analog, L-2-Amino-3-guanidinopropionic acid, L-2-Amino-3-guanidinopropionic acid hydrochloride, 4-Guanidinobutyric acid, 3-Guanidinopropionic acid. |
| Histidine | N-Boc-3-(3-methyl-4-nitrobenzyl)-L-histidine methyl ester. |
| Lysine | (S)-(−)-1-[N-(1-Ethoxycarbonyl-3-phenylpropyl)-N-trifluoroacetyl]-L-lysine, Fmoc-β-Lys(Boc)-OH, Fmoc-Lys(palmitoyl)-OH, DL-5-Hydroxylysine, (5R)-5-Hydroxy-L-lysine. |
| Glycine | Fmoc-allyl-Gly-OH, Fmoc-propargyl-Gly-OH, (±)-Boc-α-phosphonoglycine trimethyl ester, Fmoc-D-propargyl-Gly-OH, Fmoc-D-allyl-Gly-OH, Boc-D-allyl-Gly-OH, Boc-allyl-Gly-OH, Boc-D-Chg-OH, Boc-Chg-OH, N-Fmoc-iminodiacetic acid, Di-tert-butyl-iminodicarboxylate, N-Boc-iminodiacetic acid, N-(2-Hydroxyethyl)iminodiacetic acid, Iminodiacetic acid, Fmoc-N-(1-Boc-4-piperidyl)glycine, N-Lauroylsarcosine, D-α-Cyclohexylglycine, L-α-Neopentylglycine, L-C-Propargylglycine, Sarcosine, Z-D-Chg-OH, (±)-Z-α-Phosphonoglycine trimethyl ester, Sarcosine, N-(Phosphonomethyl)glycine, Z-α-Phosphonoglycine trimethyl ester, N-[Bis(methylthio)methylene]glycine methyl ester, N-(2-Furoyl)glycine, N-(2-Furfurylideneacetyl)glycine methyl ester, N-(Chloroacetyl)glycine ethyl ester, Boc-(2-indanyl)-Gly-OH, Fmoc-(2-indanyl)-Gly-OH, Fmoc-N-(2-Boc-aminoethyl)-Gly-OH, Fmoc-N-(4-Boc-aminobutyl)-Gly-OH, Fmoc-N-(2,4-dimethoxybenzyl)-Gly-OH, Boc-D-cyclopropylglycine, Boc-(S)-2-thienylglycine, Boc-(R)-2-thienylglycine, Boc-(S)-3-thienylglycine, Boc-(R)-3-thienylglycine, Boc-L-cyclopropylglycine, L-α-Cyclopropylglycine, Boc-propargyl-Gly-OH, D-Allylglycine, (2S,3R,4S)-α-(Carboxycyclopropyl)glycine, D-Propargylglycine, N-Boc-2-(4-trifluoromethyl-phenyl)-DL-glycine, Boc-D-propargylglycine, (S)-(+)-2-chlorophenylglycine methyl ester, (R)-N-Boc-4-fluorophenylglycine, (S)-N-Boc-4-fluorophenylglycine, N-(2-fluorophenyl)-N-(methylsulfonyl) glycine, N-(4-fluorophenyl)-N-(methylsulfonyl)glycine, N-(2-chlorophenyl)-N-(methylsulfonyl)glycine, Ethyl acetamidocyanoacetate, N-(4-Hydroxyphenyl)glycine. |
| Proline | trans-1-Acetyl-4-hydroxy-L-proline, N-[3-(Acetylthio)-(2S)-methylpropionyl]-L-proline, (S)-α-Allyl-proline, Boc-(S)-α-allyl-Pro-OH, Boc-α-allyl-DL-Pro-OH, N-Boc-cis-4-azido-L-proline, Boc-(S)-α-benzyl-Pro-OH, Boc-α-(2-bromobenzyl)-DL-Pro-OH, Boc-α-(4-bromobenzyl)-DL-Pro-OH, Boc-α-(2-chlorobenzyl)-DL-Pro-OH, Boc-α-(3-chlorobenzyl)-DL-Pro-OH, Boc-4-(2,2-difluorocyclopropyl)-L-proline, Boc-α-(diphenylmethyl)-DL-Pro-OH, Boc-(R)-α-(4-fluorobenzyl)-Pro-OH, Boc-(S)-α-(4-fluorobenzyl)-Pro-OH, Boc-α-(4-fluorobenzyl)-DL-Pro-OH, N-Boc-cis-4-N-Fmoc-amino-L-proline, N-Boc-trans-4-N-Fmoc-amino-L-proline, N-Boc-cis-4-hydroxy-D-proline, N-Boc-cis-4-hydroxy-L-proline, N-Boc-trans-4-hydroxy-D-proline, N-Boc-cis-4-hydroxy-L-proline methyl ester, N-Boc-trans-4-hydroxy-L-proline methyl ester, N-Boc-4- |

| Amino Acid | Exemplary Non-Natural Analogue(s) |
|---|---|
| | hydroxy-D-pyrrolidine lactone, N-Boc-4-hydroxy-L-pyrrolidine lactone, Boc-Hyp(Bzl)-OH, Boc-Hyp-OH, Boc-α-Me-DL-Pro-OH, Boc-α-(4-methylbenzyl)-DL-Pro-OH, Boc-α-(1-naphthylmethyl)-DL-Pro-OH, N-Boc-2-piperidinecarboxylic acid, (R)-(+)-N-Boc-2-piperidinecarboxylic acid, Boc-Pip-OH, Boc-α-propyl-DL-Pro-OH, Boc-α-(2-propynyl)-L-proline, Boc-(R)-4-(2-propynyl)-L-proline, N-Boc-trans-4-(p-tosyloxy)-L-proline methyl ester, Boc-(R)-4-[2-(trifluoromethyl)benzyl]-L-proline, Boc-(R)-4-[4-(trifluoromethyl)benzyl]-L-proline, Boc-(R)-α-(4-trifluoromethylbenzyl)-Pro-OH, Boc-(S)-α-(4-trifluoromethylbenzyl)-Pro-OH, 3,4-Dehydro-L-proline, 3,4-Dehydro-DL-proline, Fmoc-Hyp-OH, Fmoc-Hyp(tBu)-OH, Fmoc-Pip-OH, Fmoc-D-Pip-OH, cis-3-Hydroxy-DL-proline, cis-4-Hydroxy-D-proline, cis-4-Hydroxy-L-proline collagen synthesis inhibitor, trans-4-Hydroxy-D-proline, trans-4-Hydroxy-L-proline, trans-4-Hydroxy-L-proline, L-4-Hydroxy-proline benzyl ester hydrochloride, L-4-Hydroxyproline methyl ester, (S)-(+)-Methyl indoline-2-carboxylate, α-Methyl-L-proline, (S)-1-Z-4-oxopyrrolidine-2-carboxylic acid, L-Pipecolic acid, L-Pipecolic acid Proline homolog, Pipecolinic acid, D-Pipecolinic acid, Z-Hyp-OH. |

Non-limiting examples of substitutions for certain amino acid residues include, without limitation, those shown below.

| Amino Acid | Examplary Substition |
|---|---|
| Serine | Threonine |
| Tyrosine | Phenylalanine |
| Aspartic acid | Phosphoserine |
| Glutamic acid | Phosphoserine |
| Lysine | arginine, ornithine, diaminoproprionic acid, diaminobutyric acid |
| Arginine | Lysine |

The amino acids according to the present invention may also be optionally modified. Modifications include, for example, phosphorylation (e.g., phosphoserine, phosphotyrosine, phosphothreonine), halogenation (esp. with 3-9 halogens) (preferably with fluorine, e.g., hexafluoroleucine, hexafluorovaline), methylation (e.g., aspartic acid methyl ester, glutamic acid methyl ester, methyllysine, dimethyllysine, trimethyllysine, dimethylarginine, methylarginine, methyltryptophan), and acetylation (e.g., acetyllysine).

As will be apparent to the skilled artisan, the linkers in accordance with the present invention create a covalent bridge between an amino acid residue/analogue on one coil of the coiled-coil structure and an amino acid residue/analogue on the other coil in the coiled-coil structure. As will be apparent to the skilled artisan, virtually any covalent linker can be used, provided the appropriate spatial distance between the two linked residues is maintained. The spatial distance as used herein refers to the distance of atoms in the coiled-coil structure when in its solid state, as determined using a static molecular modeling program (e.g., UCSF Chimera) and/or by evaluating the crystal structure of the macrocycle. For linkers between g or e and g' or e' residues (Linker A, Linker D, Linker E, Linker H, linkers for $g_0$-$g'_2$, $g_1$-$g'_1$, $g_2$-$g'_0$, $e_1$-$e'_3$, $e_2$-$e'_2$, and $e_1$-$e'_1$ in Formula I, and linkers for $g_0$-$e'_1$, $g_1$-$e'_2$, $g_2$-$e'_3$, $e_1$-$g'_0$, $e_2$-$g'_1$, and $e_3$-$g'_2$ in Formula II) the appropriate spatial distance is 10-25 Å (10-11, 10-12, 10-13, 10-14, 10-15, 10-16, 10-17, 10-18, 10-19, 10-20, 10-21, 10-22, 10-23, 10-24, 11-12, 11-13, 11-14, 11-15, 11-16, 11-17, 11-18, 11-19, 11-20, 11-21, 11-22, 11-23, 11-24, 11-25, 12-13, 12-14, 12-15, 12-16, 12-17, 12-18, 12-19, 12-20, 12-21, 12-22, 12-23, 12-24, 12-25, 13-14, 13-15, 13-16, 13-17, 13-18, 13-19, 13-20, 13-21, 13-22, 13-23, 13-24, 13-25, 14-15, 14-16, 14-17, 14-18, 14-19, 14-20, 14-21, 14-22, 14-23, 14-24, 14-25, 15-16, 15-17, 15-18, 15-19, 15-20, 15-21, 15-22, 15-23, 15-24, 15-25, 16-17, 16-18, 16-19, 16-20, 16-21, 16-22, 16-23, 16-24, 16-25, 17-18, 17-19, 17-20, 17-21, 17-22, 17-23, 17-24, 17-25, 18-19, 18-20, 18-21, 18-22, 18-23, 18-24, 18-25, 19-20, 19-21, 19-22, 19-23, 19-24, 19-25, 20-21, 20-22, 20-23, 20-24, 20-25, 21-22, 21-23, 21-24, 21-25, 22-23, 22-24, 22-25, 23-24, 23-25, or 24-25 Å). In at least one embodiment, the spatial distance is 11-17 Å. In at least one embodiment, the spatial distance is 15-20 Å. For linkers between a or d and a' or d' residues (Linker B, Linker C, Linker F, Linker G, linkers for $a_1$-d', $a_2$-$d'_2$, $a_3$-d', $d_1$-$a'_3$, $d_2$-$a'_2$, and $d_3$-$a'_1$ in Formula I, and linkers for $d_1$-$d'_1$, $d_2$-$d'_2$, $d_3$-$d'_3$, $a_1$-$a'_1$, $a_2$-$a'_2$, and $a_3$-$a'_3$ in Formula II) the appropriate spatial distance is 5-15 Å (5-6, 5-7, 5-8, 5-9, 5-10, 5-11, 5-12, 5-13, 5-14, 6-7, 6-8, 6-9, 6-10, 6-11, 6-12, 6-13, 6-14, 6-15, 7-8, 7-9, 7-10, 7-11, 7-12, 7-13, 7-14, 7-15, 8-9, 8-10, 8-11, 8-12, 8-13, 8-14, 8-15, 9-10, 9-11, 9-12, 9-13, 9-14, 9-15, 10-11, 10-12, 10-13, 10-14, 10-15, 11-12, 11-13, 11-14, 11-15, 12-13, 12-14, 12-15, 13-14, 13-15, or 14-15 Å). In at least one embodiment, the spatial distance is 6-8 Å. In at least one embodiment, the spatial distance is 5-10 Å. Methods of modifying amino acid residues to facilitate attachment of a suitable linker (including replacement of an amino acid side chain with the linker) will also be apparent to the skilled artisan.

In a preferred embodiment, the two amino acids/analogues may be covalently connected to each other using alkylene, alkenylene, arylene, heteroarylene, ethers, thioethers, amides, maleimides, esters, disulfides, diselenides, —O—, —S—, —Se—, and any combination thereof. As will be apparent to the skilled artisan, the linkers may be symmetrical or asymmetrical.

Suitable examples of linkers between g or e and g' or e' residues (Linker A, Linker D, Linker E, Linker H, linkers for $g_0$-$g'_2$, $g_1$-$g'_1$, $g_2$-$g'_0$, $e_1$-$e'_3$, $e_2$-$e'_2$, and $e_3$-$e'_1$ in Formula I, and linkers for $g_0$-$e'_1$, $g_1$-$e'_2$, $g_2$-$e'_3$, $e_1$-$g'_0$, $e_2$-$g'_1$, and $e_3$-$g'_2$ in Formula II) include, without limitation, those having the formula —$Z_n$—, wherein n is a number from 1 to 25 (1, 2, 3, 4, 5, 6, 7, 8, 9, 10, 11, 12, 13, 14, 15, 16, 17, 18, 19, 20, 21, 22, 23, 24, 25, or any range within 1 and 25, including, e.g., 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-21, 2-22, 2-23, 2-24, 2-25, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 4-5, 4-6, 4-7, 4-8, 4-9, 4-10, 4-11, 4-12, 4-13, 4-14, 4-15, 4-16, 4-17, 4-18, 4-19, 4-20, 4-21, 4-22, 4-23, 4-24, 4-25, 5-6, 5-7, 5-8, 5-9, 5-10, 5-11, 5-12, 5-13, 5-14, 5-15, 5-16, 5-17, 5-18, 5-19, 5-20, 5-21, 5-22, 5-23, 5-24, 5-25, 6-10, 6-15, 6-20, 6-25, 7-10, 7-15, 7-20, 7-25, 8-10, 8-15, 8-20, 8-25, 9-10, 9-15, 9-20, 9-25, 10-15, 10-20, 10-25, 11-15, 11-20, 11-25, 12-15, 12-20, 12-25, 13-15, 13-20, 13-25, 14-15, 14-20, 14-25, 15-20, 15-25, 16-20, 16-25, 17-20, 17-25, 18-20, 18-25, 19-20, 19-25, 20-25, 21-25, 22-25, 23-25, 24-25; in at least one embodiment, n is 5-25) and each Z is independently selected at each occurrence thereof from the group consisting of alkylene, alkenylene, arylene, heteroarylene (esp. triazole-diyl, thiazole-diyl, oxazole-diyl), ethers, amides, esters, maleimides, thioethers, O, S, and Se. Some preferred examples of symmetrical linkers include, without limitation,

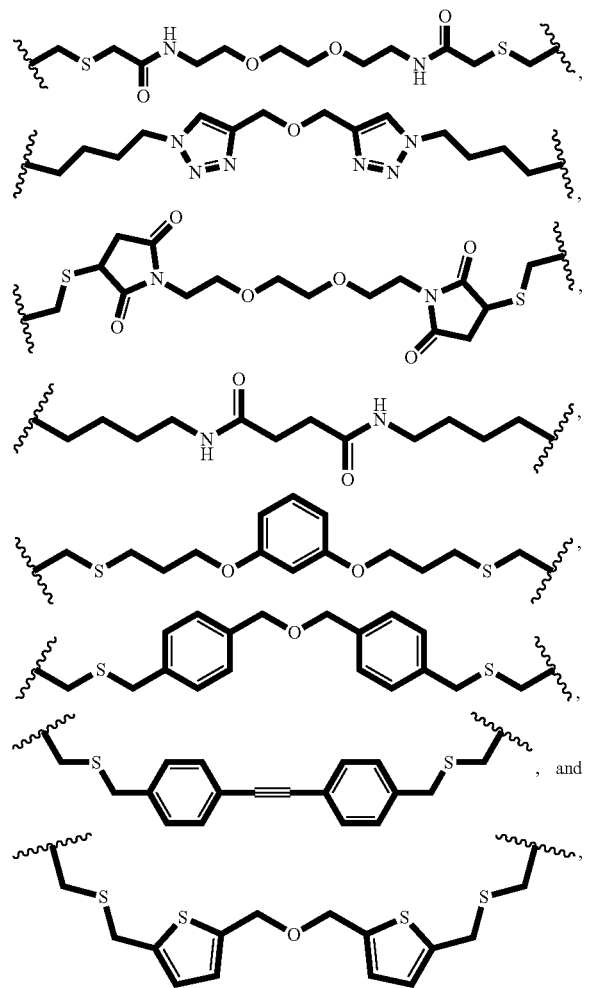

wherein each

marks a connection point to the Cα carbon in a linked residue/analogue. In at least one embodiment, the linker between g or e and g' or e' residues (Linker A, Linker D, Linker E, Linker H, linkers for $g_0$-$g'_2$, $g_1$-$g'_1$, $g_2$-$g'_0$, $e_1$-$e'_3$, $e_2$-$e'_2$, and $e_3$-$e'_1$ in Formula I, and linkers for $g_0$-$e'_1$, $g_1$-$e'_2$, $g_2$-$e'_3$, $e_1$-$g'_0$, $e_2$-$g'_1$, and $e_3$-$g'_2$ in Formula II) has the following formula

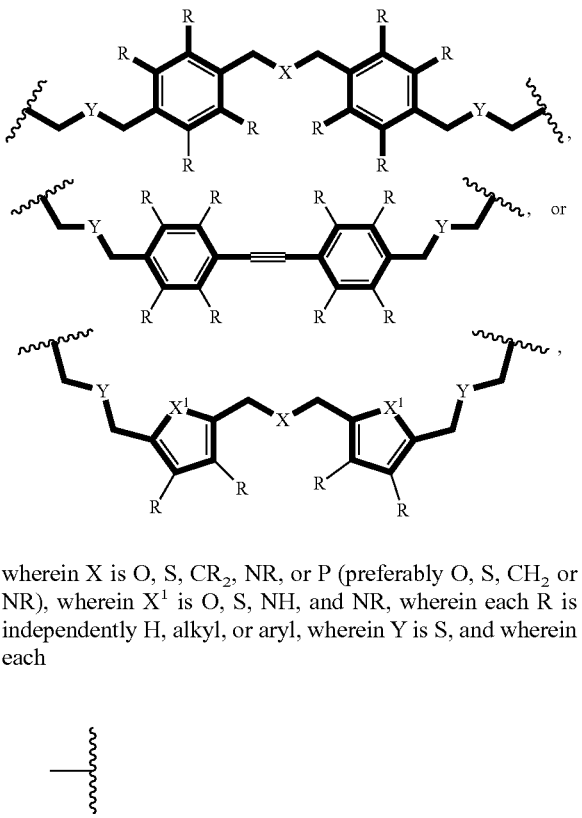

wherein X is O, S, $CR_2$, NR, or P (preferably O, S, $CH_2$ or NR), wherein $X^1$ is O, S, NH, and NR, wherein each R is independently H, alkyl, or aryl, wherein Y is S, and wherein each

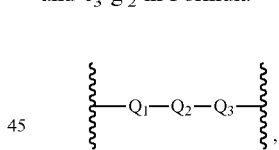

marks connection point to the Cα carbon in a linked residue/analogue.

In at least one embodiment, the linker between g or e and g' or e' residues (Linker A, Linker D, Linker E, Linker H, linkers for $g_0$-$g'_2$, $g_1$-$g'_1$, $g_2$-$g'_0$, $e_1$-$e'_3$, $e_2$-$e'_2$, and $e_3$-$e'_1$ in Formula I, and linkers for $g_0$-$e'_1$, $g_1$-$e'_2$, $g_2$-$e_3$, $e_1$-$g'_0$, $e_2$-$g'_1$, and $e_3$-$g'_2$ in Formula $$\{-Q_1-Q_2-Q_3-\}$$

wherein:
Q$_1$ is a $C_{1-8}$ alkylene or a moiety of formula ($C_{1-8}$ alkylene-X—$C_{0-8}$ alkylene)$_n$;
Q$_2$ is $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, a moiety of formula $C_{1-8}$ alkylene-X—$C_{1-8}$ alkylene, or a moiety of formula -Q$_4$-Q$_5$-Q$_6$-; wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;
Q$_3$ is a $C_{1-8}$ alkylene or a moiety of formula ($C_{1-8}$ alkylene-X—$C_{0-8}$ alkylene)$_n$;
Q$_4$ is selected from the group consisting of O, —C(O)—NR—, —NR—C(O)—, —C(O)—O—, —O—C(O)—, —C(O)—S—, —S—C(O)—, $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;

$Q_5$ is selected from the group consisting of —C(O)—NR—, —NR—C(O)—, —C(O)—O—, —O—C(O)—, —C(O)—S—, —S—C(O)—, $C_{1-8}$ alkylene, $C_{2-8}$ alkynylene, monocyclic carbocycle, fused bicyclic carbocycle, non-aromatic heterocycle, arylene, and heteroarylene, or is a moiety of formula $C_{1-8}$ alkylene-(X—$C_{1-8}$ alkylene)$_n$, wherein each of $C_{1-8}$ alkylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;

$Q_6$ is selected from the group consisting of O, —C(O)—NR—, —NR—C(O)—, —C(O)—O—, —O—C(O)—, —C(O)—S—, —S—C(O)—, $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;

each X is selected from the group consisting of O, S, CR$_2$, NR, P, $C_{2-8}$ alkynylene, arylene, and heteroarylene (preferably O, S, CH$_2$, NR, or CR≡CR);

each R is independently H, $C_{1-8}$ alkyl, or aryl;

n is 1 to 10; and each

marks a connection point to the Cα carbon in a linked residue/analogue.

In at least one embodiment, the linker between g or e and g' or e' residues (Linker A, Linker D, Linker E, Linker H, linkers for $g_0$-$g'_2$, $g_1$-$g'_1$, $g_2$-$g'_0$, $e_1$-$e'_3$, $e_2$-$e'_2$, and $e_3$-$e'_1$ in Formula I, and linkers for $g_0$-$e'_1$, $g_1$-$e'_2$, $g_2$-$e'_3$, $e_1$-$g'_0$, $e_2$-$g'_1$, and $e_3$-$g'_2$ in Formula II) has the following formula

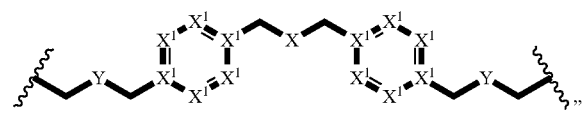

-continued

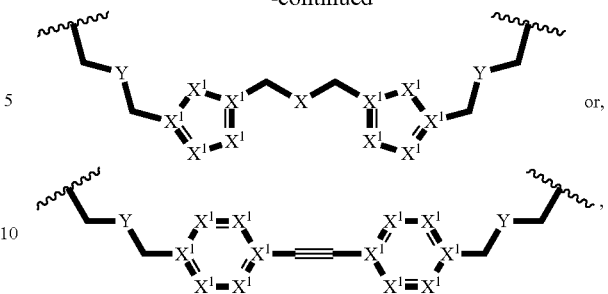

wherein X is O, S, CR$_2$, NR, or P (preferably O, S, CH$_2$ or NR), wherein X$^1$ is O, S, C, CR, N, NH, and NR, wherein each R is independently H, alkyl, or aryl, wherein Y is S, and wherein each

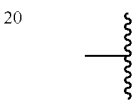

marks a connection point to the Cα carbon in a linked residue/analogue.

Preferred examples for linkers between a or d and a' or d' residues (Linker B, Linker C, Linker F, Linker G, linkers for $a_1$-$d'_3$, $a_2$-$d'_2$, $a_3$-$d'_1$, $d_1$-$a'_3$, $d_2$-$a'_2$, and $d_3$-$a'_1$ in Formula I, and linkers for $d_1$-$d'_1$, $d_2$-$d'_2$, $d_3$-$d'_3$, $a_1$-$a'_1$, $a_2$-$a'_2$, and $a_3$-$a'_3$ in Formula II) include disulfides, diselenides, $C_{1-8}$ alkylene, $C_{2-8}$ alkenylene, arylene, and heteroarylene (esp. triazole-diyl and thiazole-diyl). In a preferred embodiment, the linkers between a or d and a' or d' residues (Linker B, Linker C, Linker F, Linker G, linkers for $a_1$-$d'_3$, $a_2$-$d'_2$, $a_3$-$d'$, $d_1$-$a'_3$, $d_2$-$a'_2$, and $d_3$-$a'_1$ in Formula I, and linkers for $d_1$-$d'_1$, $d_2$-$d'_2$, $d_3$-$d'_3$, $a_1$-$a'_1$, $a_2$-$a'_2$, and $a_3$-$a'_3$ in Formula II) are a disulfide bond from cysteine/homocysteine, a diselenide from selenocysteine, an alkylene from allylglycine, or an arylene linker.

As will be apparent to the skilled artisan, the antiparallel coiled-coil structures and the parallel coiled-coil structures according to the present invention can each contain anywhere from only one of the linkers to all of the linkers. In at least one preferred embodiment, only one linker is present. In at least one preferred embodiment, only two linkers are present. In at least one preferred embodiment of the antiparallel coiled-coil structures, at least one linker between a g-g' pair or between an $e_1$-$e'$ pair (Linker A, Linker D, linkers for $g_0$-$g'$, $g_1$-$g'$, $g_2$-$g'_0$, $e_1$-$e'_3$, $e_1$-$e'_2$ and $e_1$-$e'_1$ in Formula I) is present and at least one linker between an a-d' pair or a d-a' pair (Linker B, Linker C, linkers for $a_1$-$d'_3$, $a_2$-$d'_2$, $a_3$-$d'$, $d_1$-$a'_3$, $d_2$-$a'_2$, and $d_3$-$a'_1$ in Formula I) is present. In at least one preferred embodiment of the antiparallel coiled-coil structures, one linker between a g-g' pair or between an $e_1$-$e'$ pair is present and one linker between an a-d' pair or a d-a' pair is present. In at least one preferred embodiment of the parallel coiled-coil structures, as least one linker between a $g_1$-$e'$ pair or between an $e_1$-$g'$ pair (Linker E, Linker H, linkers for $g_0$-$e'_1$, $g_1$-$e'_2$, $g_2$-$e_3$, $e_1$-$g'_0$, $e_2$-$g'_1$, and $e_3$-$g'_2$ in Formula II) is present and at least one linker between a $d_1$-$d'$ pair or between an a-a' pair (Linker F, Linker G, linkers for $d_1$-$d'_1$, $d_2$-$d'_2$, $d_3$-$d'_3$, $a_1$-$a'_1$, $a_2$-$a'_2$, and $a_3$-$a'_3$ in Formula II) is present. In at least one preferred embodiment of the parallel coiled-coil structures, one linker between a $g_1$-$e'$ pair or between an $e_1$-$g'$ pair is present and one linker between a $d_1$-$d'$ pair or between an a-a' pair is present. Typically, the coiled-coil structures will contain the minimum number of linkers necessary to stabilize the coiled-coil. This number will vary depending on the general stability of the native coiled-coil, as will be apparent to the skilled artisan. In a preferred embodiment, only one linker is present. In another preferred embodiment, only two linkers are present.

Protecting groups function primarily to protect or mask the reactivity of functional groups. Protecting groups that are suitable for the protection of an amine group are well known in the art, including without limitation, carbamates, amides, N-alkyl and N-aryl amines, imine derivatives, enamine derivatives, and N-hetero atom derivatives as described by THEODORA W. GREENE & PETER G.M. WUTS, PROTECTIVE GROUPS IN ORGANIC SYNTHESIS 494-615 (1999), which is hereby incorporated by reference in its entirety. Suitable protecting groups according to this and all aspects of the present invention include, e.g., tert-butyloxycarbonyl ("Boc"), 9-fluorenylmethyloxycarbonyl ("Fmoc"), carbobenzyloxy ("Cbz"), and trityl. Protecting groups that are suitable for the protection of an alcohol are also well known in the art. Suitable alcohol protecting groups include, without limitation, silyl ethers, esters, and alkyl/aryl ethers. Protecting groups that are suitable for the protection of a thiol group are also well known in the art. Suitable thiol protecting groups include, without limitation, aryl/alkyl thio ethers and disulfides. As will be apparent to those of ordinary skill in the art, amino acid side chains of Asn, Asp, Gln, Glu, Cys, Ser, His, Lys, Arg, Trp, or Thr will typically need to be protected while carrying out the methods described herein. Protecting groups that are suitable for protecting these amino acid side chains are also well known in the art. Methods of protecting and deprotecting functional groups vary depending on the chosen protecting group; however, these methods are well known in the art and described in THEODORA W. GREENE & PETER G.M. WUTS, PROTECTIVE GROUPS IN ORGANIC SYNTHESIS 372-450 and 494-615 (1999), which is hereby incorporated by reference in its entirety.

A "tag" as used herein includes any labeling moiety that facilitates the detection, quantitation, separation, and/or purification of the compounds of the present invention. Suitable tags include purification tags, radioactive or fluorescent labels, and enzymatic tags.

Purification tags, such as poly-histidine ($His_{6-}$), a glutathione-S-transferase (GST-), or maltose-binding protein (MBP-), can assist in compound purification or separation but can later be removed, i.e., cleaved from the compound following recovery. Protease-specific cleavage sites can be used to facilitate the removal of the purification tag. The desired product can be purified further to remove the cleaved purification tags.

Other suitable tags include radioactive labels, such as, $^{125}I$, $^{131}I$, $^{111}In$, or $^{99}TC$. Methods of radiolabeling compounds are known in the art and described in U.S. Pat. No. 5,830,431 to Srinivasan et al., which is hereby incorporated by reference in its entirety. Radioactivity is detected and quantified using a scintillation counter or autoradiography. Alternatively, the compound can be conjugated to a fluorescent tag. Suitable fluorescent tags include, without limitation, chelates (europium chelates), fluorescein and its derivatives, rhodamine and its derivatives, dansyl, Lissamine, phycoerythrin, and Texas Red. The fluorescent labels can be conjugated to the compounds using techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Enzymatic tags generally catalyze a chemical alteration of a chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., Methods for the Preparation of Enzyme—Antibody Conjugates for Use in Enzyme Immunoassay, in METHODS IN ENZYMOLOGY 147-66 (Langone et al. eds., 1981), which is hereby incorporated by reference in its entirety.

A targeting moiety according to the present invention functions to (i) promote the cellular uptake of the compound, (ii) target the compound to a particular cell or tissue type (e.g., signaling peptide sequence), or (iii) target the compound to a specific sub-cellular localization after cellular uptake (e.g., transport peptide sequence).

To promote the cellular uptake of a compound of the present invention, the targeting moiety may be a cell penetrating peptide (CPP). CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportan, protamine, maurocalcine, and M918, are suitable targeting moieties for use in the present invention and are well known in the art (see Stewart et al., "Cell-Penetrating Peptides as Delivery Vehicles for Biology and Medicine," *Organic Biomolecular Chem.* 6:2242-55 (2008), which is hereby incorporated by reference in its entirety). Additionally, methods of making CPP are described in U.S. Patent Application Publication No. 20080234183 to Hallbrink et al., which is hereby incorporated by reference in its entirety.

Another suitable targeting moiety useful for enhancing the cellular uptake of a compound is an "importation competent" signal peptide as disclosed by U.S. Pat. No. 6,043,339 to Lin et al., which is hereby incorporated by reference in its entirety. An importation competent signal peptide is generally about 10 to about 50 amino acid residues in length-typically hydrophobic residues—that render the compound capable of penetrating through the cell membrane from outside the cell to the interior of the cell. An exemplary importation competent signal peptide includes the signal peptide from Kaposi fibroblast growth factor (see U.S. Pat. No. 6,043,339 to Lin et al., which is hereby incorporated by reference in its entirety). Other suitable peptide sequences can be selected from the SIGPEP database (see von Heijne G., "SIGPEP: A Sequence Database for Secretory Signal Peptides," *Protein Seq. Data Anal.* 1(1):41-42 (1987), which is hereby incorporated by reference in its entirety).

Another suitable targeting moiety is a signal peptide sequence capable of targeting the compounds of the present invention to a particular tissue or cell type. The signaling peptide can include at least a portion of a ligand binding protein. Suitable ligand binding proteins include high-affinity antibody fragments (e.g., Fab, Fab' and F(ab')$_2$, single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor. Thus, when the modified compound is delivered intravenously or otherwise introduced into blood or lymph, the compound will adsorb to the targeted cell, and the targeted cell will internalize the compound. For example, if the target cell is a cancer cell, the compound may be conjugated to an anti-C3B(I) antibody as disclosed by U.S. Pat. No. 6,572,856 to Taylor et al., which is hereby incorporated by reference in its entirety. Alternatively, the compound may be conjugated to an alphafeto protein receptor as disclosed by U.S. Pat. No. 6,514,685 to Moro, which is hereby incorporated by reference in its entirety, or to a monoclonal GAH antibody as disclosed by U.S. Pat. No. 5,837,845 to Hosokawa, which is hereby incorporated by reference in its entirety. For targeting a compound to a cardiac cell, the compound may be conjugated to an antibody recognizing elastin microfibril interfacer (EMILIN2) (Van Hoof et al., "Identification of Cell Surface for Antibody-Based Selection of Human Embryonic Stem Cell-Derived Cardiomyocytes," *J. Proteom. Res.* 9:1610-18 (2010), which is hereby incorporated by reference in its entirety), cardiac troponin I, connexin-43, or any cardiac cell-surface membrane receptor that is known in the art. For targeting a compound to a hepatic cell, the signaling peptide may include a ligand domain specific to the hepatocyte-specific asialoglycoprotein receptor. Methods of preparing such chimeric proteins and peptides are described in U.S. Pat. No. 5,817,789 to Heartlein, et al., which is hereby incorporated by reference in its entirety.

Another suitable targeting moiety is a transport peptide that directs intracellular compartmentalization of the compound once it is internalized by a target cell or tissue. For transport to the endoplasmic reticulum (ER), for example, the compound can be conjugated to an ER transport peptide sequence. A number of such signal peptides are known in the art, including the signal peptide MMSFVSLLLVGIL-FYATEAEQLTKCEVFQ (SEQ ID NO:16). Other suitable ER signal peptides include the N-terminus endoplasmic reticulum targeting sequence of the enzyme 17β-hydroxysteroid dehydrogenase type 11 (Horiguchi et al., "Identification and Characterization of the ER/Lipid Droplet-Targeting Sequence in 17O-hydroxysteroid Dehydrogenase Type 11," *Arch. Biochem. Biophys.* 479(2):121-30 (2008), which is hereby incorporated by reference in its entirety), or any of the ER signaling peptides (including the nucleic acid sequences encoding the ER signal peptides) disclosed in U.S. Patent Application Publication No. 20080250515 to Reed et al., which is hereby incorporated by reference in its entirety. Additionally, the compound of the present invention can contain an ER retention signal, such as the retention signal KEDL (SEQ ID NO:17). Methods of modifying the compounds of the present invention to incorporate transport peptides for localization of the compounds to the ER can be carried out as described in U.S. Patent Application Publication No. 20080250515 to Reed et al., which is hereby incorporated by reference in its entirety. For transport to the nucleus, the compounds of the present invention can include a nuclear localization transport signal. Suitable nuclear transport peptide sequences are known in the art, including the nuclear transport peptide PPKKKRKV (SEQ ID NO:18). Other nuclear localization transport signals include, for example, the nuclear localization sequence of acidic fibroblast growth factor and the nuclear localization sequence of the transcription factor NF-KB p50 as disclosed by U.S. Pat. No. 6,043,339 to Lin et al., which is hereby incorporated by reference in its entirety. Other nuclear localization peptide sequences known in the art are also suitable for use in the compounds of the present invention.

Suitable transport peptide sequences for targeting to the mitochondria include MLSLRQSIRFFKPATRTLCSSRYLL (SEQ ID NO:19). Other suitable transport peptide sequences suitable for selectively targeting the compounds of the present invention to the mitochondria are disclosed in U.S. Patent Application Publication No. 20070161544 to Wipf, which is hereby incorporated by reference in its entirety.

In a preferred embodiment of the compounds of the present invention, the antiparallel coiled-coil structure is an antiparallel coiled-coil of Formula III:

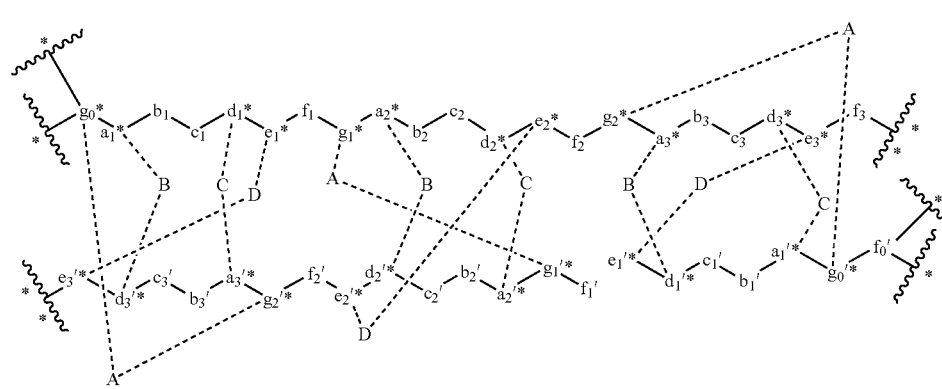

III wherein:

* represents the residue to which an optional linker may be attached;

$a_1, a_2*, a_3*, b_1, b_2, b_3, c_1, c_2, c_3, d_1*, d_2*, d_3*, e_1*, e_2*, e_3*, f_1, f_2, f_3, g_0*, g_1*, g_2*, a_1'*, a_2'*, a_3'*, b_1', b_2', b_3', c_1', c_2', c_3', d_1'*, d_2'*, d_3'*, e_1'*, e_2'*, e_3'*, f_0', f_1', f_2', g_0'*, g_1'*,$ and $g_2'*$ are each independently absent or a modified or unmodified amino acid residue or analogue thereof, with the proviso that at least seven contiguous amino acid residues/analogues are present in each coil;

$a_1*, a_2*, a_3*, d_1*, d_2*, d_3*, a_1'*, a_2'*, a_3'*, a_3'*, d_1'*, d_2'*,$ and $d_3'*$ each independently have the formula (a)

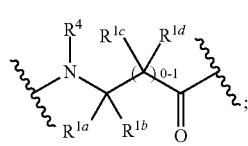

(a)

$e_1^*$, $e_2$, $e_3^*$, $g_1^*$, $g_2^*$, $e_1'$, $e_2'$, $e_3'$, $g_0'$, $g_1'^*$, and $g_2'^*$ each independently have the formula (b) and $g_0^*$ has the formula (b')

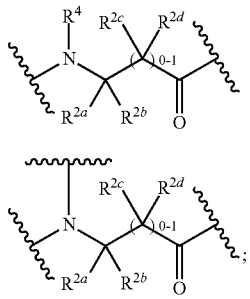

and $b_1$, $b_2$, $b_3$, $c_1$, $c_2$, $c_3$, $f_1$, $f_2$, $f_3$, $b_1'$, $b_2'$, $b_3'$, $c_1'$, $c_2'$, $c_3'$, $f_1'$, and $f_2'$ each independently have the formula (c) and $f_0'$ has the formula (c')

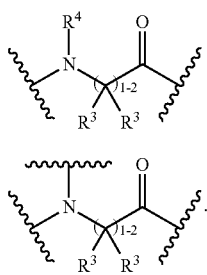

Each $R^4$ in Formula III is independently hydrogen, an alkyl, an alkenyl, an alkynyl, a cycloalkyl, a heterocyclyl, an aryl, a heteroaryl, or an arylalkyl. Preferably, $R^4$ is hydrogen.

In each residue of formula (a):
$R^{1a}$, $R^{1b}$, $R^{1c}$, and $R^{1d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, $-OR^5$, or $-SR^5$; and at least one of $R^{1a}$ and $R^{1c}$ is a side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues. When a Linker B or a Linker C is attached to a residue of formula (a), the Linker B or Linker C is attached to or replaces one of $R^{1a}$, $R^{1b}$, $R^{1c}$, and $R^{1d}$.

In a preferred embodiment, (i) one of $R^{1a}$ and $R^{1c}$ is the side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues, and (ii) $R^{1b}$, $R^{1d}$ and the other of $R^{1a}$ and $R^{1c}$ are each independently hydrogen, a $C_{1-3}$ alkyl (preferably methyl or ethyl), or a $C_{2-3}$ alkenyl (preferably ethenyl).

In each residue of formula (b):
$R^{2a}$, $R^{2b}$, $R^{2c}$, and $R^{2d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, $-OR^5$, or $-SR^5$; and at least one of $R^{2a}$ and $R^{2c}$ is an amino acid side chain. When a Linker A or a Linker D is attached to a residue of formula (b), the Linker A or Linker D is attached to or replaces one of $R^{2a}$, $R^{2b}$, $R^{2c}$, and $R^{2d}$.

In a preferred embodiment, (i) one of $R^{2a}$ and $R^{2c}$ is an amino acid side chain and (ii) $R^{2b}$, $R^{2d}$, and the other of $R^{2a}$ and $R^{2c}$ are each independently hydrogen or a $C_{1-3}$ alkyl (e.g., methyl, ethyl).

In each residue of formula (c):
each $R^3$ is independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, $-OR^5$, or $-SR^5$. In at least one embodiment, at least one $R^3$ is a side chain of a modified or unmodified amino acid.

In a preferred embodiment, residues of formula (c) are selected to facilitate molecular recognition of a target by the coiled-coil structure.

Each $R^5$ in Formula III is independently selected from the group consisting of H, —PG (where PG is a protecting group), an alkyl, an alkenyl, an alkynyl, a cycloalkyl, an aryl, a heteroaryl, a heterocyclyl, and an arylalkyl.

In a preferred embodiment of the compounds of the present invention, the parallel coiled-coil structure is a parallel coiled-coil of Formula IV:

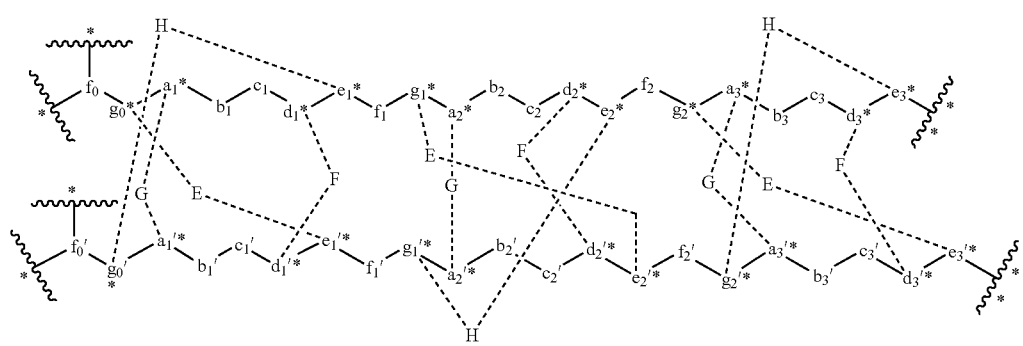

IV wherein

* represents the residue to which an optional linker may be attached;

$a_1^*, a_2^*, a_3^*, b_1, b_2, b_3, c_1, c_2, c_3, d_1^*, d_2^*, d_3^*, e_1^*, e_2^*, e_3^*, f_0, f_1, f_2, g_0^*, g_1^*, g_2^*, a_1'^*, a_2'^*, a_3'^*, b_1', b_2', b_3', c_1', c_2', c_3', d_1'^*, d_2'^*, d_3'^*, e_1'^*, e_2'^*, e_3'^*, f_0', f_1', f_2', g_0'^*, g_1'^*,$ and $g_2'^*$ are each independently absent or a modified or unmodified amino acid residue or analogue thereof, with the proviso that at least seven contiguous amino acid residues/analogues are present in each coil;

$a_1^*, a_2^*, a_3^*, d_1^*, d_2^*, d_3^*, a_1'^*, a_2'^*, a_3'^*, d_1'^*, d_2'^*,$ and $d_3'^*$ each independently have the formula (a)

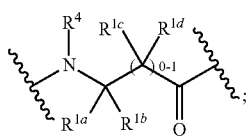
(a)

$e_1^*, e_2^*, e_3^*, g_0^*, g_1^*, g_2^*, e_1'^*, e_2'^*, e_3'^*, g_0'^*, g_1'^*,$ and $g_2'^*$ each independently have the formula (b)

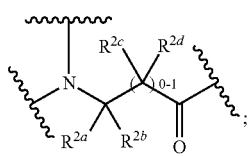
(b)

and $b_1, b_2, b_3, c_1, c_2, c_3, f_1, f_2, b_1', b_2', b_3', c_1', c_2', c_3', f_1',$ and $f_2'$ each independently have the formula (c) and $f_0$ and $f_0'$ have the formula (c')

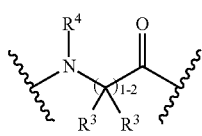
(c)

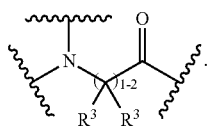
(c')

Each $R^4$ in Formula IV is independently hydrogen, an alkyl, an alkenyl, an alkynyl, a cycloalkyl, a heterocyclyl, an aryl, a heteroaryl, or an arylalkyl. Preferably, $R^4$ is hydrogen.

In each residue of formula (a):

$R^{1a}, R^{1b}, R^{1c},$ and $R^{1d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —OR$^5$, or —SR$^5$; and at least one of R$^{1a}$ and R$^{1c}$ is a side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues. When a Linker B or a Linker C is attached to a residue of formula (a), the Linker B or Linker C is attached to or replaces one of $R^{1a}, R^{1b}, R^{1c},$ and $R^{1d}$.

In a preferred embodiment, (i) one of $R^{1a}$ and $R^{1c}$ is the side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues, and (ii) $R^{1b}, R^{1d},$ and the other of $R^{1a}$ and $R^{1c}$ are each independently hydrogen, a $C_{1-3}$ alkyl (preferably methyl or ethyl), or a $C_{2-3}$ alkenyl (preferably ethenyl).

In each residue of formula (b):

$R^{2a}, R^{2b}, R^{2c},$ and $R^{2d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —OR$^5$, or —SR$^5$; and at least one of $R^{2a}$ and $R^{2c}$ is an amino acid side chain. When a Linker A or a Linker D is attached to a residue of formula (b), the Linker A or Linker D is attached to or replaces one of $R^{2a}, R^{2b}, R^{2c},$ and $R^{2d}$.

In a preferred embodiment, (i) one of $R^{2a}$ and $R^{2c}$ is an amino acid side chain and (ii) $R^{2b}, R^{2d},$ and the other of $R^{2a}$ and $R^{2c}$ are each independently hydrogen or a $C_{1-3}$ alkyl (e.g., methyl, ethyl).

In each residue of formula (c):

each $R^3$ is independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —OR$^5$, or —SR$^5$. In at least one embodiment, at least one $R^3$ is a side chain of a modified or unmodified amino acid.

In a preferred embodiment, residues of formula (c) are selected to facilitate molecular recognition of a target by the coiled-coil structure.

Each $R^5$ in Formula IV is independently selected from the group consisting of H, —PG (where PG is a protecting group), an alkyl, an alkenyl, an alkynyl, a cycloalkyl, an aryl, a heteroaryl, a heterocyclyl, and an arylalkyl.

In some at least some embodiments of the compounds of the present invention, PG is independently selected at each occurrence thereof from the group consisting of a protecting group for protection of an amine, a protecting group for protection of a thiol, and a protecting group for protection of a carboxylic acid.

In at least one embodiment of the parallel coiled-coils of the present invention, $f_0$ is any residue; $g_0$ is Trp, Met, Phe, Ala, Glu, or His; $a_1$ is Cys, HCys, Leu, Ile, allylleucine, Val, allylglycine, Thr, selenocysteine, hexafluoroleucine, or hexafluorovaline; $b_1$ is any residue; $c_1$ is Gln, Trp, Leu, Phe, Tyr, or Met; $d_1$ is Cys, HCys, Leu, Ile, allylleucine, Val, allylglycine, Thr, selenocysteine, hexafluoroleucine, or hexafluorovaline; $e_1$ is any residue; $f_1$ is any residue; $g_1$ is any residue; $a_2$ is Cys, HCys, Leu, Ile, allylleucine, Val, allylglycine, Thr, selenocysteine, hexafluoroleucine, or hexafluorovaline; $b_2$ is any residue; $c_2$ is any residue; $d_2$ is Cys, HCys, Leu, Ile, allylleucine, Val, allylglycine, Thr, selenocysteine, hexafluoroleucine, or hexafluorovaline; $e_2$ is any residue; $g'_0$ is any residue; $a'_1$ is Cys, HCys, Leu, Ile, allylleucine, Val, allylglycine, Thr, selenocysteine, hexafluoroleucine, or hexafluorovaline; $b'_1$ is His, Phe, Trp, Tyr, Val, Leu, or Ile; $c'_1$ is any residue; $d'_1$ is Cys, HCys, Leu, Ile, allylleucine, Val, allylglycine, Thr, selenocysteine, hexafluoroleucine, or hexafluorovaline; $e'_1$ is His, Phe, Trp, Tyr, Val, Leu, or Ile, $e'_1$ is any residue; $f'_1$ is any residue; $g'_1$ is any residue; $a'_2$ is Cys, HCys, Leu, Ile, allylleucine, Val, allylglycine, Thr, selenocysteine, hexafluoroleucine, or hexafluorovaline; $b'_2$ Asp, Asn, Glu, Gln, Tyr, Ser, or Thr; $c'_2$ is any residue; $d'_2$ is Cys, HCys, Leu, Ile, allylleucine, Val, allylglycine, Thr, selenocysteine, hexafluoroleucine, or hexafluorovaline, $e'_2$ is His, Phe, Trp, Tyr, Val, Leu, or Ile; $f_2$ is any residue; where any amino acid residue may be modified for attachment of Z, which is a covalent linker (e.g., a bis-triazole linker) between pair $e_2$-$g'_1$.

In at least one embodiment of the parallel coiled-coils of the present invention, $c_1$ is Glu; $d_1$ is Leu; $e_1$ is Glu; $f_1$ is Arg; $g_1$ is Glu; $a_1$ is Ile; $b_1$ is Arg; $c_1$ is Trp; $d_2$ is Leu; $e_2$ is Z; $c'_1$ is Glu; $d'_1$ is Leu; $e'_1$ is Glu; $f'_1$ is Arg; $g'_1$ is Z; $a'_2$ is Ile; $b'_2$ is Arg; $c'_2$ is Trp; $d'_2$ is Leu, $e'_2$ is Arg; where any amino acid residue may be modified for attachment of Z, which is a covalent linker (e.g., a bis-triazole linker) between pair $g_1$-$e'_2$.

In at least one embodiment of the parallel coiled-coils of the present invention, $c_1$ is Glu; $d_1$ is Cys; $e_1$ is Glu; $f_1$ is Arg; $g_1$ is Glu; $a_2$ is Ile; $b_2$ is Arg; $c_2$ is Trp; $d_2$ is Leu; $e_2$ is Z; $c'_1$ is Glu; $d'_1$ is Cys; $e'_1$ is Glu; $f'_1$ is Arg; $g'_1$ is Z; $a'_2$ is Ile; $b'_2$ is Arg; $c'_2$ is Trp; $d'_2$ is Leu, $e'_2$ is Arg; where any amino acid residue may be modified for attachment of Z, which is a covalent linker (e.g., a bis-triazole linker) between pair $g_1$-$e'_2$.

In some embodiments of the compounds of the present invention, compound comprises an antiparallel coiled-coil structure that mimics the Nervy homology two (NHR2) domain of the AML1-ETO-containing transcription factor complex (AETFC). In these embodiments, the compound is selected from the group consisting of (i) a macrostructure comprising an antiparallel coiled-coil structure that mimics the NHR2 domain and (ii) an antiparallel coiled-coil structure of Formula I that mimics the NHR2 domain. In these compounds, (i) the first strand of the antiparallel coiled-coil structure comprises at least ten contiguous modified or unmodified amino acid residues (or analogues thereof), wherein the at least ten contiguous amino acid residues/analogues have the formula $^gX_1$-$X_2$-$X_3$-$X_4$-$X_5$-$X_6$-$X_7$-$X_8$-$X_9$-$X_{10}^b$, wherein $X_1$, $X_2$, $X_3$, $X_4$, $X_5$, $X_6$, $X_7$, $X_8$, $X_9$, and $X_{10}$ are selected from the group of amino acid residues (or analogues thereof) set forth below; and (ii) the second strand of the antiparallel coiled-coil structure comprises at least ten contiguous modified or unmodified amino acid residues (or analogues thereof), wherein the at least ten contiguous amino acid residues/analogues have the formula $^{c'}X_1'$-$X_2'$-$X_3'$-$X_4'$-$X_5'$-$X_6'$-$X_7'$-$X_8'$-$X_9'$-$X_{10}^{e'}$, wherein $X_1'$, $X_2'$, $X_3'$, $X_4'$, $X_5'$, $X_6'$, $X_7'$, $X_8'$, $X_9'$, and $X_{10}'$ are selected from the group of amino acid residues (or analogues thereof) set forth below. As will be apparent to the skilled artisan, $^g$, $^b$, $^{c'}$, and $^{e'}$ indicate where the ten contiguous amino acids/analogues appear within the antiparallel coiled-coil structure (i.e., the first strand can begin at the $g_0$, $g_1$, or $g_2$ position and the second strand can begin at the $c_1'$, $c_2'$, or $c_3'$ position). As will be apparent to the skilled artisan, residues in the e/e' and g/g' positions can be optionally modified to facilitate attachment of a linker or replaced with a linker, if present. As will be apparent to the skilled artisan, residues in the a/a' and d/d' positions can be optionally modified to facilitate attachment of a linker, if present.

| NHR2 Preferred Sequences | | | |
|---|---|---|---|
| STRAND 1 | | STRAND 2 | |
| X | Amino Acid Residues[1] | X' | Amino Acid Residues[1] |
| $^gX_1$ | <u>Glu</u>, Leu, Arg, Lys, Thr, Val | $^{c'}X_1'$ | <u>Glu</u>, Asn, Leu, Gln, Met, Ala |
| $X_2$ | Cys, HCys, <u>Leu</u>, Ile, allylleucine, Val, allylglycine, Thr, selenocysteine, hexafluoroleucine, hexafluorovaline | $X_2'$ | Cys, HCys, <u>Leu</u>, Ile, allylleucine, Val, allylglycine, Thr, selenocysteine, hexafluoroleucine, hexafluorovaline |
| $X_3$ | Any residue (esp. Trp) | $X_3'$ | Any residue (esp. Trp) |
| $X_4$ | <u>His</u>, Tyr, Phe, Lys, Gln, Trp | $X_4'$ | Any residue (esp. Arg) |
| $X_5$ | Cys, HCys, <u>Leu</u>, Ile, allylleucine, Val, allylglycine, Thr, selenocysteine, hexafluoroleucine, hexafluorovaline | $X_5'$ | Ala, <u>Ser</u>, Thr, Gly, Asp |
| $X_6$ | Any residue | $X_6'$ | Cys, HCys, Leu, <u>Ile</u>, allylleucine, Val, allylglycine, Thr, selenocysteine, hexafluoroleucine, hexafluorovaline |
| $X_7$ | <u>Glu</u>, Asn, Trp, Leu, Glu, Gln | $X_7'$ | Arg, Leu, Gln, Met, Glu, Asp |
| $X_8$ | <u>Leu</u>, Met, Ala, His, Ser | $X_8'$ | Tyr, <u>Val</u>, Phe, Trp, Met |
| $X_9$ | Cys, HCys, <u>Leu</u>, Ile, allylleucine, Val, allylglycine, Thr, selenocysteine, hexafluoroleucine, hexafluorovaline | $X_9'$ | Cys, HCys, <u>Leu</u>, Ile, allylleucine, Val, allylglycine, Thr, selenocysteine, hexafluoroleucine, hexafluorovaline |
| $^bX_{10}$ | Any residue (esp. Trp) | $^eX_{10}'$ | Any residue |

[1]Underlined residues are particularly preferred.

In at least one embodiment of the antiparallel coiled-coils of the present invention, $g_1$ is Glu, Leu, Arg, Lys, Thr or Val; $a_2$ is Cys, HCys, Leu, Ile, allylleucine, Val, allylglycine, Thr, selenocysteine, hexafluoroleucine, or hexafluorovaline; $b_2$ is any residue; $c_2$ is His, Tyr, Phe, Lys, Gln, or Trp; $d_2$ is Cys, HCys, Leu, Ile, allylleucine, Val, allylglycine, Thr, selenocysteine, hexafluoroleucine, or hexafluorovaline; $e_2$ is any residue; $f_2$ is Glu, Asn, Trp, Leu, Glu, or Gln; $g_2$ is Leu, Met, Ala, His, or Ser; $a_3$ is Cys, HCys, Leu, Ile, allylleucine, Val, allylglycine, Thr, selenocysteine, hexafluoroleucine, or hexafluorovaline; $b_3$ is any residue; $c'_1$ is Glu, Asn, Leu, Gln, Met, or Ala; $d'_1$ is Cys, HCys, Leu, Ile, allylleucine, Val, allylglycine, Thr, selenocysteine, hexafluoroleucine, or hexafluorovaline; $e'_1$ is any residue; $f'_1$ is any residue; $g'_1$ is Ala, Ser, Thr, Gly, or Asp; $a'_2$ is Cys, HCys, Leu, Ile, allylleucine, Val, allylglycine, Thr, selenocysteine, hexafluoroleucine, or hexafluorovaline; $b'_2$ is Arg, Leu, Gln, Met, Glu, or Asp; $c'_2$ is Tyr, Val, Phe, Trp, or Met; $d'_2$ is Cys, HCys, Leu, Ile, allylleucine, Val, allylglycine, Thr, selenocysteine, hexafluoroleucine, or hexafluorovaline, $e'_2$ is any residue, where any amino acid residue may be modified for attachment of Z, which is a covalent linker (e.g., a bis-triazole linker) between pair g-g' or $e_2$-$e'_2$.

In at least one embodiment of the antiparallel coiled-coils of the present invention, $g_1$ is Glu, $a_2$ is Leu, $b_2$ is Trp, $c_2$ is His, $d_2$ is Leu, $e_2$ is Z, $f_2$ is Glu, $g_2$ is Leu, $a_3$ is Leu, $b_3$ is Arg, $c'_1$ is Glu, $d'_1$ is Leu, $e'_1$ is Trp, $f'_1$ is Arg, $g'_1$ is Ser, $a'_2$ is Ile, $b'_2$ is Arg, $c'_2$ is Val, $d'_2$ is Leu, $e'_2$ is Z, and each Z is a lysine residue that has been modified for attachment of a covalent linker (e.g., a bis-triazole linker) between pair $e_2$-$e'_2$.

In at least one embodiment of the antiparallel coiled-coils of the present invention, $g_1$ is Glu, $a_2$ is Leu, $b_2$ is Trp, $c_2$ is His, $d_2$ is Leu, $e_2$ is Z, $f_2$ is Glu, $g_2$ is Leu, $a_3$ is Z', $b_3$ is Arg, $c'_1$ is Glu, $d'_1$ is Z', $e'_1$ is Trp, $f'_1$ is Arg, $g'_1$ is Ser, $a'_2$ is Ile, $b'_2$ is Arg, $c'_2$ is Val, $d'_2$ is Leu, $e'_2$ is Z, each Z is a lysine residue that has been modified for attachment of a covalent linker (e.g., a bis-triazole linker) between pair $e_2$-$e'_2$, and each Z' is a cysteine residue that has been modified for attachment of a covalent linker (e.g., a disulfide linker) between pair $a_3$-$d'_1$.

In at least one embodiment of the compounds of the present invention, the compound is an NHR2 coiled-coil mimetic selected from the group consisting of CHD-NHR2-2, $CHD^{DS}$-NHR2-3, CHD-NHR2-6, and CHD-NHR2-7. CHD-NHR2-2 and $CHD^{DS}$-NHR2-3 are particularly preferred.

Another aspect of the present invention relates to pharmaceutical formulations comprising any of the above described compounds of the present invention and a pharmaceutically acceptable carrier. Acceptable pharmaceutical carriers include solutions, suspensions, emulsions, excipients, powders, or stabilizers. The carrier should be suitable for the desired mode of delivery.

In addition, the pharmaceutical formulations of the present invention may further comprise one or more pharmaceutically acceptable diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

Another aspect of the present invention is a method of inhibiting interaction between the AETFC and an NHR2 binding motif (e.g., in an E protein). This method involves contacting the transcription factor complex and/or the NHR2 binding motif with a compound of the present invention that comprises an antiparallel coiled-coil structure that mimics the NHR2 domain, as described above, under conditions effective to inhibit interaction between the AML1-ETO-containing transcription factor complex and the NHR2 binding motif. Preferably, contacting is carried out in a cell. In another preferred embodiment, contacting is carried out in a subject and contacting comprises administering the compound to the subject.

The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Another aspect of the present invention relates to a method of modulating transcription of a gene in a cell, wherein transcription of the gene is regulated by interaction between AETFC and an NHR2 binding motif. This method involves contacting the cell with a compound of the present invention that comprises an antiparallel coiled-coil structure that mimics the NHR2 domain, as described above, under conditions effective to modulate transcription of the gene. In a preferred embodiment, the cell is contacted under conditions effective to cause nuclear uptake of the compound, where the compound disrupts interaction of AETFC and the NHR2-binding domain and thereby reduces transcription of the gene.

Modulating according to this aspect of the present invention refers to up-regulating transcription of genes that are typically down-regulated by AETFC, or down-regulating transcription of genes that are typically up-regulated by AETFC. Genes typically downregulated by AETFC include, e.g., FOS, EGFR1, STYK1, MYCN, TAL1, BAALC, and 1D1. Genes typically upregulated by AETFC include, e.g., VAV1, SLA, ANXA1, PTPN12, BPI, and OGG1.

Genes whose transcription can be modulated according to this aspect of the present invention include FOS, EGFR1, STYK1, MYCN, TAL1, BAALC, 1D1, VAV1, SLA, ANXA1, PTPN12, BPI, OGG1, and those described in Sun et al., "A Stable Transcription Factor Complex Nucleated by Oligomeric AML1-ETO Controls Leukaemogenesis," *Nature* 500:93-98 (2013); Westendorf et al., "The t(8;21) Fusion Product, AML-1-ETO, Associates with C/EBP-α, Inhibits C/EBP-α-Dependent Transcription, and Blocks Granulocytic Differentiation," *Mol. Cell. Biol.* 18:322-333 (1998); Mao et al., "Functional and Physical Interactions Between AML1 Proteins and an ETS Protein, MEF: Implications for the Pathogenesis of t(8;21)-Positive Leukemias," *Mol. Cell. Biol.* 19:3635-3644 (1999); Elagib et al., "RUNX1 and GATA-1 Coexpression and Cooperation in Megakaryocytic Differentiation," *Blood* 101:4333-4341 (2003); Zhang et al., "E Protein Silencing by the Leukemogenic AML1-ETO Fusion Protein," *Science* 305:1286-1289 (2004); Gardini et al. "AML1/ETO Oncoprotein Is Directed to AML1 Binding Regions and Co-Localizes with AML1 and HEB on Its Targets," *PLoS Genet.* 4:e1000275 (2008); Guo et al., "Multivalent Binding of the ETO Corepressor to E Proteins Facilitates Dual Repression Controls Targeting Chromatin and the Basal Transcription Machinery," *Mol. Cell. Biol.* 29:2644-2657 (2009); Martens et al., "ERG and FLI1 Binding Sites Demarcate Targets for Aberrant Epigenetic Regulation by AML1-ETO in Acute Myeloid Leukemia," *Blood* 120:4038-4048 (2012); Wang et al., "The Leukemogenicity of AML1-ETO Is Dependent on Site-Specific Lysine Acetylation," *Science* 333:765-769 (2011); Shia et al., "PRMT1 Interacts with AML1-ETO to Promote Its Transcriptional Activation and Progenitor Cell Proliferative Potential," *Blood* 119:4953-4962 (2012); and Miyoshi et al., "The t(8;21) Translocation in Acute Myeloid Leukemia Results in Production of an AML1-MTG8 Fusion Transcript," *EMBO J.* 12:2715-2721 (1993), each of which is hereby incorporated by reference in its entirety.

The NHR2-mediated oligomerization of AML1-ETO has been shown to be critical for leukaemogenesis (Sun et al., "A Stable Transcription Factor Complex Nucleated by Oligomeric AML1-ETO Controls Leukaemogenesis," *Nature* 500:93-98 (2013), which is hereby incorporated by reference in its entirety). Thus, another aspect of the present invention relates to a method of treating leukemia in a subject. This method involves administering to the subject a compound of the present invention that comprises an antiparallel coiled-coil structure that mimics the NHR2 domain, as described above, under conditions effective to treat leukemia in the subject.

In all aspects of the present invention involving contacting a cell with, or administering to a subject, a compound of the present invention that comprises an antiparallel coiled-coil structure that mimics the NHR2 domain, the compound is selected from the group consisting of (i) a macrostructure comprising an antiparallel coiled-coil structure that mimics the NHR2 domain and (ii) an antiparallel coiled-coil structure of Formula I that mimics the NHR2 domain. In these compounds, (i) the first strand of the antiparallel coiled-coil structure comprises at least ten contiguous modified or unmodified amino acid residues (or analogues thereof), wherein the at least ten contiguous amino acid residues/analogues have the formula $^gX_1$-$X_2$-$X_3$-$X_4$-$X_5$-$X_6$-$X_7$-$X_8$-$X_9$-$X_{10}^b$, wherein $X_1$, $X_2$, $X_3$, $X_4$, $X_5$, $X_6$, $X_7$, $X_8$, $X_9$, and $X_{10}$ are selected from the group of amino acid residues (or analogues thereof) set forth below; and (ii) the second strand of the antiparallel coiled-coil structure comprises at least ten contiguous modified or unmodified amino acid residues (or analogues thereof), wherein the at least ten contiguous amino acid residues/analogues have the formula $^cX_1'$-$X_2'$-$X_3'$-$X_4'$-$X_5'$-$X_6'$-$X_7'$-$X_8'$-$X_9'$-$X_{10}^{e'}$, wherein $X_1'$, $X_2'$, $X_3'$, $X_4'$, $X_5'$, $X_6'$, $X_7'$, $X_8'$, $X_9'$, and $X_{10}'$ are selected from the group of amino acid residues (or analogues thereof) set forth below. As will be apparent to the skilled artisan, $^g$, $^b$, $^{c'}$, and $^{e'}$ indicate where the ten contiguous amino acids/analogues appear within the antiparallel coiled-coil structure (i.e., the first strand can begin at the $g_0$, $g_1$, or $g_2$ position and the second strand can begin at the $c_1'$, $c_2'$, or $C_3'$ position). As will be apparent to the skilled artisan, residues in the e/e' and g/g' positions can be optionally modified to facilitate attachment of a linker or replaced with a linker, if present. As will be apparent to the skilled artisan, residues in the a/a' and d/d' positions can be optionally modified to facilitate attachment of a linker, if present.

| NHR2 Preferred Sequences | | | |
| --- | --- | --- | --- |
| STRAND 1 | | STRAND 2 | |
| X | Amino Acid Residues[1] | X' | Amino Acid Residues[1] |
| $^gX_1$ | Glu, Leu, Arg, Lys, Thr, Val | $^cX_1'$ | Glu, Asn, Leu, Gln, Met, Ala |
| $X_2$ | Cys, HCys, Leu, Ile, allylleucine, Val, allylglycine, Thr, selenocysteine, hexafluoroleucine, hexafluorovaline | $X_2'$ | Cys, HCys, Leu, Ile, allylleucine, Val, allylglycine, Thr, selenocysteine, hexafluoroleucine, hexafluorovaline |
| $X_3$ | Any residue (esp. Trp) | $X_3'$ | Any residue (esp. Trp) |

NHR2 Preferred Sequences

| STRAND 1 | | STRAND 2 | |
|---|---|---|---|
| X | Amino Acid Residues[1] | X' | Amino Acid Residues[1] |
| $X_4$ | His, Tyr, Phe, Lys, Gln, Trp | $X_4'$ | Any residue (esp. Arg) |
| $X_5$ | Cys, HCys, Leu, Ile, allylleucine, Val, allylglycine, Thr, selenocysteine, hexafluoroleucine, hexafluorovaline | $X_5'$ | Ala, Ser, Thr, Gly, Asp |
| $X_6$ | Any residue | $X_6'$ | Cys, HCys, Leu, Ile, allylleucine, Val, allylglycine, Thr, selenocysteine, hexafluoroleucine, hexafluorovaline |
| $X_7$ | Glu, Asn, Trp, Leu, Glu, Gln | $X_7'$ | Arg, Leu, Gln, Met, Glu, Asp |
| $X_8$ | Leu, Met, Ala, His, Ser | $X_8'$ | Tyr, Val, Phe, Trp, Met |
| $X_9$ | Cys, HCys, Leu, Ile, allylleucine, Val, allylglycine, Thr, selenocysteine, hexafluoroleucine, hexafluorovaline | $X_9'$ | Cys, HCys, Leu, Ile, allylleucine, Val, allylglycine, Thr, selenocysteine, hexafluoroleucine, hexafluorovaline |
| $^bX_{10}$ | Any residue (esp. Trp) | $^{e'}X_{10}'$ | Any residue |

[1]Underlined residues are particularly preferred.

In at least one embodiment of all aspects of the present invention involving contacting a cell with, or administering to a subject, a compound of the present invention that comprises an antiparallel coiled-coil structure, $g_1$ is Glu, Leu, Arg, Lys, Thr or Val; $a_2$ is Cys, HCys, Leu, Ile, allylleucine, Val, allylglycine, Thr, selenocysteine, hexafluoroleucine, or hexafluorovaline; $b_2$ is any residue; $c_2$ is His, Tyr, Phe, Lys, Gln, or Trp; $d_2$ is Cys, HCys, Leu, Ile, allylleucine, Val, allylglycine, Thr, selenocysteine, hexafluoroleucine, or hexafluorovaline; $e_2$ is any residue; $f_2$ is Glu, Asn, Trp, Leu, Glu, or Gln; $g_2$ is Leu, Met, Ala, His, or Ser; $a_3$ is Cys, HCys, Leu, Ile, allylleucine, Val, allylglycine, Thr, selenocysteine, hexafluoroleucine, or hexafluorovaline; $b_3$ is any residue; $c'_1$ is Glu, Asn, Leu, Gln, Met, or Ala; $d'_1$ is Cys, HCys, Leu, Ile, allylleucine, Val, allylglycine, Thr, selenocysteine, hexafluoroleucine, or hexafluorovaline; $e'_1$ is any residue; $f'_1$ is any residue; $g'_1$ is Ala, Ser, Thr, Gly, or Asp; $a'_2$ is Cys, HCys, Leu, Ile, allylleucine, Val, allylglycine, Thr, selenocysteine, hexafluoroleucine, or hexafluorovaline; $b'_2$ is Arg, Leu, Gln, Met, Glu, or Asp; $c'_2$ is Tyr, Val, Phe, Trp, or Met; $d'_2$ is Cys, HCys, Leu, Ile, allylleucine, Val, allylglycine, Thr, selenocysteine, hexafluoroleucine, or hexafluorovaline, $e'_2$ is any residue, where any amino acid residue may be modified for attachment of Z, which is a covalent linker (e.g., a bis-triazole linker) between pair g-g' or $e_2$-$e'_2$.

In at least one embodiment of all aspects of the present invention involving contacting a cell with, or administering to a subject, a compound of the present invention that comprises an antiparallel coiled-coil structure, $g_1$ is Glu, $a_2$ is Leu, $b_2$ is Trp, $c_2$ is His, $d_2$ is Leu, $e_2$ is Z, $f_2$ is Glu, $g_2$ is Leu, $a_3$ is Leu, $b_3$ is Arg, $c'_1$ is Glu, $d'_1$ is Leu, $e'_1$ is Trp, $f'_1$ is Arg, $g'_1$ is Ser, $a'_2$ is Ile, $b'_2$ is Arg, $c'_2$ is Val, $d'_2$ is Leu, $e'_2$ is Z, and each Z is a lysine residue that has been modified for attachment of a covalent linker (e.g., a bis-triazole linker) between pair $e_2$-$e'_2$.

In at least one embodiment of all aspects of the present invention involving contacting a cell with, or administering to a subject, a compound of the present invention that comprises an antiparallel coiled-coil structure, $g_1$ is Glu, $a_2$ is Leu, $b_2$ is Trp, $c_2$ is His, $d_2$ is Leu, $e_2$ is Z, $f_2$ is Glu, $g_2$ is Leu, $a_3$ is Z', $b_3$ is Arg, $c'_1$ is Glu, $d'_1$ is Z', $e'_1$ is Trp, $f'_1$ is Arg, $g'_1$ is Ser, $a'_2$ is Ile, $b'_2$ is Arg, $c'_2$ is Val, $d'_2$ is Leu, $e'_2$ is Z, each Z is a lysine residue that has been modified for attachment of a covalent linker (e.g., a bis-triazole linker) between pair $e_2$-$e'_2$, and each Z' is a cysteine residue that has been modified for attachment of a covalent linker (e.g., a disulfide linker) between pair $a_3$-$d'_1$.

In at least one embodiment of all aspects of the present invention involving contacting a cell with, or administering to a subject, a compound of the present invention that comprises an antiparallel coiled-coil structure that mimics the NHR2 domain, the compound is an NHR2 coiled-coil mimetic selected from the group consisting of CHD-NHR2-2, CHD$^{DS}$-NHR2-3, CHD-NHR2-6, and CHD-NHR2-7 (esp. CHD-NHR2-2 or CHD$^{DS}$-NHR2-3).

In all aspects of the present invention involving contacting a cell, suitable cells include, without limitation, mammalian cells (e.g., human cells, cat cells, dog cells, horse cells, cattle cells, goat cells, sheep cells, pig cells, mice cells, rat cells) and avian cells (e.g., chicken cells). In at least one preferred embodiment, the cells are leukemia cells (esp. acute myeloid leukemia cells, t(8;21)-positive leukemia cells).

In all aspects of the present invention involving a subject, suitable subjects include mammals (e.g., humans, cats, dogs, horses, cattle, goats, sheeps, pigs, mice, rats) and birds (e.g., chickens). In at least one preferred embodiment, the subject has leukemia (esp. acute myeloid leukemia, t(8;21)-positive leukemia).

In all aspects of the present invention directed to methods involving contacting a cell with one or more compounds, contacting can be carried out using methods that will be apparent to the skilled artisan, and can be done in vitro or in vivo.

One approach for delivering agents into cells involves the use of liposomes. Basically, this involves providing a liposome which includes agent(s) to be delivered, and then contacting the target cell, tissue, or organ with the liposomes under conditions effective for delivery of the agent into the cell, tissue, or organ.

This liposome delivery system can also be made to accumulate at a target organ, tissue, or cell via active targeting (e.g., by incorporating an antibody or hormone on the surface of the liposomal vehicle). This can be achieved according to known methods.

An alternative approach for delivery of protein- or polypeptide-containing agents involves the conjugation of the desired agent to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of agents involves preparation of chimeric agents according to U.S. Pat. No. 5,817,789 to Heartlein et al., which is hereby incorporated by reference in its entirety. The chimeric agent can include a ligand domain and the agent (e.g., a compound of the invention). The ligand domain is specific for receptors located on a target cell. Thus, when the chimeric agent is delivered intravenously or otherwise introduced into blood or lymph, the chimeric agent will adsorb to the targeted cell, and the targeted cell will internalize the chimeric agent.

Compounds of the present invention may be delivered directly to the targeted cell/tissue/organ.

Additionally and/or alternatively, the compounds may be administered to a non-targeted area along with one or more agents that facilitate migration of the compounds to (and/or uptake by) a targeted tissue, organ, or cell. As will be apparent to one of ordinary skill in the art, the compound itself can be modified to facilitate its transport to a target tissue, organ, or cell, including its transport across the blood-brain barrier; and/or to facilitate its uptake by a target cell (e.g., its transport across cell membranes). In a preferred embodiment, the peptide of the invention is modified, and/or delivered with an appropriate vehicle, to facilitate its delivery to the nucleus of the target cell (Wender et al., "The Design, Synthesis, and Evaluation of Molecules That Enable or Enhance Cellular Uptake: Peptoid Molecular Transporters," *Proc. Nat'l Acad. Sci. USA* 97:13003-08 (2000); Roberts, "Buyer's Guide to Protein Transduction Reagents," *Scientist* 18:42-43 (2004); Joliot & Prochiantz, "Transduction Peptides: From Technology to Physiology," *Nat. Cell Biol.* 6:189-96 (2004), each of which is hereby incorporated by reference in its entirety).

The present invention may be further illustrated by reference to the following examples.

EXAMPLES

Example 1—General Materials and Methods

Research grade solvents and reagents were used without further purification. Fmoc amino acids and peptide synthesis reagents were purchased from Novabiochem and Chem-Impex International. Fmoc-azido amino acids were synthesized as previously described (Lau et al., *Synlett* 1917 (2011); Sminia et al., *Synlett* 2643 (2012), which are hereby incorporated by reference in their entirety).

Example 2—Synthesis of Hydrogen Bond Surrogate Coiled-Coil Mimic (AB-1)

Hydrogen bond surrogate coiled-coil mimic AB-1 was synthesized as shown in Scheme 1 below.

Scheme 1

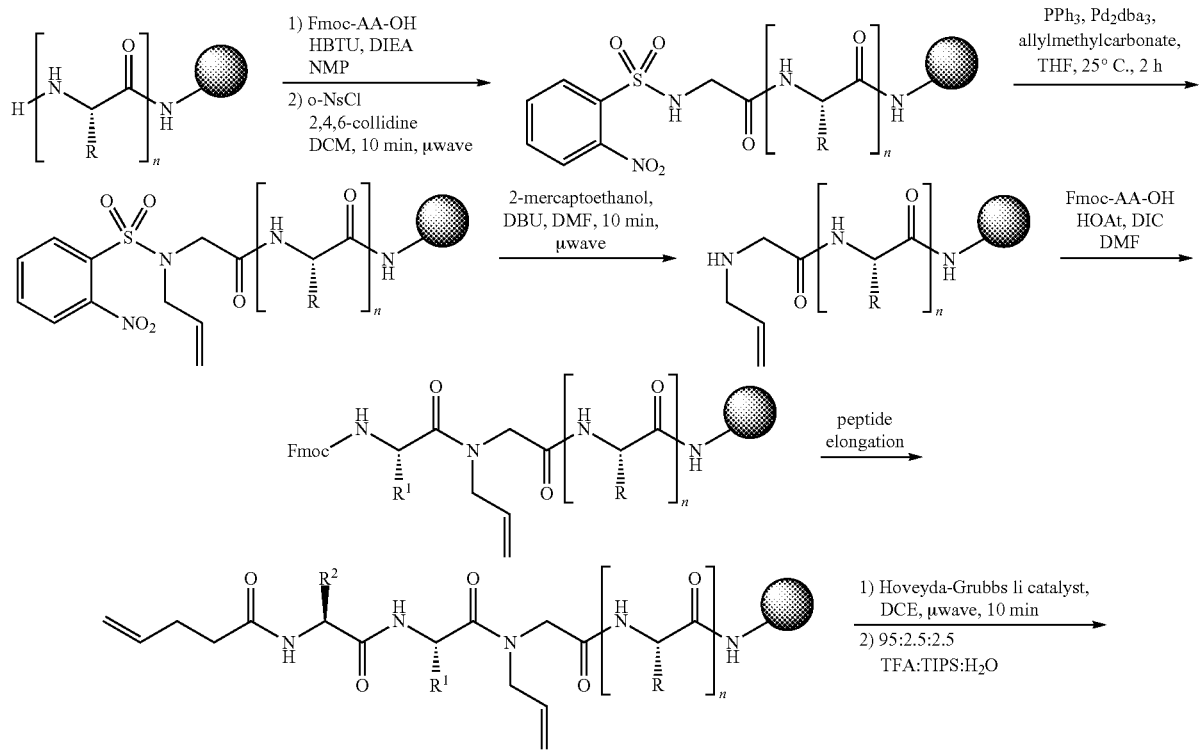

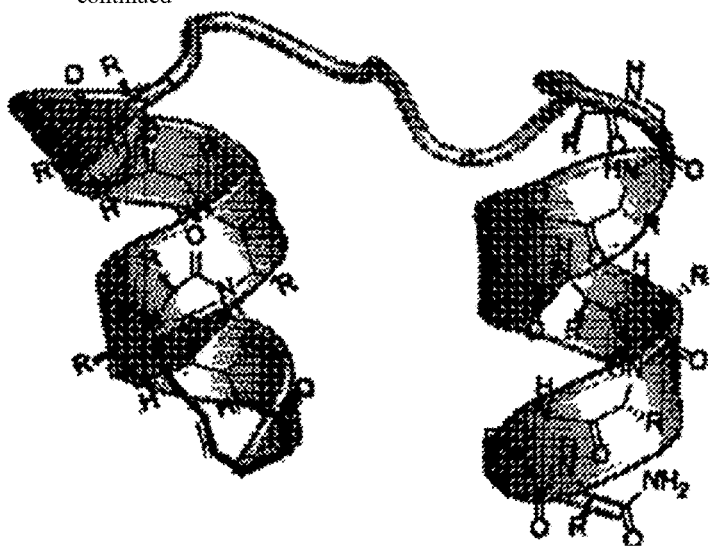

HBS peptides were synthesized as previously described (Patgiri et al., Org. Biomol. Chem. 8:1773 (2010), which is hereby incorporated by reference in its entirety). Peptide sequences up to the i+3rd residue of the parent strand were synthesized on solid phase on a CEM® Liberty Peptide Synthesizer. A solution containing premixed o-nitrobenzesulfonyl chloride (10 eq) and 2,4,6-collidine (10 eq) in DCM was added to resin containing Fmoc-deprotected peptide. Resin was washed sequentially with dichloromethane, dimethylformamide, and diethyl ether (3×5 mL each). Resin was dried overnight under vacuum. Dried resin, PPh3, and $Pd_2(dba)_3$ were flushed under inert argon for 30 minutes. The resin with reactants was swelled in THF, and allymethylcarbonate was added to the reaction vessel. The solution was agitated at room temperature for 2 hours under argon to afford allylated peptide. Resin was filtered and washed with DCM, DMF, 0.2 M sodium diethylcarbamate trihydrate in NMP, and diethyl ether (3×5 mL). The nosyl protecting group was then removed by the addition of 1,8-diazabicyclo [5.4.0]undec-7-ene (DBU, 5 eq) and 2-mercaptoethanol (10 eq) in DMF. Resin was washed with DMF, DCM, and diethyl ether (3×5 mL) and treated with the desired Fmoc amino acid (20 eq), DIC (20 eq) and HOAt (10 eq) in DMF. The reaction was allowed to agitate at room temperature for 12 to 16 hours. Resin containing elongated peptide was washed, and coupled to the desired Fmoc amino acid residue (5 eq) and 4-pentenoic acid (5 eq) with HBTU (5 eq) and DIEA (10 eq) in DMF. Ring-closing metathesis of bis-olefin 9 was performed with Hoveyda-Grubbs II catalyst (20 mol %) in 1,2-dichloroethane under microwave irradiation at 120° C. for 10 min as previously described (Miller et al., Curr. Prot. Chem. Biol. 6:101 (2014); Patgiri et al., Nat. Prot. 5:1857 (2010), which are hereby incorporated by reference in their entirety). The ring-closing reaction was monitored by MALDI-TOF. Peptides were cleaved from the resin using 95% trifluoroacetic acid, 2.5% TIPS, and 2.5% $H_2O$, and purified by reversed-phase HPLC (gradient 15-60 acetonitrile/water with 0.1% TFA over 60 min) and characterized by MALDI-TOF.

Example 3—Synthesis of Macrocycle Coiled-Coil Mimic (AB-2)

Macrocycle coiled-coil mimic AB-2 was synthesized as shown in Scheme 2 below.

Scheme 2

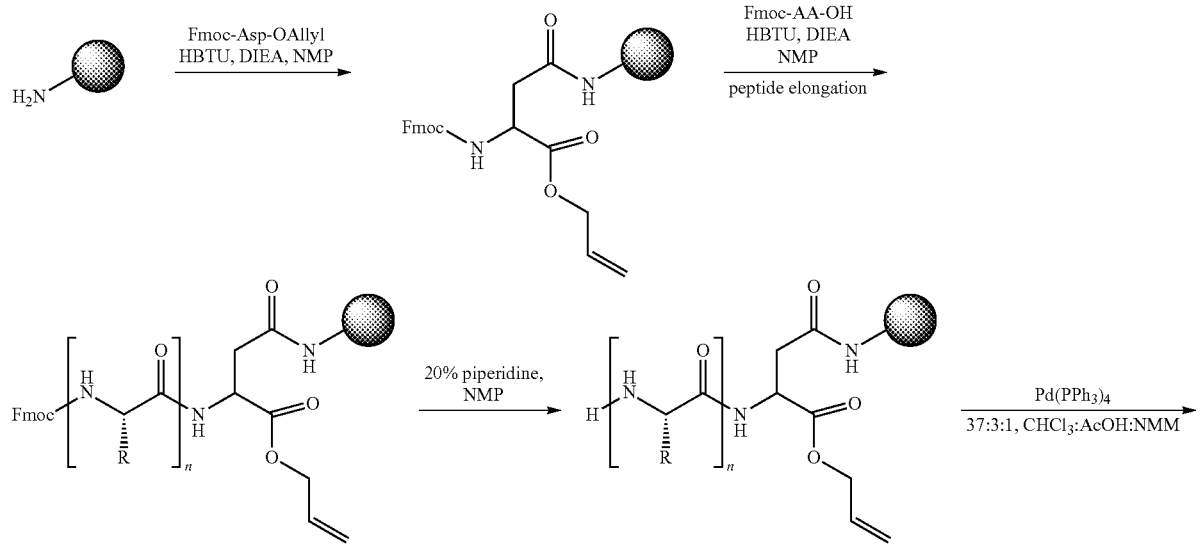

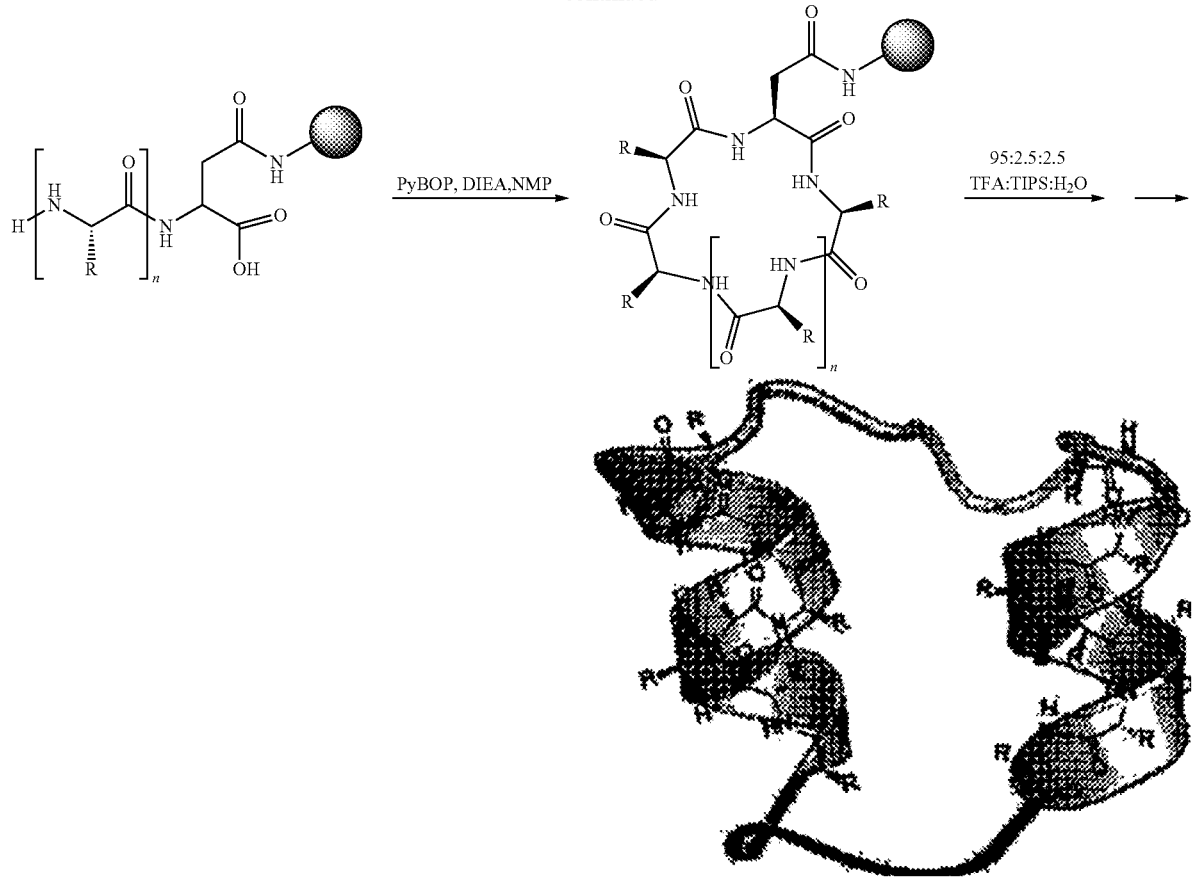

PEG RAM/resin 0.4 mmol/g was swelled in DMF and preloaded with Fmoc-Asp-OAllyl(1 eq), HBTU(1.5 eq), and diisopropylethylamine (1.5 eq) for 1 hour. The resin was then N-acetyl capped with 0.5 M acetic anhydride (2×5 mL) and the loading was modified to 0.2 mmol/g loading as assessed by % loading. Solid phase peptide synthesis was performed using standard Fmoc solid phase chemistry on a CEM® Liberty Peptide Synthesizer. The resin bearing the parent peptide was transferred to a fritted polypropylene SPE tube. Following N-terminal deprotection with 20% piperidine in NMP (2×5 mL) and washing with dichloromethane, methanol, and dimethylformamide (3×5 mL each), allyl deprotection was performed using Pd(PPh$_3$)$_4$ (3 eq) in a solution of chloroform: acetic acid: N-methylmorpholine (37:3:1). After 3 hours, the resin was washed again with dichloromethane, methanol and dimethylformamide (3×5 mL each). Addition of PyBOP (1.5 eq) and DIPEA (1.5 eq) yielded complete macrocyclization with no observed linear product. Peptides were cleaved from the resin using 95% trifluoroacetic acid, 2.5% TIPS, and 2.5% H$_2$O, and purified by reversed-phase HPLC (gradient 15-60 acetonitrile/water with 0.1% TFA over 60 min) and characterized by MALDI-TOF.

Example 4—Synthesis of Disulfide Coiled-Coil Mimic (AB-3)

Disulfide coiled-coiled mimic AB-3 was synthesized as shown in Scheme 3 below.

Scheme 3

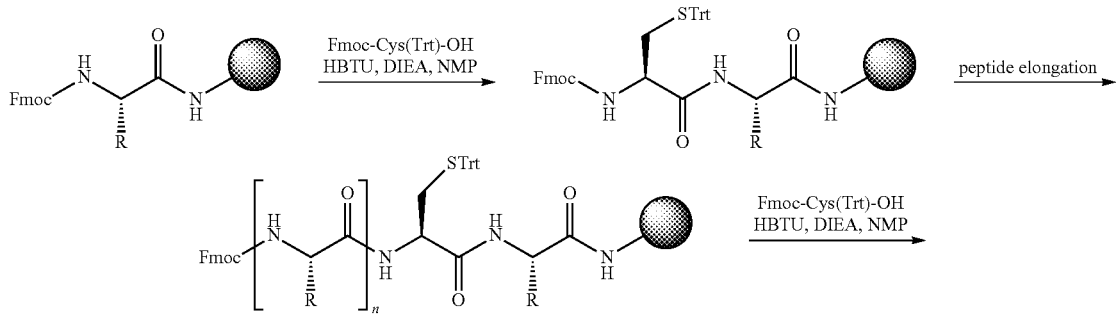

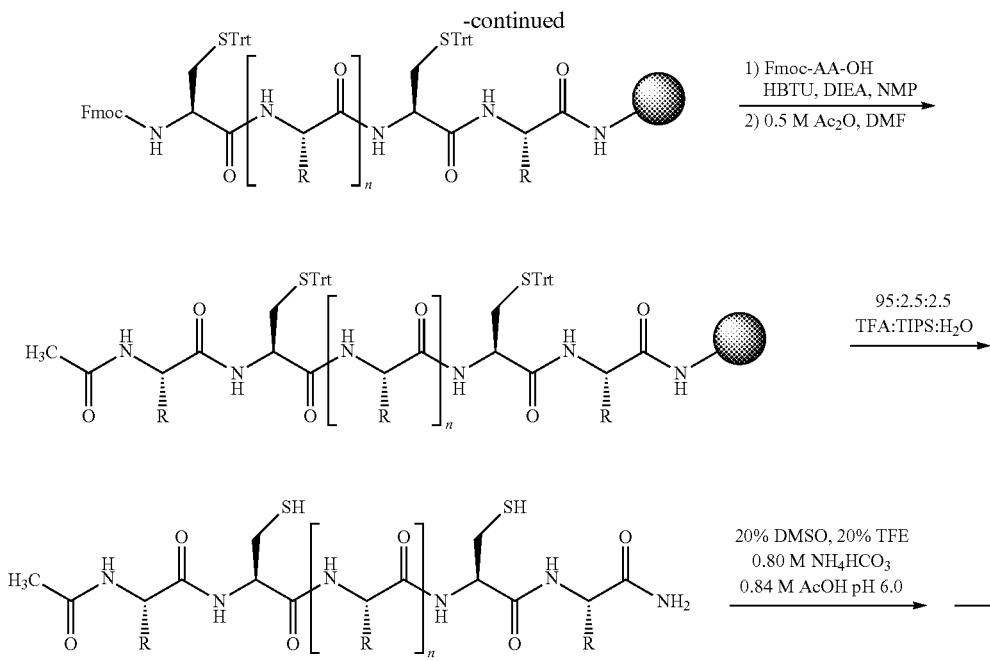

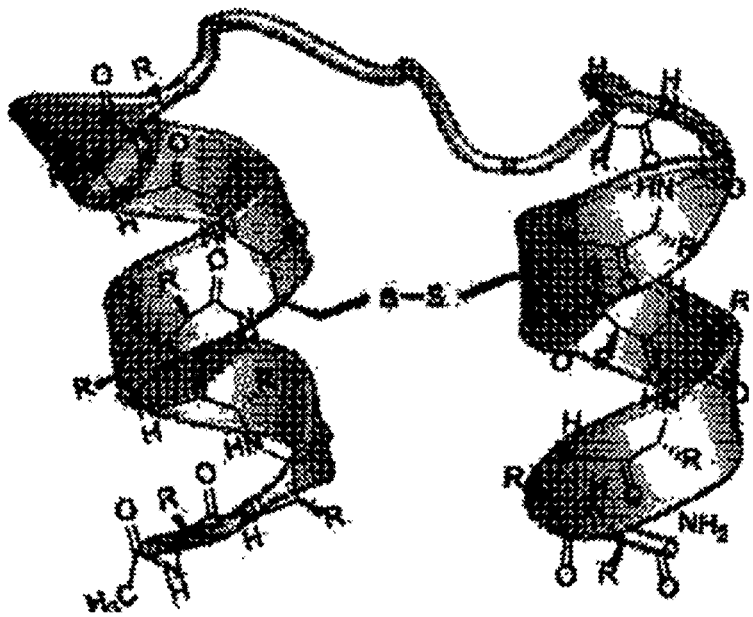

Parent peptide (0.25 mmol) was synthesized on a CEM® Liberty Peptide Synthesizer using standard Fmoc solid phase chemistry with Knorr Amide MBHA resin, and N-acetyl capped with 0.5 M acetic anhydride in DMF (2×5 mL), resulting in resin-bound coiled-coil mimic. The peptide was treated with a solution containing 95% trifluoroacetic acid, 2.5% TIPS, and 2.5% H₂O. After 3 hours, the reaction mixture was filter and concentrated in vacuo. The crude solid was precipitated with cold diethyl ether and dried under a stream of nitrogen gas. Peptides were purified by reversed-phase HPLC (gradient 15-60 acetonitrile/water with 0.1% TFA over 60 min), and after lyophiliziation yielded bisthiol as a white powder. The bis thiol was oxidized with 20% DMSO, 20% TFE in 0.8 M ammonium bicarbonate and 0.84 M acetic acid (pH 6.0), affording only intramolecular disulfide formation as monitored by MALDI-TOF (Tam et al., *J. Am. Chem. Soc.* 113:6657 (1991); Miller et al., *Proc. Natl. Acad. Sci. USA* 111:6636 (2014), which are hereby incorporated by reference in their entirety). 10-30 mg purified product recovered from 0.25 mmol scale.

Example 5—Synthesis of Crosslinked Helix Dimer Coiled-Coil Mimics (AB-4, AB-5, and AB-6))

Crosslinked helix dimer coiled-coiled mimic AB-4 was synthesized as shown in Scheme 4 below.

Scheme 4
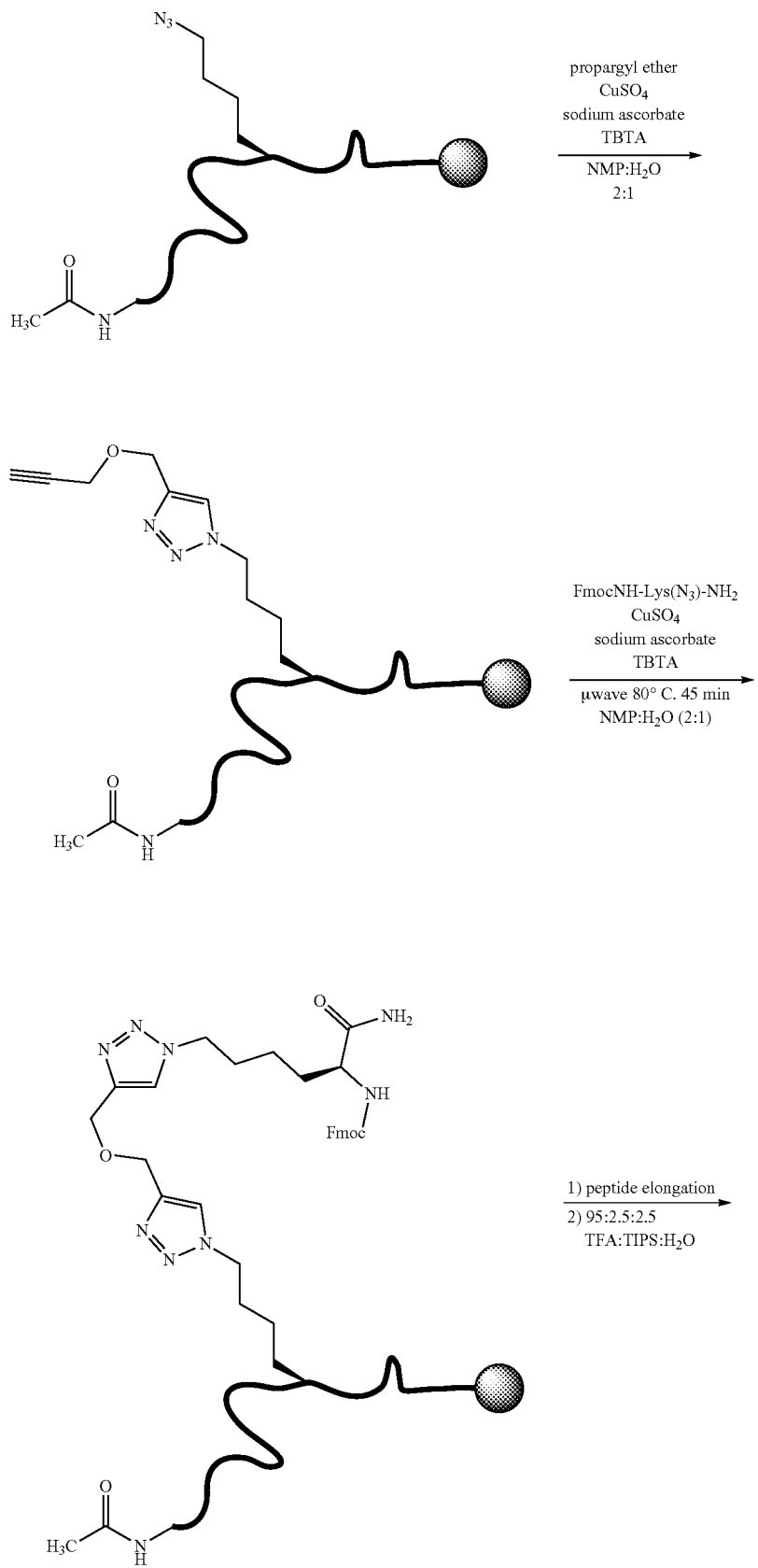

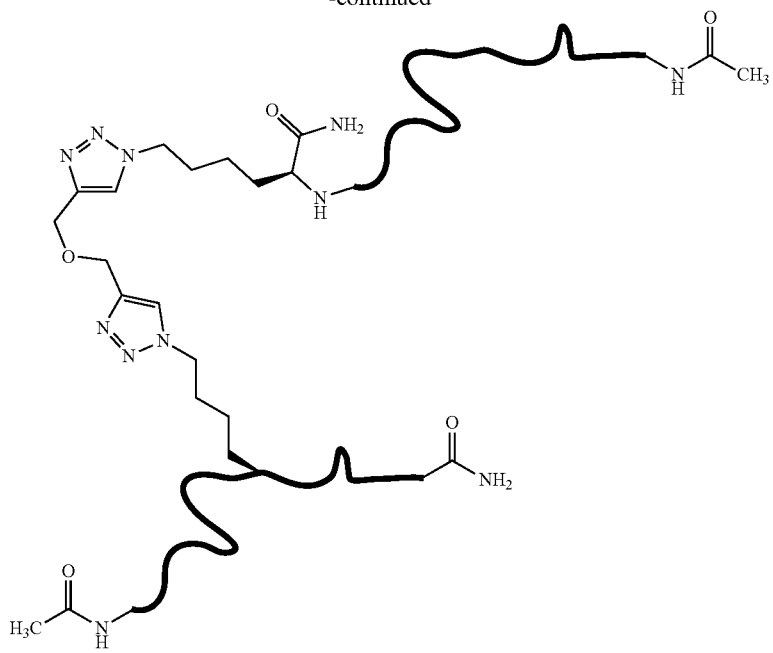

Parent peptide (0.25 mmol) was synthesized on a CEM® Liberty Peptide Synthesizer using standard Fmoc solid phase chemistry with Knorr Amide MBHA resin. The resin bearing the parent peptide was transferred to a fritted polypropylene SPE tube, washed, and transferred to a microwave tube. The resin was subsequently swelled in 3 mL of NMP and the bisalkyne propargyl ether (257 µL, 2.5 mmol, 10 eq) was added.

A solution of CuSO$_4$ (20 mg, 0.125 mmol, 0.5 eq) dissolved in 500 µL of water was separately prepared. To this solution, Tris[(1-benzyl-1H-1,2,3-triazol-4-yl)methyl]amine (132 mg, 0.25 mmol, 1 eq) dissolved in 1 mL of NMP was added. This mixture was added to a solution of sodium ascorbate (495 mg, 2.5 mmol, 10 eq) prepared in 1.5 mL of water. The resulting mixture was pipetted into the microwave tube containing propargyl ether and peptide. A magnetic stir bar was added, and the reaction mixture was subjected to microwave irradiation at 80° C. for 45 minutes, after which the resin was transferred to a fritted polypropylene SPE tube and washed with a 20 mM solution of sodium diethyldithiocarbamate in water (3×15 mL) followed by NMP (3×15 mL). A microcleavage of resin (95% trifluoroacetic acid, 2.5% TIPS, and 2.5% H$_2$O) showed the starting material to be consumed after one reaction.

Following the initial CuAAC reaction, the mono-triazole peptide was transferred to another microwave tube containing CuSO$_4$ (20 mg, 0.125 mmol, 0.5 eq), sodium ascorbate (149 mg, 0.75 mmol, 3 eq), Fmoc-azidolysine-NH$_2$ (294 mg, 0.75 mmol, 3 eq), and Tris[(1-benzyl-1H-1,2,3-triazol-4-yl)methyl]amine (132 mg, 0.25 mmol, 1 eq) in prepared solution as described above. The resulting reaction mixture was subjected to microwave irradiation at 80° C. for 45 minutes, after which the resin was transferred to a fritted polypropylene SPE tube and washed as described above. A microcleavage of resin (95% trifluoroacetic acid, 2.5% TIPS, and 2.5% H$_2$O) showed the starting material to be consumed after one reaction.

The resulting on-resin peptide was added to the CEM® Liberty microwave peptide synthesizer. The sequence was continued using standard Fmoc solid phase chemistry and N-acetyl capped with 0.5 M acetic anhydride in DMF (2×5 mL), resulting in resin-bound coiled-coil mimic. The peptide was treated with a solution containing 95% trifluoroacetic acid, 2.5% TIPS, and 2.5% H$_2$O. After 3 hours, the reaction mixture was filtered and concentrated in vacuo. The crude solid was precipitated with cold diethyl ether and dried under a stream of nitrogen gas. HPLC purification (gradient 15-60 acetonitrile/water with 0.1% TFA over 60 minutes) and lyophiliziation yielded peptide as a white powder, which was characterized by MALDI-TOF. CHD-peptides yield, sequence dependently, 20-40 mg of peptide from a 0.25 mmol scale.

AB-5 and AB-6 were synthesized in a similar manner.

Example 6—Synthesis of Crosslinked Helix Dimer$^{DS}$ Coiled-Coil Mimics

Crosslinked Helix Dimer$^{DS}$ Coiled-coil Mimics were synthesized as shown in Scheme 5 below.

Scheme 5
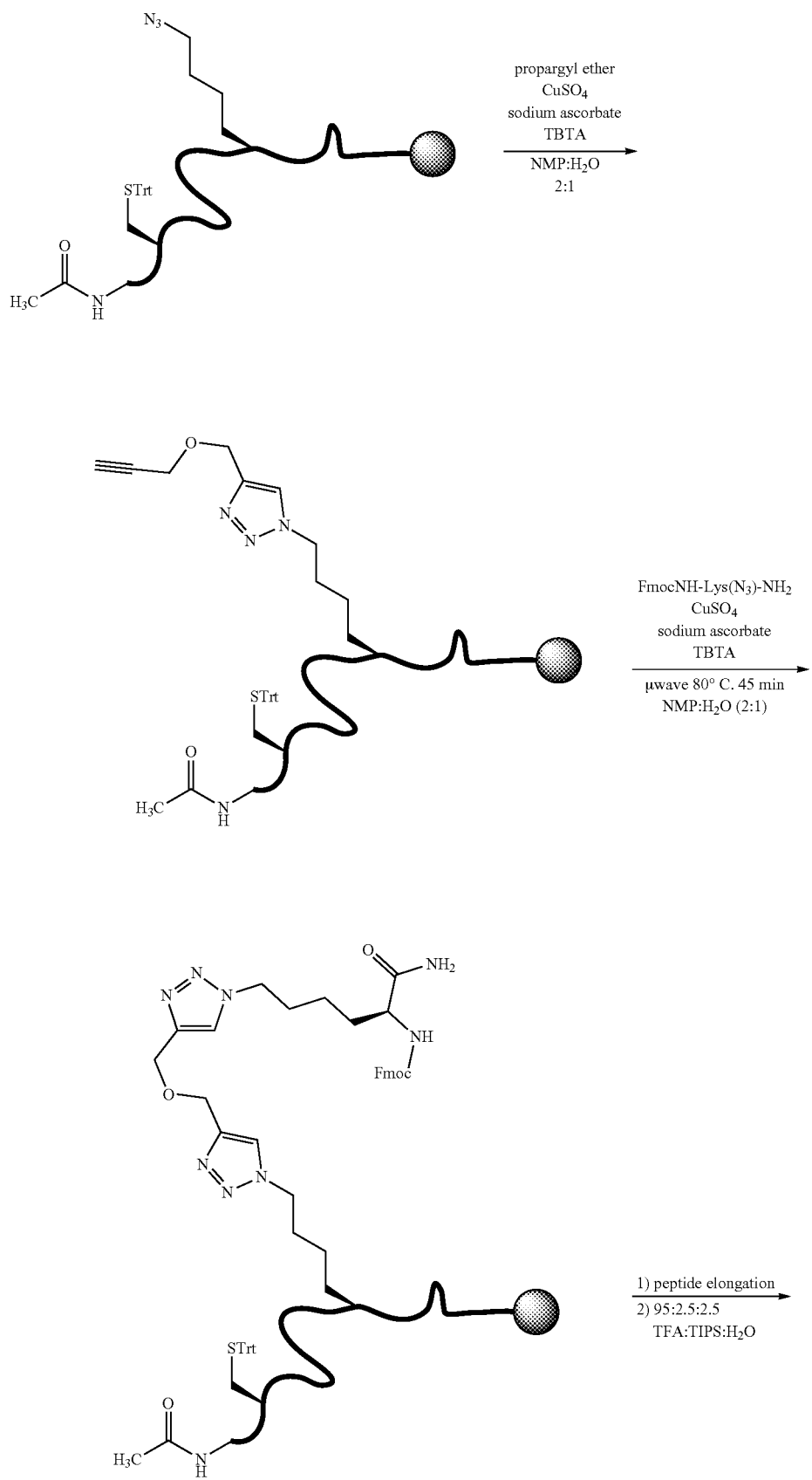

-continued

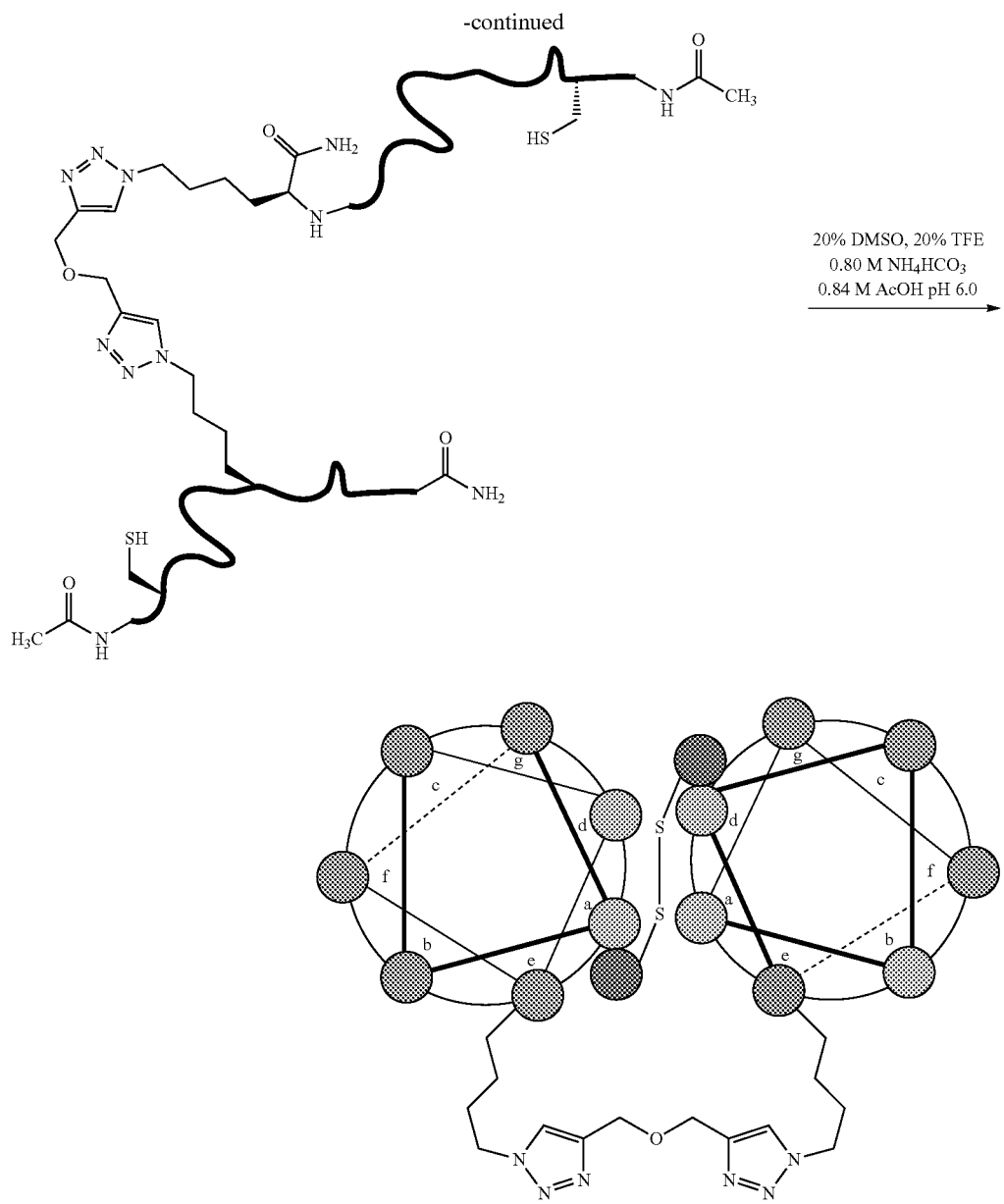

Parent peptide (0.25 mmol) was synthesized as described above where upon elongation, consecutive CuAAC reactions were implemented, and further elongated using standard Fmoc solid phase chemistry to afford the dithiol cross-linked helix dimer (CHD$^{DT}$). After N-acetyl capping with 0.5 M acetic anhydrided in DMF (2×5 mL), the CHD$^{DT}$-peptide was cleaved from resin using 94% trifluoroacetic acid, 2.5% 1,2-ethanedithiol, 2.5% H$_2$O, and 1% triisopropylsilane. The resulting peptide was precipitated with cold diethyl ether and dried under a stream of nitrogen gas. Crude peptide was purified by reversed-phase HPLC (gradient 15-60 acetonitrile/water with 0.1% TFA over 60 min), and after lyophilization yielded bisthiol as a white powder. The bisthiol was oxidized with 20% DMSO, 20% TFE in 0.8 M ammonium bicarbonate and 0.84 M acetic acid, pH 6.0 affording only intramolecular disulfide formation as monitored by MALDI-TOF (Tam et al., *J. Am. Chem. Soc.* 113:6657 (1991); Miller et al., *Proc. Natl. Acad. Sci. USA* 111:6636 (2014), which are hereby incorporated by reference in their entirety).

Example 7—Analytical HPLC and Mass Spectrometry

Figure 1:
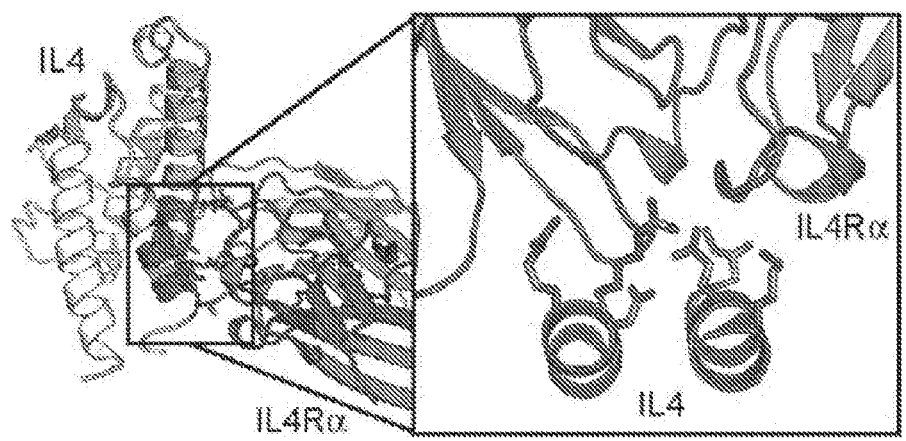
FIG. 1 shows an example of a protein complex that utilizes residues from both helices of a dimeric coiled-coil domain to target the partner protein. The model depicts the complex between IL-4 and IL-4 receptor alpha chain (PDB code 1IAR).
Figure 2A:
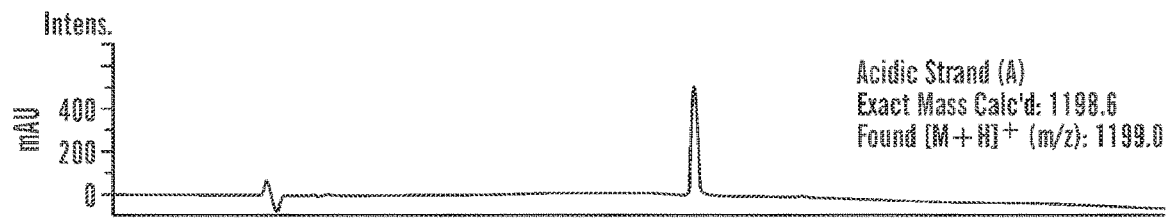
FIGS. 2A-P are analytical HPLC traces of peptide A (FIG. 2A), peptide B (FIG. 2B), constrained peptides AB-1, AB-2, and AB-3 (FIGS. 2C-E, respectively), coiled-coil mimics AB-4, AB-5, and AB-6 (FIGS. 2F-H, respectively), and NHR2 mimics CHD-NHR2-1, CHD-NHR2-2, CHD-NHR2-6, CHD-NHR2-7, CHD$^{DS}$-NHR2-3, CHD$^{DS}$-NHR2-4, CHD$^{DS}$-NHR2-5, and CHD$^{DT}$-NHR2-3 (FIGS. 2I-P, respectively).
Figure 2B:
Figure 2C:
Figure 2D:
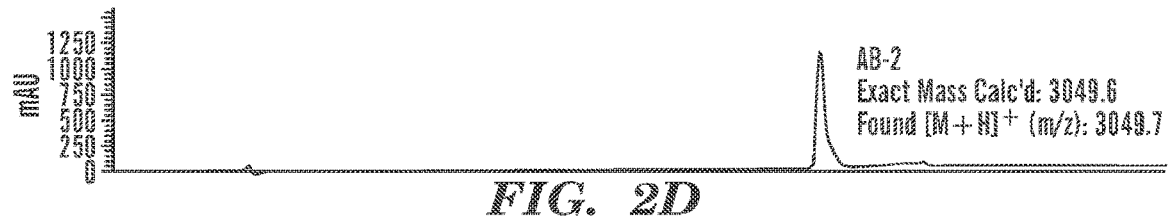
Figure 2E:
Figure 2F:
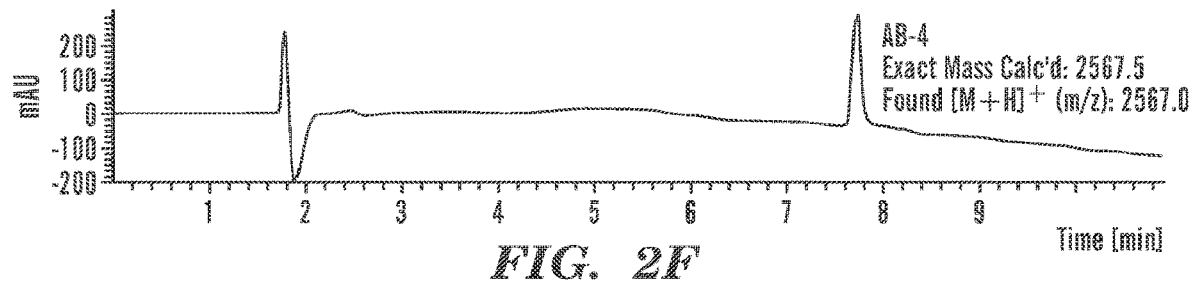
Figure 2G:
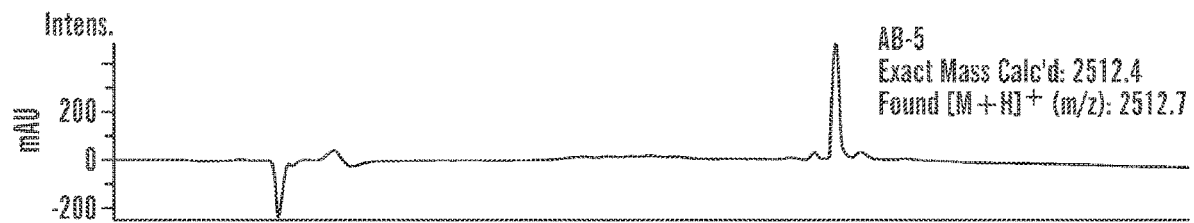
Figure 2H:
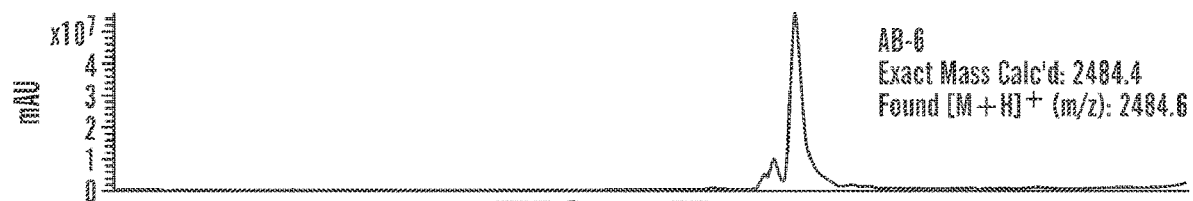
Figure 2I:
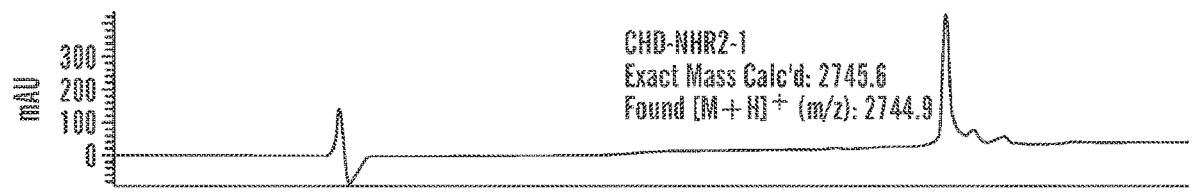
Figure 2J:
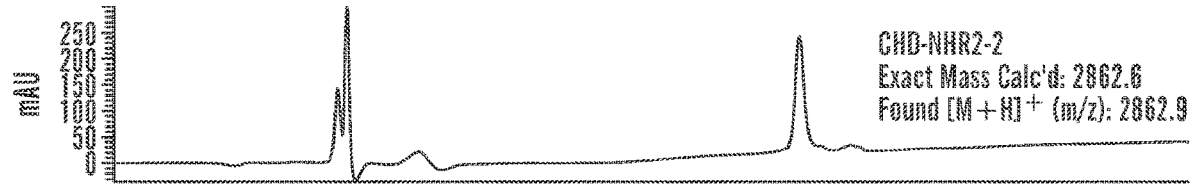
Figure 2K:
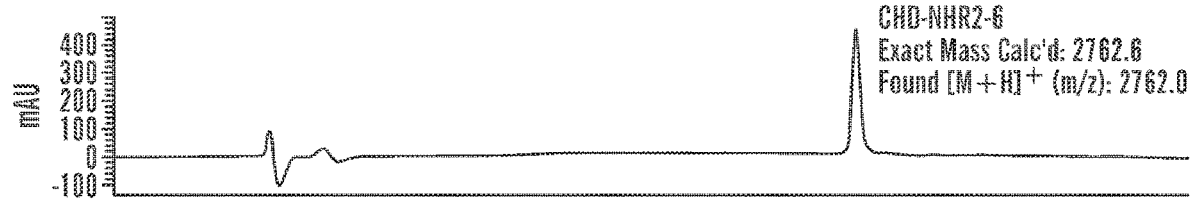
Figure 2L:
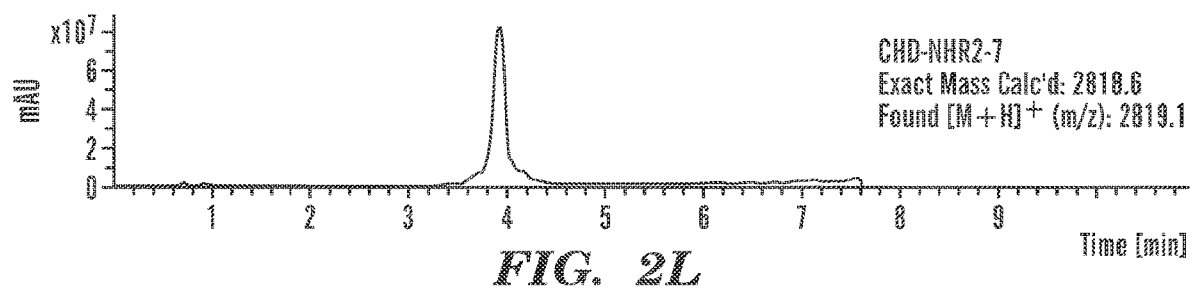
Figure 2M:
Figure 2N:
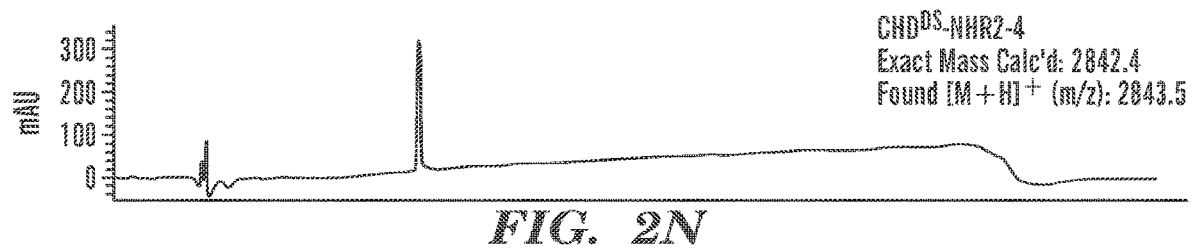
Figure 2O:
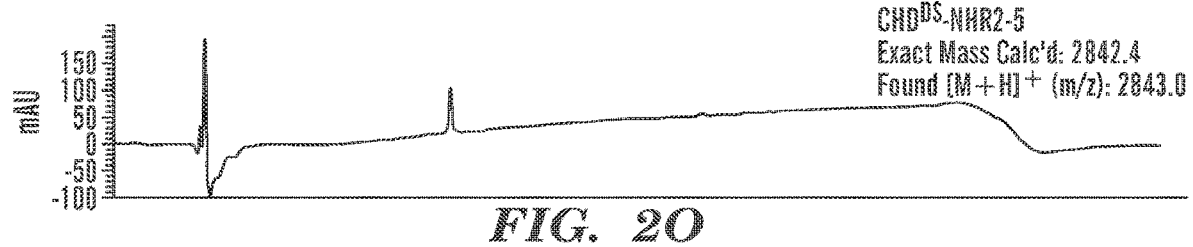
Figure 2P:
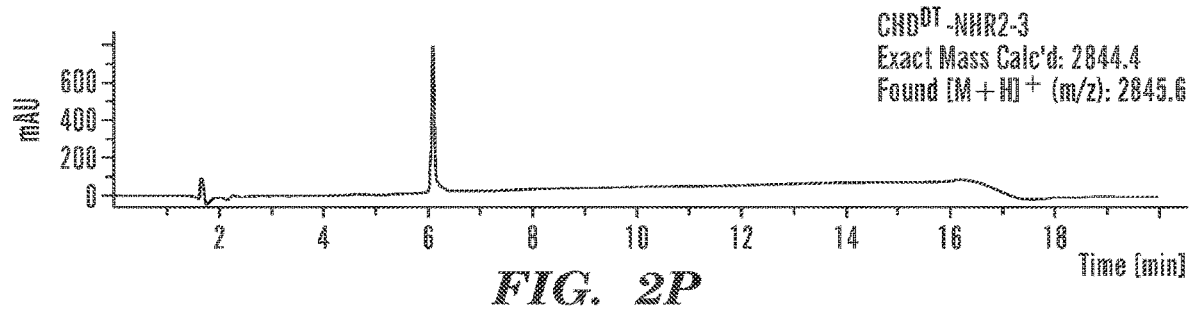

Analytical HPLC traces of peptides were obtained at 220 nm from a gradient of 10% B to 90% B over 10 min on an XTerra RP18 3.5 µm 2.1×150 mm column (Part No. 186000410); A: 0.1% aqueous TFA, B: acetonitrile; flow rate 400 µL/min. Exact masses were found using a Bruker Matrix-assisted laser desorption/ionization (MALDI-TOF) instrument. 10-30 mg purified product recovered from 0.25 mmol scale. See FIGS. 2A-2P.

Example 8—CD Spectroscopy

CD spectra were recorded on an AVIV 202SF CD spectrometer equipped with a temperature controller using 1 mm length cells and a scan speed of 5 nm/min. The spectra were averaged over 8 scans with the background subtracted according to the analogueous experimental conditions. Each sample was prepared in a 50 mM potassium fluoride solution in water (pH 7.4) with a final concentration of 20 µM. The concentrations of each peptide was determined by the UV absorption of tryptophan residues at 280 nm. See FIGS. 3A-3B.

Example 9—NMR Spectroscopy

Figure 4:
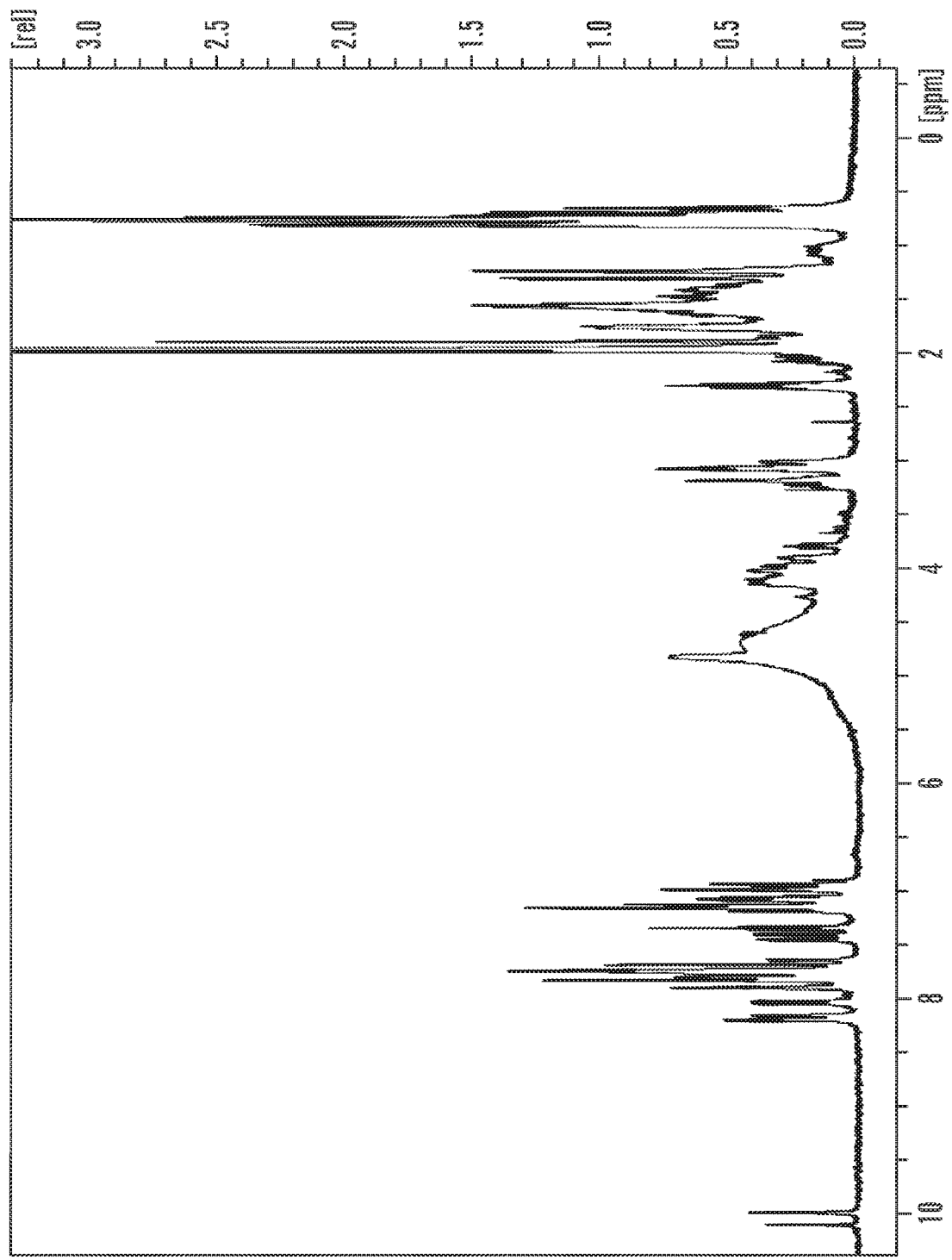
FIG. 4 is the $^1$H NMR spectrum of AB-4.

All experiments were carried out on a Bruker Avance 600 MHz spectrometer at 25° C. A 500 µM solution of AB-4 was prepared in 400 µL of 10% $d_3$-$CH_3CN$ in $H_2O$ with 0.1% trifluoroacetic acid (pH=5). Proton NMR, TOCSY, and NOESY spectra were used to assign amide protons (see Table 2 and Table 3 below). Solvent supression was achieved with a 3919 Watergate pulse sequence. All 2D spectra were recorded by collecting 4092 complex data points in the t2 domain by averaging 64 scans and 128 increments in the t1 domain with the States-TPPI mode. TOCSY experiments were performed with a mixing time of 80 ms, while NOESY experiments were performed with a mixing time of 300 ms. All NMR data were processed and analyzed using the Bruker TOPSPIN program. The original free induction decays were zero-filled to give a final matrix of 2048 by 2048 real data points. A 90 sine-squared window function was applied in both dimensions. Nucleaver Overhauser effect (NOE) cross-peaks are listed in Table 3 below. See FIG. 4 (HNMR), FIG. 5A (NOESY amide), FIG. 6 (NOESY fingerprint), and FIG. 5B (TOCSY amide to side chain).

TABLE 2

$^1$H NMR assignments and chemical shifts (δ, ppm) for AB-4 (298 K) in 10% d3-$CH_3CN$ in $D_2O$ (pH 5), and calculated dihedral angles, Φ, derived from $^3J_{NHC\alpha H}$ coupling constants.

| Residue | Φ° | NH | Hα | Hβ | Hγ | Hδ | Hε |
|---|---|---|---|---|---|---|---|
| E (A1) | −53.86 | 7.824 | 4.10 | N/A | N/A | N/A | N/A |
| L (A2) | −52.67 | 8.217 | 4.15 | 1.89 | N/A | 0.756 | N/A |
| A (A3) | −52.67 | 8.06 | 4.03 | 1.54 | N/A | N/A | N/A |
| E (A4) | −55.60 | 7.907 | 3.97 | 1.96 | 2.31 | N/A | N/A |
| L (A5) | −57.84 | 7.75 | 4.03 | 1.58 | N/A | N/A | N/A |
| Z (A6) | −52.07 | 7.16 | 4.06 | 1.76 | 1.57 | N/A | 3.08 |
| W (A7) | −51.47 | 7.65 | 4.48 | 3.19 | N/A | N/A | N/A |
| R (A8) | −57.29 | 7.85 | 3.9 | 1.58 | 1.04 | N/A | N/A |
| L (A9) | −52.67 | 7.818 | 4.10 | 1.44 | 1.39 | 1.38δ | 1.29δ |
| L (B1) | −55.60 | 7.76 | 3.80 | 2.05 | 1.41 | 1.04 | N/A |
| W (B2) | −55.60 | 7.91 | 4.38 | 3.19 | N/A | N/A | N/A |
| E (B3) | −56.73 | 8.18 | 3.98 | N/A | N/A | N/A | N/A |
| R (B4) | −52.07 | 7.143 | 4.04 | N/A | N/A | N/A | N/A |
| I (B5) | −53.27 | 7.77 | 3.92 | 1.76 | N/A | 0.74 | N/A |
| A (B6) | −55.60 | 8.03 | 3.97 | 1.24 | N/A | N/A | N/A |
| R (B7) | −55.60 | 8.2 | 4.12 | N/A | N/A | N/A | N/A |
| L (B8) | −49.62 | 7.78 | 4.13 | 1.60 | N/A | 0.76 | N/A |
| Z (B9) | −58.38 | 7.1 | 4.04 | 1.66 | 1.39 | N/A | 3.5 |

$^3J_{NHC\alpha H}$ coupling constants were obtained from TOCSY spectrum (Wang et al., *J. Biomol. NMR* 10: 373 (1997), which is hereby incorporated by reference in its entirety).
φ angles were calculated by applying the Pardi parameterized Karplus equation (Pardi et al., *J. Mol. Biol.* 180: 741 (1984), which is hereby incorporated by reference in its entirety).

TABLE 3

Observed NOE crosspeaks from NOESY spectra of AB-4.

| Residue | | Chemical shift, ppm | | |
|---|---|---|---|---|
| Atom 1 | Atom 2 | Atom 1 | Atom 2 | NOE intensity |
| E(A1)-NH | E(A1)-Hα | 7.82 | 4.10 | strong |
| E(A1)-Hα | L(A5)-Hβ | 4.10 | 1.58 | weak |

TABLE 3-continued

Observed NOE crosspeaks from NOESY spectra of AB-4.

| Residue | | Chemical shift, ppm | | |
|---|---|---|---|---|
| Atom 1 | Atom 2 | Atom 1 | Atom 2 | NOE intensity |
| L(A2)-NH | L(A2)-Hα | 8.216 | 4.15 | strong |
| L(A2)-Hα | L(A2)-Hβ | 4.15 | 1.89 | medium |
| L(A2)-Hα | A(A3)-Hβ | 4.15 | 1.54 | weak |
| L(A2)-Hα | L(A2)-Hβ | 4.15 | 1.898 | weak |
| A(A3)-NH | A(A3)-Hα | 8.06 | 4.12 | strong |
| A(A3)-NH | Z(A6)-Hα | 8.06 | 4.06 | weak |
| A(A3)-NH | E(A4)-Hα | 8.06 | 4.06 | medium |
| A(A3)-NH | A(A3)-Hβ | 8.06 | 1.54 | medium |
| E(A4)-NH | E(A4)-Hα | 7.907 | 4.06 | strong |
| E(A4)-NH | E(A4)-Hγ | 7.907 | 2.31 | weak |
| E(A4)-NH | E(A4)-Hβ | 7.907 | 1.96 | strong |
| E(A4)-Hα | E(A4)-Hβ | 4.06 | 1.96 | strong |
| L(A5)-NH | L(A4)-Hα | 7.75 | 4.03 | strong |
| L(A5)-Hα | I(B5)-Hβ | 4.03 | 1.76 | weak |
| Z(A6)-NH | Z(A6)-Hα | 7.16 | 4.06 | strong |
| Z(A6)-Hα | Z(A6)-Hβ | 4.06 | 1.758 | medium |
| Z(A6)-Hα | Z(A6)-Hε | 4.06 | 3.08 | strong |
| W(A7)-NH | W(A7)-Hα | 7.65 | 4.48 | strong |
| W(A7)-NH | R(A8)-Hα | 7.65 | 3.9 | medium |
| W(A7)-Hα | W(A7)-Hβ | 4.48 | 3.19 | strong |
| R(A8)-NH | R(A8)-Hα | 7.85 | 4.48 | strong |
| R(A8)-NH | L(A9)-Hα | 7.85 | 3.9 | medium |
| R(A8)-NH | R(A8)-Hγ | 7.85 | 1.04 | medium |
| R(A8)-NH | R(A8)-Hβ | 7.85 | 1.58 | medium |
| L(A9)-NH | L(A9)-Hα | 7.82 | 4.10 | strong |
| L(A9)-NH | L(B1)-Hα | 7.82 | 3.8 | weak |
| L(A9)-NH | L(A9)-Hβ | 7.82 | 1.44 | medium |
| L(A9)-NH | L(A9)-Hγ | 7.82 | 1.41 | strong |
| L(A9)-NH | L(A9)-Hδ | 7.82 | 1.38 | medium |
| L(A9)-Hδ | L(B1)-Hγ | 1.38 | 1.04 | weak |
| L(A9)-Hα | I(B5)-Hβ | 4.10 | 1.758 | weak |
| L(B1)-NH | L(B1)-Hα | 7.76 | 3.8 | strong |
| L(B1)-NH | W(B2)-Hα | 7.76 | 3.19 | strong |
| L(B1)-NH | L(B1)-Hβ | 7.76 | 2.05 | weak |
| L(B1)-NH | L(B1)-Hγ | 7.76 | 1.41 | strong |
| L(B1)-NH | L(B1)-Hδ | 7.76 | 1.04 | medium |
| L(B1)-Hα | I(B5)-Hβ | 3.80 | 1.758 | weak |
| L(B1)-Hγ | L(B1)-Hδ | 1.41 | 1.04 | medium |
| W(B2)-NH | W(B2)-Hα | 7.91 | 4.38 | strong |
| W(B2)-NH | E(B3)-Hα | 7.91 | 3.98 | medium |
| W(B2)-NH | W(B2)-Hβ | 7.91 | 3.19 | strong |
| E(B3)-NH | E(B3)-Hα | 8.18 | 3.98 | medium |
| E(B3)-NH | A(B6)-Hα | 8.18 | 8.03 | weak |
| E(B3)-Hα | A(B6)-Hα | 3.98 | 1.24 | weak |
| R(B4)-NH | R(B4)-Hα | 7.143 | 4.04 | strong |
| R(B4)-Hα | I(B5)-Hβ | 4.04 | 1.76 | weak |
| I(B5)-NH | I(B5)-Hα | 7.77 | 3.92 | strong |
| I(B5)-NH | A(B6)-Hα | 7.77 | 3.97 | medium |
| I(B5)-NH | I(B5)-Hβ | 7.77 | 1.76 | strong |
| I(B5)-NH | A(B6)-Hβ | 7.77 | 1.04 | strong |
| I(B5)-Hβ | I(B5)-Hδ | 1.76 | 0.74 | weak |
| I(B5)-Hα | L(B1)-Hβ | 3.92 | 2.05 | weak |
| A(B6)-NH | A(B6)-Hα | 8.03 | 3.97 | strong |
| A(B6)-NH | A(B6)-Hβ | 8.03 | 1.24 | strong |
| A(B6)-Hα | A(B6)-Hβ | 3.97 | 1.24 | weak |
| R(B7)-NH | R(B7)-Hα | 8.20 | 4.12 | strong |
| R(B7)-Hα | R(B7)-Hβ | 4.12 | 1.58 | weak |
| L(B8)-NH | L(B8)-Hα | 7.78 | 4.13 | strong |
| L(B8)-NH | L(B8)-Hβ | 7.78 | 1.60 | weak |
| L(B8)-NH | L(B8)-Hδ | 7.78 | 0.77 | weak |
| L(B8)-Hβ | L(A1)-Hδ | 1.60 | 0.756 | weak |
| L(B8)-Hα | Z(B9)-HHβ | 4.13 | 1.66 | weak |
| Z(B9)-NH | Z(B9)-Hα | 7.1 | 4.04 | strong |

Example 10—NMR Structure Calculation

The solution NMR structure of AB-4 was computed using Monte Carlo conformational search in Macromodel 2015. The Merck Molecular Force Field (MMFF) was applied to the AB-4 peptide with water as an explicit solvent. A total of 70 conformers were obtained using 65 NOESY and 18 dihedral angle (Φ) constraints. The 20 lowest energy structures show minimal overall deviation from each other. Distance constraints were implemented in the structural model according to observed NOE crosspeaks: strong (2.5 Å), medium (4.0 Å), and weak (5.5 Å). The $^3J_{NHCH\alpha}$ coupling constants were used to calculate the Φ angles from the Karplus equation.

Example 11—Protein Expression and Purification

GST-labeled NHR2 protein was expressed and purified as previously reported (Sun et al., Nature 500:93 (2013); Bartel et al., Biomed. Res. Int. 2013:297692 (2013), which are hereby incorporated by reference in their entirety). The pGEX4T-3-NHR2 fusion vector was transformed into BL21 (DE3) competent E. coli (Novagen) in LB media. Protein production was induced with 1 mM IPTG at $OD_{600}$ of 0.75 for 4 hours at 25° C. Production of the desired GST-NHR2 fusion product was verified by SDS-PAGE. Cells were harvested and resuspended in lysis buffer (50 mM Tris pH 7.5, 150 mM NaCl, 0.05% TritonX 100) with 10 mg/mL Leupeptin A, 1 mg/mL Pepstatin A, 500 μM PMSF, 1 mM DTT, and 0.5% glycerol (Sigma). Cell pellets were lysed via sonication and centrifuged at 4° C. at 5,000 rpm for 40 minutes. The bacterial supernatant was poured over pre-equilibrated glutathione Sepharose beads (G-Biosciences) and allowed to bind for 1 hour at 25° C. Nonspecific binding proteins were removed from resin using washed buffer (100 mM Tris pH 8.0, 0.5% glycerol, 1 mM DTT), and the fusion protein GST-NHR2 was eluted with buffer (100 mM Tris pH 8.0, 0.5% glycerol, 1 mM DTT, 10 mM glutathione). Purity was assessed using SDS-PAGE.

Example 12—Peptide Binding Assay

The relative affinity of native GST-tagged NHR2 protein and CHD-NHR2 peptides was determined using a fluorescence polarization based direct binding assay with fluorescein-labeled N2B peptide, flu-N2B (see FIG. 7). The polarization experiments were performed with a DTX 880 Multimode Detector (Beckman) at 25° C., with excitation and emission wavelengths at 485 and 525 nm, respectively. Each binding experiment was prepared in 96-well plates in assay buffer: 10 mM Tris 20 mM NaCl pH=7.4 with 0.1% pluronic F-68 (Sigma). The binding affinity ($K_D$) values reported for each CHD peptide and GST-NHR2 were performed in triplicate, and were determined by fitting the experimental data to a sigmoidal dose-response nonlinear regression model in GraphPad Prism 6.0.

Figure 8:
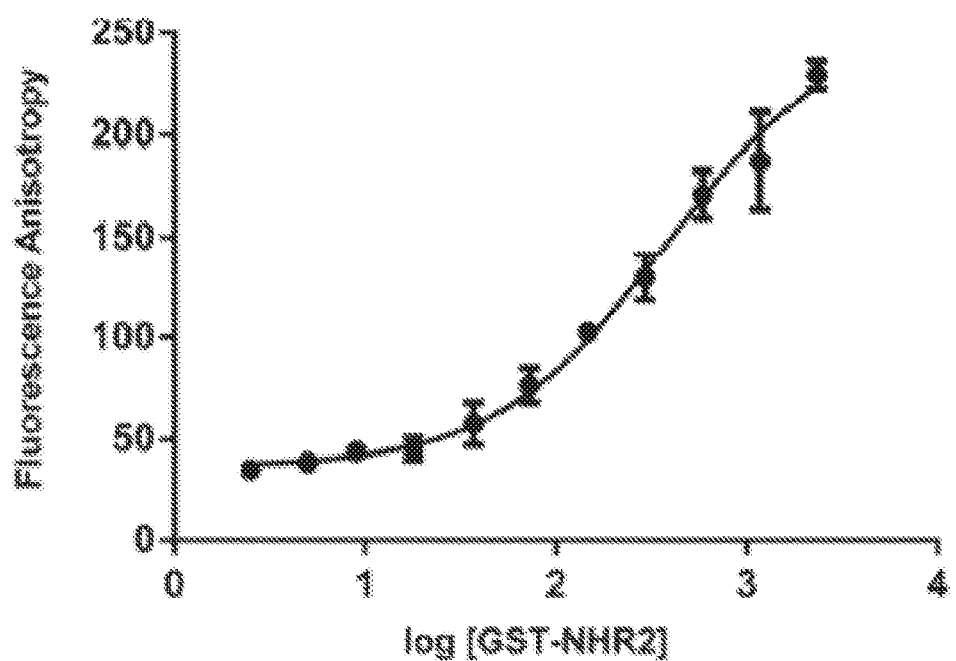
FIG. 8 is the saturation binding curve of NR$_{482-551}$ with flu-N2B. K$_D$=363±60 M. Literature reported: 380±18 M (Sun et al., *Nature* 500:93 (2013), which is hereby incorporated by reference in its entirety).
Figure 9A:
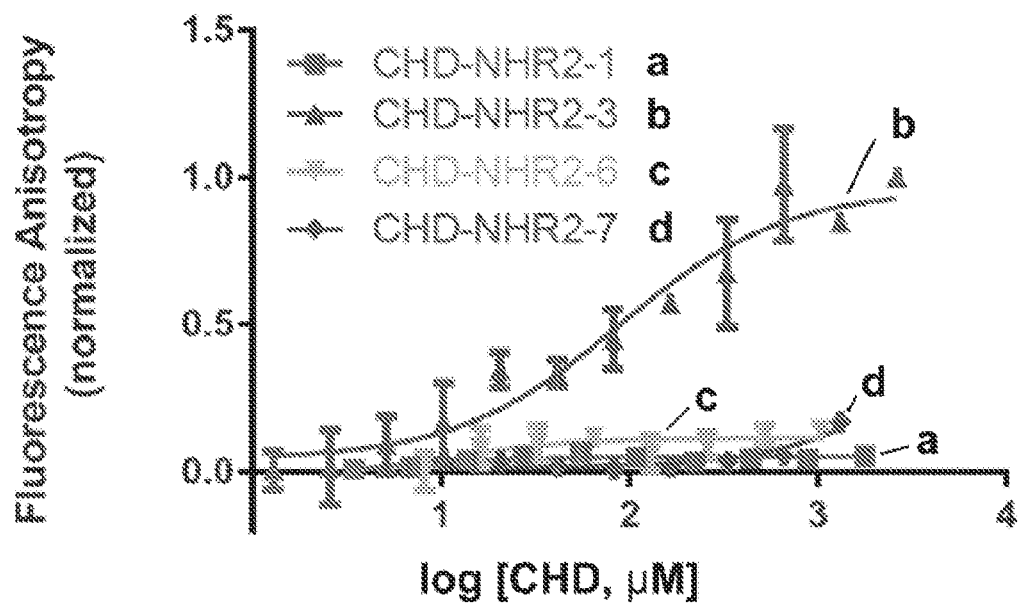
FIGS. 9A-B are graphs of the saturation binding of flu-N2B with designed CHD mimetics and a native control.
Figure 9B:
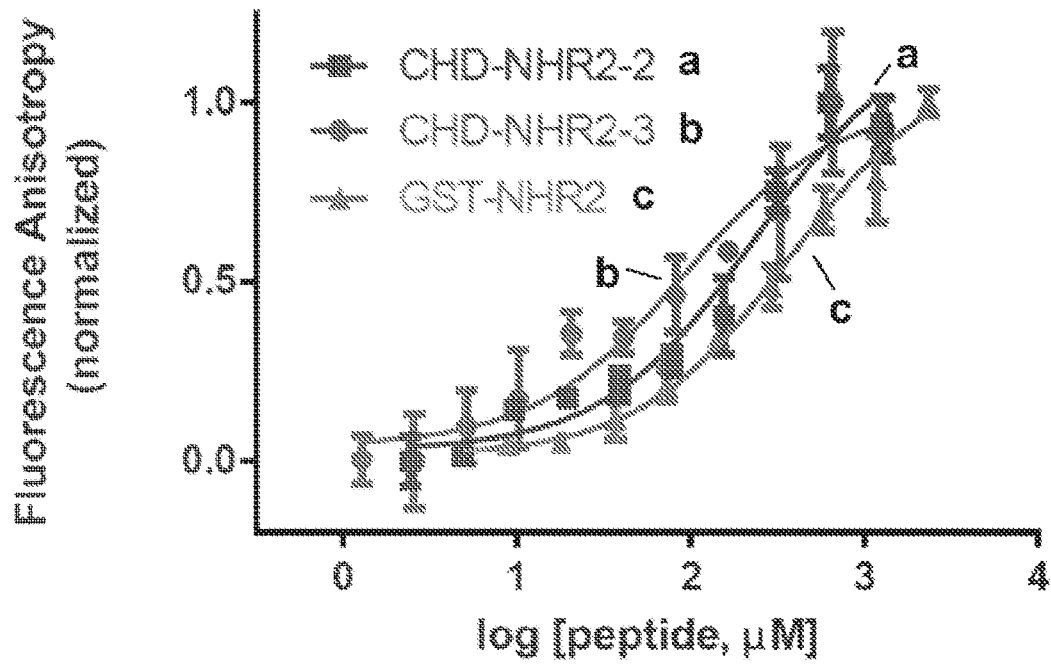
Figure 10D:
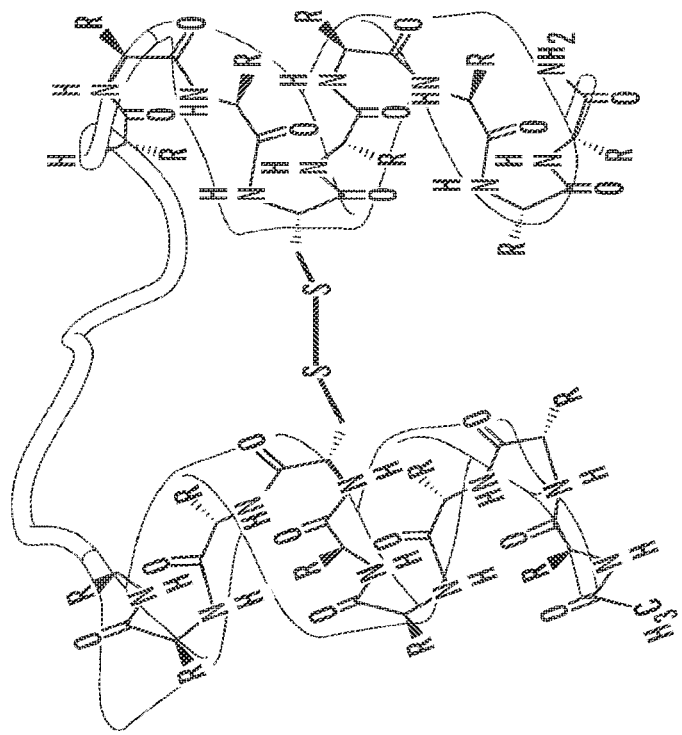

The affinity of flu-N2B for its native partner GST-NHR2 was first determined. Addition of serially diluted concentrations of GST-NHR2 from 2.35 mM to 2.5 M into 100 nM of flu-N2b in assay buffer afforded the saturation binding curve (FIG. 8) in agreement with previously reported results (Sun et al., Nature 500:93 (2013), which is hereby incorporated by reference in their entirety). The affinity of flu-N2b for each CHD-NHR2 peptide was prepared in the same manner (FIGS. 9A-B). $K_D$ was calculated using equation 1 below.

$$K_D=(R_T\times(1-F_{SB})+L_{ST}\times F_{SB}^2)/F_{SB}-L_{ST})\quad 1$$

where,
$R_T$=Total concentration of NHR2
$L_{ST}$=Total concentration of fluorescent peptide
$F_{SB}$=Fraction of bound fluorescent peptide Example 13—Evaluation of Four General Strategies for Coiled-Coil Stabilization Coiled-coils consist of heptad repeats with critical hydrophobic contacts at the a and d positions and ionic residues at the e and g positions. It was hypothesized that a helix capable of a minimum of three a/d hydrophobic contacts (or 1.5 heptads) provides a reasonable starting point for development of minimal coiled-coil mimics. It was postulated that strategies that stabilize such short helix dimers would also be applicable for longer chains since coiled-coil stability increases with number of contacts (Lau et al., J. Biol. Chem. 259:13253 (1984), which is hereby incorporated by reference in its entirety). Short, helical dimers can project side chains for biomolecular recognition only if individual helices are packed against each other (Crick, Acta Crystallographica 6:689 (1953), which is hereby incorporated by reference in its entirety). Four different approaches for the de novo design of minimal coiled-coil mimics for the stabilization of a model sequence were envisioned (FIGS. 10B-10E). The model sequence incorporates favorable hydrophobic residues at a/d positions as well as judicioulsly placed inter- and intrastrand ionic interactions to enhance both the helix and the dimer stability. A hydrophobic interface following the recently described design rules for vertical triads was created (Hadley et al., Proc. Nat. Acad. Sci. USA 105:530 (2008), which is hereby incorporated by reference in its entirety). Gellman and Woolfson and coworkers suggest that placement of Leu-Ile-Leu residues at a-a'-a positions contributes significantly to helical dimer stability because of optimal packing interactions (Hadley et al., Proc. Natl. Acad. Sci. USA 105:530 (2008), which is hereby incorporated by reference in its entirety). Intra- and inter-helical salt bridges were positioned at appropriate positions to enhance stability of coiled-coiled assemblies (Burkhard et al., Trends Cell Biol. 11:82 (2001); Woolfson, Adv. Protein Chem. 70:79 (2005); Mason et al., ChemBiochem 5:170 (2004), which are hereby incorporated by reference in their entirety). These design considerations led to peptide sequences A: Ac-ELAELEWRL-$NH_2$ (SEQ ID NO:1) and B: Ac-LWERIARLR-$NH_2$(SEQ ID NO:2). Potential inter- and intrastrand interactions between A and B in the context of an antiparallel coiled-coil are depicted in FIG. 10A.

Seminal work investigating the stabilities of minimal, de novo-designed coiled-coils suggests that designed peptides (A and B) would not spontaneously assemble in aqueous solution (Lau et al., J. Biol. Chem. 259:13253 (1984); Burkhard et al., Protein Sci. 9:2294 (2000), which are hereby incorporated by reference in their entirety), because (a) short peptides do not adopt stable helical conformations (Scholtz et al., FASEB J. 6:A345 (1992); Zimm et al., J. Chem. Phys. 31:526 (1959), which are hereby incorporated by reference in their entirety) and (b) short helices do not create enough contacts to favor dimer assembly. Circular dichroism spectroscopy was used to assess the conformational stability of peptides. CD provides a distinct signature for α-helices with a maximum near 190 nm and minima at 208 and 222 nm (Kallenbach et al., in CIRCULAR DICHROISM AND THE CONFORMATIONAL ANALYSIS OF BIOMOLECULES 201-260 (Gerald D. Fasman ed., 1996), which is hereby incorporated by reference in its entirety). The relative helicity of peptides is typically estimated by the mean residue ellipticity at 222 nm (Kallenbach et al., in CIRCULAR DICHROISM AND THE CONFORMATIONAL ANALYSIS OF BIOMOLECULES 201-260 (Gerald D. Fasman ed., 1996); Manning et al., Biopolymers 31:569 (1991), which are hereby incorporated by reference in their entirety), although these estimates are often not accurate for short helices (Shepherd et al., J. Am. Chem. Soc. 127:2974 (2005); Chin et al., Proc. Natl. Acad. Sci. U.S.A. 99:15416 (2002); Wang et al., J. Am. Chem. Soc. 128:9248 (2006), which are hereby incorporated by reference in their entirety).

Figure 3A:
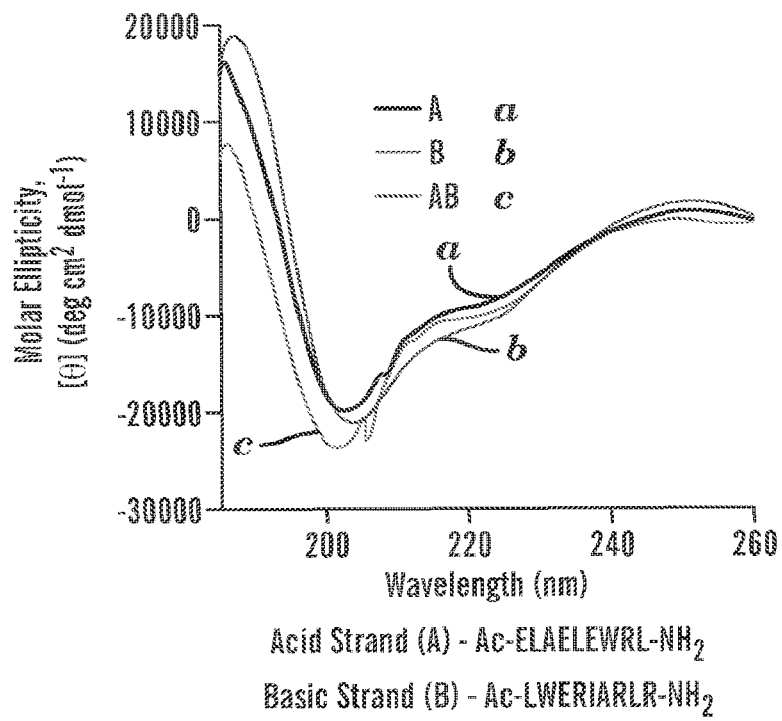
FIGS. 3A-B show CD spectra of unconstrained peptides A (SEQ ID NO:1) and B (SEQ ID NO:2), equimolar mixture of A and B peptides (FIG. 3A), and constrained peptides AB-1 (SEQ ID NO:3), AB-2 (SEQ ID NO:4), and AB-3 (SEQ ID NO:5) (FIG. 3B). CD spectra were acquired in 50 mM aqueous KF, pH 7.4.

The ratio of the 222 and 208 nm bands offers an additional gauge of α-helicity. The origin and effect of peptide sequence on this ratio remains ill-defined (Kallenbach et al., in CIRCULAR DICHROISM AND THE CONFORMATIONAL ANALYSIS OF BIOMOLECULES 201-260 (Gerald D. Fasman ed., 1996), which is hereby incorporated by reference in its entirety), but a ratio of ≥1 is expected of stable α-helices (Wallimann et al., J. Am. Chem. Soc. 125:1203 (2003), which is hereby incorporated by reference in its entirety). CD results displayed nonhelical signatures for each individual peptide (A and B), and their equimolar mixture at 20 M concentration (FIG. 3A).

The potential of four synthetic strategies to create conformationally defined coiled-coil mimics was evaluated (FIGS. 10B-10E). The minimal mimetic design was built on the following key hypotheses: (a) stabilization of individual helices will enhance stability of the dimeric assembly, and coil formation in an attached peptide can be nucleated with a preformed helix (Torres et al., ChemBiochem 9:1701 (2008); Houston et al., J. Mol. Biol. 262:270 (1996); Litowski et al., J. Biol. Chem. 277:37272 (2002), which are hereby incorporated by reference in their entirety). (b) Macrocyclization of the dimeric scaffold would aid interpeptide contacts and helix formation. (c) Noncovalent interhelical contacts can be strengthened by substitution with covalent bonds (Patgiri et al., Acc. Chem. Res. 41:1289 (2008); Zhou et al., Biochemistry 32:3178 (1993); Haney et al., Chemistry 19:11342 (2013), which are hereby incorporated by reference in their entirety). Each of these models was systematically evaluated. Studies revealed that replacement of an interhelical ionic bond with a covalent bond provides a general and versatile approach for stabilization of short helix dimers. The constrained, antiparallel coiled-coil mimics were extensively characterized by circular dichroism (CD) and 2D NMR spectroscopies, and then the design was applied to the modulation of a PPI involved in leukaemogenesis, where complex formation depends on coiled-coil assembly.

Figure 3B:
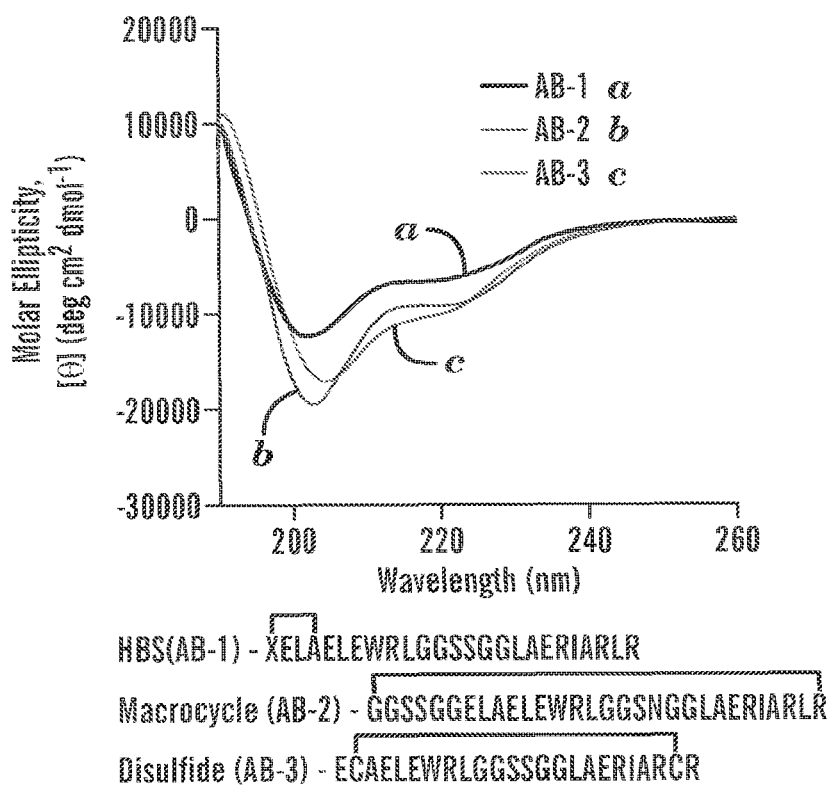

Whether a preformed helix could nucleate helical conformation in an attached peptide was first determined. The hydrogen bond surrogate (HBS) (Wallimann et al., J. Am. Chem. Soc. 125:1203 (2003); Patgiri et al., Acc. Chem. Res. 41:1289 (2008), which are hereby incorporated by reference in their entirety) strategy was utilized to stabilize the helical conformation in peptide A, and a GGSSGG (SEQ ID NO:20) linker (Hadley et al., Proc. Natl. Acad. Sci. USA 105:530 (2008), which is hereby incorporated by reference in its entirety) was installed between HBS-A helix and peptide B to synthesize AB-1 as a potential antiparallel helix-loop-helix motif (FIG. 10B). However, CD studies indicated a weakly helical signature in AB-1 reminiscent of a single short helix stabilized by the HBS approach (FIG. 3B).

Figure 10C:
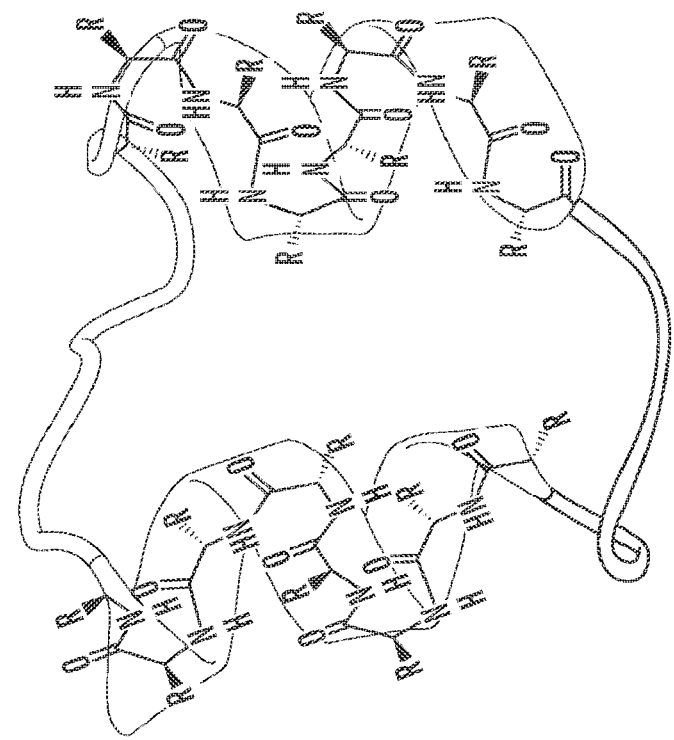

It was next tested whether macrocycliclization of peptides A and B with two loops (GGSSGG (SEQ ID NO:20) and GGSNGG (SEQ ID NO:21)) (AB-2: cyclo(GGSSGGE-LAELEWRLGGSNGGLAERIARLR (SEQ ID NO:4)) could induce helical dimer association in both sequences (FIG. 10C). This scaffold would potentially limit fraying at all four peptide termini while promoting interstrand hydrophobic interactions. However, CD spectroscopy again revealed minimal helicity suggesting that macrocyclization did not lead to a significant conformational stability relative to the HBS strategy (FIG. 3B). Subsequently, it was determined whether an interhelical-disulfide linkage in place of hydrophobic pairing would lead to a stable helix dimer (FIG. 10D). Hodges and coworkers have previously demonstrated that mutation of hydrophobic residues to create disulfide bridges with cysteine residues increases coiled-coil stability while preserving coiled-coil structure (Zhou et al., Biochemistry 32:3178 (1993), which is hereby incorporated by reference in its entirety). Their seminal work serves as the basis of the present disulfide design. A bis-cysteine peptide (AB-3: ECAELEWRLGGSSGGLAERIARCR (SEQ ID NO:5)) was synthesized on resin followed by disulfide formation and characterized its helical content by CD (FIG. 3B). Analysis revealed that this approach also did not provise significant helical stabilization in short sequences.

Figure 10E:
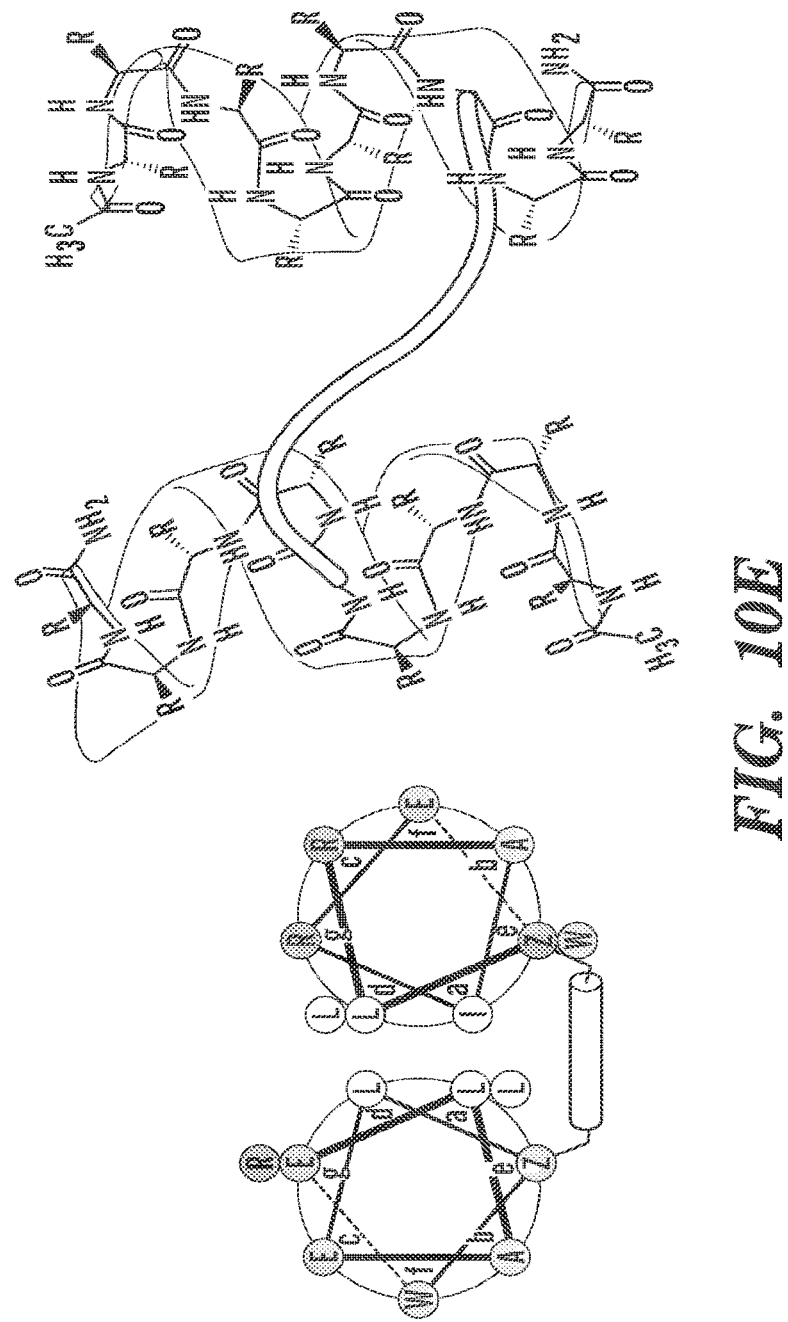

Salt-bridge networks contribute significantly to coiled-coil chain alignment as well as to general helix stability (Woolfson, Adv. Protein Chem. 70:79 (2005); O'Shea et al., Cell 68:699 (1992); Steinmetz et al., Proc. Natl. Acad. Sci. USA 104:7062 (2007), which are hereby incorporated by reference in their entirety); although there is debate (Lavigne et al., Science 271:1136 (1996); Lumb et al., Science 268:436 (1995), which are hereby incorporated by reference in their entirety), individual salt-bridges are thought to stabilize helices and coiled-coils by ≤0.5 kcal/mol (Spek et al., Protein Sci. 7:2431 (1998); Zhou et al., J Mol. Biol. 237:500 (1994); Marqusee et al., Proc. Natl. Acad. Sci. U.S.A. 84:8898 (1987), which are hereby incorporated by reference in their entirety). It was envisioned that replacement of a weak interhelical ionic bond at g/g' or e/e' positions with a covalent bond would offer an attractive option for stabilizing helical dimers (FIG. 10E). Bis-trizole linkers formed via copper catalyzed azide-alkyne cycloaddition reaction (Meldal et al., Chem. Rev. 108:2952 (2008); Rostovtsev et al., Angew. Chem. Int. Ed. 4:2596 (2002), which are hereby incorporated by reference in their entirety) were designed to constrain peptides A and B (FIGS. 11A-D) (Torres et al., ChemBiochem 9:1701 (2008); Horne et al., J. Am. Chem. Soc. 126:15366 (2004); Angell et al., Chem. Soc. Rev. 36:1674 (2007); Holub et al., Chem. Soc. Rev. 39:1325 (2010), which are hereby incorporated by reference in their entirety). Bis-triazole bridges of varying lengths resulting from azidoalanine, azidohomoalanine, and azidolysine residues were incorporated at positions e/e' to obtain dimers AB-4, AB-5, and AB-6, respectively (see FIG. 11A). The azido side chains were reacted with propargyl ether to obtain the bis-triazole linkers. Solid-phase synthesis of AB-4-AB-6 is described in Example 5 supra. CD analysis reveals that replacement of an ionic bond with a covalent linkage has a dramatic effect on the conformational stability in a linker length dependent manner (FIG. 11B). Based on the intensity of the 222 nm minimum and 222/208 nm ratio, AB-4 and AB-5 constructs derived from azidolysine and azidohomoalanine were found to be significantly more helical than AB-6.

Figure 5:
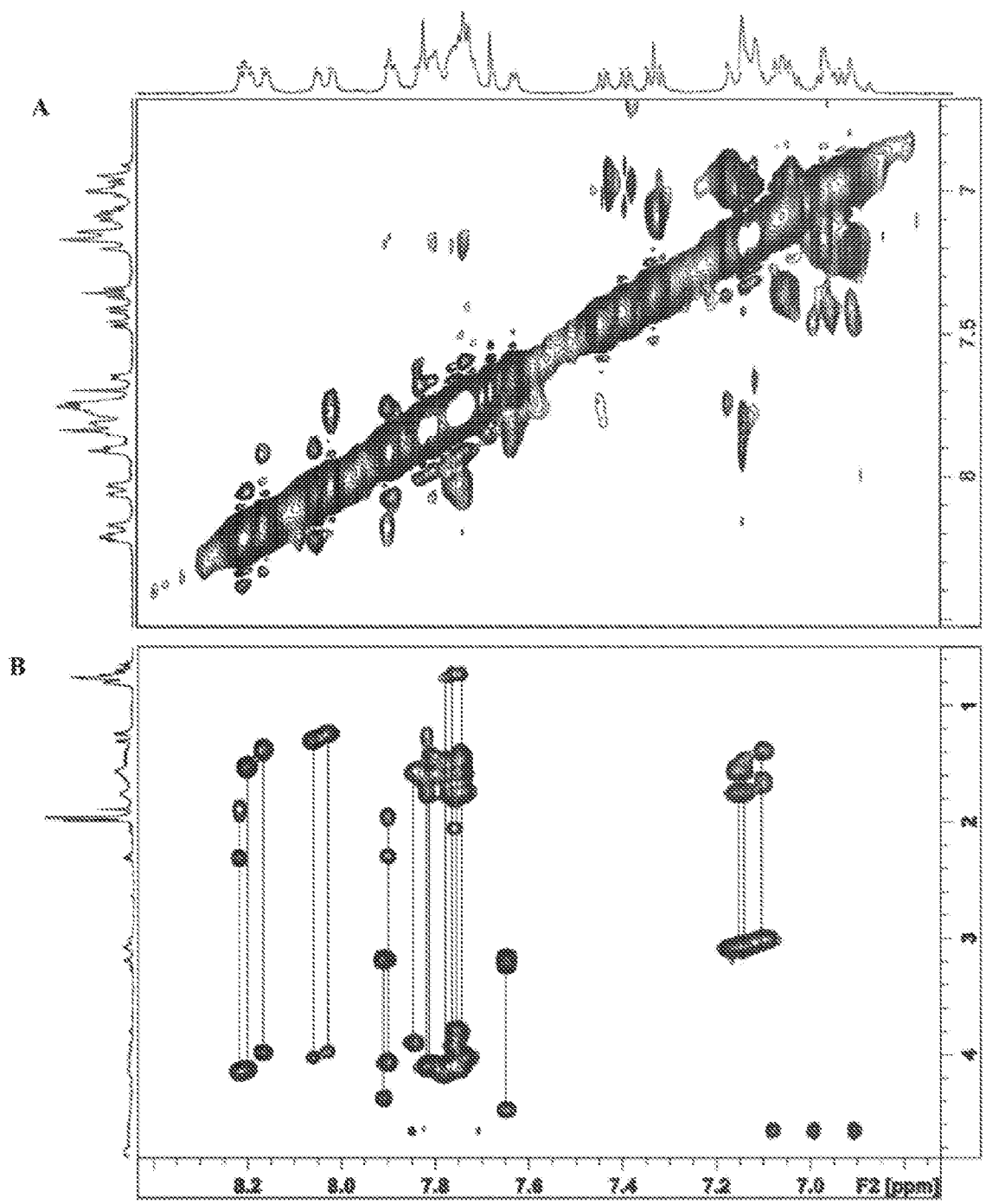
FIGS. 5A-B are NMR spectra showing the amide region of NOESY (FIG. 5A) and amide to side-chain connectivity of TOCSY (FIG. 5B) of AB-4.
Figure 6:
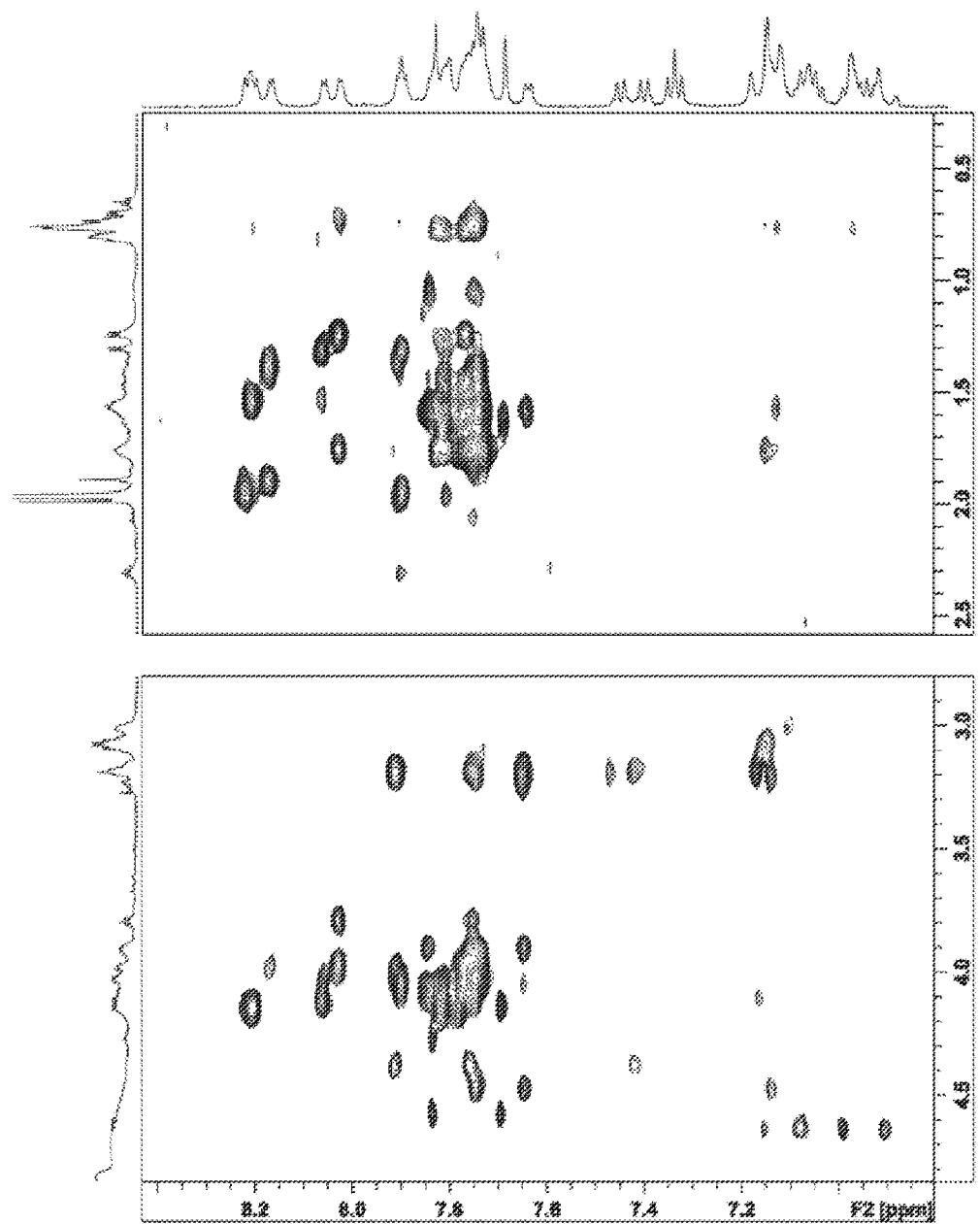
FIG. 6 is an NMR spectrum showing the fingerprint region of NOESY from AB-4.

The conformational stability of the crosslinked helix dimer (CHD) AB-4 (FIG. 11C) was further assessed using a combination of 1D NMR, total correlation spectroscopy (TOCSY), and nuclear Overhauser effect spectroscopy (NOESY) in 10% d3-$CH_3CN$ in $H_2O$ with 0.1% TFA (pH 5). Addition of 10% acetonitrile was found to be necessary to limit aggregation of the peptide at the 0.5 mM concentration needed for NMR. The NOESY spectrum revealed NOE crosspeaks indicative of a helical tertiary structure, showing sequential dNN (i, i+1) and several medium range NOEs (dαN (i, i+3)) suggestive of stable α-helices (FIGS. 5A-B). Additionally, the backbone dihedral angles (Φ) calculated from $^3J_{NHCH\alpha}$ coupling constants fall in the range expected for canonical α-helices (Kurt Wüthrich, NMR OF PROTEINS AND NUCLEIC ACIDS (1986), which is hereby incorporated by reference in its entirety). The dihedral angles found for the crosslinked azidolysine residues did not differ from those calculated for the rest of the residues in the helical dimer. A structural model of AB-4 was calculated using 65 NOESY crosspeaks and 18 (constraints (FIG. 11D).

Example 14—Coiled-Coil Mimics of Nervy Homology Two (NHR2) Domain of the AML1-ETO-Containing Transcription Factor Complex (AETFC)

To establish that the CHD strategy can be translated from a designed sequence to a native protein coiled-coil, mimics of Nervy homology two (NHR2) domain of the AML1-ETO-containing transcription factor complex (AETFC) which interacts with NHR2-binding (N2B) motif of E-proteins (Sun et al., Nature 500:93 (2013), which is hereby incorporated by reference in its entirety), were developed. This complex is critical for leukaemogenesis and features a dimeric, antiparallel coiled-coil from NHR2 at the interface to engage N2B (FIG. 12A). Computational alanine scanning (see Table 4 below) and experimental mutagenesis data (Sun et al., Nature 500:93 (2013), which is hereby incorporated by reference in its entirety), reveal residues E501, H504, L508, V522, and S525 as key for binding.

TABLE 4

Analysis of NHR2-N2B interaction. Hot spot residues were identified through computational alanine scanning (Kortemme et al., Sci. Signal. 2004:p12 (2004); Sun et al., Nature 500:93 (2013), which are hereby incorporated by reference in their entirety).

| Sequence | ΔΔG from Rosetta analysis in kcal/mol |
|---|---|
| 501 - EWKHLDHLLN (SEQ ID NO: 22) | E501 (1.41) H504 (1.81) L508 (1.40) |
| 518 - KTRRSLTVLR (SEQ ID NO: 23) | V525 (1.05) S522 (H-bonding) |

To investigate the potential of a bis-triazole bridge to induce stable, dimeric helical conformation in an NHR2 sequence, azidolysine residues were inserted at the e/e' position of the native sequence to obtain CHD-NHR2-1: $^g$EWKHLZHLLN$^{b/c'}$KTRRSLTVLZ$^{e'}$ (SEQ ID NO:6/SEQ ID NO:7) (FIG. 12B, top). CD spectroscopy showed this construct to be largely non-helical (FIG. 12C). This result was attributed to the missing stabilizing contribution from the hydrophobic vertical triad since the native sequence contains potentially disruptive large tryptophan and polar threeonine within the interior of its hydrophobic core (Liu et al., Proc. Natl. Acad. Sci. USA 101:16156 (2004); Akey et al., Biochemistry 40:6352 (2001), which are hereby incorporated by reference in their entirety). The native sequence also contains two positively charged residues near the amino terminus, which likely reduce the helical stability. CHD-NHR2-1 was redesigned to include the optimal hydrophobic residues from AB-4 and intrahelical salt-bridges at the i and i+3 positions while preserving the native residues that interact with N2B to obtain CHD-NHR2-2: $^g$ELWHLZELLR$^{b/c'}$ELWRSIRVLZ$^{e'}$ (SEQ ID NO:9) (FIG. 12B, middle). The redesigned sequence is significantly more helical than the parent, as ascertained by the intensity of the 222 nm minimum and the ratio of the 222 nm and 208 nm bands (FIG. 12C). However, the overall helical stability of this native sequence remained low ($\theta_{222}$<10,000) as compared to the designed sequence AB-4 ($\theta_{222}$=14,000). This result prompted the reevaluation of the stabilization approach to determine whether further constraints can be placed to stabilize the dimer in the context of difficult biological sequences. Placement of more than one linker at the g/g' position is not desirable as it would influence the binding surface. Although the internal disulfide bridge did not offer significant stability in the context of a flexible tether (AB-3), it was sought to determine the effect of interhelical disulfide bonds in enhancing stability of triazole crosslinked dimer CHD-NHR2-2.

Disulfide bridges may be placed at different a/d positions within CHD-NHR2-2 such that they are located adjacent to the triazole link at e/e' positions or farther away (FIG. 12D and FIGS. 13A-C). It was conjectured that placement of the disulfide bond farthest away from the triazole bridge would have the highest impact on helix stability, as the designed salt bridge surrogate may not be an optimal helix nucleator (Patgiri et al.,"Acc. Chem. Res. 41:1289 (2008), which is hereby incorporated by reference in its entirety). The results support this hypothesis. CHD$^{DS}$-NHR2-3 $^g$ELWHLZELCR$^{b/c'}$ECWRSIRVLZ$^{e'}$ (SEQ ID NO:10/SEQ ID NO:11)) (FIG. 12B, bottom) in which the disulfide is located distal from the triazole bridge is significantly more helical, according to CD spectroscopy, than CHD$^{DS}$-NHR2-4 $^g$ELWHCZELLR$^{b/c'}$ELWRSCRVLZ$^{e'}$ (SEQ ID NO:12/SEQ ID NO:13)) and CHD$^{DS}$-NHR2-5 ($^g$ECWHLZELLR$^{b/c'}$ELWRSIRVCZ$^{e'}$ (SEQ ID NO:14/SEQ ID NO:15)) where the disulfide bonds are placed near the triazole linker (FIGS. 3A-C). CHD$^{DS}$-NHR2-3 is also significantly more helical than CHD-NHR2-2, with the overall CD signature similar in intensity to that of the artificial construct AB-4 (FIG. 12C).

The binding affinities of the designed NHR2 mimetics were determined to correlate their molecular recognition attributes with the conformational stability. Previously described fluorescence polarization assay with a fluorescein-labeled N2B peptide was utilized to evaluate binding of the crosslinked dimers as compared to the native NHR2 coiled-coil (NHR2$_{482-551}$) (Sun et al., Nature 500:93 (2013), which is hereby incorporated by reference in its entirety). The native NHR2 domain binds to the N2B peptide in agreement with published results ($K_d$=356±90 μM), while CHD-NHR2-1, CHD-NHR2-2, and CHD$^{DS}$-NHR2-3 target N2B with $K_d$ values of >10,000 μM, 212±80 μM, 66±20 μM respectively, highlighting the influence of conformational stability on molecular recognition (see Table 5 below). As expected, the doubly crosslinked dimer, with higher conformational stability, binds to the target with the highest affinity. The five-fold enhanced affinity of the much shorter CHD$^{DS}$-NHR2-3 (20 residues) mimetic versus the native NHR2 coiled-coil (138 residues) is notable and supports the present design principles.

TABLE 5

Sequences and binding affinities of the native NHR2 coiled-coil and the crosslinked helix dimer (CHD) mimics.

| Compound | Sequence$^a$ | $K_d$ (μM)$^b$ |
|---|---|---|
| NHR2 | GST-NHR2(482-551) | 356 ± 90 |
| CHD-NHR2-1 | EWKHLZHLLN/KTRRSLTVLZ (SEQ ID NO: 6/SEQ ID NO: 7) | >10,000 |
| CHD-NHR2-2 | ELWHLZELLR/ELWRSIRVLZ (SEQ ID NO: 8/SEQ ID NO: 9) | 212 ± 80 |

TABLE 5-continued

Sequences and binding affinities of the native
NHR2 coiled-coil and the crosslinked helix
dimer (CHD) mimics.

| Compound | Sequence[a] | $K_d$ (µM)[b] |
|---|---|---|
| CHD[DS]-NHR2-3 | ELWHLZELCR/ECWRSIRVLZ (SEQ ID NO: 10/SEQ ID NO: 11) | 66 ± 20 |
| CHD-NHR2-6 | ALWHLZEALR/ELWRSIRVLZ (SEQ ID NO: 24/SEQ ID NO: 9) | >3000 |
| CHD-NHR2-7 | ELWHLZELLR/ELWRAIRALZ (SEQ ID NO: 8/SEQ ID NO: 25) | >3000 |

[a]Z = azidolysine-derived bis-triazole linker; alanine mutations are underlined.
[b]Binding affinity calculated using a fluorescence polarization assay with fluorescein-labeled N2B peptide.

It was next investigated whether contacts from both helices are require for binding to N2B peptide—i.e., if the dimeric construct is necessary for interacting with the target peptide. Residues S522 and V525 on one helix strand and E501 and L508 on the opposite strand are suggested to be critical for binding. CHD-NHR2-6 (S522A/V525A) and CHD-NHR2-7 (E501A/L508A) were designed as controls for CHD-NHR2-2, and contain alanine mutations on one strand per dimer while retaining CHD-NHR2-2 sequence on the other strand (see Table 5 above). Both control constructs bound N2B with diminished affinity ($K_d$>3000 µM) supporting the requirement of critical residues on each helical strand and the present hypothesis that a dimer is needed to engage such PPIs.

In summary, various stabilization strategies to design minimal mimics of helical tertiary structures were investigated. The present studies reveal that judicious replacement of interhelical ionic contacts with a covalent linkages and substitution of internal hydrophobic interactions with disulfide bonds afford stable dimeric helical conformations in difficult biological sequences. The design principles were applied to the stabilization of short sequences from a biological assembly to evaluate the potential of the minimal mimetics to reproduce native binding interactions of much longer protein coiled-coils. The present studies illustrate that the mimetics are capable of participating in biomolecular recognition with high specificity as mutation of specific residues abrogated binding. We previously examined coiled-coils and helix bundles that mediate complex formation to create a platform for the discovery of potential tertiary structure mimetics and identified critical features of these helical interfaces with respect to coiled-coil and other helical PPIs (Watkins et al., "Protein-Protein Interactions Mediated by Helical Tertiary Structure Motifs," *J Am. Chem. Soc.* 137:11622-11630 (2015), which is hereby incorporated by reference in its entirety). Analysis revealed that more than 300 biomedically relevant complexes in the current Protein Data Bank will require a helix dimer or coiled-coil mimic for inhibition, because the hot spot residues reside on two neighboring helices (Watkins et al., "Protein-Protein Interactions Mediated by Helical Tertiary Structure Motifs," *J Am. Chem. Soc.* 137:11622-11630 (2015), which is hereby incorporated by reference in its entirety). Given the ubiquity of coiled-coil mediated PPIs (Watkins et al., "Protein-Protein Interactions Mediated by Helical Tertiary Structure Motifs," *J Am. Chem. Soc.* 137:11622-11630 (2015), which is hereby incorporated by reference in its entirety), it is expected that coiled-coil mimics will prove to be useful leads for ligand design.

Example 15—Additional Linker

Coiled-coil mimetics containing the following linker have also been synthesized, using a brominated precursor and coupling the precursor to cysteine side chains.

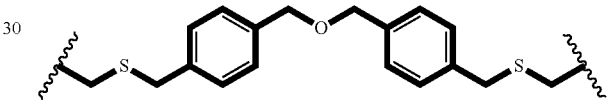

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A macrostructure comprising:

(i) an antiparallel coiled-coil structure of formula:

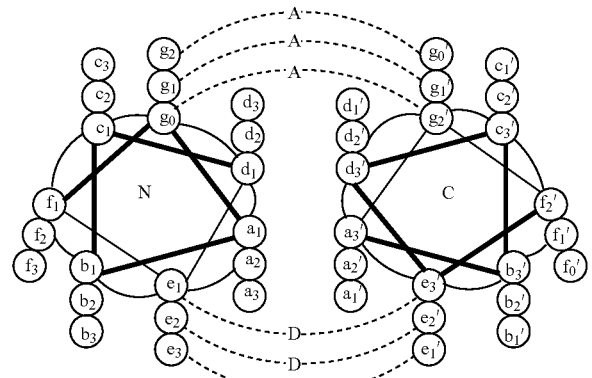

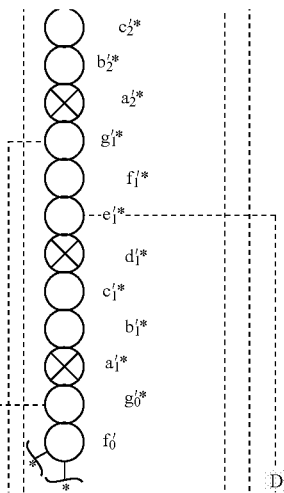

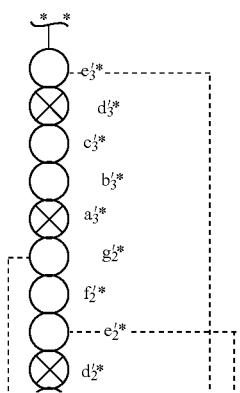

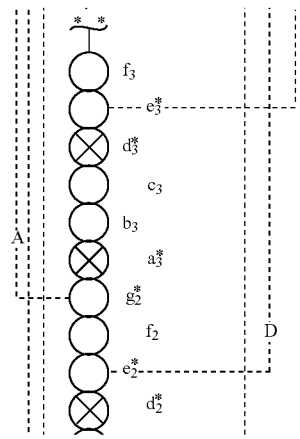

-continued

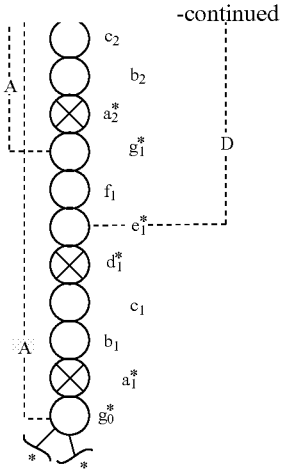

(two-dimensional view);

wherein:
each ○ and each ⊗ is independently absent or a modified or unmodified amino acid residue or analogue thereof, with the proviso that ten to thirty contiguous amino acid residues/analogues are present in each coil, wherein
  a, b, c, d, e, f, g, a', b', c', d', e', f', and g' indicate the location of the amino acid residues/analogues within the coiled-coil structure and
each ⊗ amino acid residue is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues;

each ⌐ ¬ is absent or a covalent linker (Linker) between two amino acid residues/analogues, wherein:
  each Linker A is independently a linker between a g* amino acid residue and a g'* amino acid residue, wherein the length of the linker is such that the spatial distance between the Cα position of the g* amino acid residue and the Cα position of the g'* amino acid residue is 10-25 Å;
  each Linker D is independently a linker between an e* amino acid residue and an e'* amino acid residue, wherein the length of the linker is such that the spatial distance between the Cα position of the e* amino acid residue and the Cα position of the e'* amino acid residue is 10-25 Å;
  and
  at least one Linker A or Linker D is present;

each

is a point of attachment from a terminal nitrogen to H, —$PG_1$, —C(O)R, —C(O)$NR_2$, —C(O)$NH_2$, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein $PG_1$ is a protecting group for protection of an amine; and each

is a point of attachment from a terminal carbonyl to H, —$OPG_2$, —$NPG_2$, —OR, —OH, —$NR_2$, —$NH_2$, —NRC(O)$C_{1-6}$ alkyl, —NHC(O)$C_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein $PG_2$ is a protecting group for protection of a carboxylic acid;

or (ii) a parallel coiled-coil structure of formula:

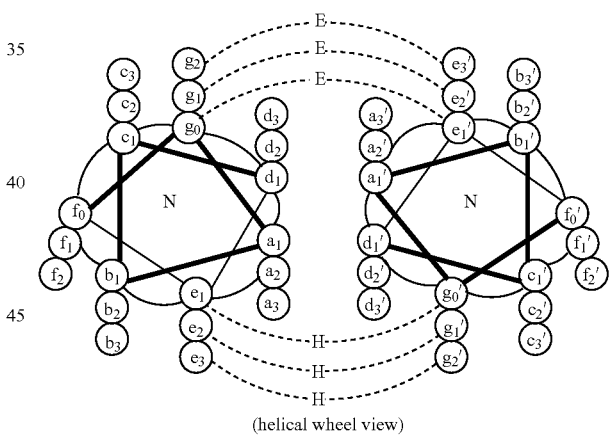

(helical wheel view)

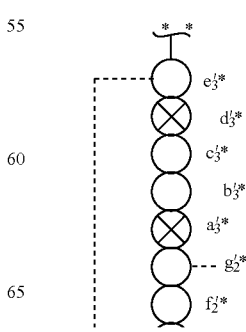

-continued

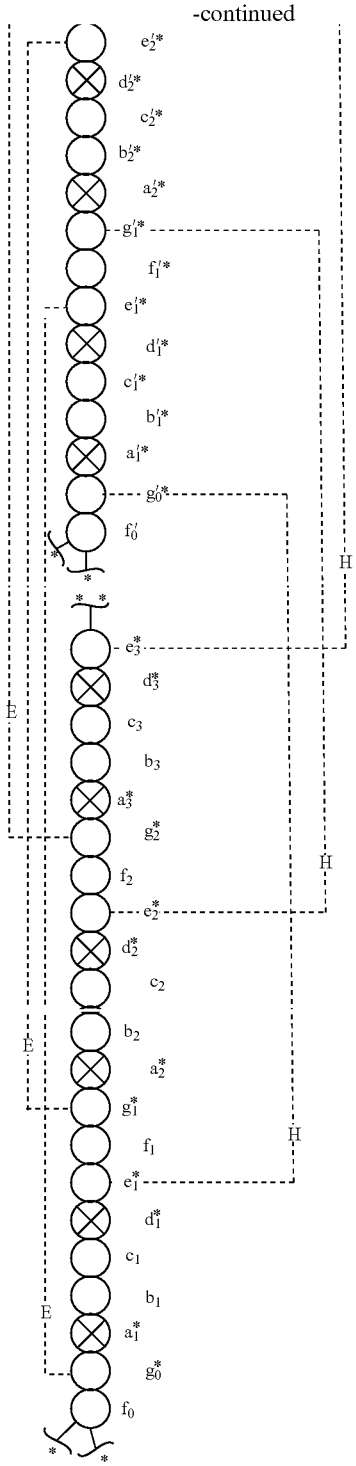

(two-dimensional view);

wherein:
each ○ and each ⊗ s independently absent or a modified or unmodified amino acid residue or analogue thereof, with the proviso that ten to thirty contiguous amino acid residues/analogues are present in each coil, wherein
a, b, c, d, e, f, g, a', b', c', d', e', f', and g' indicate the location of the amino acid residues/analogues within the coiled-coil structure and each ⊗ amino acid residue is a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues;

each  is absent or a covalent linker (Linker) between two amino acid residues/analogues, wherein:
each Linker E is independently a linker between a g* amino acid residue and an e'* amino acid residue, wherein the length of the linker is such that the spatial distance between the Cα position of the g* amino acid residue and the Cα position of the e'* amino acid residue is 10-25 Å;
each Linker H is independently a linker between an e* amino acid residue and a g'* amino acid residue, wherein the length of the linker is such that the spatial distance between the Cα position of the e* amino acid residue and the Cα position of the g'* amino acid residue is 10-25 Å; and
at least one Linker E or Linker H is present; and
each

is a point of attachment from a terminal nitrogen to H, —$PG_1$, —C(O)R, —C(O)$NR_2$, —C(O)$NH_2$, —R, —C(O)OR, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein $PG_1$ is a protecting group for protection of an amine; and each

is a point of attachment from a terminal carbonyl to H, —$OPG_2$, —$NPG_2$, —OR, —OH, —$NR_2$, —$NH_2$, —NRC(O)$C_{1-6}$ alkyl, —NHC(O)$C_{1-6}$ alkyl, an amino acid, a peptide, a tag, or a targeting moiety, where each R is independently hydrogen, an alkyl, an alkenyl, an alkynyl, a cycloalkyl, an aryl, a heteroaryl, a heterocyclyl, an arylalkyl, a peptide, a targeting moiety, or a tag; and wherein $PG_2$ is a protecting group for protection of a carboxylic acid.

2. The macrostructure of claim 1, wherein each Linker is independently selected from the group consisting of alkylene, alkenylene, arylene, heteroarylene, ethers, thioethers, amides, maleimides, esters, disulfides, diselenides, —O—, —S—, —Se—, and any combination thereof.

3. The macrostructure of claim 2, wherein at least one of Linker A, Linker D, Linker E, and Linker H has the formula —$Z_n$—, wherein n is a number from 1 to 25 and each Z is independently selected at each occurrence thereof from the group consisting of alkylene, alkenylene, arylene, heteroarylene, triazole-diyl, thiazole-diyl, oxazole-diyl, ethers, amides, esters, maleimides, thioethers, O, S, and Se.

4. The macrostructure of claim 3, wherein the at least one of Linker A, Linker D, Linker E, and Linker H is independently selected from the group consisting of

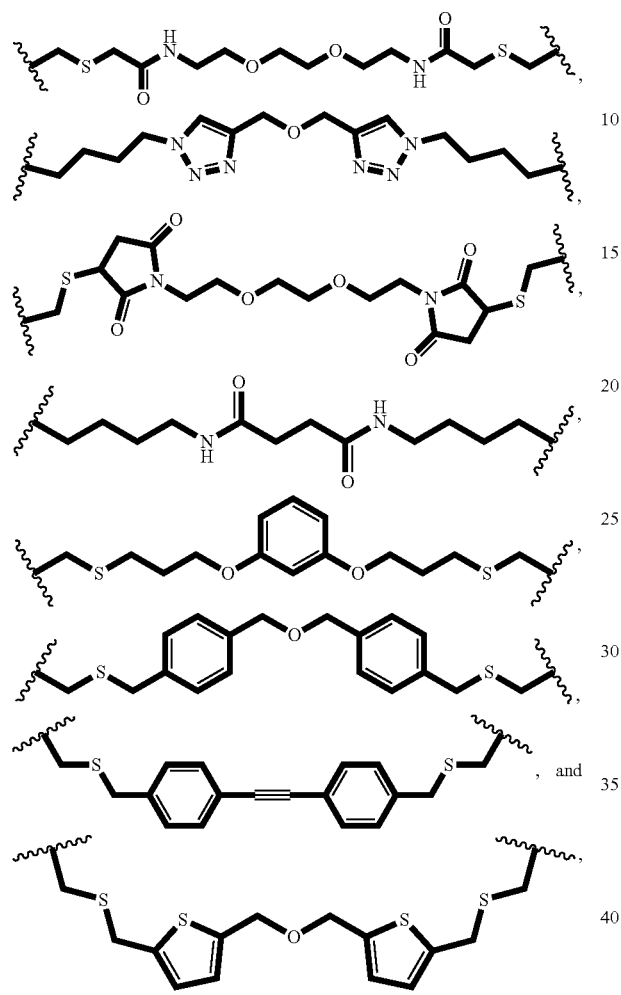

wherein each

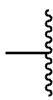

marks a connection point to the Cα carbon in a linked residue/analogue.

5. The macrostructure of claim 3, wherein the at least one of Linker A, Linker D, Linker E, and Linker H:
(i) has the formula

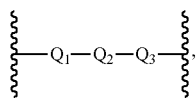

wherein:
$Q_1$ is a $C_{1-8}$ alkylene or a moiety of formula $(C_{1-8}$ alkylene-X—$C_{0-8}$ alkylene$)_n$;

$Q_2$ is $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, a moiety of formula $C_{1-8}$ alkylene-X—$C_{1-8}$ alkylene, or a moiety of formula -$Q_4$-$Q_5$-$Q_6$-; wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;

$Q_3$ is a $C_{1-8}$ alkylene or a moiety of formula $(C_{1-8}$ alkylene-X—$C_{0-8}$ alkylene$)_n$;

$Q_4$ is selected from the group consisting of O, —C(O)—NR—, —NR—C(O)—, —C(O)—O—, —O—C(O)—, —C(O)—S—, —S—C(O)—, $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;

$Q_5$ is selected from the group consisting of —C(O)—NR—, —NR—C(O)—, —C(O)—O—, —O—C(O)—, —C(O)—S—, —S—C(O)—, $C_{1-8}$ alkylene, $C_{2-8}$ alkynylene, monocyclic carbocycle, fused bicyclic carbocycle, non-aromatic heterocycle, arylene, and heteroarylene, or is a moiety of formula $C_{1-8}$ alkylene-(X—$C_{1-8}$ alkylene$)_n$, wherein each of $C_{1-8}$ alkylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;

$Q_6$ is selected from the group consisting of O, —C(O)—NR—, —NR—C(O)—, —C(O)—O—, —O—C(O)—, —C(O)—S—, —S—C(O)—, $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene, wherein each $C_{1-8}$ alkylene, $C_{2-8}$ alkenylene, $C_{2-8}$ alkynylene, monocyclic carbocycle, fused bicyclic carbocycle, non-aromatic heterocycle, arylene, and heteroarylene can be optionally substituted from 1 to 4 (1, 2, 3, or 4) times with substituents independently selected at each occurrence thereof from the group consisting of H, halogen, $C_{1-8}$ alkyl, =C(O), NHR, N(R)$_2$, OR, and SR;

each X is selected from the group consisting of O, S, CR$_2$, NR, P, C$_{2-8}$ alkynylene, arylene, and heteroarylene (preferably O, S, CH$_2$, NR, or CR≡CR);

each R is independently H, C$_{1-8}$ alkyl, or aryl;

n is 1 to 10; and each

marks a connection point to the Cα carbon in a linked residue/analogue;

(ii) has the following formula

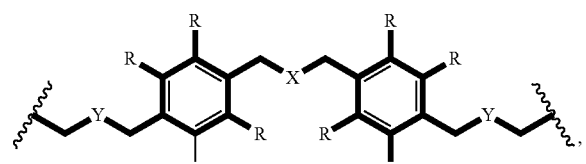

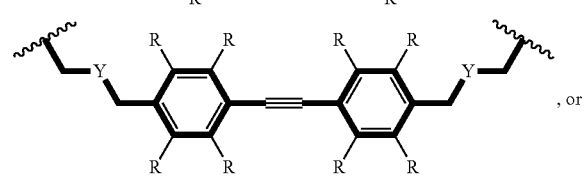

, or

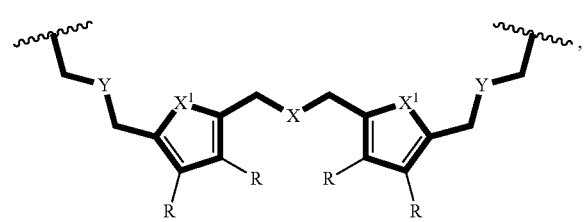

wherein X is O, S, CR$_2$, NR, or P (preferably O, S, CH$_2$ or NR), wherein X is O, S, NH, and NR, wherein each R is independently H, alkyl, or aryl, wherein Y is S, and wherein each

marks a connection point to the Cα carbon in a linked residue/analogue; or (iii) has the following formula

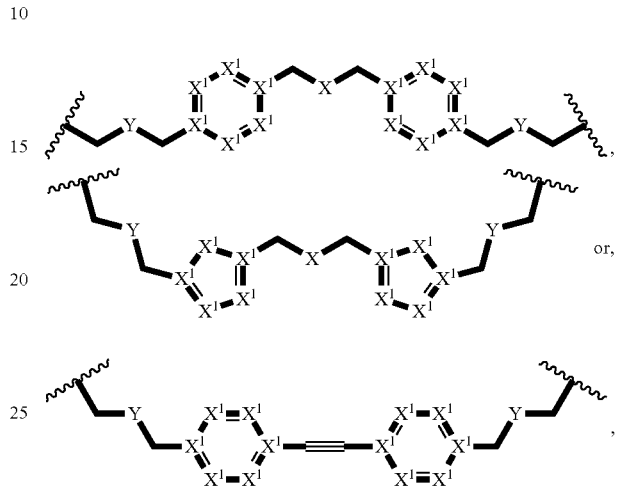

wherein X is O, S, CR$_2$, NR, or P (preferably O, S, CH$_2$ or NR), wherein X$^1$ is O, S, C, CR, N, NH, and NR, wherein each R is independently H, alkyl, or aryl, wherein Y is S, and wherein each

marks a connection point to the Cα carbon in a linked residue/analogue.

6. The macrostructure of claim 1, wherein one Linker is present.

7. The macrostructure of claim 1, wherein two Linkers are present.

8. The macrostructure of claim 1, wherein the antiparallel coiled-coil structure is an antiparallel coiled-coil of Formula III:

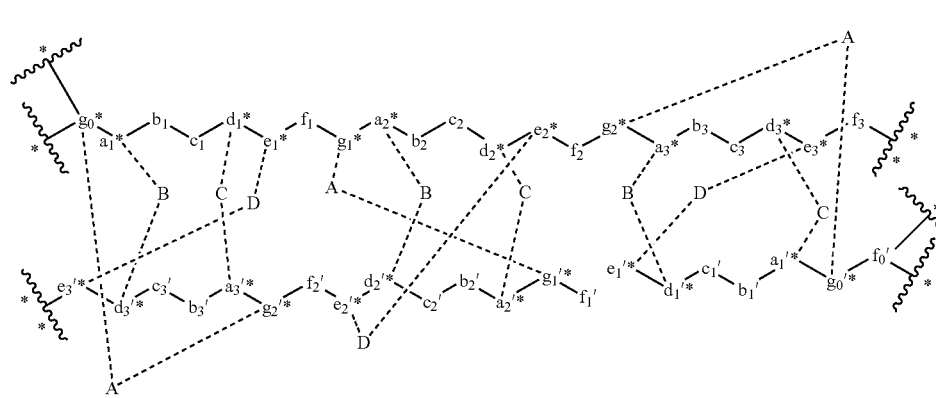

III wherein:

$a_1^*, a_2^*, a_3^*, b_1, b_2, b_3, c_1, c_2, c_3, d_1^*, d_2^*, d_3^*, e_1^*, e_2^*, e_3^*, f_1, f_2, f_3, g_0^*, g_1^*, g_2^*, a_1'^*, a_2'^*, a_3'^*, b_1', b_2', b_3', c_1', c_2', c_3', d_1'^*, d_2'^*, d_3'^*, e_1'^*, e_2'^*, e_3'^*, f_0', f_1', f_2', g_0'^*, g_1'^*,$ and $g_2'^*$ are each independently absent or a modified or unmodified amino acid residue or analogue thereof, with the proviso that ten to thirty contiguous amino acid residues/analogues are present in each coil;

$a_1^*, a_2^*, a_3^*, d_1^*, d_2^*, d_3^*, a_1'^*, a_2'^*, a_3'^*, d_1'^*, d_2'^*,$ and $d_3'^*$ each independently have the formula (a)

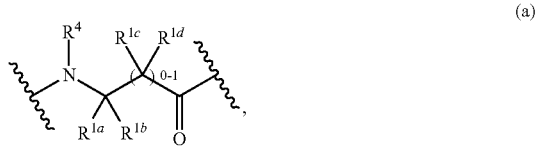

(a)

wherein:

$R^{1a}, R^{1b}, R^{1c},$ and $R^{1d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, $-OR^5$, or $-SR^5$; and at least one of $R^{1a}$ and $R^{1c}$ is a side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues; and $e_1^*, e_2^*, e_3^*, g_1^*, g_2^*, e_1'^*, e_2'^*, e_3'^*, g_0'^*, g_1'^*,$ and $g_2'^*$ each independently have the formula (b) and $g_0^*$ has the formula (b')

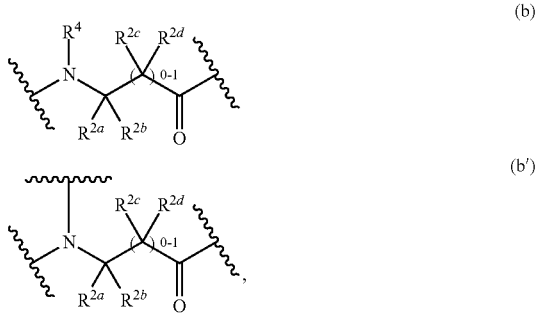

wherein:

$R^{2a}, R^{2b}, R^{2c},$ and $R^{2d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, $-OR^5$, or $-SR^5$; and at least one of $R^{2a}$ and $R^{2c}$ is an amino acid side chain; and when a Linker A or a Linker D is attached to a residue of formula (b), the Linker A or Linker D is attached to or replaces one of $R^{2a}, R^{2b}, R^{2c},$ and $R^{2d}$;

$b_1, b_2, b_3, c_1, c_2, c_3, f_1, f_2, f_3, b_1', b_2', b_3', c_1', c_2', c_3', f_1',$ and $f_2'$ each independently have the formula (c) and $f_0'$ has the formula (c')

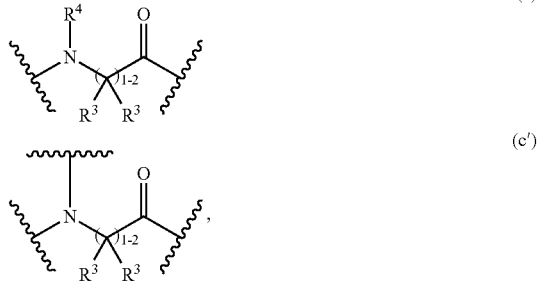

wherein each $R^3$ is independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, $-OR^5$, or $-SR^5$;

each $R^4$ is independently hydrogen, an alkyl, an alkenyl, an alkynyl, a cycloalkyl, a heterocyclyl, an aryl, a heteroaryl, or an arylalkyl; and each $R^5$ in Formula III is independently selected from the group consisting of H, —PG (where PG is a protecting group), an alkyl, an alkenyl, an alkynyl, a cycloalkyl, an aryl, a heteroaryl, a heterocyclyl, and an arylalkyl.

9. The macrostructure of claim 8, wherein at least one of the following conditions is met:

(A) in at least one residue of formula (a), (i) one of $R^{1a}$ and $R^{1c}$ is the side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues, and (ii) $R^{1b}, R^{1d},$ and the other of $R^{1a}$ and $R^{1c}$ are each independently hydrogen, a $C_{1-3}$ alkyl, or a $C_{2-3}$ alkenyl;

(B) in at least one residue of formula (b), (i) one of $R^{2a}$ and $R^{2c}$ is an amino acid side chain and (ii) $R^{2b}, R^{2d},$ and the other of $R^{2a}$ and $R^{2c}$ are each independently hydrogen or a $C_{1-3}$ alkyl.

10. The macrostructure of claim 1, wherein the parallel coiled-coil structure is a parallel coiled-coil of Formula IV:

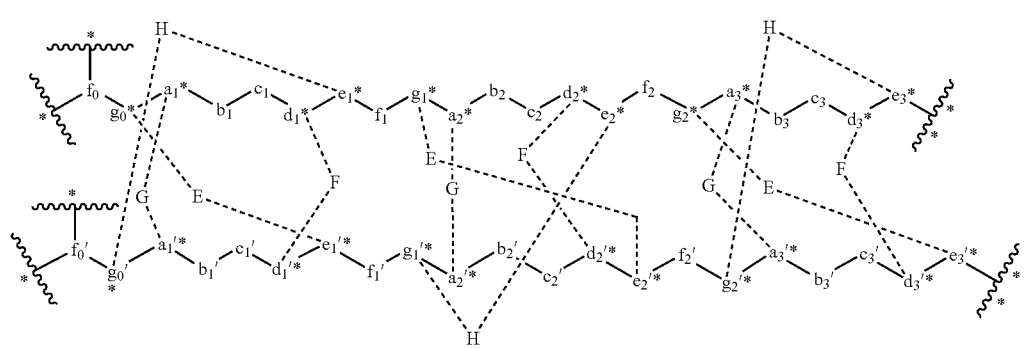

IV wherein:

$a_1^*, a_2^*, a_3^*, b_1, b_2, b_3, c_1, c_2, c_3, d_1^*, d_2^*, d_3^*, e_1^*, e_2^*, e_3^*, f_0, f_1, f_2, f_3, g_0^*, g_1^*, g_2^*, a_1'^*, a_2'^*, a_3'^*, b_1', b_2', b_3', c_1', c_2', c_3', d_1'^*, d_2'^*, d_3'^*, e_1'^*, e_2'^*, e_3'^*, f_0', f_1', f_2', g_0'^*, g_1'^*$, and $g_2'^*$ are each independently absent or a modified or unmodified amino acid residue or analogue thereof, with the proviso that ten to thirty contiguous amino acid residues/analogues are present in each coil;

$a_1^*, a_2^*, a_3^*, d_1^*, d_2^*, d_3^*, a_1'^*, a_2'^*, a_3'^*, d_1'^*, d_2'^*,$ and $d_3'^*$ each independently have the formula (a)

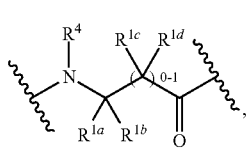

(a)

wherein:

$R^{1a}, R^{1b}, R^{1c}$, and $R^{1d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —$OR^5$, or —$SR^5$; and at least one of $R^{1a}$ and $R^{1c}$ is a side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues; and $e_1^*, e_2^*, e_3^*, g_0^*, g_1^*, g_2^*, e_1'^*, e_2'^*, e_3'^*, g_0'^*, g_1'^*$, and $g_2'^*$ each independently have the formula (b)

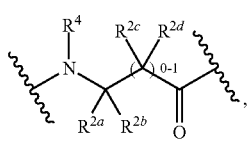

(b)

wherein:

$R^{2a}, R^{2b}, R^{2c}$, and $R^{2d}$ are each independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —$OR^5$, or —$SR^5$; and at least one of $R^{2a}$ and $R^{2c}$ is an amino acid side chain; and when a Linker E or a Linker H is attached to a residue of formula (b), the Linker E or a Linker H is attached to or replaces one of $R^{2a}, R^{2b}, R^{2c}$, and $R^{2d}$;

$b_1, b_2, b_3, c_1, c_2, c_3, f_1, f_2, b_1', b_2', b_3', c_1', c_2', c_3', f_1'$, and $f_2'$ each independently have the formula (c) and $f_0$ and $f_0'$ have the formula (c')

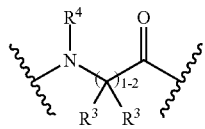

(c)

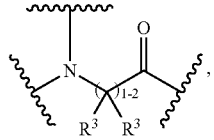

(c')

wherein each $R^3$ is independently hydrogen, an amino acid side chain, an alkyl, an alkenyl, an alkynyl, a cycloalkyl, a heterocyclyl, an aryl, a heteroaryl, or an arylalkyl, wherein each amino acid side chain, alkyl, alkenyl, alkynyl, cycloalkyl, heterocyclyl, aryl, heteroaryl, and arylalkyl can be optionally substituted with H, an alkyl, an alkenyl, an alkynyl, an azide, —$OR^5$, or —$SR^5$;

each $R^4$ is independently hydrogen, an alkyl, an alkenyl, an alkynyl, a cycloalkyl, a heterocyclyl, an aryl, a heteroaryl, or an arylalkyl; and each $R^5$ is independently selected from the group consisting of H, —PG (where PG is a protecting group), an alkyl, an alkenyl, an alkynyl, a cycloalkyl, an aryl, a heteroaryl, a heterocyclyl, and an arylalkyl.

11. The macrostructure of claim 10, wherein at least one of the following conditions is met:

(A) in at least one residue of formula (a), (i) one of $R^{1a}$ and $R^{1c}$ is the side chain of a modified or unmodified amino acid selected from the group consisting of cysteine, homocysteine, selenocysteine, leucine, isoleucine, hexafluoroleucine, valine, hexafluorovaline, allylglycine, threonine, and analogues of each of the preceding residues, and (ii) $R^{1b}, R^{1d}$ and the other of $R^{1a}$ and $R^{1c}$ are each independently hydrogen, a $C_{1-3}$ alkyl, or a $C_{2-3}$ alkenyl;

(B) in at least one residue of formula (b), (i) one of $R^{2a}$ and $R^{2c}$ is an amino acid side chain and (ii) $R^{2b}, R^{2d}$, and the other of $R^{2a}$ and $R^{2c}$ are each independently hydrogen or a $C_{1-3}$ alkyl.

12. The macrostructure of claim 1, wherein the macrostructure comprises the antiparallel coiled-coil structure.

13. The macrostructure of claim 12, wherein:

(i) the first strand of the antiparallel coiled-coil structure comprises at least ten contiguous modified or unmodified amino acid residues (or analogues thereof), wherein the at least ten contiguous amino acid residues/analogues have the formula $^gX_1\text{-}X_2\text{-}X_3\text{-}X_4\text{-}X_5\text{-}X_6\text{-}X_7\text{-}X_8\text{-}X_9\text{-}X_{10}^b$, wherein $X_1$ is Glu, Leu, Arg, Lys, Thr, or Val (or analogues of each of the preceding residues); $X_2$ is Cys, HCys, Leu, Ile, allylleucine, Val, allylglycine, Thr, selenocysteine, hexafluoroleucine, or hexafluorovaline (or analogues of each of the preceding residues); $X_3$ is any residue/analogue; $X_4$ is His, Tyr, Phe, Lys, Gln, or Trp (or analogues of each of the preceding residues); $X_5$ is Cys, HCys, Leu, Ile, allylleucine, Val, allylglycine, Thr, selenocysteine, hexafluoroleucine, or hexafluorovaline (or analogues of each of the preceding residues); $X_6$ is any residue/analogue; $X_7$ is Glu, Asn, Trp, Leu, Glu, or Gln (or analogues of each of the preceding residues); $X_8$ is Leu, Met, Ala, His, or Ser (or analogues of each of the preceding residues); $X_9$ is Cys, HCys, Leu, Ile, allylleucine, Val, allylglycine, Thr, selenocysteine, hexafluoroleucine, or hexafluorovaline (or analogues of each of the preceding residues); and $X_{10}$ is any residue/analogue;

(ii) the second strand of the antiparallel coiled-coil structure comprises at least ten contiguous modified or unmodified amino acid residues (or analogues thereof), wherein the at least ten contiguous amino acid residues/analogues have the formula $^{e}X_1'\text{-}X_2'\text{-}X_3'\text{-}X_4'\text{-}X_5'\text{-}X_6'\text{-}X_7'\text{-}X_8'\text{-}X_9'\text{-}X_{10}^{e'}$, wherein $X_1'$ is Glu, Asn, Leu, Gln, Met, or Ala (or analogues of each of the preceding residues); $X_2'$ is Cys, HCys, Leu, Ile, allylleucine, Val, allylglycine, Thr, selenocysteine, hexafluoroleucine, or hexafluorovaline (or analogues of each of the preceding residues); $X_3'$ is any residue/analogue; $X_4'$ is any residue/analogue; $X_5'$ is Ala, Ser, Thr, Gly, or Asp (or analogues of each of the preceding residues); $X_6'$ is Cys, HCys, Leu, Ile, allylleucine, Val, allylglycine, Thr, selenocysteine, hexafluoroleucine, or hexafluorovaline (or analogues of each of the preceding residues); $X_7'$ is Arg, Leu, Gln, Met, Glu, or Asp (or analogues of each of the preceding residues); $X_8'$ is Tyr, Val, Phe, Trp, or Met (or analogues of each of the preceding residues); $X_9'$ is Cys, HCys, Leu, Ile, allylleucine, Val, allylglycine, Thr, selenocysteine, hexafluoroleucine, or hexafluorovaline (or analogues of each of the preceding residues); and $X_{10}'$ is any residue/analogue;

(iii) $^g$, $^b$, $^{c'}$, and $^{e'}$ indicate where the ten contiguous amino acids/analogues appear within the antiparallel coiled-coil structure;

(iv) residues in the e/e' and g/g' positions can be optionally modified to facilitate attachment of a Linker or replaced with a Linker, if present; and (v) residues in the a/a' and d/d' positions can be optionally modified to facilitate attachment of a Linker, if present.

14. The macrostructure of claim 13, wherein:

(i) $X_1$ is Glu (or analogue thereof); $X_2$ is Leu (or analogue thereof); $X_3$ is Trp (or analogue thereof); $X_4$ is His (or analogue thereof); $X_5$ is Leu (or analogue thereof); $X_6$ is any residue/analogue; $X_7$ is Glu (or analogue thereof); $X_8$ is Leu (or analogue thereof); $X_9$ is Leu (or analogue thereof); and $X_{10}$ is Trp (or analogue thereof);

(ii) $X_1'$ is Glu (or analogue thereof); $X_2'$ is Leu (or analogue thereof); $X_3'$ is Trp (or analogue thereof); $X_4'$ is Arg (or analogue thereof); $X_5'$ is Ser (or analogue thereof); $X_6'$ is Ile (or analogue thereof); $X_7'$ is Arg (or analogue thereof); $X_8'$ is Val (or analogue thereof); $X_9'$ is Leu (or analogue thereof); and $X_{10}'$ is any residue/analogue.

15. The macrostructure of claim 1, wherein the macrostructure is CHD-NHR2-2.

16. The macrostructure of claim 1, wherein the macrostructure is CHD$^{DS}$-NHR2-3.

17. The macrostructure of claim 1, wherein the macrostructure comprises the parallel coiled-coil structure.

* * * * *

UNITED STATES PATENT AND TRADEMARK OFFICE
CERTIFICATE OF CORRECTION

PATENT NO. : 10,851,133 B2  
APPLICATION NO. : 15/580987  
DATED : December 1, 2020  
INVENTOR(S) : Arora and Wuo Page 1 of 3

It is certified that error appears in the above-identified patent and that said Letters Patent is hereby corrected as shown below:

In the Claims

At Claim 1, Column 105, Line 56, delete "$c'_3$*" and insert --$c'_3$-- in its place.
At Claim 1, Column 105, Line 57, delete "$b'_3$*" and insert --$b'_3$-- in its place.
At Claim 1, Column 105, Line 61, delete "$f'_2$*" and insert --$f'_2$-- in its place.
At Claim 1, Column 106, Line 28, delete "$c'_2$*" and insert --$c'_2$-- in its place.
At Claim 1, Column 106, Line 29, delete "$b'_2$*" and insert --$b'_2$-- in its place.
At Claim 1, Column 106, Line 33, delete "$f'_1$*" and insert --$f'_1$-- in its place.
At Claim 1, Column 106, Line 38, delete "$c'_1$*" and insert --$c'_1$-- in its place.
At Claim 1, Column 106, Line 39, delete "$b'_1$*" and insert --$b'_1$-- in its place.
At Claim 1, Column 108, Line 60, delete "$c'_3$*" and insert --$c'_3$-- in its place.
At Claim 1, Column 108, Line 61, delete "$b'_3$*" and insert --$b'_3$-- in its place.
At Claim 1, Column 108, Line 66, delete "$f'_2$*" and insert --$f'_2$-- in its place.
At Claim 1, Column 109, Line 5, delete "$c'_2$*" and insert --$c'_2$-- in its place.
At Claim 1, Column 109, Line 6, delete "$b'_2$*" and insert --$b'_2$-- in its place.
At Claim 1, Column 109, Line 11, delete "$f'_1$*" and insert --$f'_1$-- in its place.
At Claim 1, Column 109, Line 15, delete "$c'_1$*" and insert --$c'_1$-- in its place.
At Claim 1, Column 109, Line 16, delete "$b'_1$*" and insert --$b'_1$-- in its place.
At Claim 5, Column 113, Line 47, delete "X" and insert --$X^1$-- in its place.

Signed and Sealed this  
Twenty-first Day of February, 2023

Katherine Kelly Vidal

Katherine Kelly Vidal  
*Director of the United States Patent and Trademark Office*

CERTIFICATE OF CORRECTION (continued)
U.S. Pat. No. 10,851,133 B2

At Claim 8, Columns 113-114, Line 50, delete the following chemical formula:

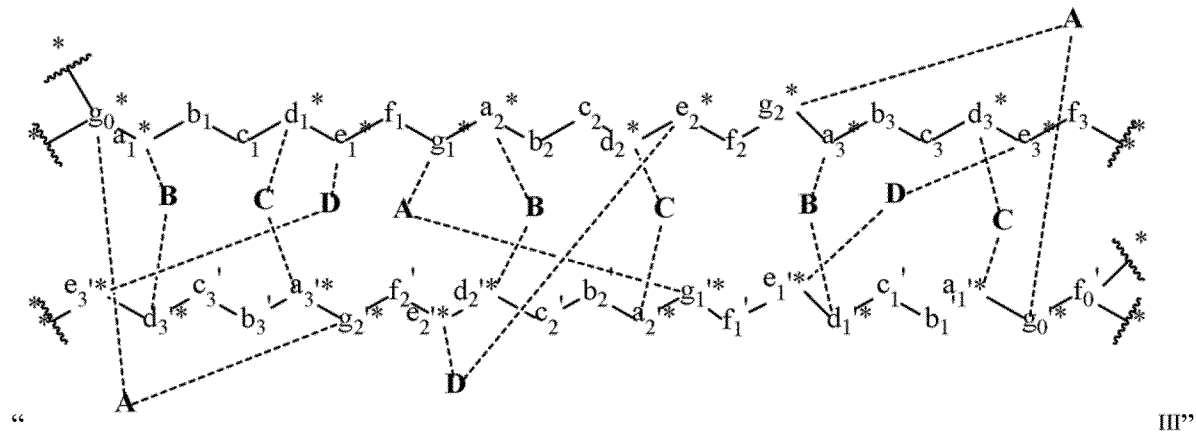

" III"

And insert the following chemical formula in its place:

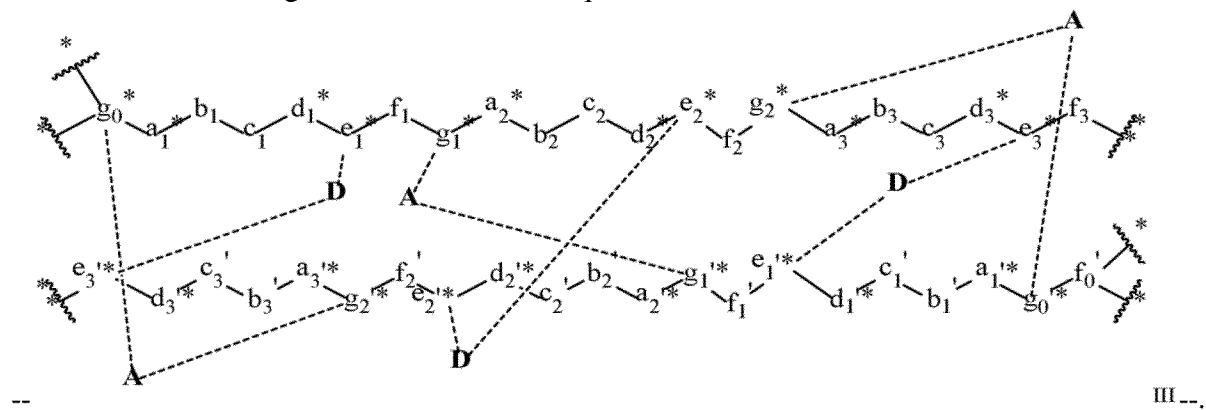

-- III --.

At Claim 10, Columns 115-116, Line 53, delete the following chemical formula:

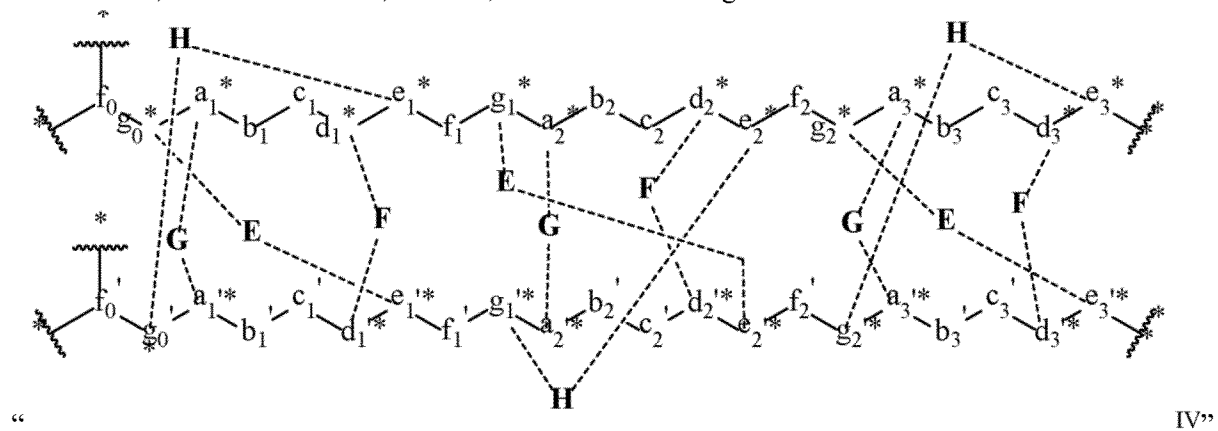

" IV"

CERTIFICATE OF CORRECTION (continued)
U.S. Pat. No. 10,851,133 B2

And insert the following chemical formula in its place:

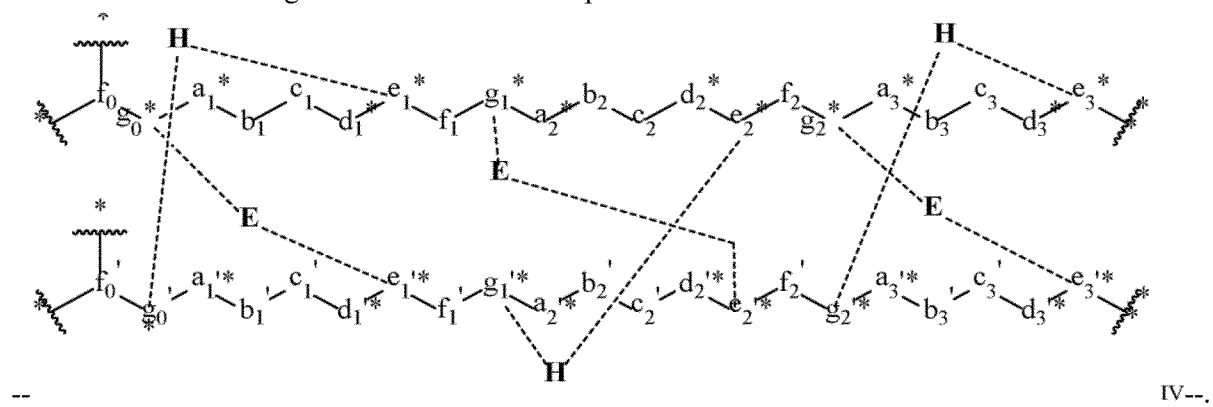

--                                         IV--.